US012637498B2

(12) United States Patent
Qu et al.

(10) Patent No.: US 12,637,498 B2

(45) Date of Patent: May 26, 2026

(54) PDLIM2 AS A BIOMARKER FOR CANCER AND AS AN ANTI-CANCER TREATMENT TARGET

(71) Applicant: UNIVERSITY OF PITTSBURGH—OF THE COMMONWEALTH SYSTEM OF HIGHER EDUCATION, Pittsburgh, PA (US)

(72) Inventors: Zhaoxia Qu, Pittsburgh, PA (US); Gutian Xiao, Pittsburg, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1170 days.

(21) Appl. No.: 17/576,112

(22) Filed: Jan. 14, 2022

(65) Prior Publication Data

US 2022/0135634 A1 May 5, 2022

Related U.S. Application Data

(63) Continuation of application No. PCT/US2020/042814, filed on Jul. 20, 2020.

(60) Provisional application No. 62/876,433, filed on Jul. 19, 2019.

(51) Int. Cl.

| | |
|---|---|
| ***A61K 31/337*** | (2006.01) |
| ***A61K 45/06*** | (2006.01) |
| ***A61P 35/00*** | (2006.01) |
| ***C07K 14/47*** | (2006.01) |
| ***C07K 16/28*** | (2006.01) |

(52) U.S. Cl.

CPC .......... *C07K 14/4703* (2013.01); *A61K 45/06* (2013.01); *A61P 35/00* (2018.01); *C07K 16/2818* (2013.01); *C07K 16/2827* (2013.01)

(58) Field of Classification Search

CPC .................................................... A61K 31/337

See application file for complete search history.

(56) References Cited

U.S. PATENT DOCUMENTS

| | | | |
|---|---|---|---|
| 5,399,346 | A | 3/1995 | Anderson et al. |
| 2014/0221229 | A1 | 8/2014 | Ostrer et al. |
| 2017/0007573 | A1 | 1/2017 | Nezami |
| 2018/0256522 | A1 | 9/2018 | Polymeropoulos et al. |
| 2018/0346989 | A1 | 12/2018 | Li et al. |

FOREIGN PATENT DOCUMENTS

| | | | |
|---|---|---|---|
| WO | WO 2009/016507 | A2 | 2/2009 |
| WO | WO 2009/074970 | A2 | 6/2009 |
| WO | WO 2016/077347 | A1 | 5/2016 |

OTHER PUBLICATIONS

Connolly et al. Clinical Cancer Research, 2017, 23(11): 2691-2701.*

Zhu et al. Cancer Research, 2001, 61(4): 1327-1333.*

Anderson, "Prospects for Human Gene Therapy," Science 226(4673):401-409 (1984).

Basseres et al., "Requirement of the NF-κB Subunit p65/RelA for K-Ras-Induced Lung Tumorigenesis," Cancer Res. 70(9): 3537-3546 (2010).

Blömer et al., "Highly Efficient and Sustained Gene Transfer in Adult Neurons with a Lentivirus Vector," Journal of Virology 71(9):6641-6649 (1997).

Boch, "TALEs of genome targeting: New tools for site-specific genome targeting in human cells are generated from TALE proteins," Nature Biotechnology; 29(2):135-136 (2011).

Bregni et al., "Human Peripheral Blood Hematopoietic Progenitors Are Optimal Targets of Retroviral-Mediated Gene Transfer," Blood 80(6):1418-1422 (1992).

Brigham et al., "Rapid Communication: In vivo Transfection of Murine Lungs with a Functioning Prokaryotic Gene Using a Liposome Vehicle," Am. J. Med. Sci. 298:278 (1989).

Butte et al., "PD-L1 interacts specifically with B7-1 to inhibit T cell proliferation," Immunity, 27(1):111-122 (2007).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

Chaudhri et al., "PD-L1 binds to B7-1 only In Cis on the same cell surface," *Cancer Immunol. Res.* 6(8), 921-929 (2018).

Chen, "Co-inhibitory molecules of the B7-CD28 family in the control of T-cell immunity," Nat Rev Immunol, 4:336-347 (2004).

Cornetta et al., "Gene Transfer into Primates and Prospects for Gene Therapy in Humans," Progress in Nucleic Acid Research and Molecular Biology 36:311-322 (1987).

(Continued)

*Primary Examiner* — Rei Tsang Shiao

(74) *Attorney, Agent, or Firm* — Baker Botts L.L.P.

(57) ABSTRACT

The present disclosure provides methods and compositions for treating cancer (e.g., lung cancer) in a subject by increasing the expression of PDZ-LIM domain containing protein 2 (PDLIM2) in the subject, or a functional fragment thereof. The present disclosure further provides methods of using PDLIM2 as a marker for determining and monitoring a subject's responsiveness to an anti-cancer treatment, providing a prognosis about a cancer in a subject, and selecting an effective anti-cancer treatment for a subject. The present disclosure also provides in vitro methods of screening anti-cancer agents by assessing whether the expression of PDLIM2 is restored by an anti-cancer agent in a cancer cell.

12 Claims, 143 Drawing Sheets

Figure 1A:
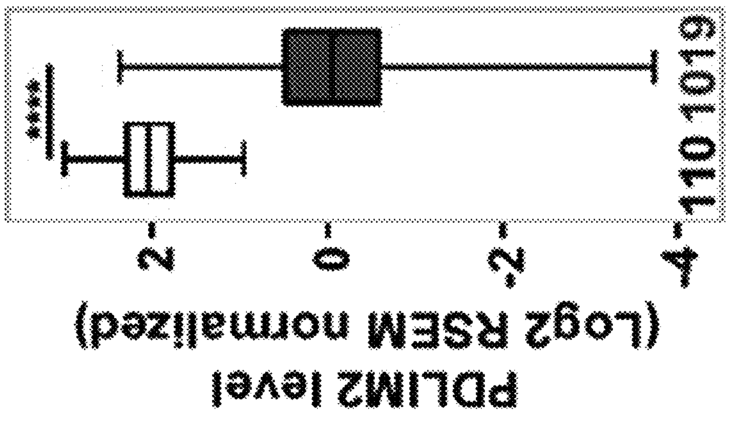

Specification includes a Sequence Listing.

(56) References Cited

OTHER PUBLICATIONS

Danos et al., "Safe and efficient generation of recombinant retroviruses with amphotropic and ecotropic host ranges," PNAS USA 85:6460-6464 (1988).
Durai et al., "Zinc finger nucleases: custom-designed molecular scissors for genome engineering of plant and mammalian cells," Nucleic Acids Res.; 33 (18): 5978-90 (2005).
Eglitis et al., "Retroviral Vectors for Introduction of Genes into Mammalian Cells," BioTechniques 6(7):608-614 (1988).
Friedmann, "Progress toward Human Gene Therapy," Science 244(4910):1275-1281 (1989).
Fu et al., "Molecular determinants of PDLIM2 in suppressing HTLV-I Tax-mediated tumorigenesis," Onocogene, 29(49):6499-6507 (2010).
Gettinger et al., "Five-Year Follow-Up of Nivolumab in Previously Treated Advanced Non-Small-Cell Lung Cancer: Results From the CA209-003 Study," J. Clin. Oncol. 36(17), 1675-1684 (2018).
Gordon et al., "PD-1 expression by tumor-associated macrophages inhibits phagocytosis and tumor immunity," Nature, 545:495-499 (2017).
Hokuto et al., "Stat-3 is required for pulmonary homeostasis during hyperoxia," J. Clin. Invest. 113(1), 28-37 (2004).
Houghton et al., "Neutrophil Elastase-Mediated Degradation of IRS-1 Accelerates Lung Tumor Growth," Nat. Med. 16(2), 219-223 (2010).
Hughes et al., "Retroviral Gene Transfer to Primitive Normal and Leukemic Hematopoietic Cells Using Clinically Applicable Procedures," J. Clin. Invest. 89:1817-1824 (1992).
International Search Report and Written Opinion for International Patent Application No. PCT/US2020/042814 dated Dec. 8, 2020.
Jackson et al., "Analysis of lung tumor initiation and progression using conditional expression of oncogenic K-ras," Genes Dev. 15(24), 3243-3248 (2001).
Johnson, "Gene Therapy for Cystic Fribrosis," Chest 107:77S-83S (1995).
Keir et al., "PD-1 and Its Ligands in Tolerance and Immunity," Annu. Rev. Immunol., 26:677-704 (2008).
Kido et al., "Use of a retroviral vector with an internal opsin promoter to direct gene expression to retinal protoreceptor cells," Current Eye Research 15:833-844 (1996).
Lawless et al., "Oxidative stress induced lung cancer and COPD: opportunities for epigenetic therapy," J Cell Mol Med 13:2800-2821 (2009).
Lee et al., "Targeted chromosomal deletions in human cells using zinc finger nucleases," Genome Res 20 (1):81-89 (2010) doi:10.1101/gr.099747.109.
Le Gal La Salle et al., "An Adenovirus Vector for Gene Transfer into Neurons and Glia in the Brain," Science 259(5097):988-990 (1993).
Li et al., "NF-κB RelA renders tumor-associated macrophages resistant to and capable of directly suppressing CD8+ T cells for tumor promotion," Oncoimmunology 7, e1435250 (2018).
Liou et al., "Reactive oxygen species in cancer," Free Radic Res, 44(5):479-496 (2010).
Loughran et al., "Mystique Is a New Insulin-like Growth Factor-I-regulated PDZ-LIM Domain Protein That Promotes Cell Attachment and Migration and Suppresses Anchorage-independent Growth," Mol Biol Cell., 16(4): 1811-1822 (2005).
Lundstrom et al., "New frontiers in oncolytic viruses: optimizing and selecting for virus strains with improved efficacy," Biologics. 2018; 12: 43-60 (2018).
Miller, "Retrovirus Packaging Cells," Human Gene Therapy 1:5-14 (1990).
Miller et al., "Improved Retroviral Vectors for Gene Transfer and Expression," Biotechniques 7(9):980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miyoshi et al., "Stable and efficient gene transfer into the retina using an HIV-based lentiviral vector," PNAS USA 94:10319-10323 (1997).
Moen, "Directions in Gene Therapy," Blood Cells 17:407-416 (1991).
Naldini et al., "In Vivo Gene Delivery and Stable Transduction of Nondividing Cells by a Lentiviral Vector," Science 272(5259):263-267 (1996).
Ono et al., "Plasmid DNAs directly injected into mouse brain with lipofectin can be incorporated and expressed by brain cells," Neuroscience Letters, 117:259-263 (1990).
Qing et al., "Endoproteolytic processing of C-terminally truncated NF-κB2 precursors at κB-containing promoters," Proc. Natl. Acad. Sci. USA 104, 5324-5329 (2007).
Qu et al., "Interleukin-6 prevents the initiation but enhances the progression of lung cancer," Cancer Res., 75(16): 3209-3215 (2015).
Qu et al., "PDLIM2 restricts Th1 and Th17 differentiation and prevents autoimmune disease," Cell Biosci. 2, 23 (2012).
Qu et al., Epigenetic Repression of PDZ-LIM Domain-containing Protein 2, *Implications for the Biology and Treatment of Breast Cancer**, J Biol Chem, 285(16): 11786-11792 (2010).
Qu et al., "DNA methylation-dependent repression of PDZ-LIM domaincontaining protein 2 in colon cancer and its role as a potential therapeutic target," Cancer Res. 70(5): 1766-1772 (2010).
Reck et al., "Pembrolizumab versus Chemotherapy for PD-L1-Positive Non-Small-Cell Lung Cancer," N. Engl. J. Med. 375, 1823-1833 (2016).
Riley et al., Recent Advances in Nanomaterials for Gene Delivery—A Review, Nanomaterials (Basel)., 7(5): 94 (2017).
Rosenberg et al., "Gene Transfer into Humans," N. Engl. J. Med 323(9):570-578 (1990).
Rountree et al., "DNA methylation, chromatin inheritance, and cancer," Oncogene 20, 3156-3165 (2001).
Schildberg et al., "Coinhibitory pathways in the B7-CD28 ligand-receptor family," Immunity, 44(5): 955-972 (2016).
Sharp, "Gene Therapy," The Lancet 337: 1277-1278 (1991).
Siegel et al., "Cancer Statistics, 2018," CA Cancer J. Clin. 68, 7-30 (2018).
Straubinger et al., "Liposomes as Carriers for Intracellular Delivery of Nucleic Acids," Methods in Enzymology, 101:512-527 (1983).
Steinbrecher et al.,"Loss of Epithelial RelA Results in Deregulated Intestinal Proliferative/Apoptotic Homeostasis and Susceptibility to Inflammation," J. Immunol. 180, 2588-2599 (2008).
Sugiura et al., "Restriction of PD-1 function by cis-PD-L1/CD80 interactions is required for optimal T cell responses," Science, 364, 558-566 (2019).
Sun et al., "Identification of tumor immune infiltration-associated lncRNAs for improving prognosis and immunotherapy response of patients with non-small cell lung cancer," J Immunother Cancer 8(1): e000110 (2020).
Sun et al., "Causative role of PDLIM2 epigenetic repression in lung cancer and therapeutic resistance," Nat Commun, 10:5324 (2019).
Sun et al., "Murine Bronchoalveolar Lavage," Bio. Protoc. 7, pii: e2287 (2017).
Sun et al., "NF-κB1 p105 suppresses lung tumorigenesis through the Tpl2 kinase but independently of its NF-κB function," Oncogene 35(18): 2299-2310 (2016).
Sun et al., "Oncovirus Kaposi Sarcoma Herpesvirus (KSHV) Represses Tumor Suppressor PDLIM2 to Persistently Activate Nuclear Factor κB (NF-κB) and STAT3 Transcription Factors for Tumorigenesis and Tumor Maintenance*," J Biol Chem 290(12): 7362-7368 (2015).
Tanaka et al., "PDLIM2 inhibits T helper 17 cell development and granulomatous inflammation through degradation of STAT3," Sci Signal 4, ra85 (2011).
Tanaka et al., "PDLIM2-mediated termination of transcription factor NF-κB activation by intranuclear sequestration and degradation of the p65 subunit," Nat. Immunol. 8, 584-591 (2007).
Tanaka et al., "SLIM Is a Nuclear Ubiquitin E3 Ligase that Negatively Regulates STAT Signaling," Immunity 22, 729-736 (2005).

(56) References Cited

OTHER PUBLICATIONS

Tolstoshev et al., "Gene expression using retroviral vectors," Current Opinion in Biotechnology 1:55-61 (1990).
Torrado et al., "Pdlim2, a Novel PDZ-LIM Domain Protein, Interacts with α-Actinins and Filamin A," Invest. Ophthalmol. Vis. Sci. 45, 3955-3963 (2004).
Vanoirbeek et al., "PDLIM2 expression is driven by vitamin D and is involved in the pro-adhesion, and anti-migration and -invasion activity of vitamin D," Oncogene, 33, 1904-1911 (2014).
Vokes et al., "Nivolumab versus docetaxel in previously treated advanced non-small-cell lung cancer (CheckMate 017 and CheckMate 057): 3-year update and outcomes in patients with liver metastases," Ann. Oncol. 29, 959-965 (2018).
Wolff et al., "Direct Gene Transfer into Mouse Muscle in Vivo," Science 247(4949):1465-1468 (1990).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Wu et al., "Receptor-mediated Gene Delivery and Expression in Vivo," Journal of Biological Chemistry, 263(29):14621-14624 (1988).
Xiao et al., "NF-κB and cancer: a paradigm of Yin-Yang," Am. J. Cancer Res. 1, 192-221 (2011).
Xu et al., "Evidence for type II cells as cells of origin of K-Ras-induced distal lung adenocarcinoma," Proc. Natl. Acad. Sci. USA 109, 4910-4915 (2012).
Xu et al., "Correction of the enzyme deficiency in hematopoietic cells of Gaucher patients using a clinically acceptable retroviral supernatant transduction protocol," Exp. Hemat. 22:223-230 (1994).
Yan et al., "PDLIM2 suppresses human T-cell leukemia virus type I Tax-mediated tumorigenesis by targeting Tax into the nuclear matrix for proteasomal degradation," Blood 113(18), 4370-4380 (2009).
Yan et al., "Human T-Cell Leukemia Virus Type I-Mediated Repression of PDZ-LIM Domain-Containing Protein 2 Involves DNA Methylation But Independent of the Viral Oncoprotein Tax[1]," Neoplasia. 11(10): 1036-1041 (2009).
Yu et al., "STATs in cancer inflammation and immunity: a leading role for STAT3," Nat Rev Cancer 9, 798-809 (2009).
Zhao et al., "PD-L1:CD80 Cis-Heterodimer Triggers the Co-stimulatory Receptor CD28 While Repressing the Inhibitory PD-1 and CTLA-4 Pathways," Immunity, 51(6):1059-1073 (2019).
Zhao et al., "Epigenetic repression of PDZ-LIM domain-containing protein 2 promotes ovarian cancer via NOS2-derived nitric oxide signaling," Oncotarget, 7(2): 1408-1420; p. 1410, second column, first and second paragraphs; p. 1411, first column, first and second paragraphs; p. 1411, second column, first paragraph; DOI: 10.18632/oncotarget.6368 (2015).
Zhou et al., "Myeloid STAT3 promotes lung tumorigenesis by transforming tumor immunosurveillance into tumor-promoting inflammation," Cancer Immunol. Res. 5(3): 257-268 (2017).
Zhou et al., "The Bach Family of Transcription Factors: A Comprehensive Review," Clin Rev Allergy Immunol, 50:345-356 (2016).
Zhou et al., "Differential roles of STAT3 in the initiation and growth of lung cancer," Oncogene 34(29): 3804-3814 (2015).

* cited by examiner

Relative cell growth (fold)
Calu-6
H727
H460
A549
Vec
PDLIM2

MAD109

Migratory cells

Invasive cells
H460
A549

| Cycle | 1 | 2 | 3 | 4 |
|---|---|---|---|---|
| Time (Day) | 1~9 | 10~18 | 19~27 | 28~36 |
| Paclitaxel (nM) | 10 | 10 | 100 | 100 |

Correlation between PDLIM2 and genes involved in T cell activation (P00053)

| Gene | Pearson r | *p*-value |
|---|---|---|
| B2M | 0.3409 | < 0.0001 |
| CD247 | 0.3046 | < 0.0001 |
| CD28 | 0.4021 | < 0.0001 |
| CD3E | 0.3089 | < 0.0001 |
| CD74 | 0.4859 | < 0.0001 |
| CD80 | 0.3716 | < 0.0001 |
| CD86 | 0.3791 | < 0.0001 |
| GRAP2 | 0.3225 | < 0.0001 |
| HLA-DMA | 0.4589 | < 0.0001 |
| HLA-DMB | 0.4150 | < 0.0001 |
| HLA-DOA | 0.4222 | < 0.0001 |
| HLA-DPA1 | 0.4629 | < 0.0001 |
| HLA-DQA1 | 0.3774 | < 0.0001 |
| HLA-DQA2 | 0.3552 | < 0.0001 |
| HLA-DRA | 0.4501 | < 0.0001 |
| LAT | 0.3257 | < 0.0001 |
| LCP2 | 0.3904 | < 0.0001 |
| NFATC1 | 0.3020 | < 0.0001 |
| NFATC2 | 0.3326 | < 0.0001 |
| PIK3CD | 0.3903 | < 0.0001 |
| PIK3CG | 0.3515 | < 0.0001 |
| PPP3CC | 0.4455 | < 0.0001 |
| PTPRC | 0.3684 | < 0.0001 |
| RAC2 | 0.4019 | < 0.0001 |
| VAV1 | 0.3748 | < 0.0001 |
| WAS | 0.4732 | < 0.0001 |
| ZAP70 | 0.3217 | < 0.0001 |

Figure 14A

Correlation between PDLIM2 and HLA Class I antigen presentation-related gen

| Gene | Pearson r | *p*-value |
|---|---|---|
| HLA-A | 0.3336 | < 0.0001 |
| HLA-B | 0.3678 | < 0.0001 |
| HLA-C | 0.3738 | < 0.0001 |
| HLA-E | 0.4285 | < 0.0001 |
| HLA-F | 0.4096 | < 0.0001 |
| HLA-G | 0.3027 | < 0.0001 |
| B2M | 0.3409 | < 0.0001 |
| TAP1 | 0.1062 | 0.0007 |
| TAP2 | 0.1573 | < 0.0001 |
| TAPBP | 0.2714 | < 0.0001 |
| CALR | -0.0160 | 0.6092 |
| CANX | 0.0060 | 0.8479 |
| PDIA3 | -0.0722 | 0.0213 |

| | |
|---|---|
| Consensus BACH1-binding motif | TGA$^{C}/_{G}$TCA$^{G}/_{T}$C |
| *pdlim2* promoter (+212/+220) | TGAGTCATG |
Figure 35A
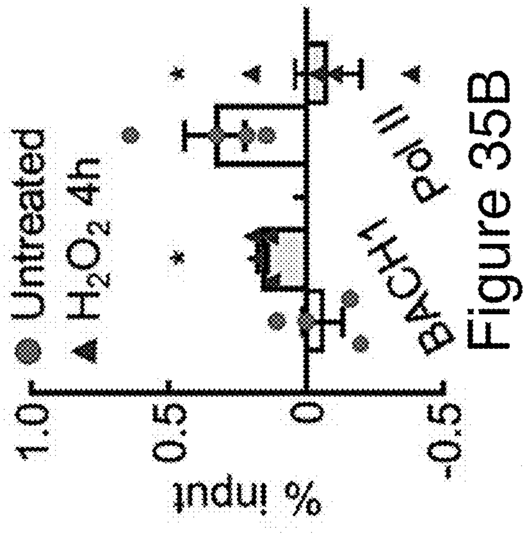
Figure 35B
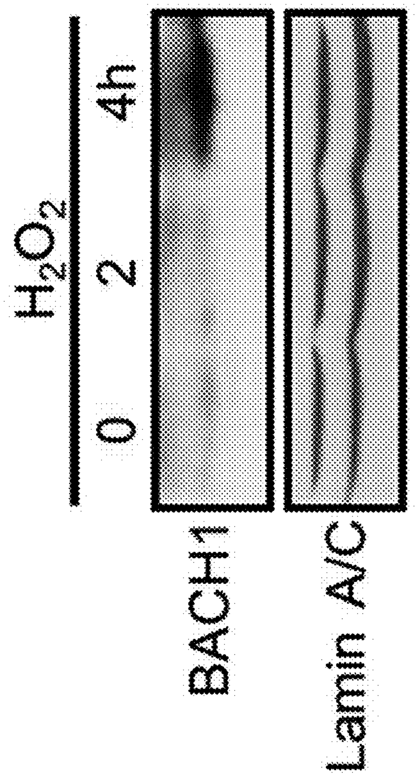
Figure 35C
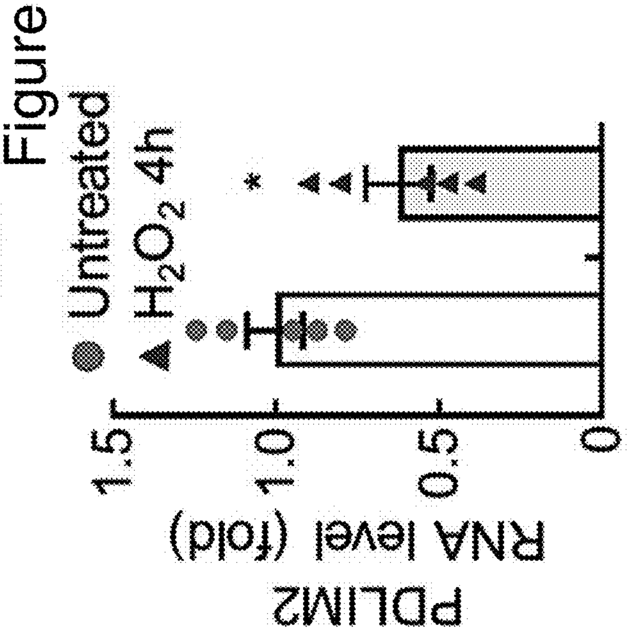
Figure 35D

SEQUENCE LISTING

<160> NUMBER OF SEQ ID NOS: 54

<210> SEQ ID NO 1
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 1
ccgagccaca tcgctcagac ac 22

<210> SEQ ID NO 2
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 2
gtgaccaggc gcccaatacg ac 22

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
gtatggcgtt gacggtggat gtg 23

<210> SEQ ID NO 4
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 4
ggaggtcagc gtccttggct tt 22

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
actacgacgg ggatgttgga 20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
cagcattggc tttgtgaggg 20

<210> SEQ ID NO 7
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 7
atgtgtgtgg agagcgtcaa cc 22

<210> SEQ ID NO 8
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 8
tgagcagagt cttcagagac agcc 24

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
gcctttggac acgcacgacg 20

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 10
agcccacttg gtccacctgg tt 22

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
gcgaggtcgg aatggatctt 20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
gccaaagttc ccaccaccat 20

<210> SEQ ID NO 13
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 13
gaatgaccac ctagagcctt gg 22

<210> SEQ ID NO 14
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 14
tgttcccata gagttccaca aaag 24

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
tgacgacccc atagaggaac a 21

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
cgcactttct ccgcagtttc 20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
gctgcgaagt ggaaaccatc 20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
gcacttctgt tcctcgcaga 20

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19
tggcatttgc tgaacgcatt t 21

<210> SEQ ID NO 20

<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 20
agtgcagcca ggtctaattg t 21

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
ggcttctggt gaaatcgcat 20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
gcaggctcac tgctctcata 20

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 23
acccgcgagc acagcttctt tg 22

<210> SEQ ID NO 24
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 24
ctttgcacat gccggagccg ttg 23

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
agtgccagcc tcgtcccgta 20

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
caggcgccca atacggccaa 20

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
gagaacatgc tacacgcgga 20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
ggagccctgg aatctggttg 20

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
aggctggtga agcagagaga 20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
atgtcagcag ggtagaagcc 20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
ctaccaggtt ctccagagcg 20

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
ttgtccaggt gccgaaagtc 20

<210> SEQ ID NO 33
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 33
aaagaggtcc tgatggagag tccac 25

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34
gctcctggga cctgccgagt a 21

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
agattcagca cgagcagtca 20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
gggctcaacc agtccattgt 20

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
caaaatgcca gaggcggatg 20

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
catggagggt gggttggaaa 20

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
cctgctgtca cttgctacgg 20

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
cactaacgca agcaggtcca 20

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
ccttgcttca ggcgtctgtg 20

<210> SEQ ID NO 42
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 42
cttgaaatct gctggctcgc 20

<210> SEQ ID NO 43
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 43
ctgtgaggaa gagttcgccg atgctgaaga ggagggagag 40

<210> SEQ ID NO 44
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 44
ctctccctcc tcttcagcat cggcgaactc ttcctcacag 40

<210> SEQ ID NO 45
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 45
tgctgctcaa ctatggtctc tattcaagag atagagacca tagttgagca gcttttttc 59

<210> SEQ ID NO 46
<211> LENGTH: 63
<212> TYPE: DNA
<213> ORGANISM: Artificial Sequence
<220> FEATURE:

<223> OTHER INFORMATION: Synthetic polynucleotide

<400> SEQUENCE: 46
tcgagaaaaa agctgctcaa ctatggtctc tatctcttga atagagacca tagttgagca 60
gca 63

<210> SEQ ID NO 47
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 47
gggcggccgc aagatggcgc agacgcagg 29

<210> SEQ ID NO 48
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 48
agggatcctc aggccaactt gacctcctc 29

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
gaagtgaaac cgggctgagg 20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
gccaaaggga gaaggagagg 20

<210> SEQ ID NO 51
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 51
agaggagttt atatatattt agg 23

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
tacctaacaa ccctctctcc 20

-continued

```
<210> SEQ ID NO 53
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 53

agaggagttt atatatattt agg                                    23


<210> SEQ ID NO 54
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 54

tacctaacaa ccctctctcc                                        20
```

PDLIM2 AS A BIOMARKER FOR CANCER AND AS AN ANTI-CANCER TREATMENT TARGET

CROSS-REFERENCED TO RELATED APPLICATIONS

This application is a Continuation of International Patent Application No. PCT/US2020/042814, filed Jul. 20, 2020, which claims priority to U.S. Provisional Application No. 62/876,433, filed Jul. 19, 2019, the contents of each of which are incorporated by reference in their entireties, and to each of which priority is claimed.

GRANT INFORMATION

This invention was made with government support under grant numbers CA047904, CA189703, CA172090, and CA175252 awarded by the National Institute of Health. The government has certain rights in the invention.

SEQUENCE LISTINGS

The specification further incorporates by reference the Sequence Listing submitted herewith via EFS on Jan. 14, 2022. Pursuant to 37 C.F.R. § 1.52(e)(5), the Sequence Listing text file, identified as 0723960892SL.txt, is 11,084 bytes and was created on Jan. 14, 2022. The Sequence Listing, electronically filed herewith, does not extend beyond the scope of the specification and thus does not contain new matter.

1. TECHNICAL FIELD

The present disclosure provides PDZ-LIM domain containing protein 2 (PDLIM2) based methods and kits for treating cancer (e.g., lung cancer). The present disclosure further provides methods and kits of using PDLIM2 as a biomarker for the diagnosis and prognosis of cancer, and for the selection of effective cancer treatments.

2. BACKGROUND

Lung cancer, the leading cause of cancer deaths, has been largely resistant to certain therapies, including conventional chemotherapy and an immune checkpoint PD-1 blockade therapy (Siegel et al., *CA Cancer J. Clin.* 68, 7-30 (2018); Vokes et al., *Ann. Oncol.* 29, 959-965 (2018); Reck et al., *N. Engl. J. Med.* 375, 1823-1833 (2016); Gettinger et al., *J. Clin. Oncol.* 36, 1675-1684 (2018)).

Thus, there remain needs for anti-cancer treatments that improve a subject's responsiveness to the existing treatments for lung cancer, and for biomarkers that identify subjects that are responsive to the existing anti-cancer treatments.

3. SUMMARY

The present disclosure provides methods and compositions for treating cancer (e.g., lung cancer) in a subject by increasing the expression of PDLIM2, or a functional fragment thereof, in the subject. It is based, at least in part, on the discoveries that PDLIM2 is repressed in various cancers, and is associated with poor prognosis. Restoration of PDLIM2 in vivo suppresses primary tumor growth and tumor metastasis and sensitizes tumor cells to anti-cancer treatments, such as chemotherapy and immune checkpoint blockade therapy.

In one aspect, the presently disclosed subject matter provides a method for treating a subject having a cancer, comprising administering to the subject an agent for increasing the expression of PDZ-LIM domain containing protein 2 (PDLIM2), or a functional fragment thereof, in the subject. In certain embodiments, the agent is an epigenetic modulating agent. In certain embodiments, the epigenetic modulating agent is selected from DNA methyltransferase inhibitors, histone deacetylase inhibitors, and any combinations thereof. In certain embodiments, the DNA methyltransferase inhibitor is selected from 5-azadeoxycitidine, 5-aza-cytidine, SGI-110, procainamide, epigallocathechin 3-gallate, RG108, hydralazine, and derivatives thereof, and combinations thereof. In certain embodiments, the histone deacetylase inhibitor is selected from HDAC1 inhibitors, HDAC2 inhibitors, HDAC3 inhibitors, pan-HDAC inhibitors, and combinations thereof. In certain embodiments, the histone deacetylase inhibitor is selected from entinostat, trichostatin A, vorinostat, panobinostat, romidepsin, belinostat, derivatives thereof, and combinations thereof.

In another aspect, the presently disclosed subject matter provides a method for treating a subject having a cancer, comprising administering to the subject a genetic engineering system for increasing the expression of PDLIM2, or a functional fragment thereof, in the subject.

In certain embodiments, the genetic engineering system knocks down or knocks out at least one negative regulator of the PDLIM2 gene. In certain embodiments, wherein the genetic engineering system knocks in at least one PDLIM2 gene, or a functional fragment thereof. In certain embodiments, the genetic engineering system knocks in at least one positive regulator of the PDLIM2. In certain embodiments, the genetic engineering system knocks out at least one negative cis-element of the PDLIM2 gene. In certain embodiments, the genetic engineering system knocks in at least one positive cis-element of the PDLIM2 gene. In certain embodiments, the genetic engineering system modulates the promoter and/or enhancer of the PDLIM2 gene.

In certain embodiments, the genetic engineering system comprises a CRISPR/Cas system, a zinc-finger nuclease (ZFN) system, a transcription activator-like effector nuclease (TALEN) system), or an interfering RNA. In certain embodiments, the genetic engineering system comprises a CRISPR/Cas system. In certain embodiments, the genetic engineering system knocks down or knocks out at least one microRNA that targets PDLIM2 mRNA. In certain embodiments, the genetic engineering system comprises an oligonucleotide that has a complementary sequence to the microRNA. In certain embodiments, the oligonucleotide is a small interference RNA (siRNA), and/or a short hairpin RNA (shRNA).

In certain embodiments, wherein the genetic engineering system comprises a nucleic acid encoding a PDLIM2 gene, a positive regulator of PDLIM2, an inhibitor of a PDLIM2 negative regulator, a functional fragment thereof, or combination thereof. In certain embodiments, the nucleic acid is DNA or RNA. In certain embodiments, the nucleic acid is a plasmid or a nanoplasmid. In certain embodiments, the nucleic acid is a messenger RNA. In certain embodiments, the nucleic acid comprises a promoter.

In certain embodiments, the genetic engineering system comprises a viral vector. In certain embodiments, the viral vector is a lentivirus, a retrovirus, an adenovirus, an adenoassociated virus, or an oncolytic-vaccinia virus. In certain embodiments, the viral vector is a retrovirus.

In certain embodiments, the genetic engineering system comprises a non-viral vector. In certain embodiments, the non-viral vector comprises nanoparticles. In certain embodiments, the nanoparticles comprise cationic polymers.

In certain embodiments, the increasing the expression of PDLIM2, or a functional fragment thereof, restores PDLIM2 function. In certain embodiments, the expression of PDLIM2, or a functional fragment thereof, includes the level of PDLIM2 mRNA and/or the level of PDLIM2 protein.

In certain embodiments, the method further comprises administering the agent or the genetic engineering system to a tumor cell of the subject. In certain embodiments, the method further comprises administering the agent or the genetic engineering system to a non-tumor cell of the subject. In certain embodiments, the non-tumor cell is a tumor-associated cell.

In certain embodiments, the method further comprises administering a second anti-cancer treatment to the subject. In certain embodiments, the second anti-cancer treatment is a chemotherapy, a radiotherapy, a targeted drug therapy, an immunotherapy, or a combination thereof. In certain embodiments, wherein the second anti-cancer treatment is a combination of chemotherapy and immunotherapy.

In certain embodiments, the chemotherapy comprises administering a chemotherapeutic agent to the subject. In certain embodiments, the chemotherapeutic agent is selected from cisplatin, carboplatin, docetaxel, gemcitabine, paclitaxel, paclitaxel, vinorelbine, pemetrexed, analogues and derivative thereof, and combinations thereof. In certain embodiments, the immune therapy comprises administering an immune checkpoint inhibitor to the subject. In certain embodiments, the second anti-cancer treatment comprises administer to the subject the chemotherapeutic agent and the immune checkpoint inhibitor. In certain embodiments, the immune checkpoint inhibitor is selected from anti-PD1 antibodies, anti-PD-L1 antibodies, anti-CTLA-4 antibodies, and any combinations thereof.

In another aspect, the presently disclosed subject matter provides a method for diagnosing a cancer, comprising (a) determining the level of a PDLIM2 biomarker in a sample from a subject; (b) comparing the level of the PDLIM2 biomarker to a reference level; and (c) diagnosing the subject as having a risk of the cancer if the level of the PDLIM2 biomarker is lower than the reference level. In certain embodiments, the method further comprises diagnosing the subject as not having a risk of the cancer if the level of the PDLIM2 biomarker is higher than the reference level.

In another aspect, the presently disclosed subject matter provides a method for determining a prognosis of a cancer, comprising (a) determining the level of a PDLIM2 biomarker in a sample from a subject; (b) comparing the level of the PDLIM2 biomarker to a reference level; and (c) determining that the subject has a poor prognosis if the level of the PDLIM2 biomarker is lower than the reference level.

In certain embodiment, the method further comprises determining that the subject has a good prognosis if the level of the PDLIM2 biomarker is higher than the reference level. In certain embodiments, the poor prognosis indicates non-survival of the subject within 5 years.

In another aspect, the presently disclosed subject matter provides a method for predicting a subject's responsiveness to an anti-cancer treatment, comprising (a) determining the level of a PDLIM2 biomarker in a sample from a subject; (b) comparing the level of the PDLIM2 biomarker to a reference level; and (c) predicting that the subject will be responsive to the anti-cancer treatment if the PDLIM2 biomarker is higher than the reference level.

In certain embodiments, the method further comprises treating the subject with the anti-cancer treatment if the subject is predicted to be responsive to the anti-cancer treatment. In certain embodiments, the method further comprises predicting that the subject will not be responsive to the anti-cancer treatment if the PDLIM2 biomarker is lower than the reference level. In certain embodiments, the method further comprises increasing the expression of PDLIM2 in the subject if the subject is predicted to be not responsive to the anti-cancer treatment. In certain embodiments, the expression of PDLIM2 is increased by administering to the subject an agent or a genetic modulating system that increases the expression of PDLIM2. In certain embodiments, the reference level is the level of the PDLIM2 biomarker in a population of healthy individuals free of the cancer.

In another aspect, the presently disclosed subject matter provide a method for monitoring a subject's responsiveness to an anti-cancer treatment, comprising (a) determining the level of a PDLIM2 biomarker in a sample obtained from the subject before receiving the anti-cancer treatment; (b) determining the level of the PDLIM2 biomarker in a sample obtained from the subject during or after receiving the anti-cancer treatment; (c) comparing the levels of the biomarker in the samples; and (d) determining that the subject is responsive to the anti-cancer treatment if the level of the PDLIM2 biomarker increases during or after receiving the anti-cancer treatment. In certain embodiments, the method further comprises determining that the subject is not responsive to the anti-cancer treatment if the level of the PDLIM2 biomarker decreases during or after receiving the anti-cancer treatment.

In certain embodiments, the PDLIM2 biomarker is a PDLIM2 gene methylation profile, a PDLIM2 mRNA, a PDLIM2 protein, or a combination thereof. In certain embodiments, the anti-cancer treatment is a chemotherapy, a radiotherapy, a targeted drug therapy, an immune therapy, or a combination thereof. In certain embodiments, the chemotherapy comprises administering a chemotherapeutic agent to the subject. In certain embodiments, the immune therapy comprises administering an immune checkpoint inhibitor to the subject.

In certain embodiments, the sample comprises tumor cells of the subject. In certain embodiments, the sample comprises non-tumor cells of the subject. In certain embodiments, the non-tumor cells are tumor-associated cells. In certain embodiments, the subject is a human subject.

In certain embodiments, the cancer is a lung cancer. In certain embodiments, wherein the cancer is selected from bladder urothelial carcinoma, cervical squamous cell carcinoma and endocervical adenocarcinoma, cholangiocarcinoma, colon adenocarcinoma, head and neck squamous cell carcinoma, kidney chromophobe, kidney renal papillary cell carcinoma, liver hepatocellular carcinoma, lung adenocarcinoma, lung squamous cell carcinoma, prostate adenocarcinoma, rectum adenocarcinoma, stomach adenocarcinoma, and uterine corpus endometrial carcinoma.

In another aspect, the presently disclosed subject matter provides a method for screening for candidate compounds for treating cancer, comprising (a) providing a population of cells comprising tumor cells, non-tumor cells, tumor-associated cells, or combinations thereof; (b) contacting the cells with a test compound; (c) measuring the expression of PDLIM2 in the cells; and (d) selecting the test compound, if the expression of PDLIM2 is higher than a reference level.

In another aspect, the present disclosure provides a kit for diagnosing a cancer, including a detector for determining the level of a PDLIM2 biomarker.

In another aspect, the present disclosure provides a kit for determining a prognosis of a cancer, including a detector for determining the level of a PDLIM2 biomarker.

In another aspect, the present disclosure provides a kit for predicting a subject's responsiveness to an anti-cancer treatment, including a detector for determining the level of a PDLIM2 biomarker.

In another aspect, the present disclosure provides a kit for monitoring a subject's responsiveness to an anti-cancer treatment, including a detector for determining the level of a PDLIM2 biomarker.

4. BRIEF DESCRIPTION OF THE DRAWINGS

Figure 1B:
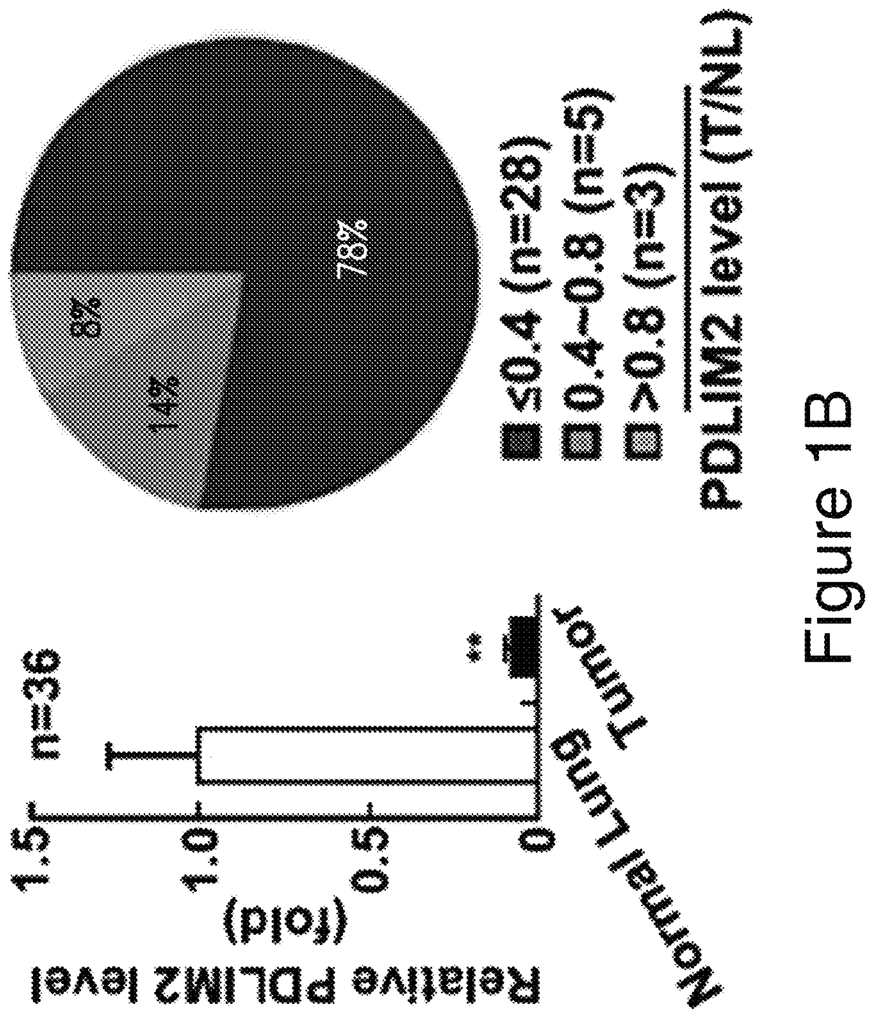
Figure 1C:
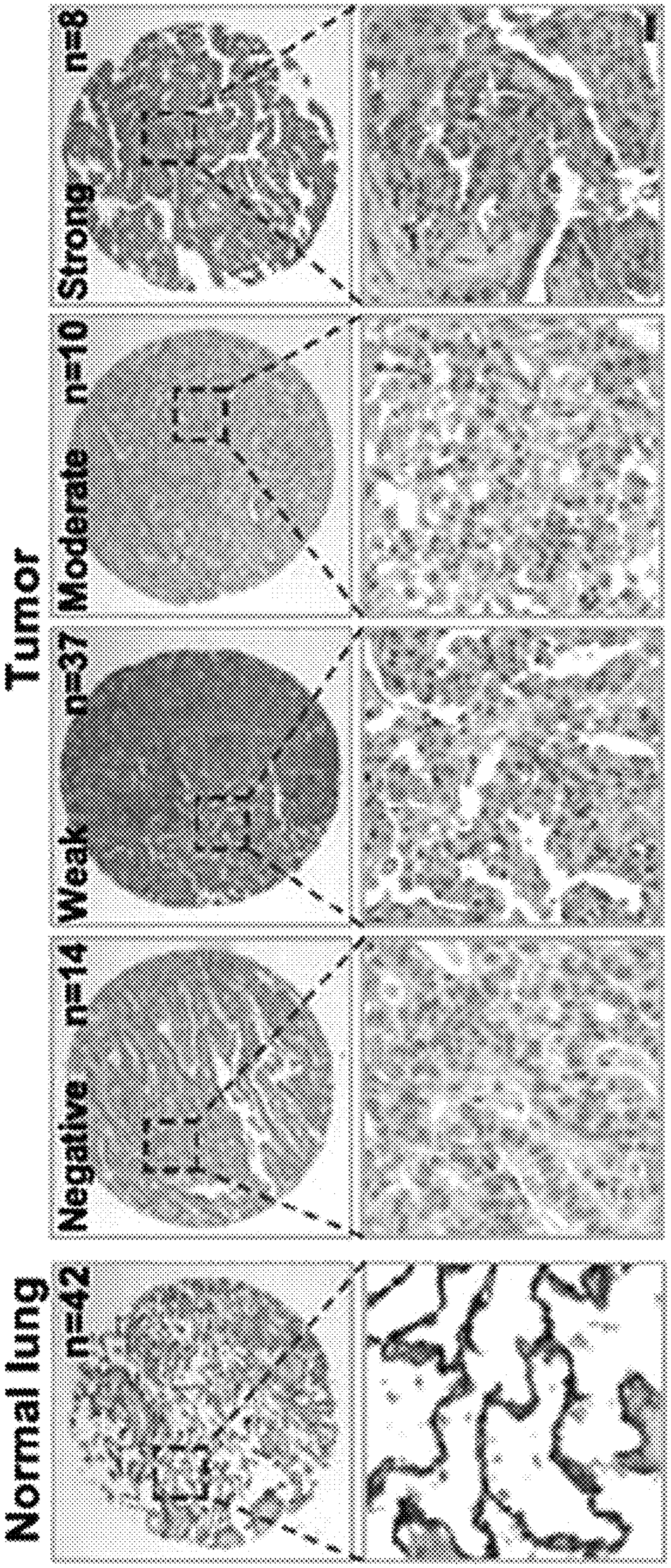
Figure 1D:
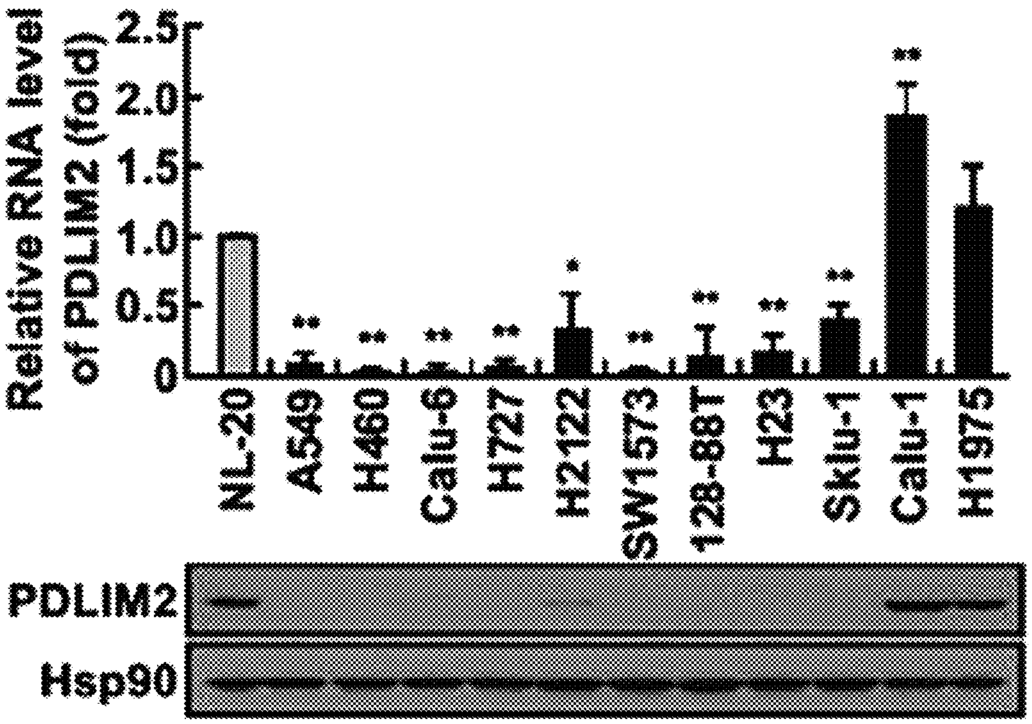
Figure 1E:
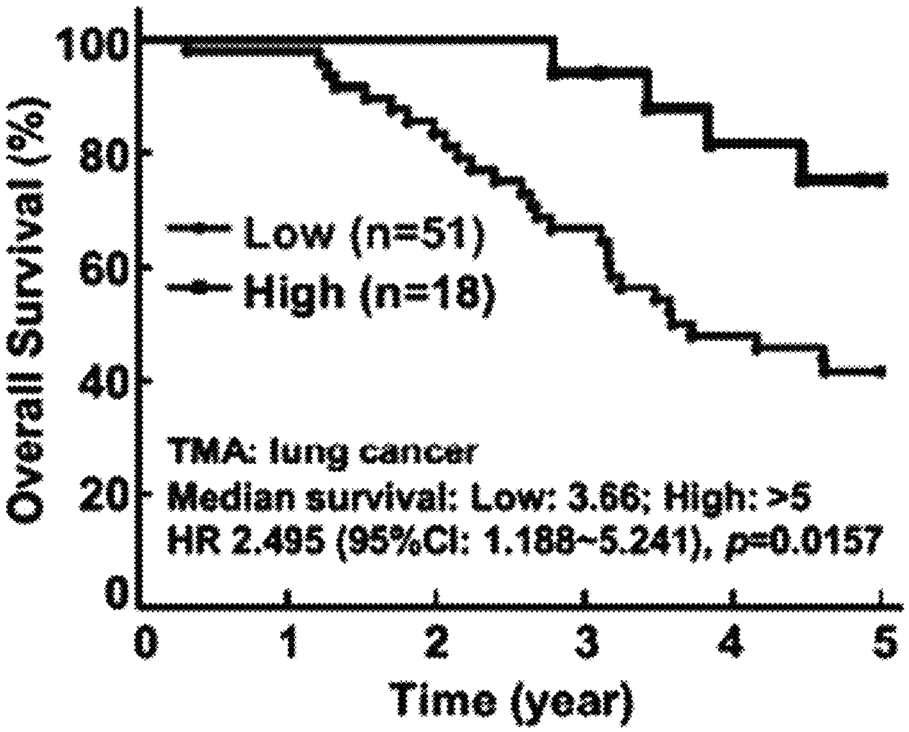
Figure 1F:
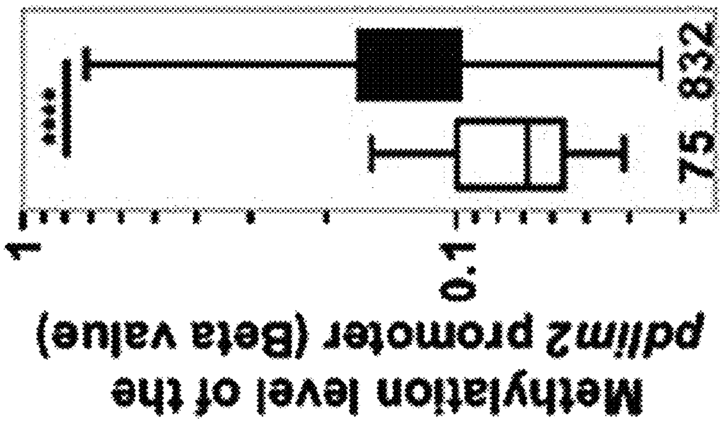
Figure 1G:
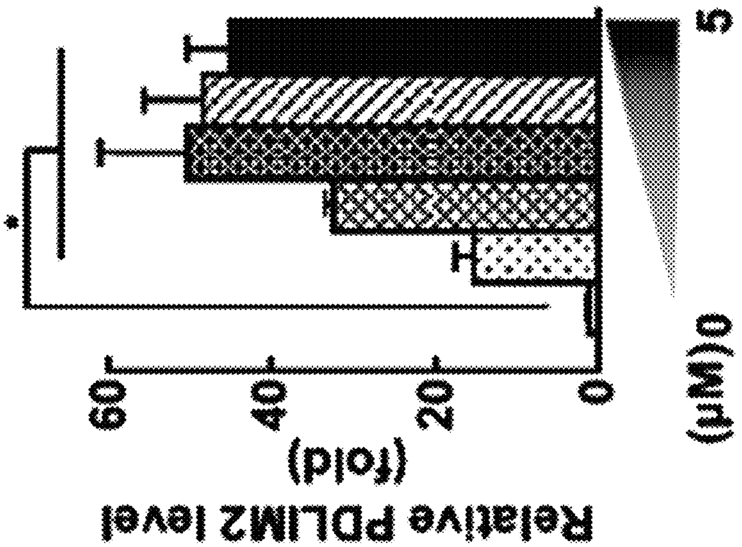
Figure 1H:
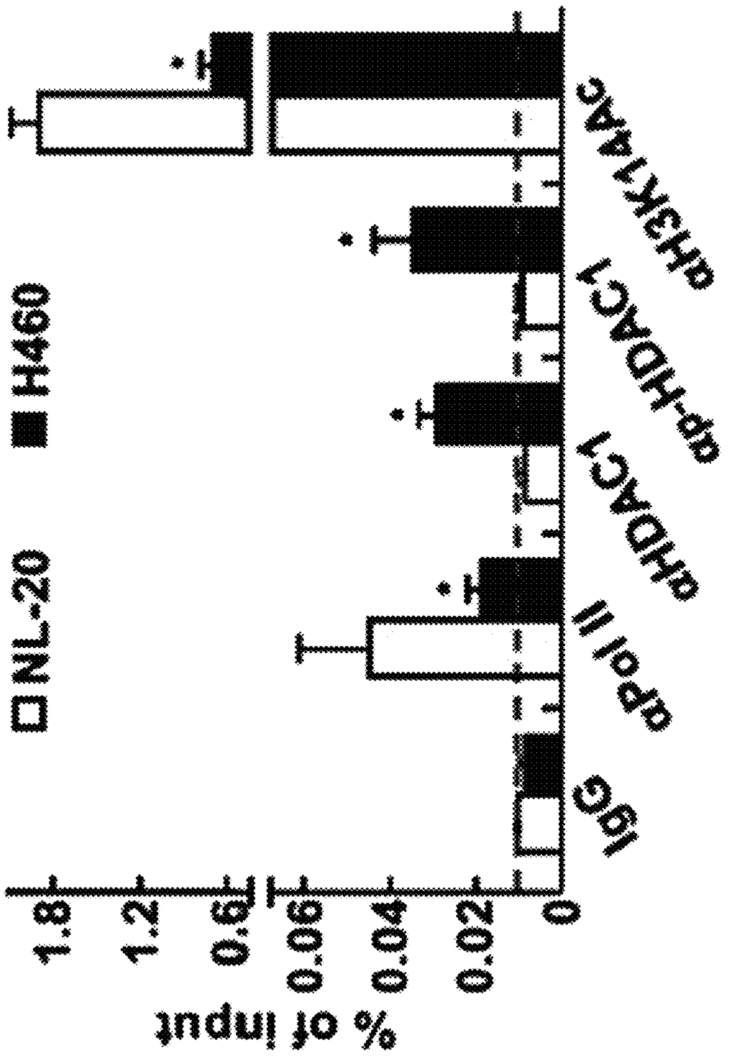
Figure 1I:
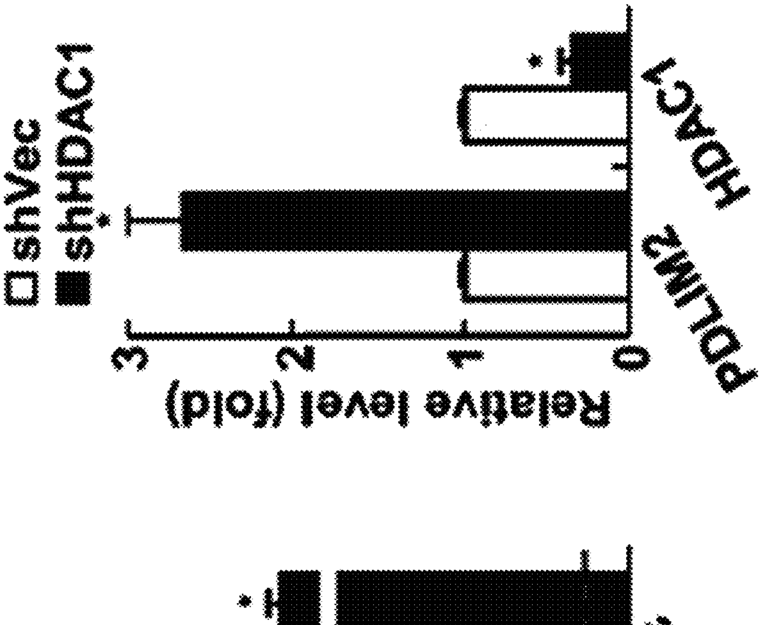
Figure 1L:
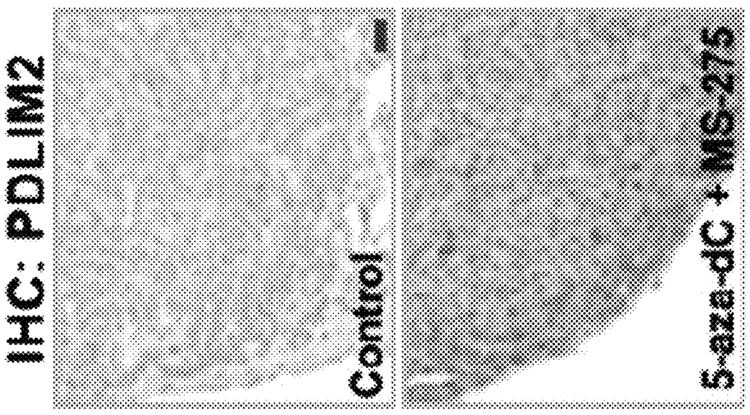
Figure 1K:
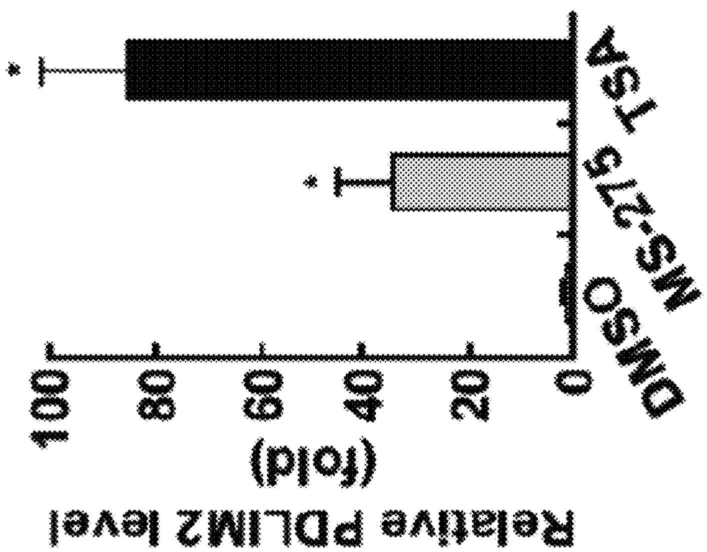
Figure 1J:
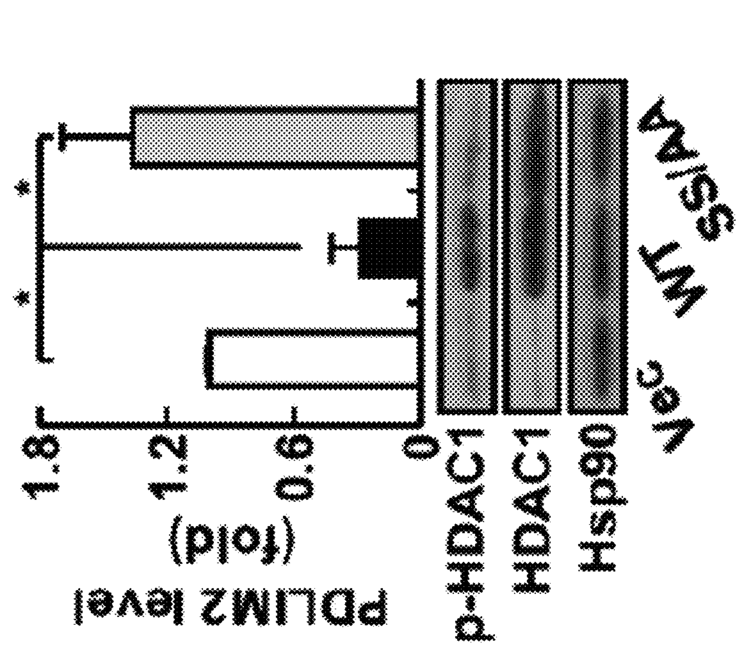

FIGS. 1A-1L provide that PDLIM2 is epigenetically repressed in human lung cancer, which is associated with poor prognosis. FIG. 1A provides TCGA data showing PDLIM2 repression in human lung cancer. Light column and dark column stand for normal lung tissues and lung cancer tissues, respectively. Sample numbers are indicated. FIG. 1B provides quantitative RT-PCR (qPCR) analysis showing PDLIM2 repression in human lung cancer. Matched normal lung tissues from the same patients were used as controls. FIG. 1C provides lung tumor tissue microarray (TMA) assay showing PDLIM2 repression in human lung cancer. Representatives of normal tissues as well as lung cancer tissues with different intensities of PDLIM2 IHC staining are provided. The intensities of PDLIM2 IHC staining were measured by ImageJ. Scale bar, 20 μm. FIG. 1D provides qPCR and immunoblotting (IB) analysis showing PDLIM2 repression in human lung cancer cell lines (n≥3). NL-20 is a normal human lung epithelial cell line; others are human lung cancer cell lines. FIG. 1E provides Kaplan-Meier patient survival curve showing a positive association between PDLIM2 expression and patient survival based on the TMA assay in FIG. 1C. FIG. 1F provides TCGA data showing increased methylation of the pdlim2 promoter in human lung cancer. Light column and dark column stand for normal lung tissues and lung cancer tissues, respectively. Sample numbers are indicated. FIG. 1G provides qPCR analysis showing PDLIM2 recovery in A549 human lung cancer cells by 5-aza-dC (n=3). FIG. 1H provides chromatin immunoprecipitation (ChIP) assay showing increased HDAC1 and in particular its phosphorylation form but decreased RNA polymerase II (Pol II) and histone H3K14 acetylation (H3K14Ac) at the pdlim2 promoter in H460 human lung cancer cells (n≥3). FIG. 1I provides qPCR analysis showing PDLIM2 recovery in H460 cells by HDAC1 knockdown (n=3). FIG. 1J provides qPCR analysis showing PDLIM2 repression by ectopic HDAC1 (WT) but not its phosphorylation deficient mutant (SS/AA) in human lung cancer cells H460 (n=3). The expression levels of HDAC1 and its mutant were detected by IB. FIG. 1K provides qPCR analysis showing PDLIM2 recovery in H460 cells by MS-275 and TSA (n≥3). FIG. 1L provides IHC staining showing PDLIM2 recovery in mouse lung tumor by 5-aza-dC and MS-275 in urethane model. Scale bar, 20 μm. In FIGS. 1A, 1B, 1D, 1F-1K, * p<0.05,  p<0.01, ** p<0.0001, Student's t test.

Figure 2B:
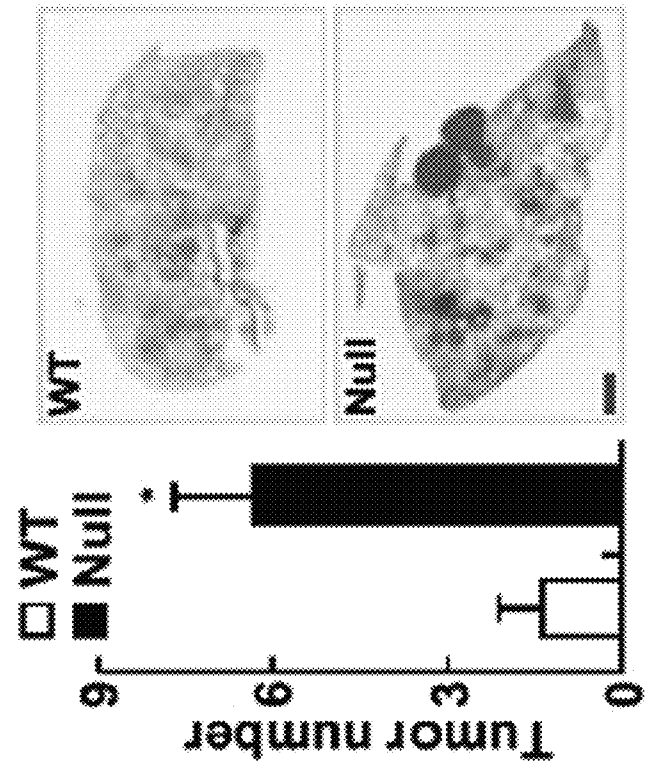
Figure 2A:
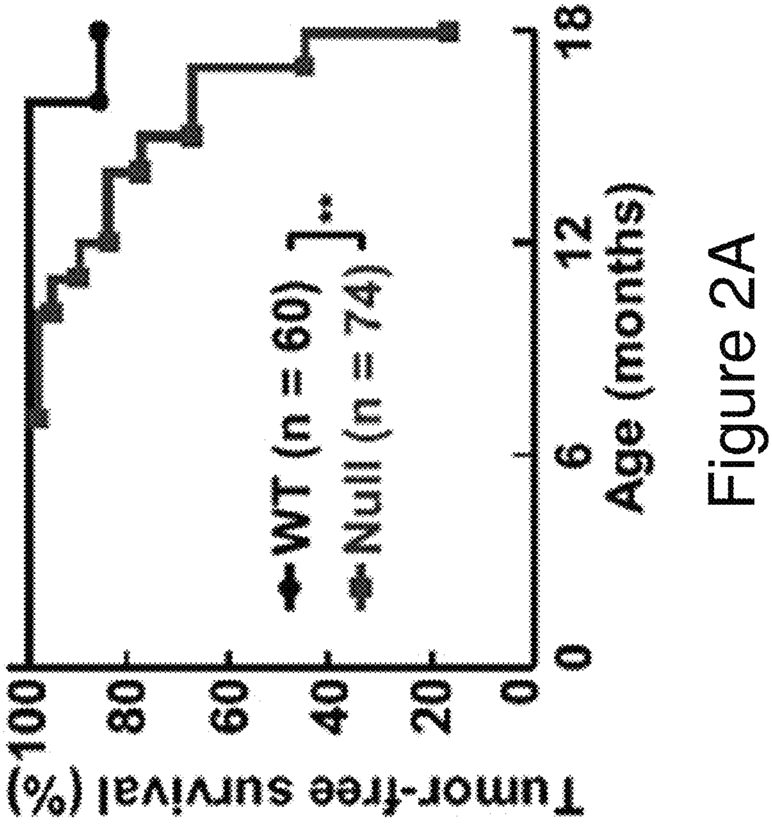
Figure 2D:
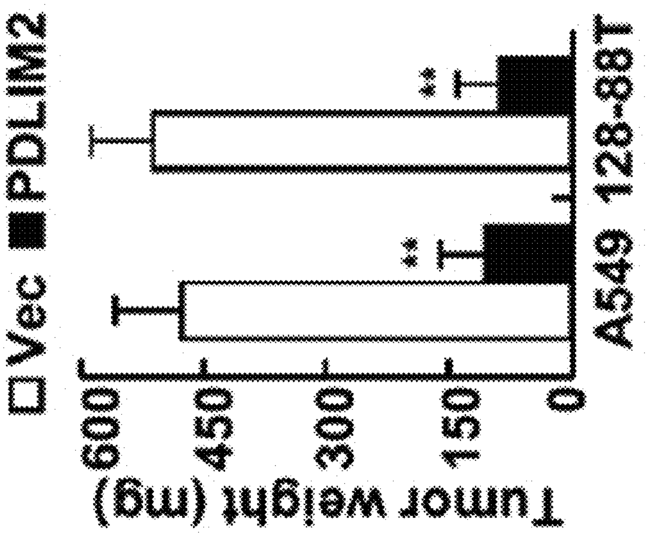
Figure 2C:
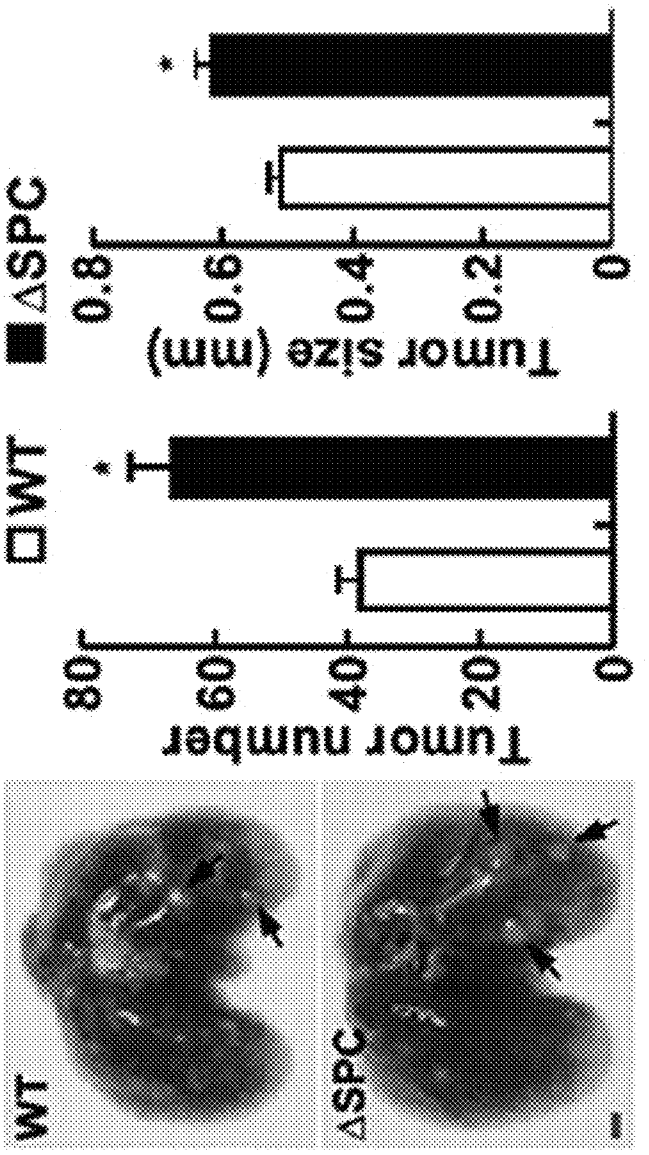
Figure 2E:
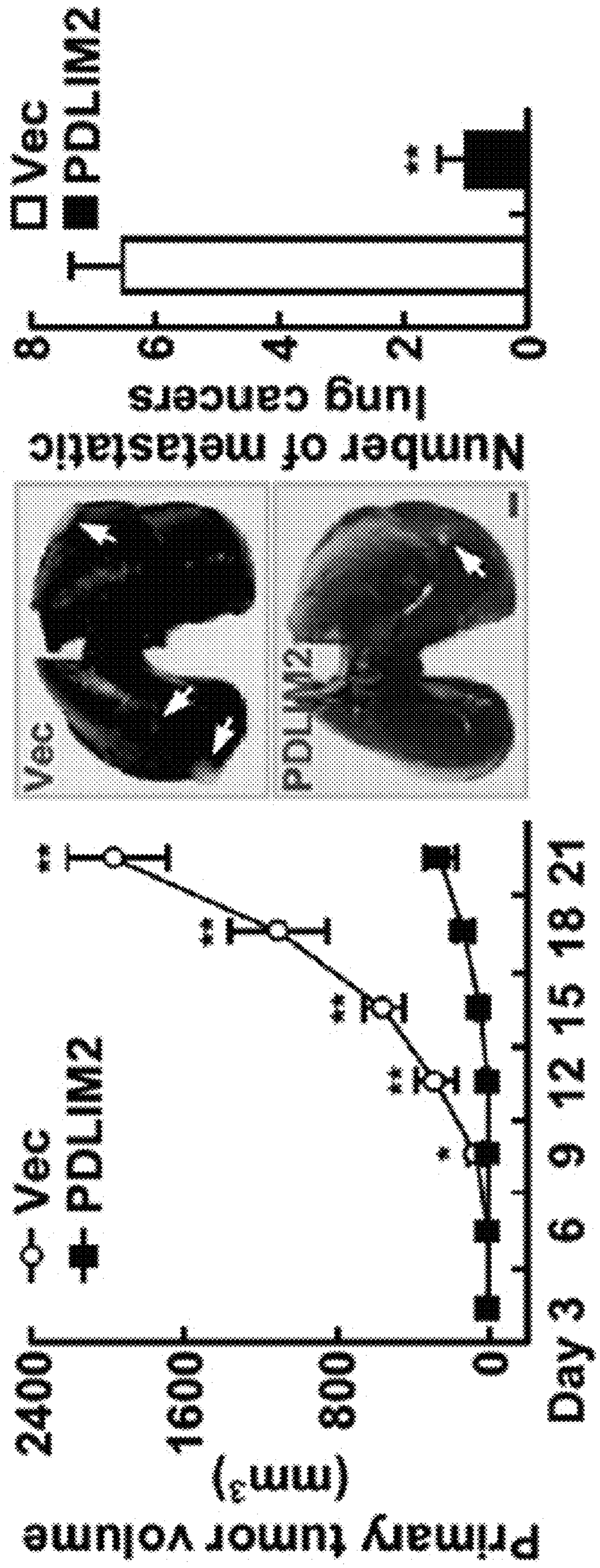
Figure 2G:
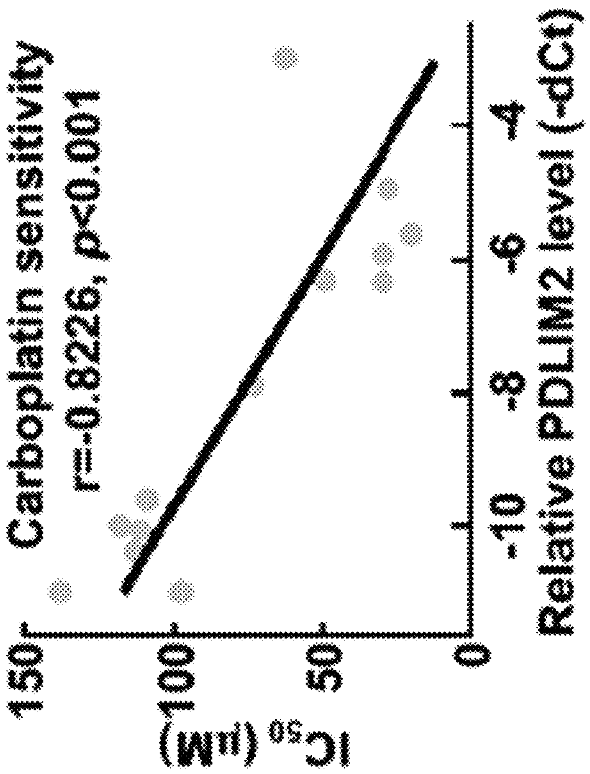
Figure 2F:
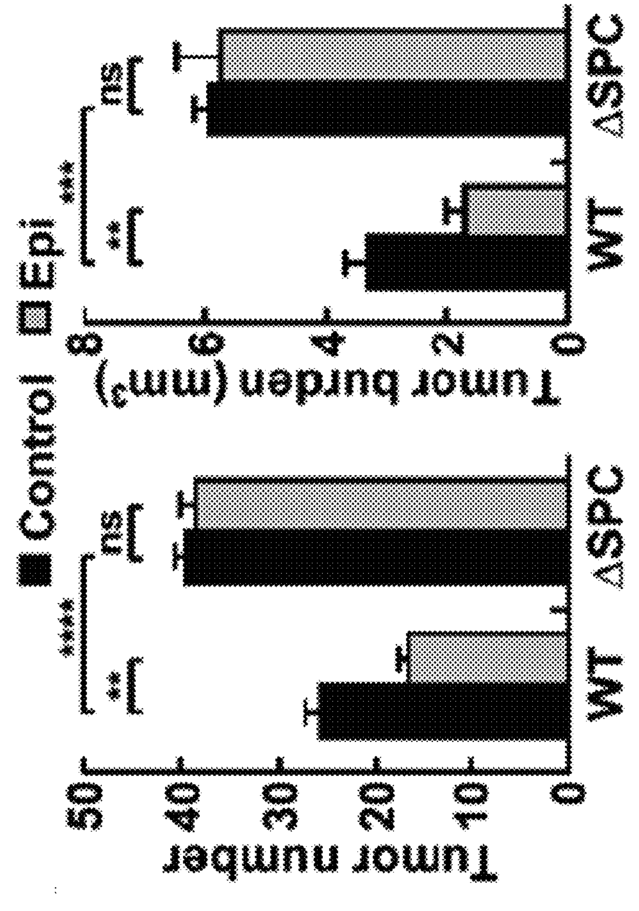
Figure 2I:
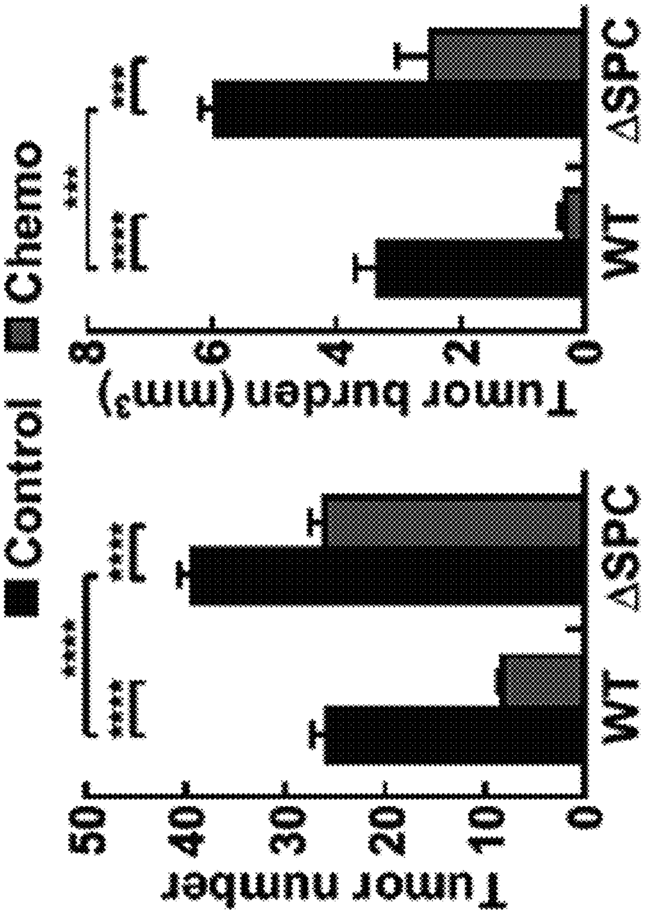
Figure 2H:
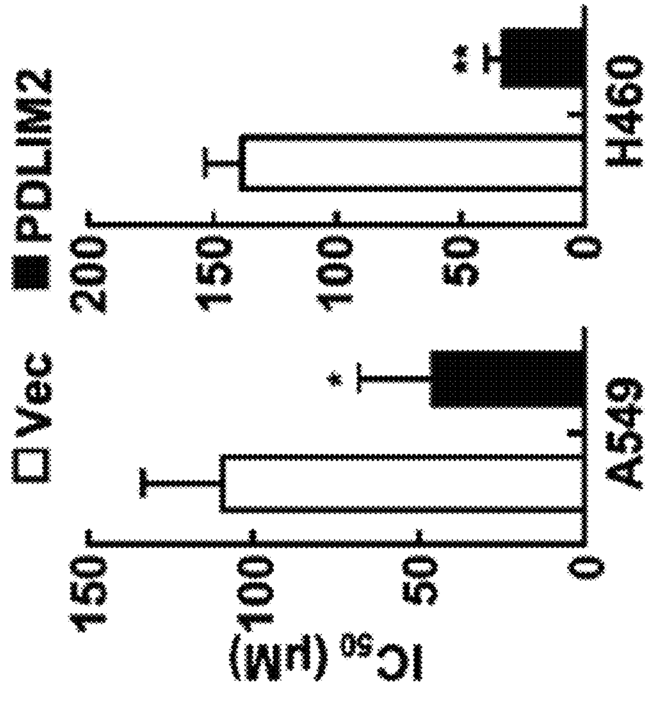
Figure 2K:
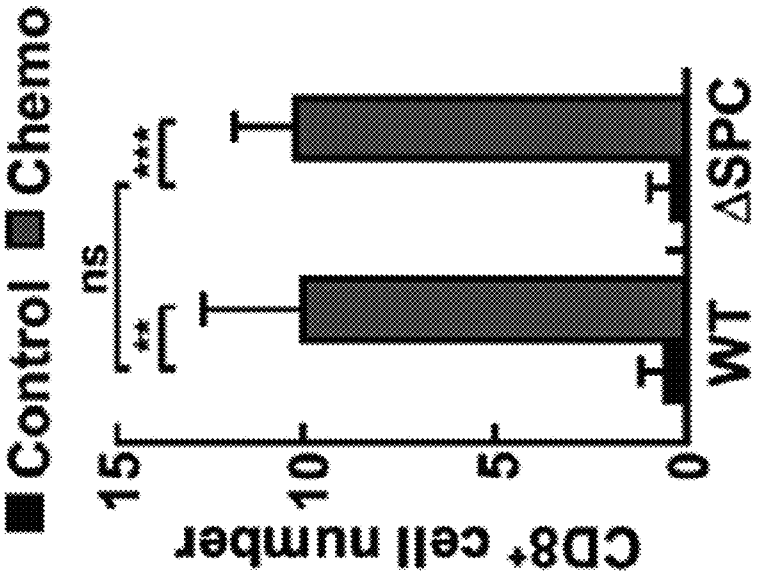
Figure 2J:
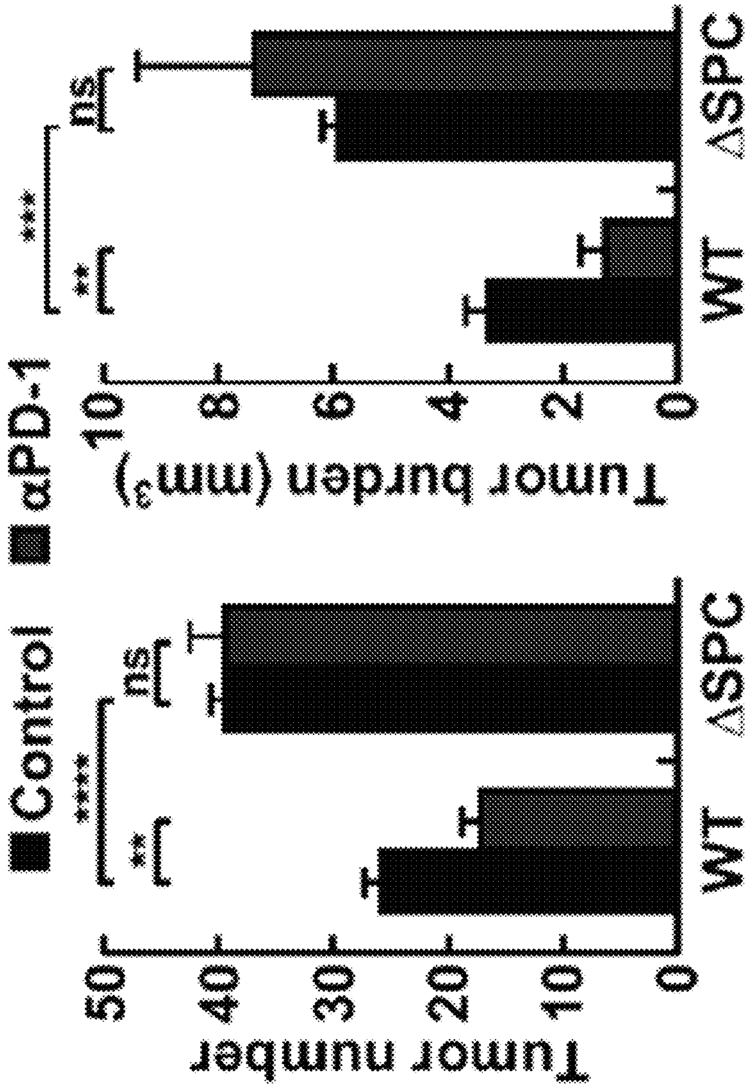
Figure 2L:
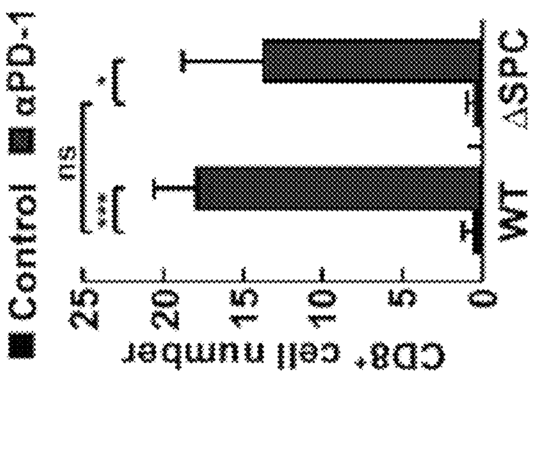
Figure 2M:
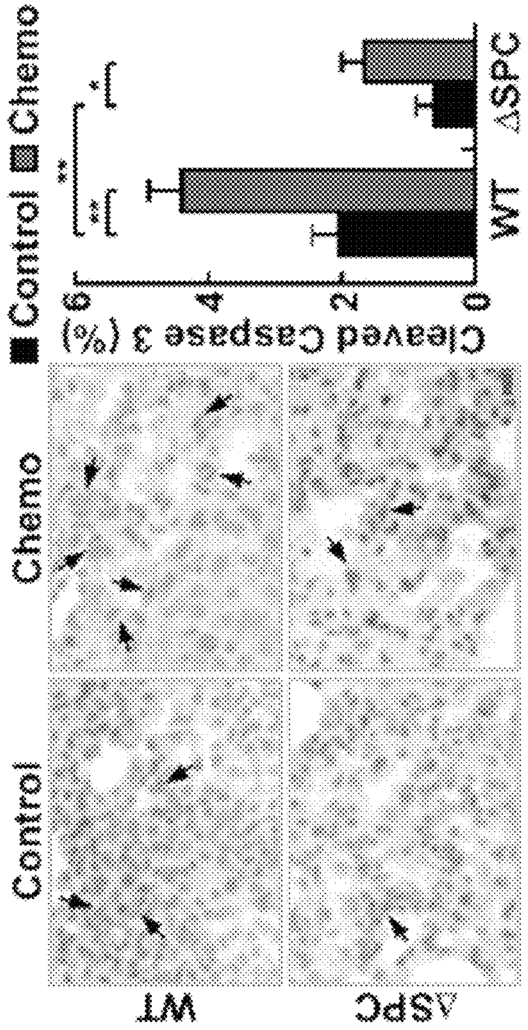
Figure 2N:
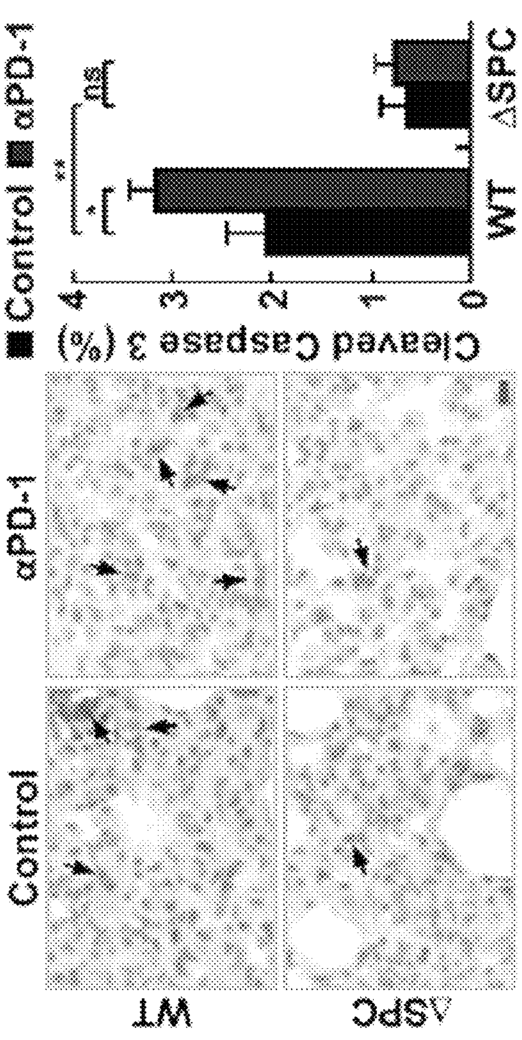

FIGS. 2A-2N provide that PDLIM2 was a bona fide lung tumor suppressor particularly important for therapeutic responses. FIG. 2A provides Kaplan-Meier tumor-free survival curve showing increased spontaneous tumors in PDLIM2-null mice. FIG. 2B provides K-Ras$^{G12D}$ model showing increased lung tumors in PDLIM2-null mice (n≥5). Scale bar, 1 mm. FIG. 2C provides urethane model showing increased lung tumor numbers and sizes in ASPC mice (n=4). Scale bar, 1 mm. FIG. 2D provides SCID mouse xenograft model showing decreased lung tumor sizes by PDLIM2 reconstitution (n=3). FIG. 2E provides MAD109 syngeneic mouse model showing decreased primary tumor formation and lung metastasis by PDLIM2 reconstitution (n=4). Scale bar, 1 mm. FIG. 2F provides urethane model showing complete resistance of lung cancer to the 5-aza-dC and MS275 combination therapy (Epi) in ASPC mice (n≥4). FIG. 2G provides in vitro IC$_{50}$ assay showing a negative association between PDLIM2 expression and carboplatin sensitivity in human lung cancer cells. FIG. 2H provides in vitro IC$_{50}$ assay showing increased carboplatin sensitivity of human lung cancer cells by PDLIM2 reconstitution. FIG. 2I provides urethane model showing increased resistance to the carboplatin and paclitaxel combination therapy (Chemo) of lung cancer in ASPC mice (n=6). FIG. 2J provides urethane model showing complete resistance of lung cancer to PD-1 blockade therapy in ΔSPC mice (n≥5). FIG. 2K provides IHC staining of CD8 showing no difference in basal or chemo-induced TILs in ΔSPC and WT mice (urethane model) (n=3). FIG. 2L provides IHC staining of CD8 showing no difference in basal or anti-PD-1-induced TILs in ΔSPC and WT mice (urethane model) (n=3). FIG. 2M provides IHC staining of cleaved caspase 3 showing decreased basal or chemo-induced apoptosis of lung cancer cells in ΔSPC mice (urethane model)(n=3). Scale bar, 10 μm. FIG. 2N provides IHC staining of cleaved caspase 3 showing complete prevention of lung cancer cell apoptosis by anti-PD-1 treatment in ΔSPC mice (urethane model) (n=3). Scale bar, 10 μm. In FIGS. 2A-2F, 2H-2N, * p<0.05,  p<0.01, * p<0.001, **** p<0.0001, ns, no significant difference, Student's t test.

Figure 3B:
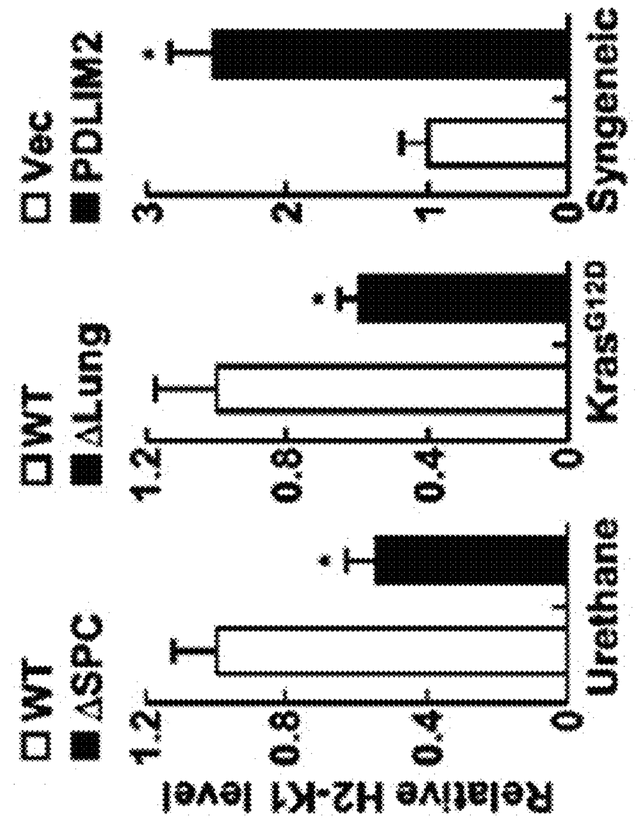
Figure 3A:
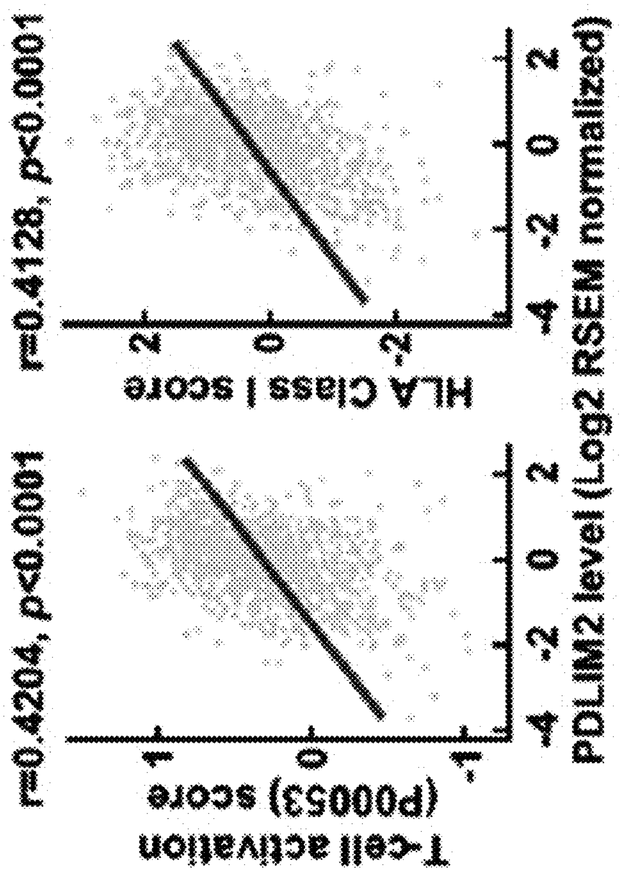
Figure 3C:
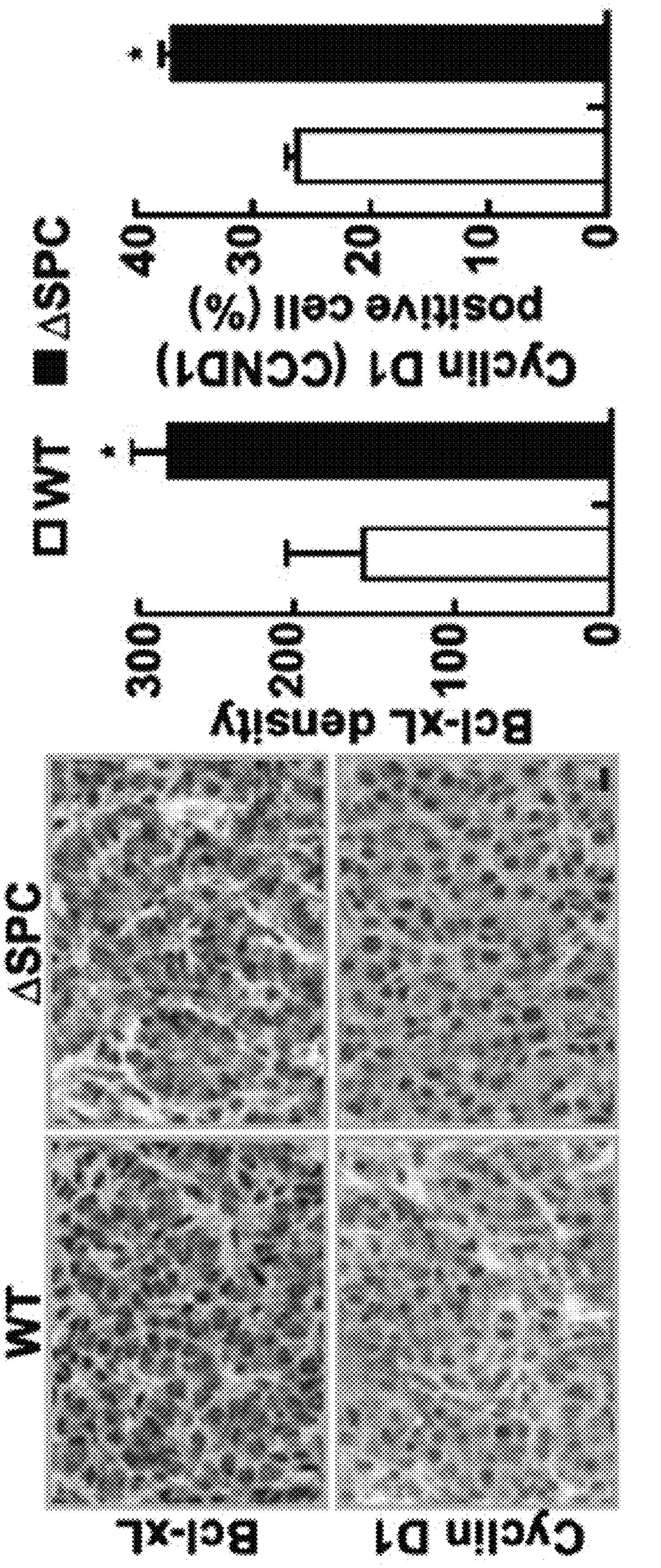
Figure 3F:
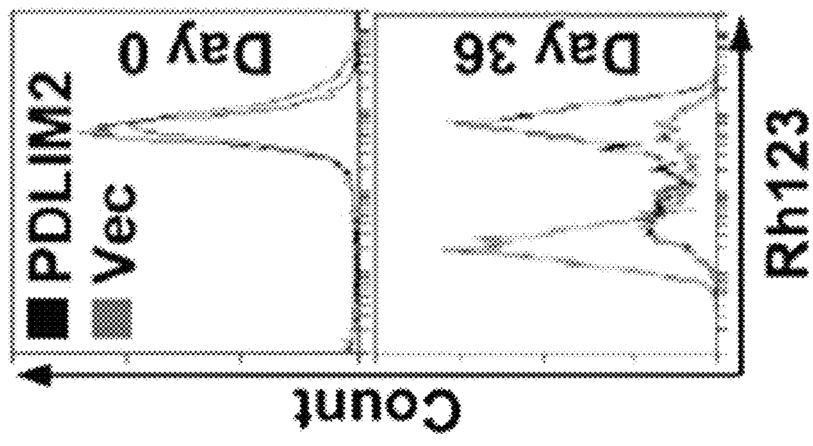
Figure 3E:
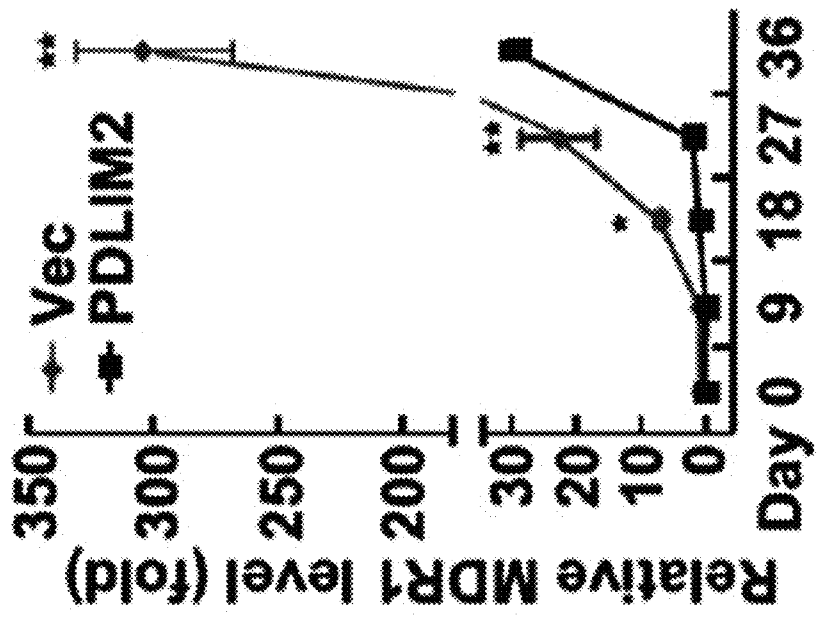
Figure 3D:
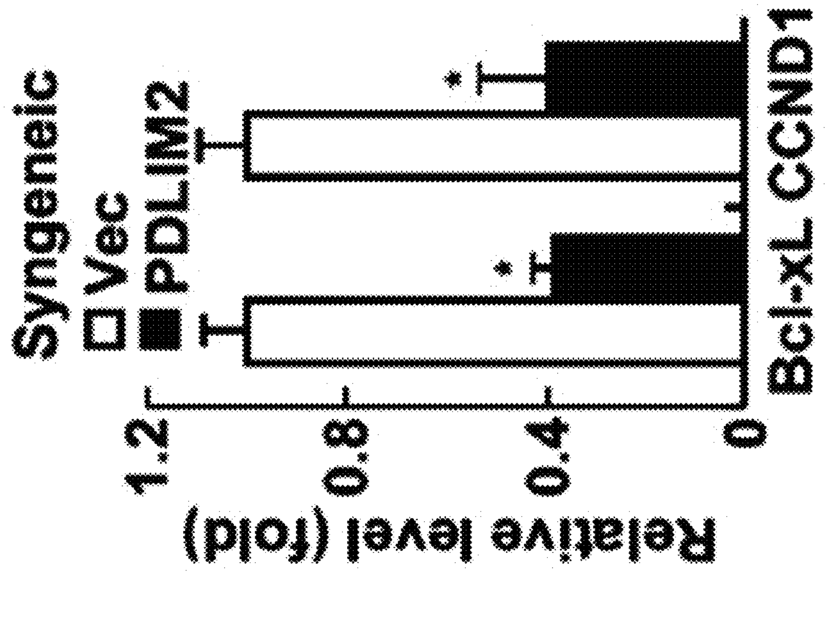
Figure 3G:
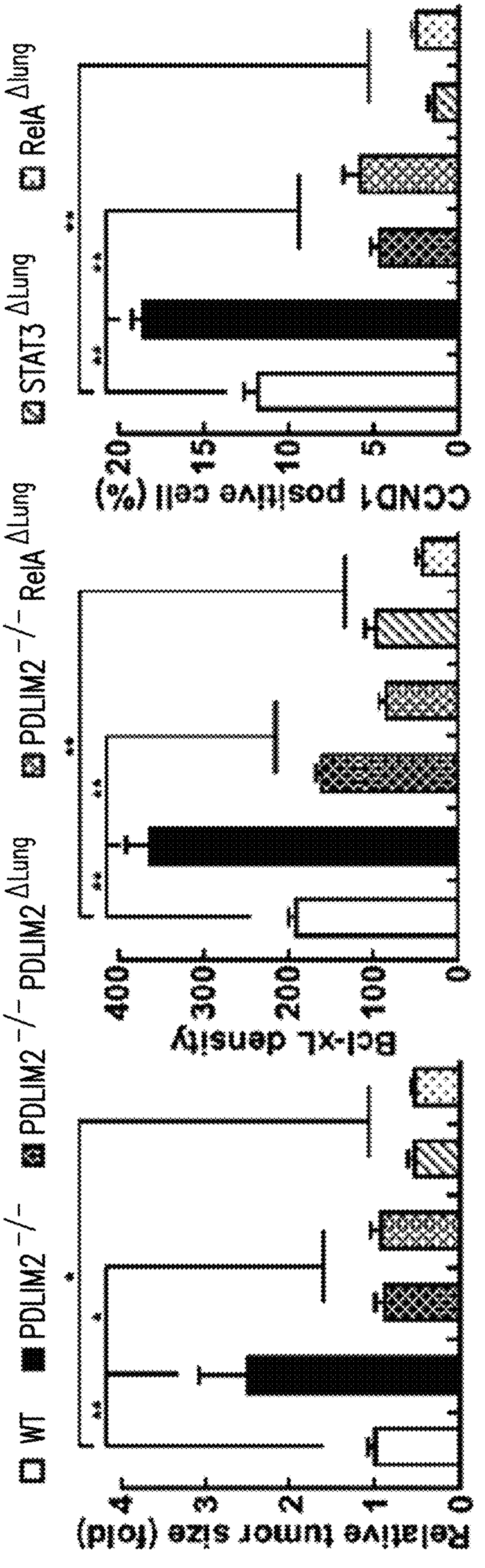
Figure 3H:
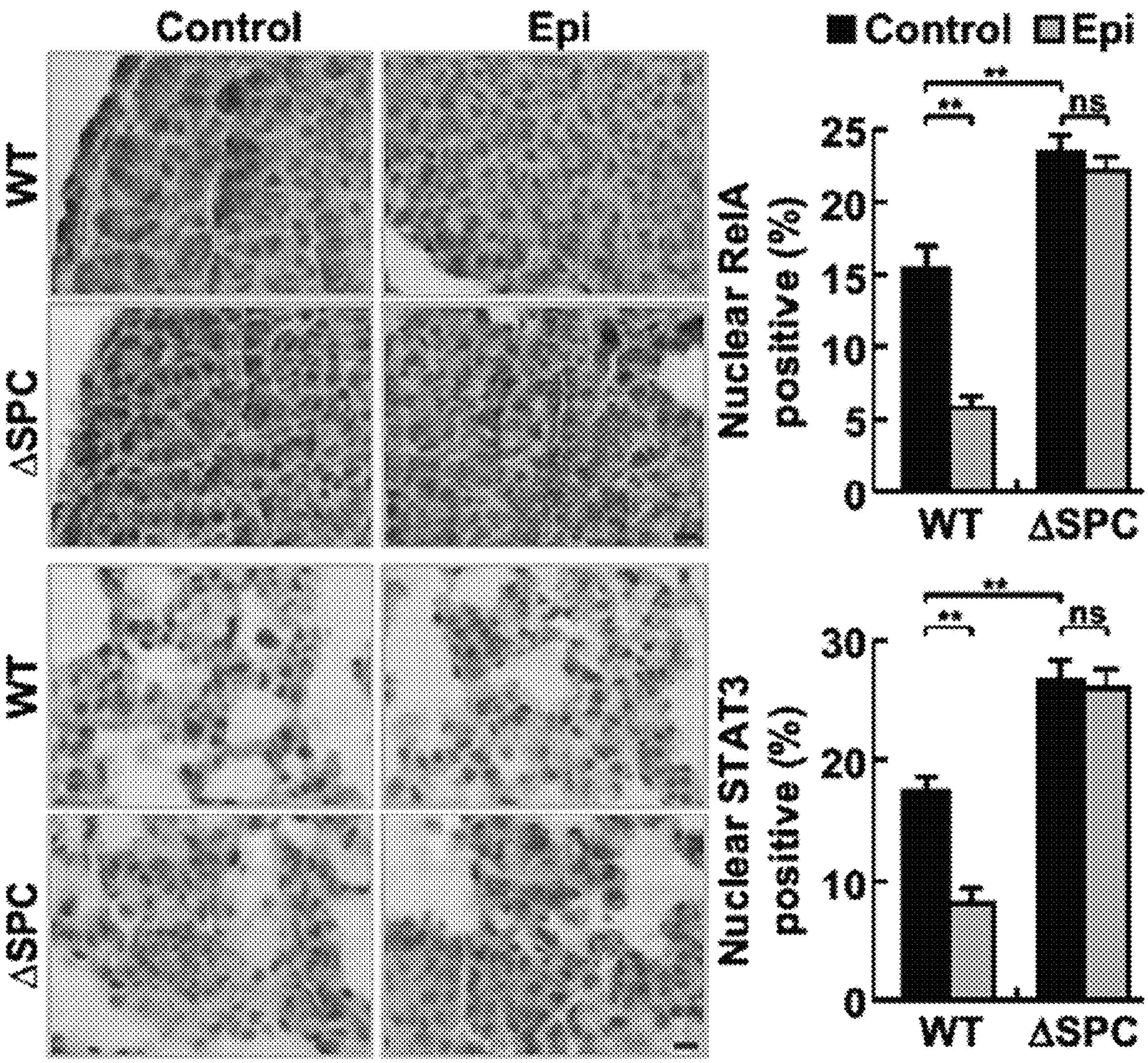
Figure 3I:
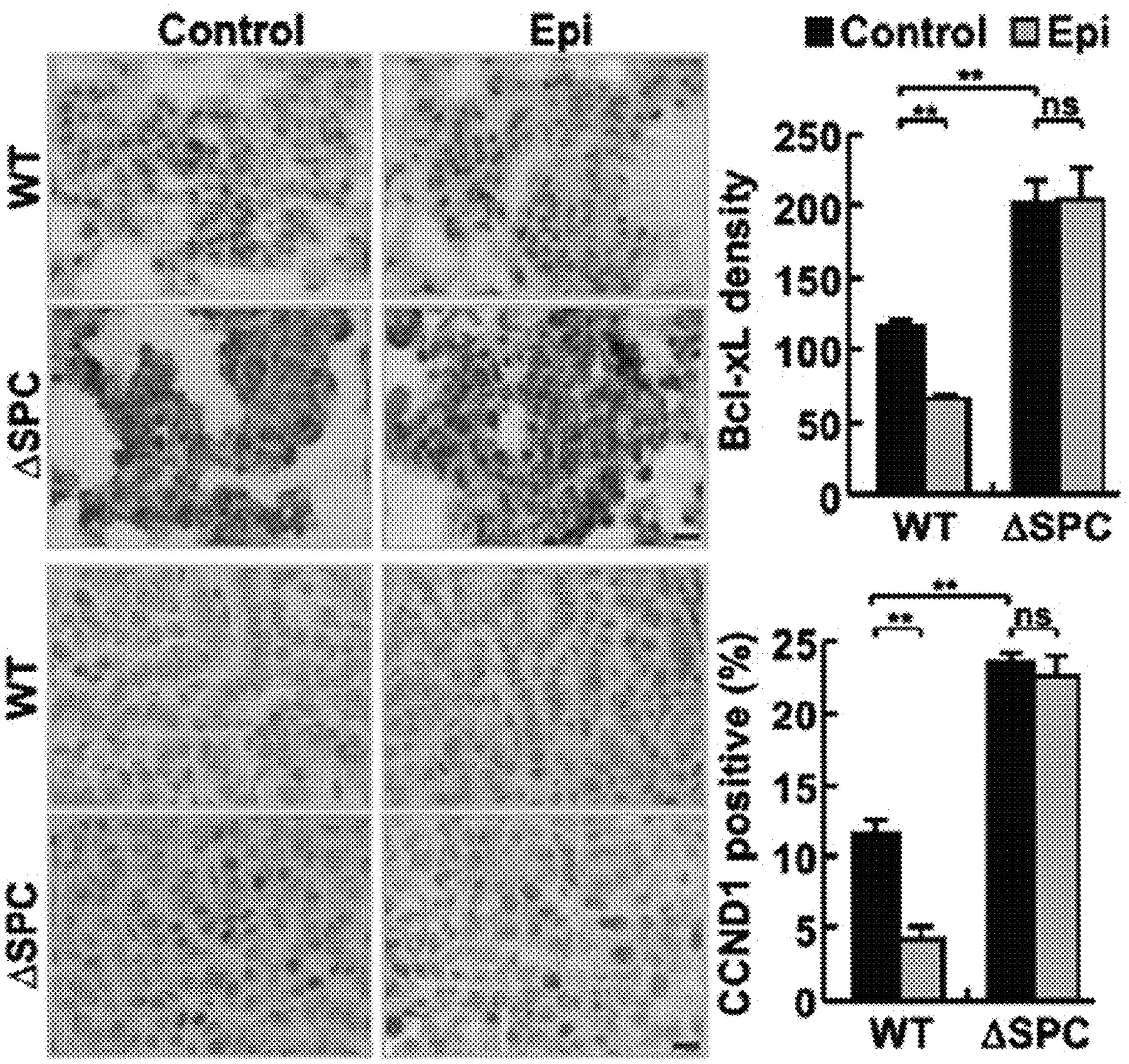
Figure 3J:
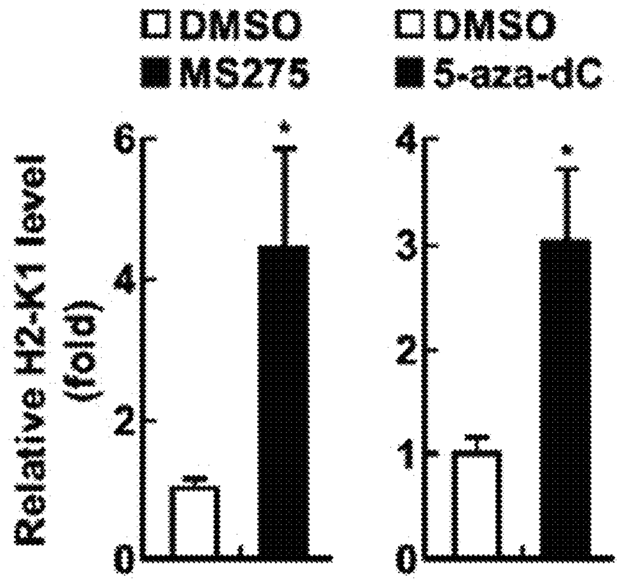

FIGS. 3A-3J provide that PDLIM2 suppressed RelA and STAT3 to increase MHC-I and repress MDR1 and cancer genes for lung cancer suppression. FIG. 3A provides TCGA data showing a positive association between PDLIM2 expression and T-cell activation or MHC-I expression in human lung cancer. FIG. 3B provides qPCR showing decreased MHC-I expression in lung cancer by PDLIM2 deletion in urethane and K-Ras$^{G12D}$ models, and increased MHC-I expression by PDLIM2 reconstitution in MAD109 syngeneic mouse model (n≥3). FIG. 3C provides IHC staining showing increased Bcl-xL and Cyclin D1 in lung cancer by PDLIM2 deletion in urethane model (n≥3). Scale bar, 10 μm. FIG. 3D provides qPCR showing decreased Bcl-xL and Cyclin D1 expression by PDLIM2 reconstitution in MAD109 syngeneic mouse model (n=3). FIG. 3E provides qPCR showing repression of paclitaxel induction of MDR1 in A549 lung cancer cells by PDLIM2 reconstitution. FIG. 3F provides FACS of Rhodamine 123 (Rh123) showing prevention of drug efflux from A549 lung cancer cells by PDLIM2 reconstitution. FIG. 3G provides RelA or STAT3 deletion from lung cancer in K-Ras$^{G12D}$ model suppressed the increased lung cancer in PDLIM2$^{-/-}$ mice by. WT mice (n=10), PDLIM2$^{-/-}$ mice (n=7), PDLIM2$^{-/-}$STAT3$^{\Delta Lung}$ mice (n=6), PDLIM2–/–RelA$^{\Delta Lung}$ mice (n=5), STAT3$^{\Delta Lung}$ mice (n=12), RelA$^{\Delta Lung}$ mice (n=2). FIG. 3H provides IHC staining showing no effect of epigenetic treatment on the nuclear RelA and STAT3 expression in lung cancers in ΔSPC mice (urethane model) (n≥3). Scale bar, 10 μm. FIG. 3I provides IHC staining showing no effect of epigenetic treatment on the Bcl-xL and Cyclin D1 expression in lung cancers in ΔSPC mice (urethane model) (n=3). Scale bar, 10 μm. FIG. 3J provides qPCR showing increased MHC-I expression in MAD109 lung cancer cells by the indicated epigenetic drugs (n=4). In FIGS. 3B-3E,3G-3J, * p<0.05, ** p<0.01, ns, no significant difference, Student's t test.

Figure 4B:
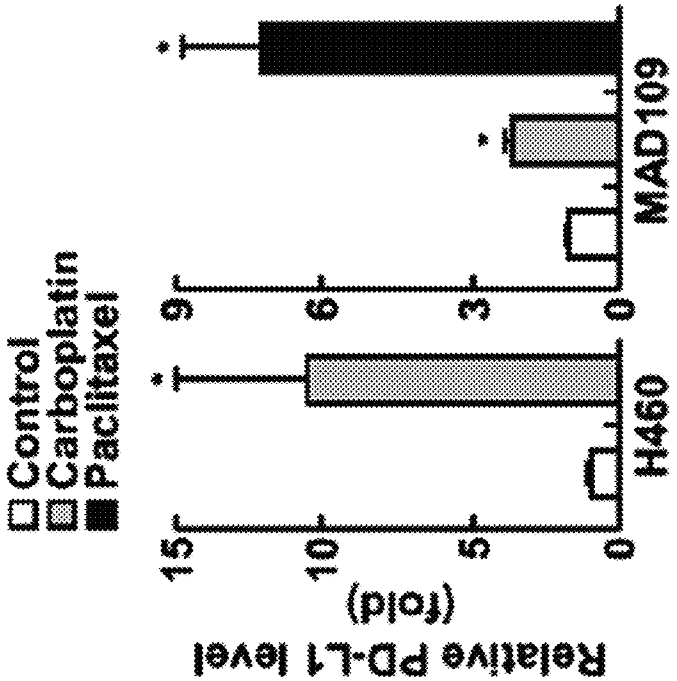
Figure 4A:
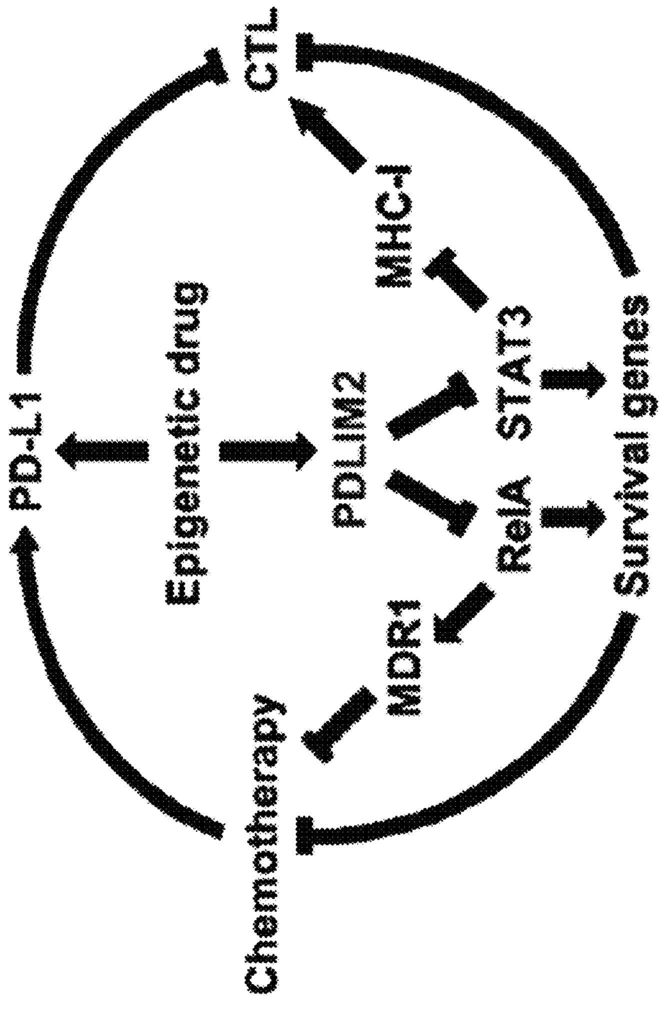
Figure 4D:
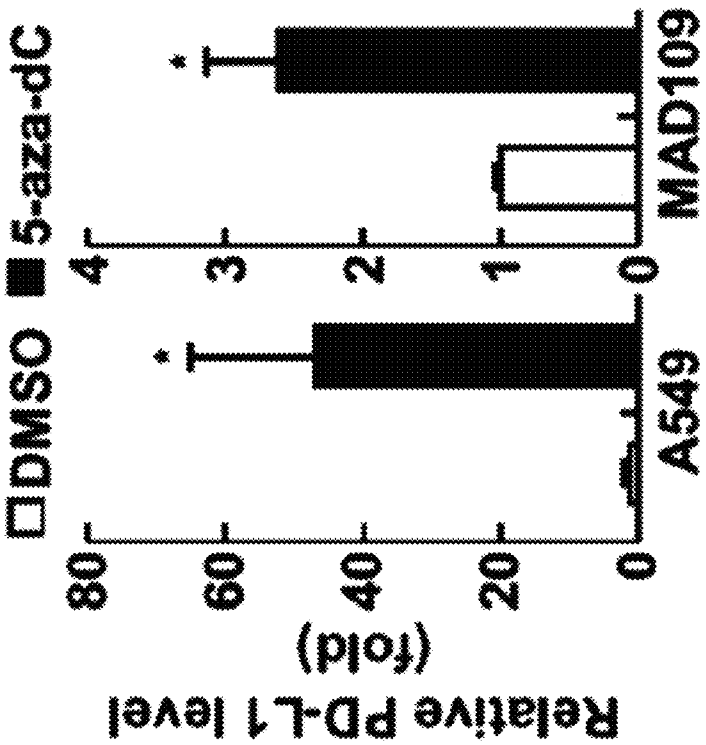
Figure 4C:
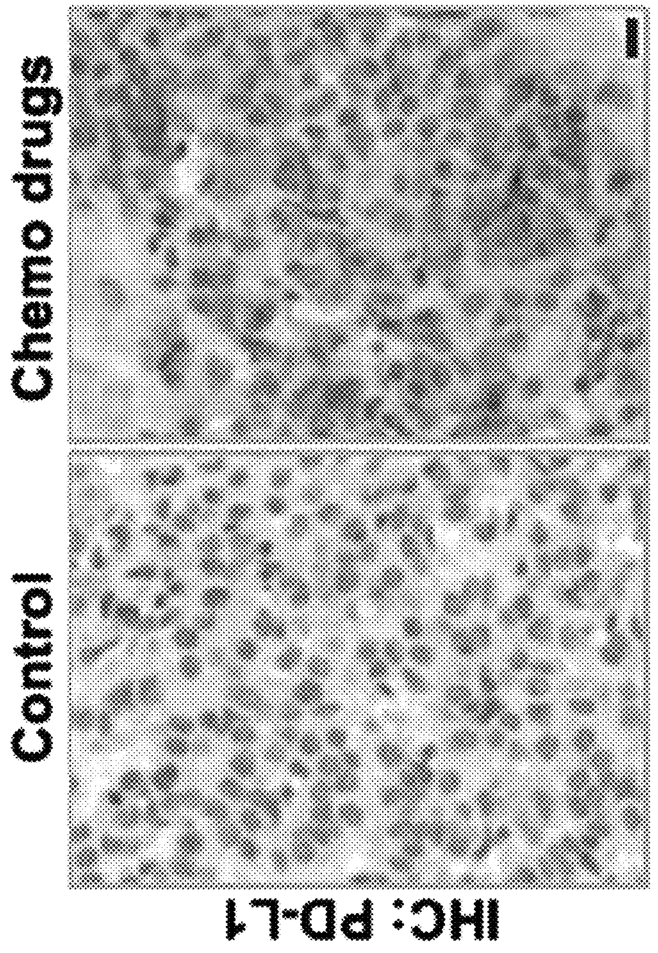
Figure 4F:
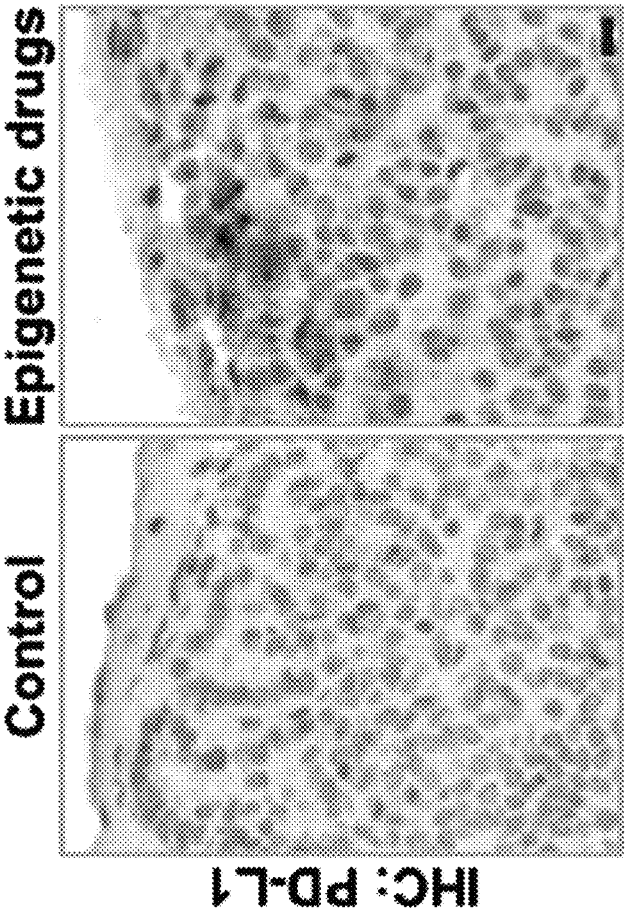
Figure 4E:
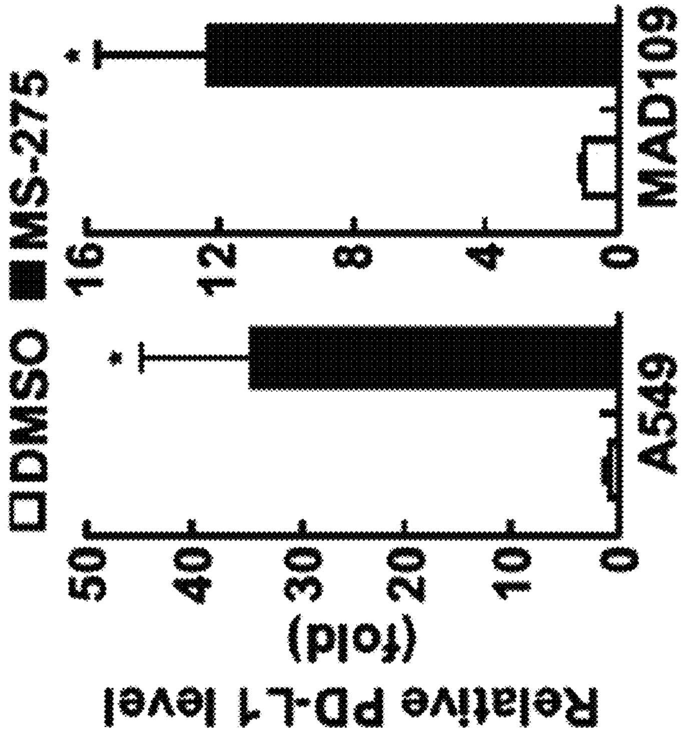
Figure 4G:
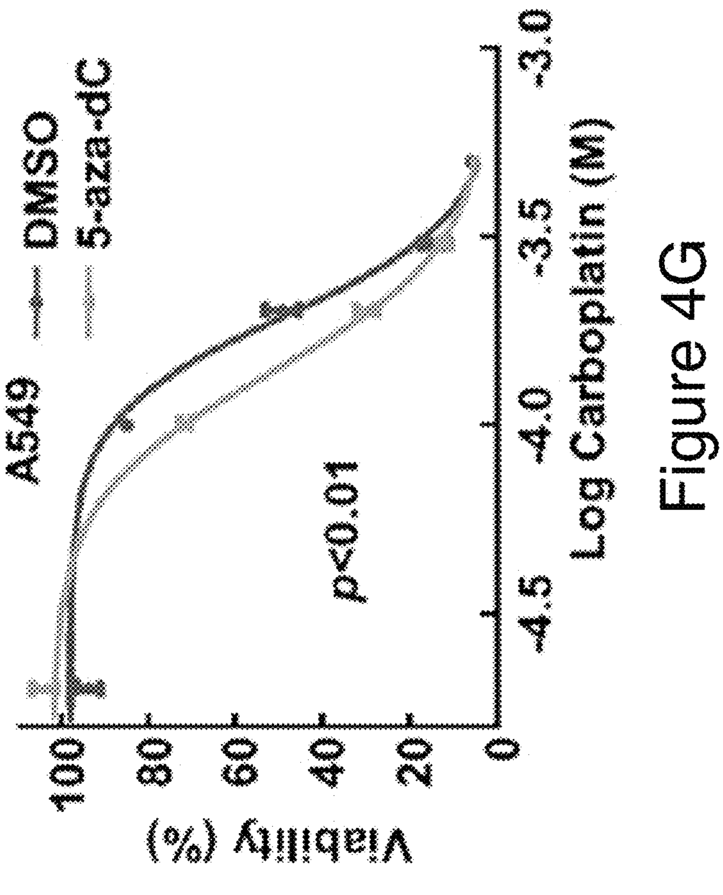
Figure 4H:
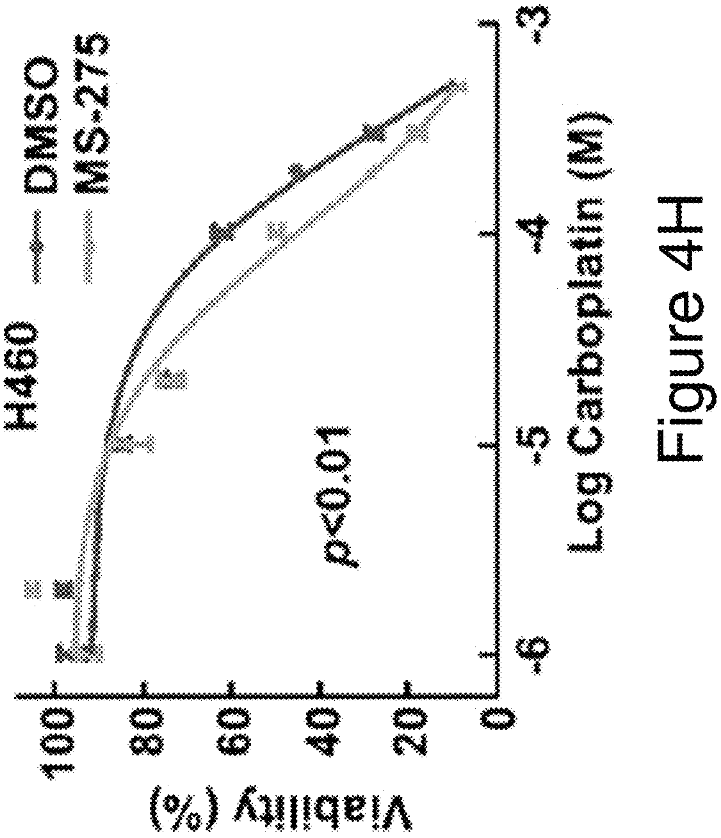
Figure 4I:
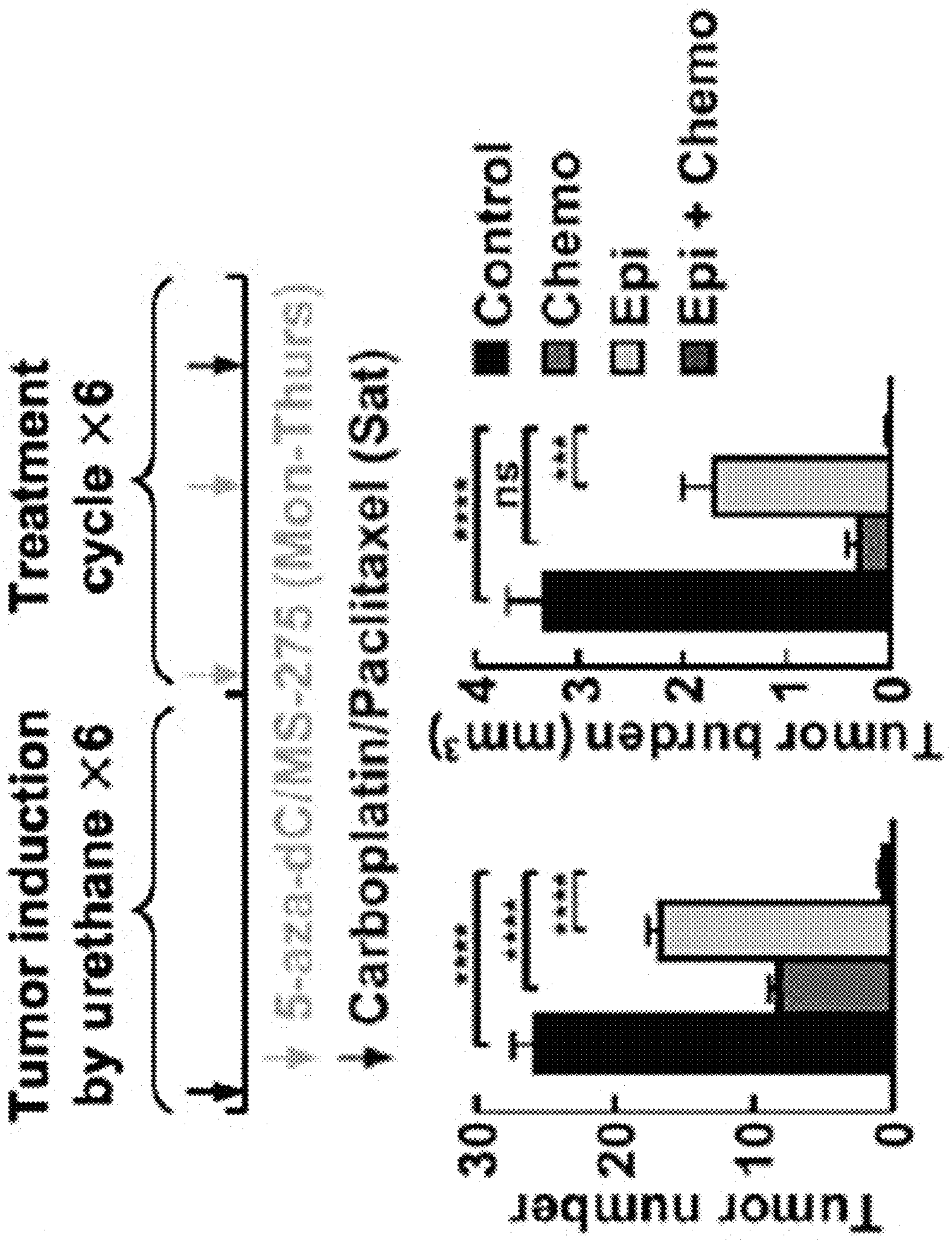
Figure 4J:
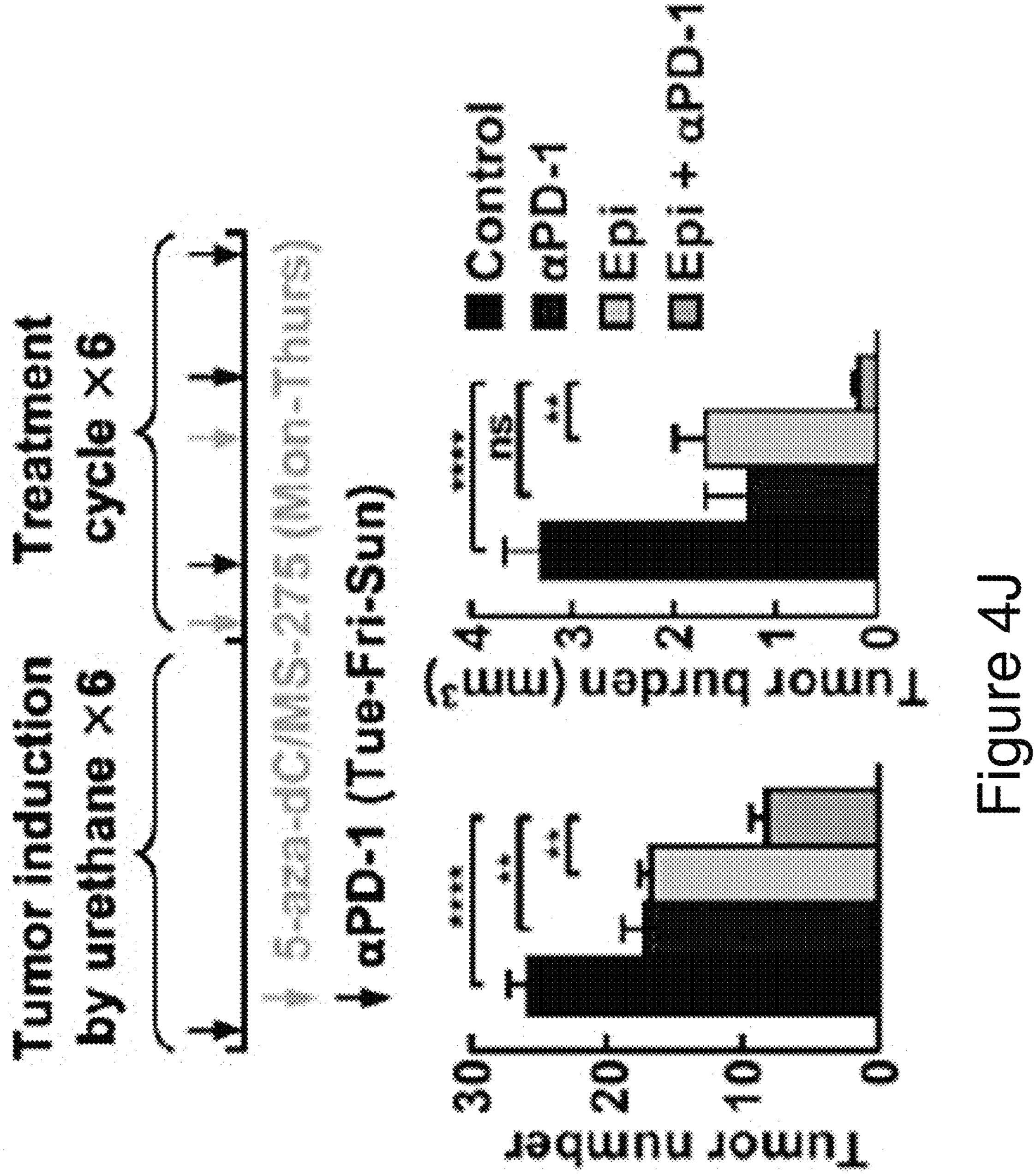
Figure 4K:
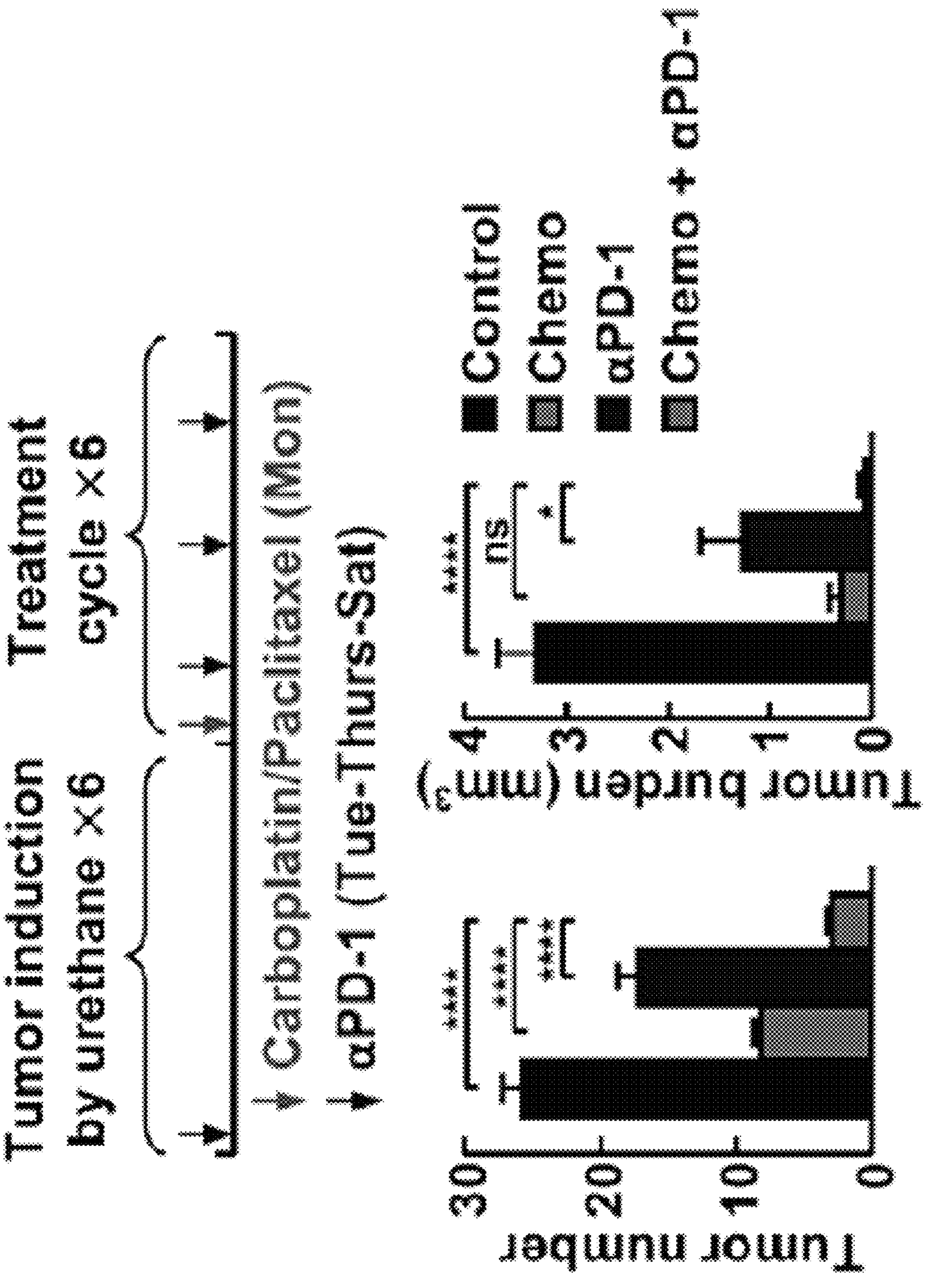

FIGS. 4A-4K provide that epigenetic agents, chemotherapeutic drugs and anti-PD-1 synergized in lung cancer treatment. FIG. 4A provides mechanistic rationale for combination therapy using anti-PD-1, chemotherapeutic drugs and epigenetic agents. FIG. 4B provides qPCR showing PD-L1 induction in lung cancer cells by carboplatin and paclitaxel (n=3). FIG. 4C provides IHC staining showing PD-L1 induction in lung cancer by carboplatin and paclitaxel in urethane model. Scale bar, 10 μm. FIG. 4D provides qPCR showing PD-L1 induction in lung cancer cells by 5-aza-dC (n≥3). FIG. 4E provides qPCR showing PD-L1 induction in lung cancer cells by MS-275 (n≥3). FIG. 4F provides IHC staining showing PD-L1 induction in lung cancer by 5-aza-dC and MS-275 in urethane model. Scale bar, 10 μm. FIG. 4G provides in vitro $IC_{50}$ assay showing increased carboplatin sensitivity of A549 human lung cancer cells by 5-aza-dC (n=3). FIG. 4H provides In vitro $IC_{50}$ assay showing increased carboplatin sensitivity of H460 human lung cancer cells by MS-275 (n=3). FIG. 4I provides complete remission of almost all lung cancers by combination epigenetic and chemo therapy in urethane model (n≥4). FIG. 4J provides increased lung cancer treatment of combination epigenetic and anti-PD-1 therapy in urethane model (n≥4). FIG. 4K provides increased lung cancer treatment of combination chemo and anti-PD-1 therapy in urethane model (n≥4). In FIGS. 4B, 4D, 4E, 4G-4I, * p<0.05,  p<0.01, * p<0.001, **** p<0.0001, ns, no significant difference, Student's t test.

Figure 5A:
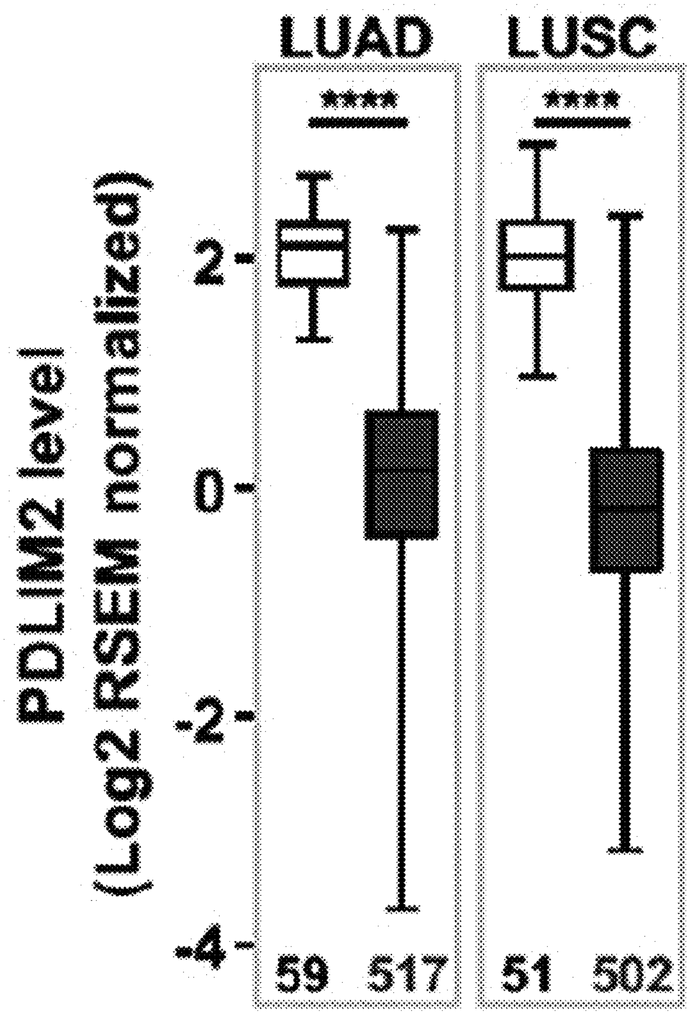
Figure 5B:
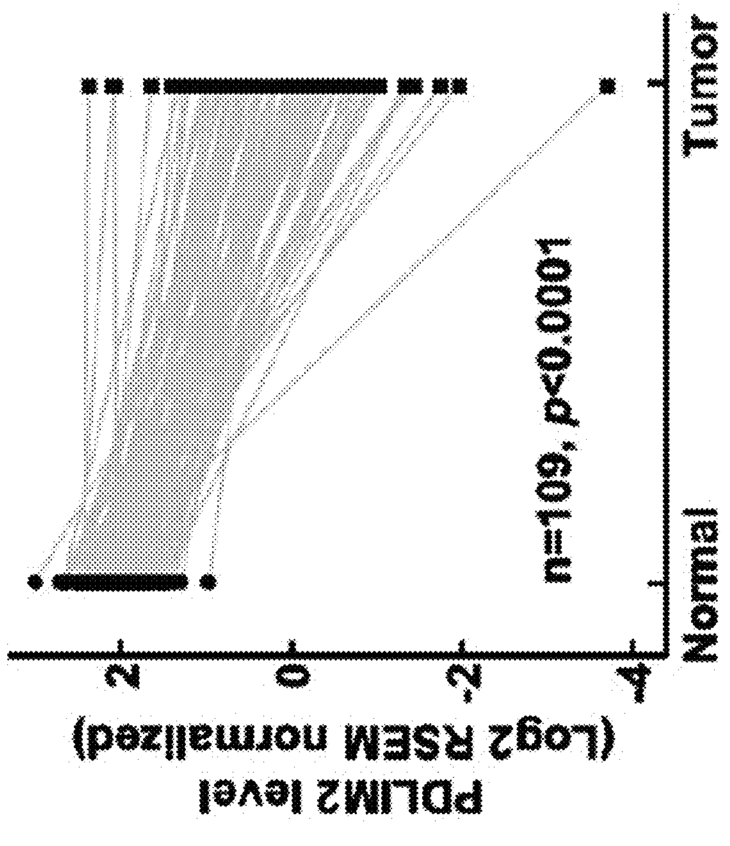
Figure 5C:
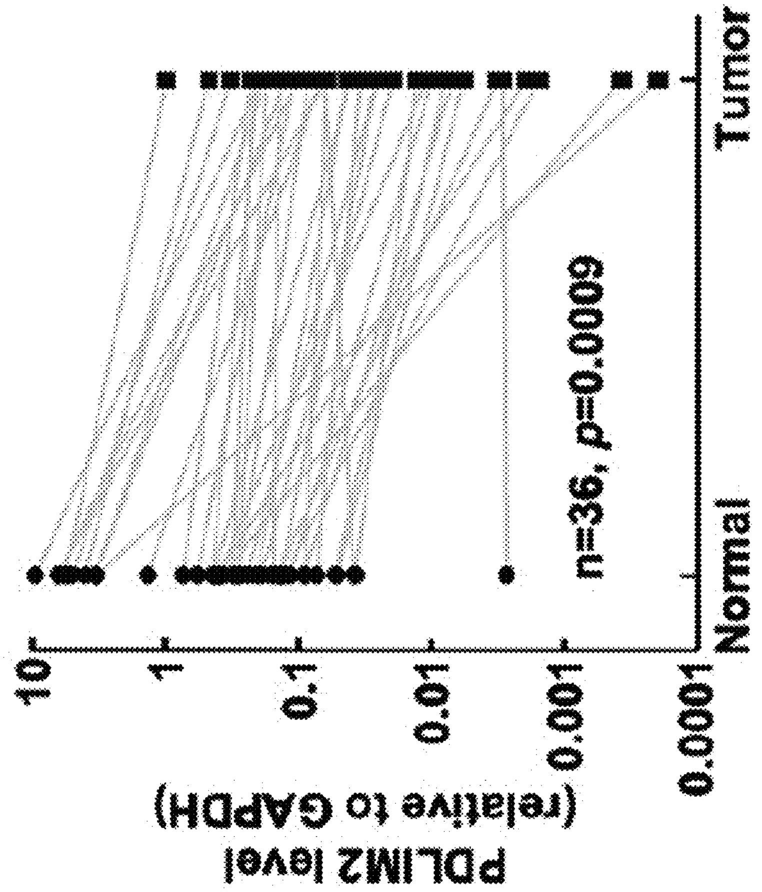
Figure 5D:
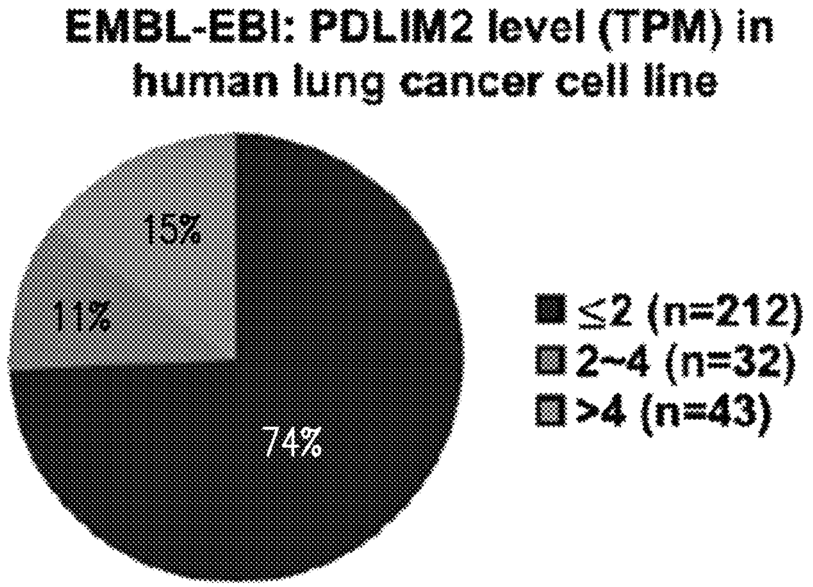
Figure 5E:
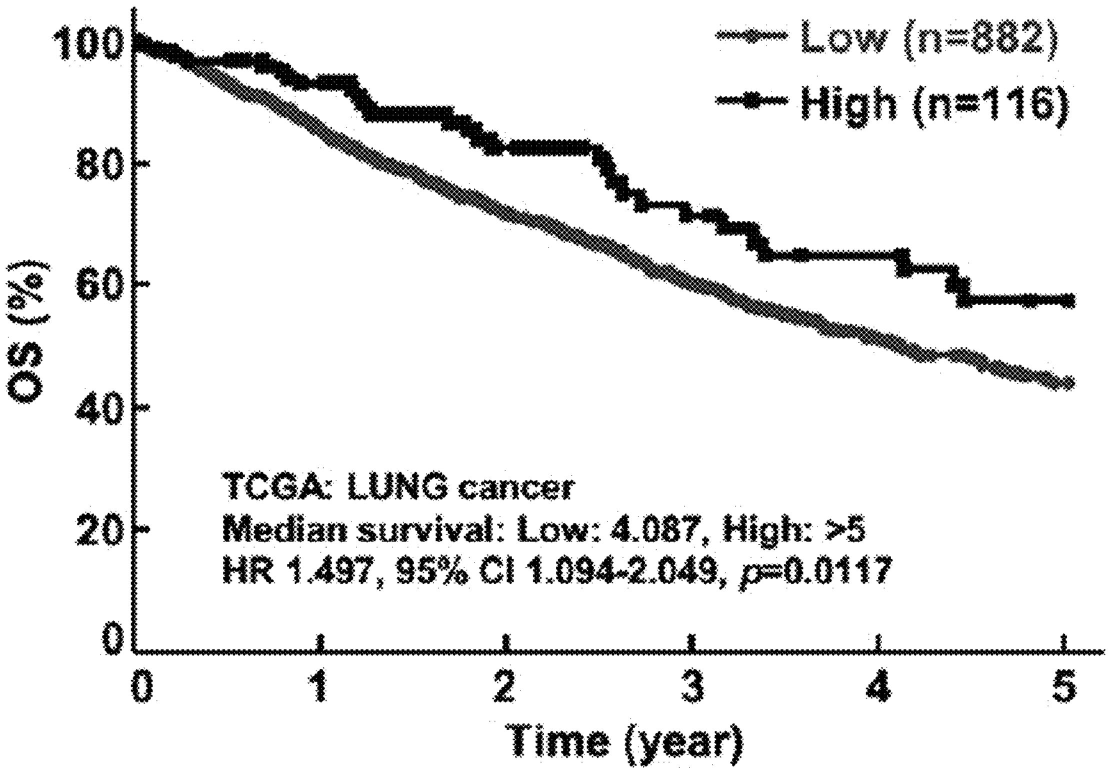
Figure 5F:
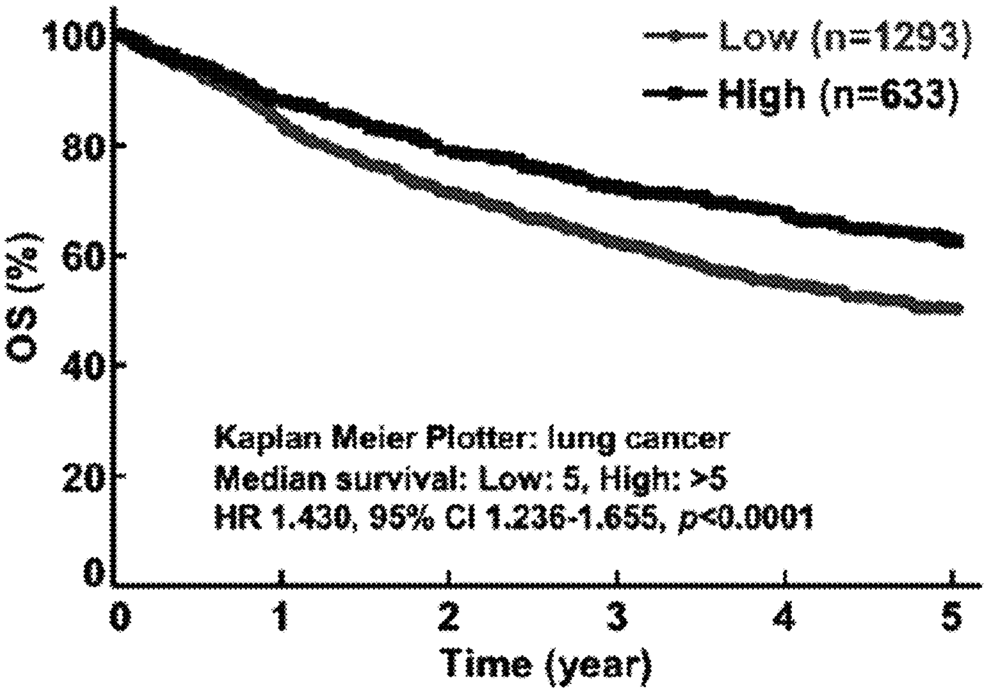
Figure 5G:
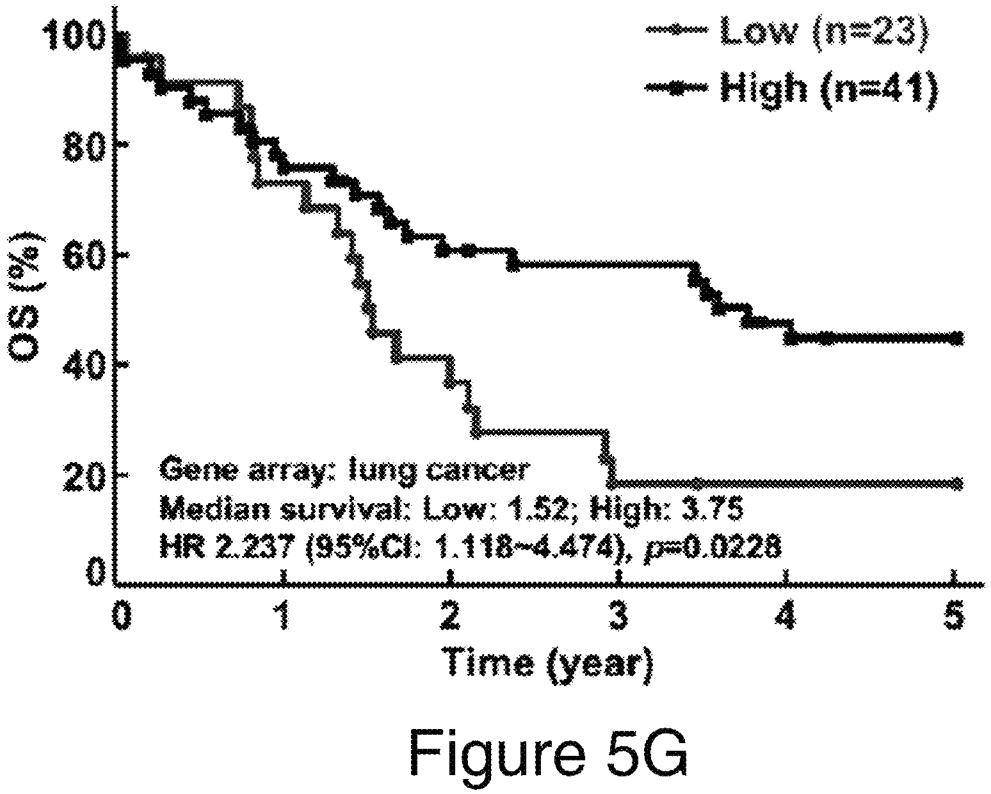
Figure 5H:
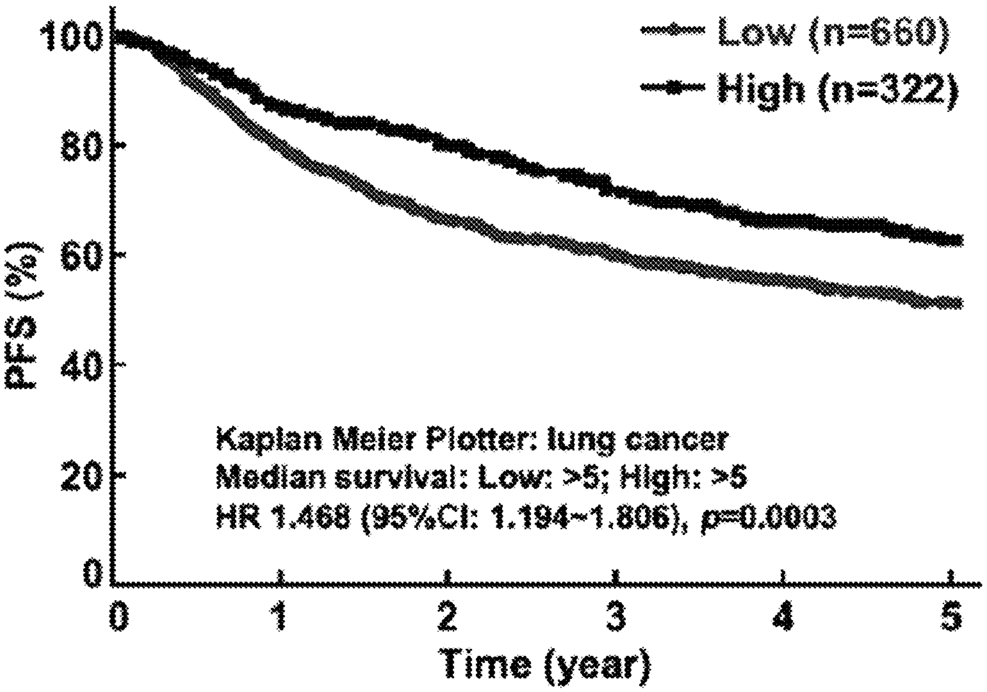
Figure 5I:
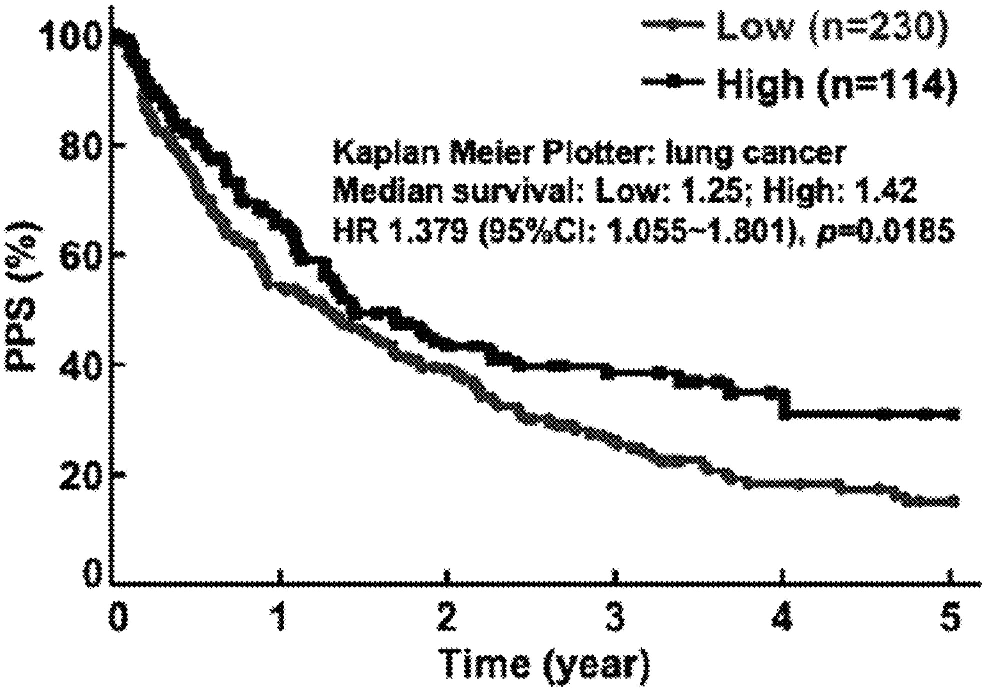

FIGS. 5A-5I provide that PDLIM2 was repressed in human lung cancer, which is associated with poor prognosis. FIG. 5A provides TCGA data showing PDLIM2 repression in human lung adenocarcinoma (LUAD) and squamous cell carcinoma (LUSC). Light column and dark column stand for normal lung tissues and lung cancer tissues, respectively. Sample numbers are indicated. **** p<0.0001. FIG. 5B provides TCGA data showing PDLIM2 repression in human lung cancer using paired lung cancer tissues and adjacent normal tissues from the same patients. FIG. 5C provides qPCR analysis showing PDLIM2 repression in human lung cancer using paired lung cancer tissues and adjacent normal tissues from the same patients. FIG. 5D provides EMBL-EBI data showing PDLIM2 repression in human lung cancer cell lines. FIG. 5E provides Kaplan-Meier patient survival curve of TCGA data showing a positive association between PDLIM2 expression and patient overall survival (OS). FIG. 5F provides Kaplan-Meier patient survival curve generated from Kaplan-Meier Plotter showing a positive association between PDLIM2 expression and patient OS. FIG. 5G provides Kaplan-Meier patient survival curve of gene array showing a positive association between PDLIM2 expression and patient OS. FIG. 5H provides Kaplan-Meier patient survival curve generated from Kaplan-Meier Plotter showing a positive association between PDLIM2 expression and progression free survival (PFS) of lung cancer patients. FIG. 5I provides Kaplan-Meier patient survival curve generated from Kaplan-Meier Plotter showing a positive association between PDLIM2 expression and post progression survival (PPS) of lung cancer patients.

Figure 6:
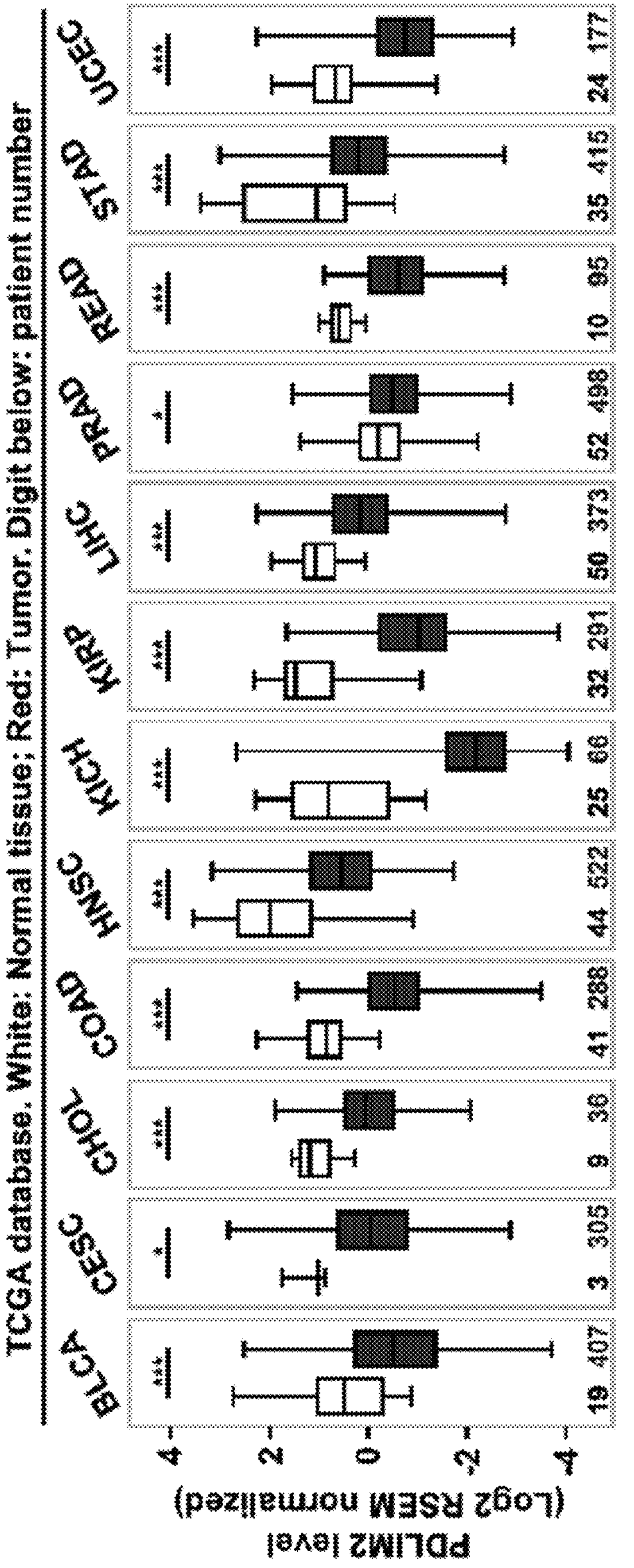

FIG. 6 provides that PDLIM2 was repressed in various human cancers. TCGA data showing PDLIM2 repression in the indicated human cancers. Light columns and dark columns stand for normal tissues and cancer tissues, respectively. Sample numbers are also indicated. BLCA, Bladder Carcinoma; CESC, Cervical Squamous Cell Carcinoma; CHOL, Cholangiocarcinoma; COAD, Colon Adenocarcinoma; HNSC, Head and Neck Squamous Cell Carcinoma; KICH, Kidney Chromophobe; KIRP, Kidney Renal Papillary Cell Carcinoma; LIHC, Liver Hepatocellular Carcinoma; PRAD, Prostate Adenocarcinoma; READ, Rectum Adenocarcinoma; STAD, Stomach Adenocarcinoma; UCEC, Uterine Corpus Endometrial Carcinoma. * p<0.05, * p<0.001, ** p<0.0001.

Figure 7A:
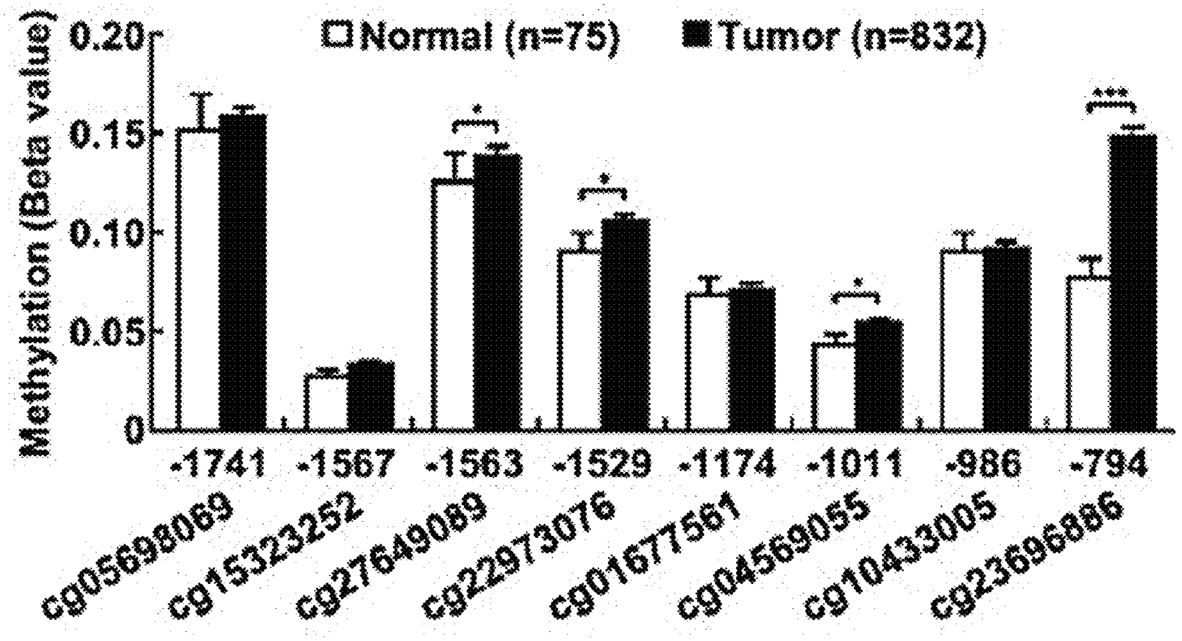
Figure 7B:
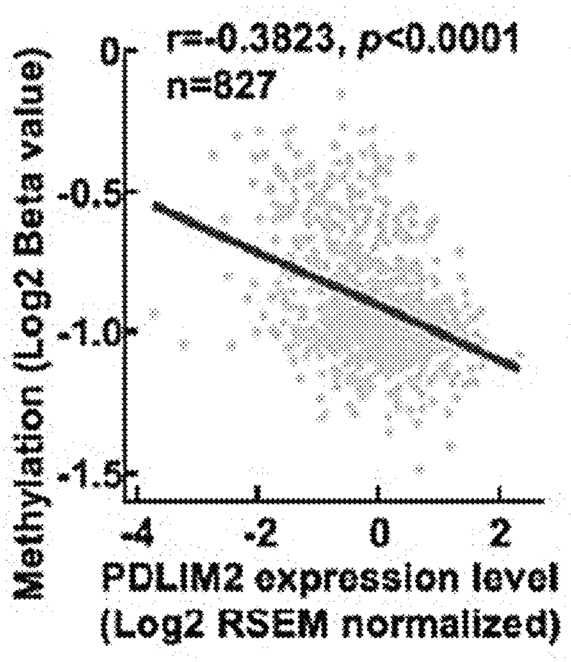
Figure 7C:
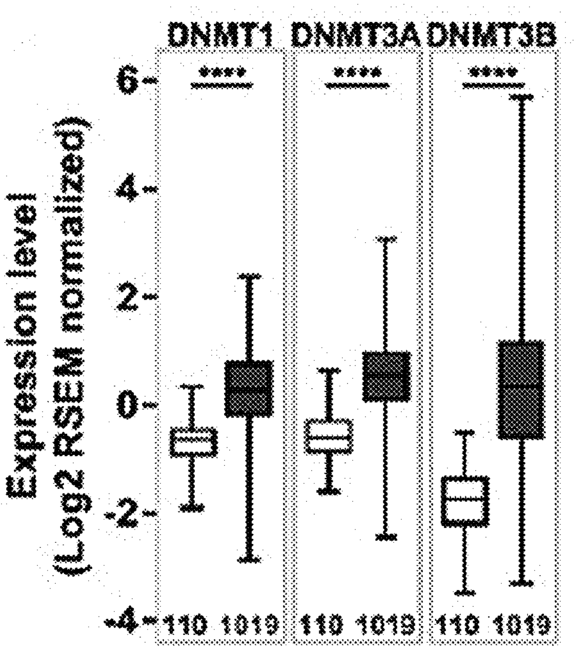
Figure 7D:
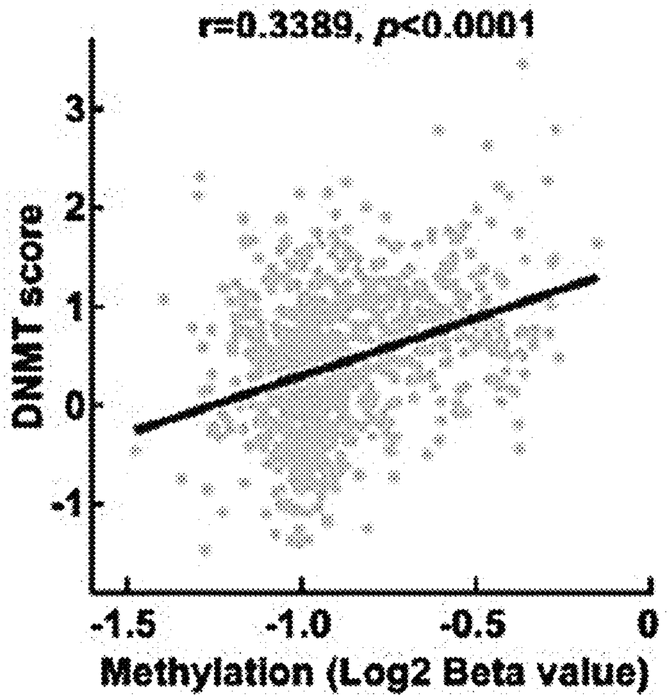
Figure 7E:
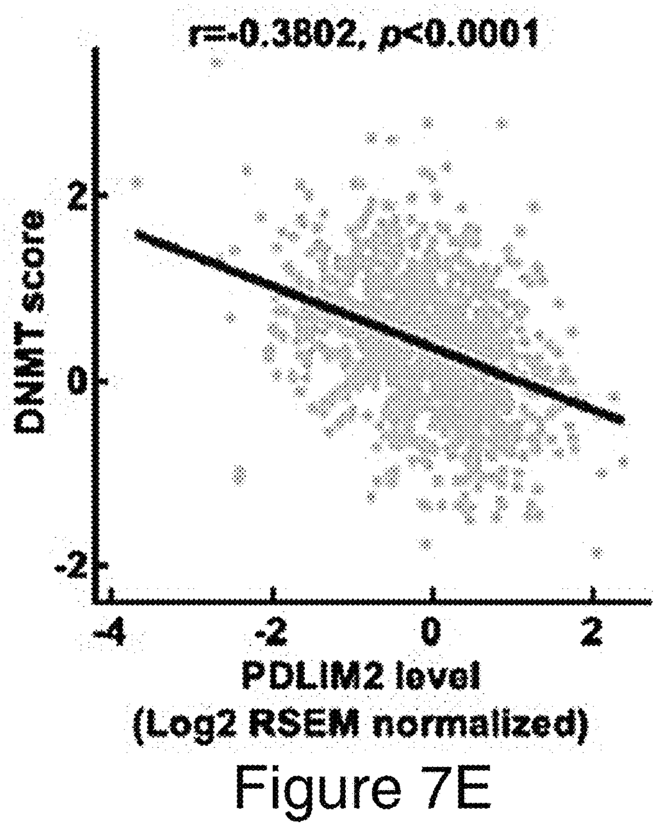
Figure 7F:
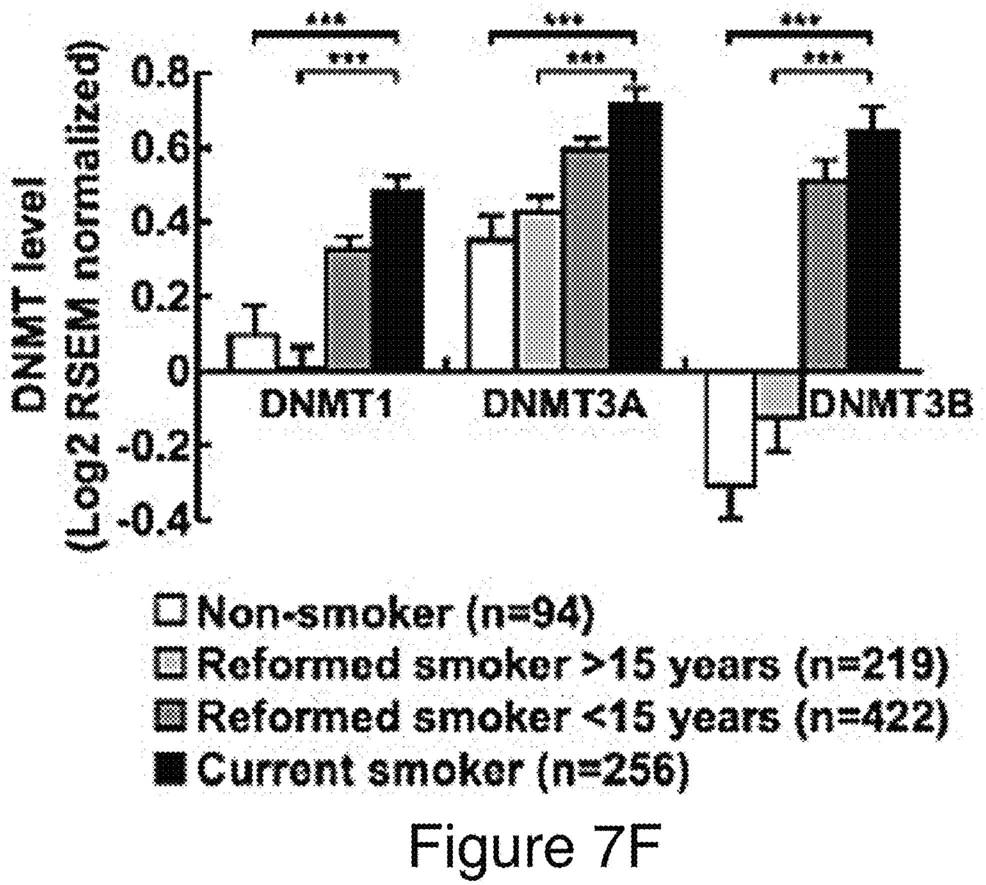
Figure 7G:
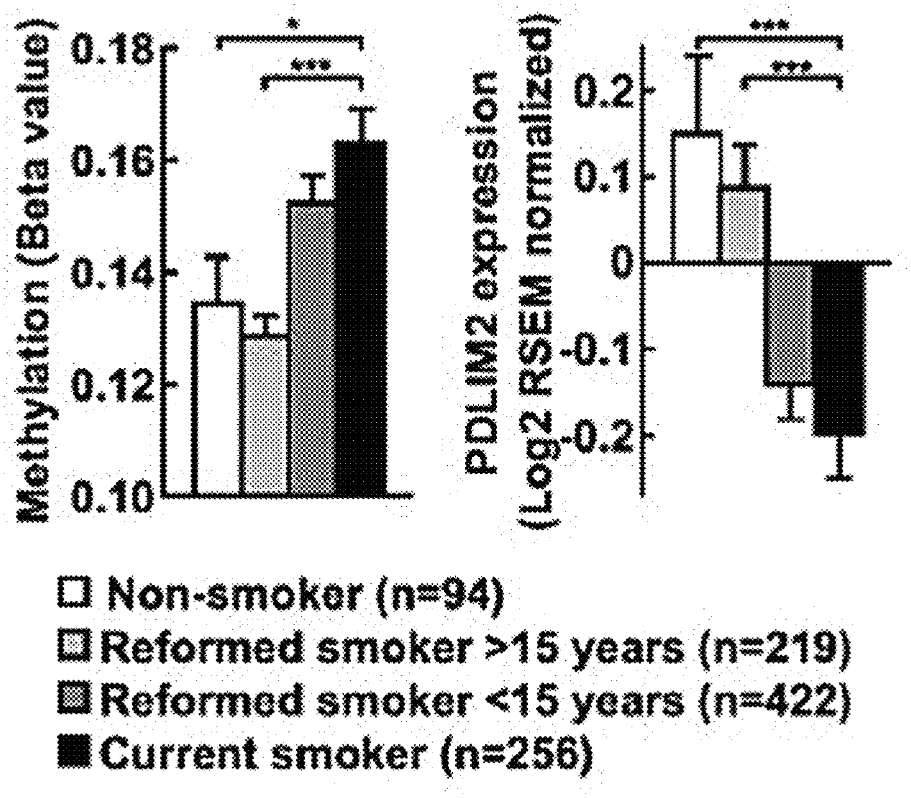
Figure 7H:
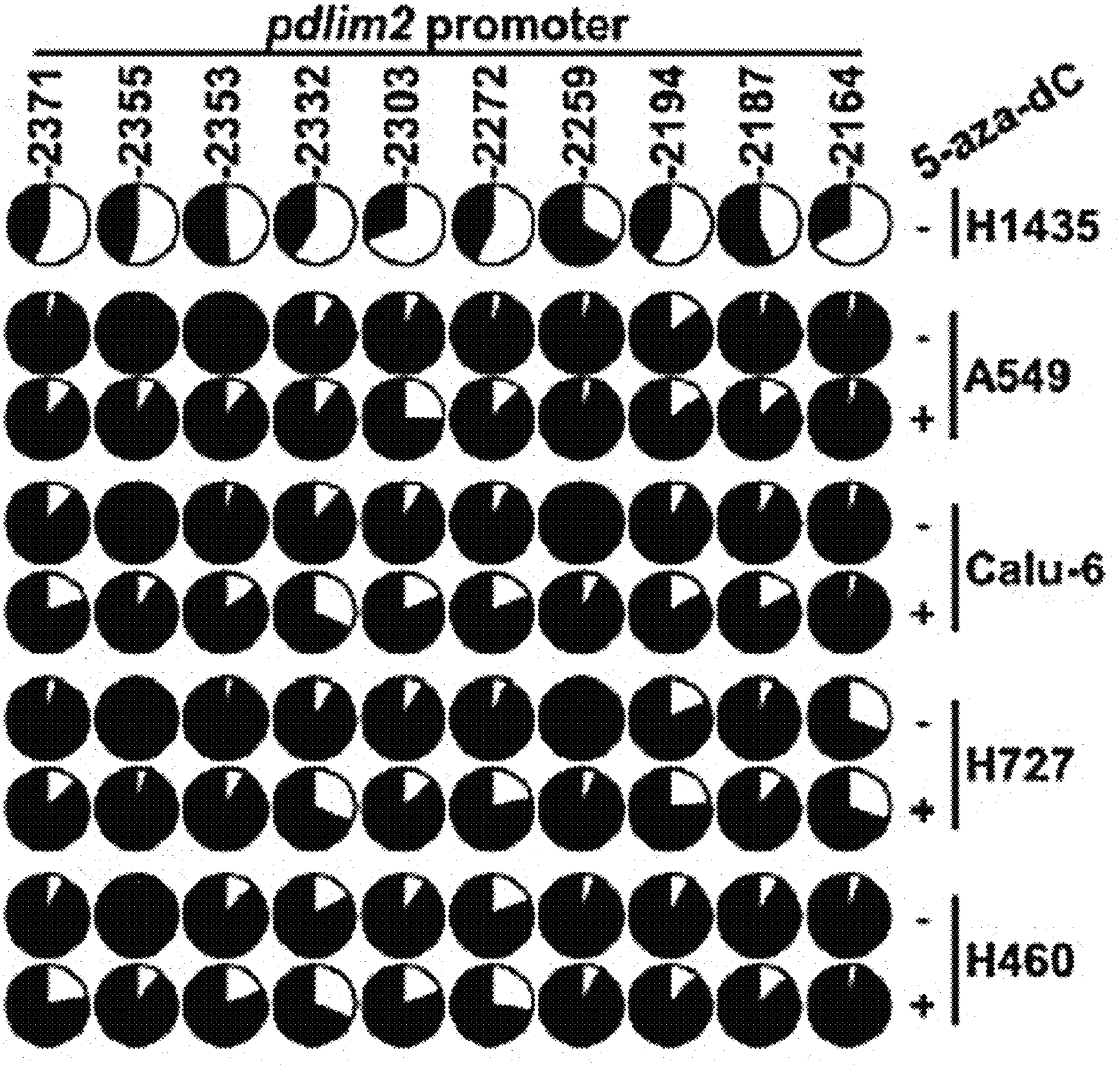
Figure 7I:
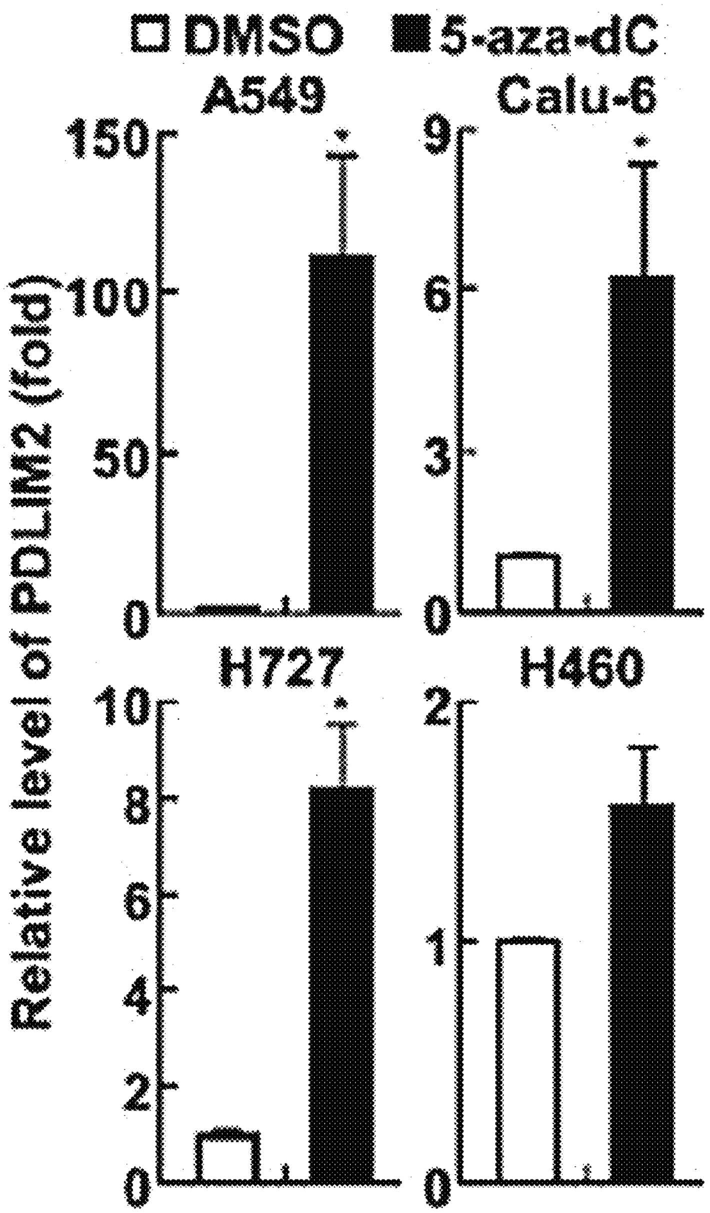

FIGS. 7A-7I provide that PDLIM2 repression in human lung cancer involved promoter methylation by DNMTs. FIG. 7A provides TCGA data showing increased CpG methylation of the pdlim2 promoter in human lung cancer. The position of CpG nucleotides relative to the PDLIM2 transcription initiation site (+1) and their probes was indicated at the bottom. * p<0.05, * p<0.001. FIG. 7B provides TCGA data showing a negative association between PDLIM2 expression and its promoter methylation in human lung cancer. FIG. 7C provides TCGA data showing increased DNMT expression in human lung cancer. Light column and dark column stand for normal lung tissues and lung cancer tissues, respectively. Sample numbers are indicated.  p<0.0001. FIG. 7D provides TCGA data showing positive associations between DNMT expression and pdlim2 promoter methylation in human lung cancer. FIG. 7E provides TCGA data showing negative associations between DNMT and PDLIM2 expression in human lung cancer. FIG. 7F provides TCGA data showing positive associations between smoking and DNMT expression in human lung cancer. * p<0.001. FIG. 7G provides TCGA data showing positive associations between smoking and pdlim2 promoter methylation and negative association between smoking and PDLIM2 expression in human lung cancer. * p<0.05, *** p<0.001. FIG. 7H provides bisulfite genomic DNA sequencing showing de-methylation of the pdlim2 promoter in the indicated human lung cancer cell lines by 5-aza-dC. Each circle represents a CpG site; open circles represent unmethylated CpG dinucleotides, and filled circles represent methylated CpG sites. The ratios of the filled area in circles represent percentiles of the methylation in the CpG sites. The position of each CpG nucleotide relative to the PDLIM2 transcription initiation site (+1) is indicated at the top. FIG. 7I provides qPCR analysis showing PDLIM2 induction in the indicated human lung cancer cell lines by 5-aza-dC (n=3). * p<0.05.

Figure 8B:
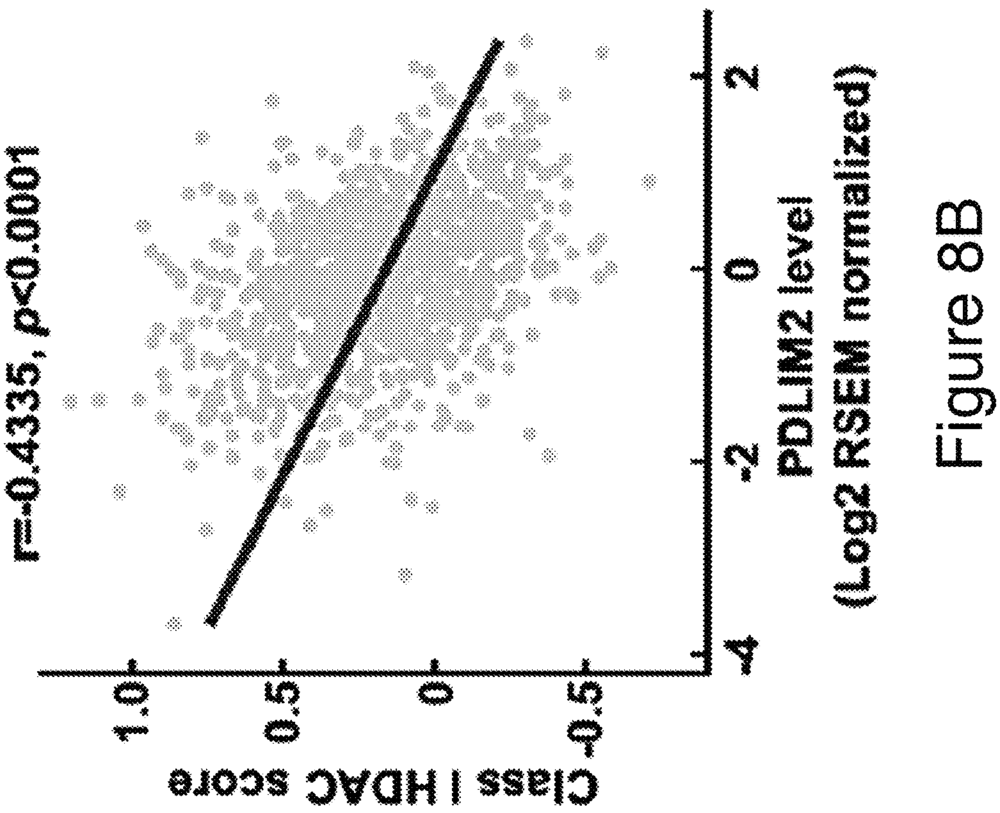
Figure 8A:
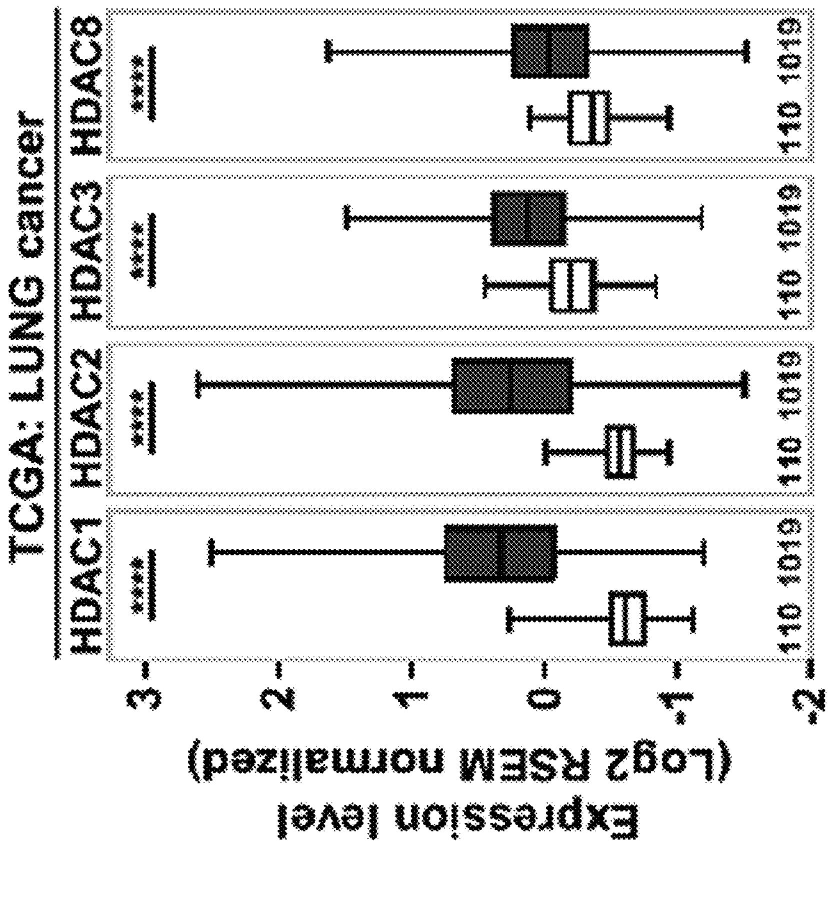
Figure 8C:
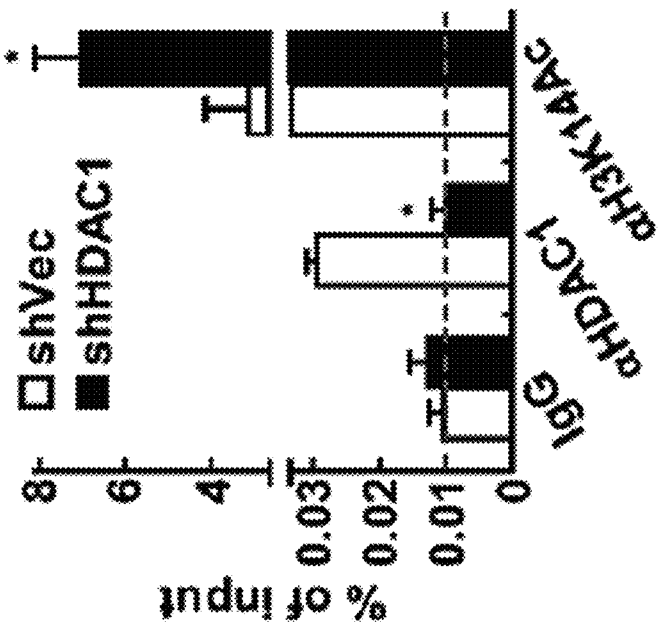
Figure 8D:
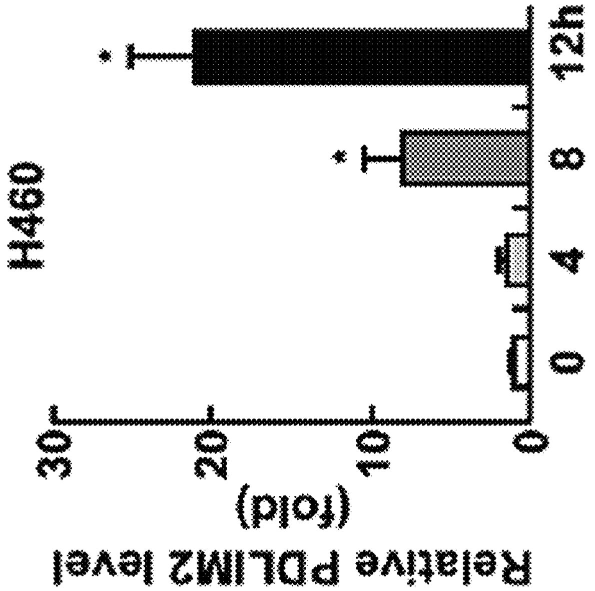
Figure 8F:
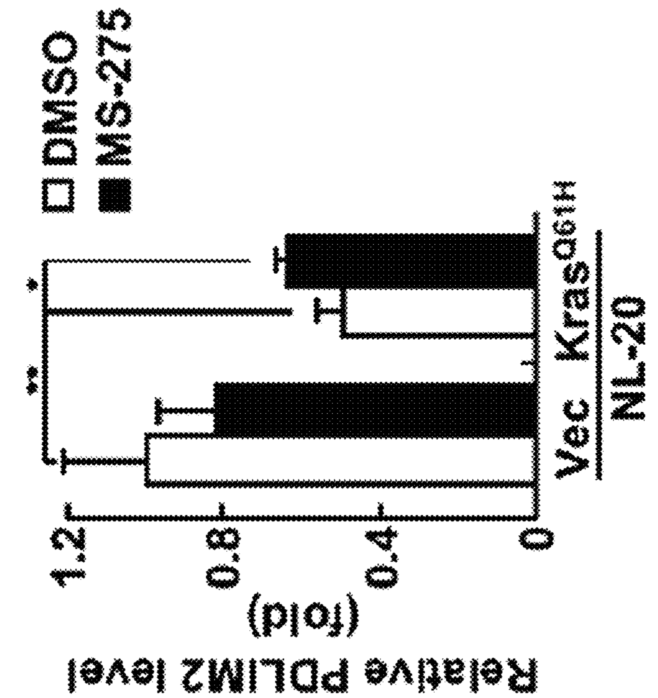
Figure 8E:
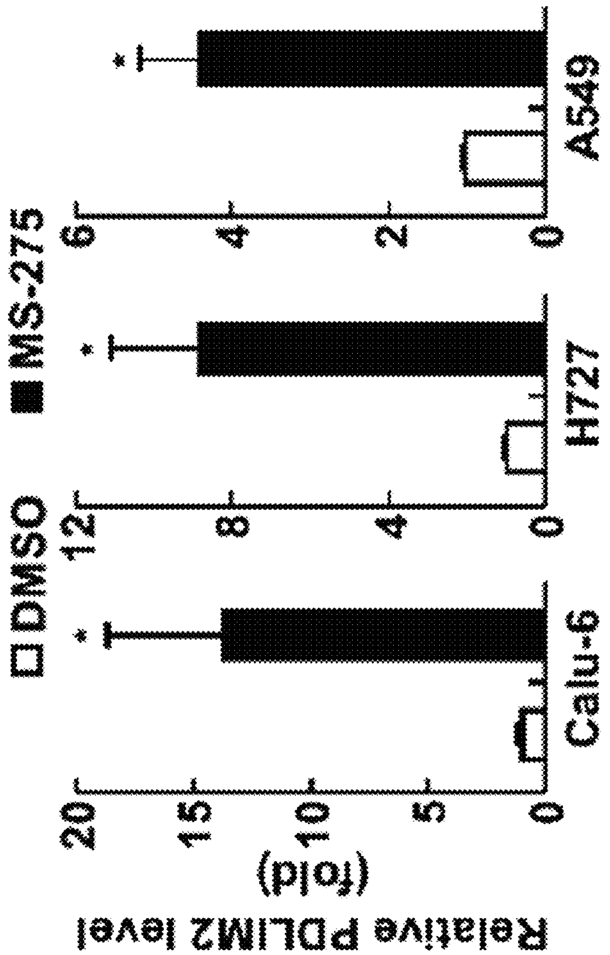

FIGS. 8A-8F provide that PDLIM2 repression in human lung cancer involved promoter histone deacetylation by HDACs. FIG. 8A provides TCGA data showing increased HDAC expression in human lung cancer. Light columns and dark columns stand for normal lung tissues and lung cancer tissues, respectively. Sample numbers are indicated. **** p<0.0001. FIG. 8B provides TCGA data showing negative associations between HDAC and PDLIM2 expression in human lung cancer. FIG. 8C provides ChIP assay showing increased H3K14 acetylation at the pdlim2 promoter in H460 human lung cancer cells by HDAC1 knockdown (n=3). * p<0.05. FIG. 8D provides qPCR analysis showing time-dependent induction of PDLIM2 in H460 human lung cancer cells by MS-275 treatment (n=3). * p<0.05. FIG. 8E provides qPCR analysis showing MS-275 induction of PDLIM2 in the indicated human lung cancer cell lines (n≥3). * p<0.05. FIG. 8F provides qPCR analysis showing PDLIM2 repression by oncogenic K-$Ras^{Q61H}$ mutant and PDLIM2 re-induction by MS-275 in the normal human lung epithelial cell line NL-20 (n=3). * p<0.05, ** p<0.01.

Figures 9A, 9B, 9C, 9D:
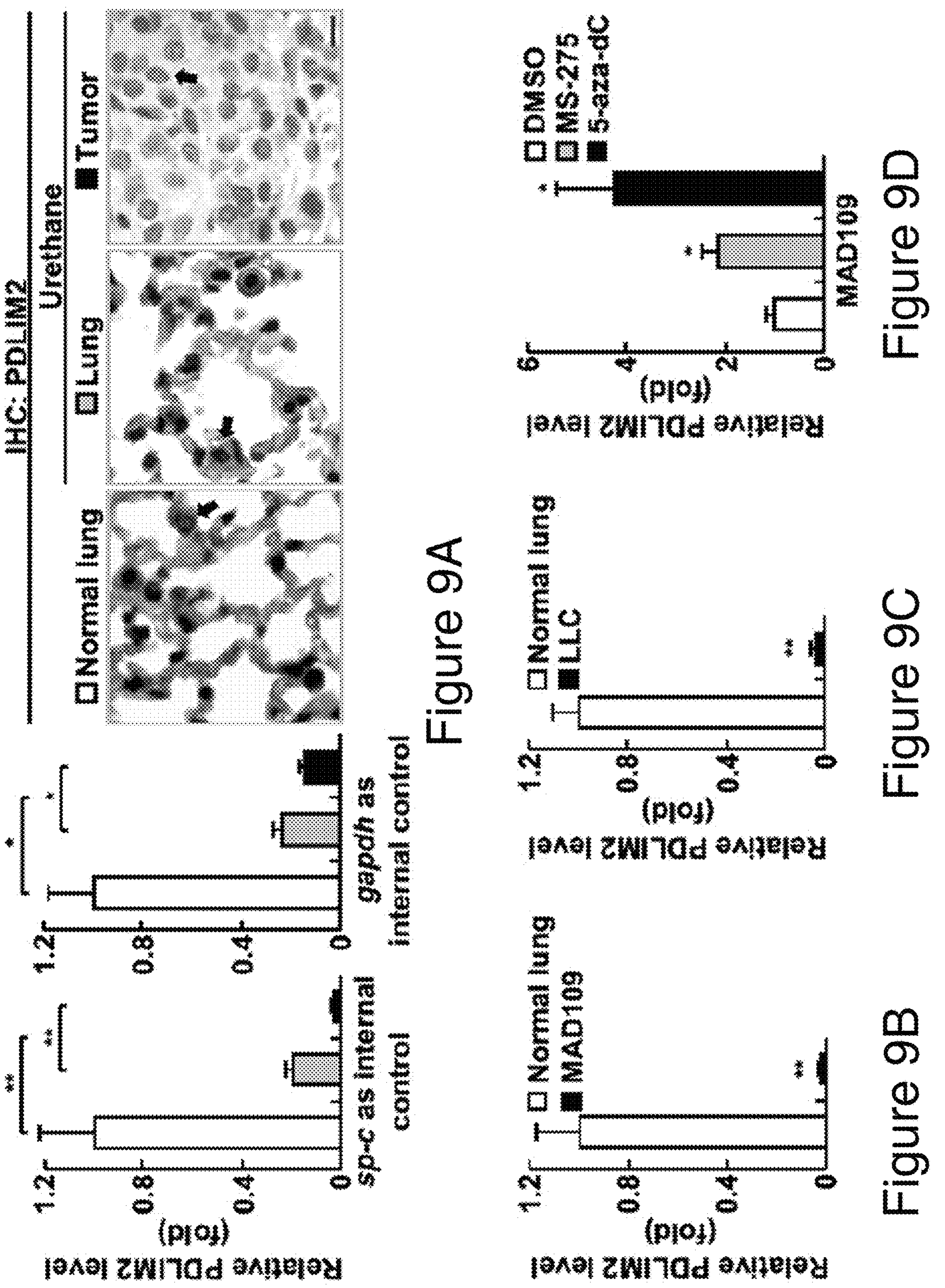

FIGS. 9A-9D provide that PDLIM2 was epigenetically repressed in mouse lung cancer. FIG. 9A provides qPCR and IHC staining analysis showing PDLIM2 repression in lung cancer induced by urethane in FVB/N mice (n≥3). Normal lung tissues from untreated mice as well as adjacent normal lung tissues from the same mice with lung tumors were used as controls. Representative lung epithelial and tumor cells are indicated by arrows. Scale bar, 10 μm. * $p<0.05$,  $p<0.01$. FIG. 9B provides qPCR analysis showing PDLIM2 repression in mouse lung cancer cell line MAD109 derived from a BALB/c mouse. Normal lung tissues from BALB/c mice were used as controls (n≥3).  $p<0.01$. FIG. 9C provides qPCR analysis showing PDLIM2 repression in mouse lung cancer cell line LLC derived from a C57BL/6 mouse (n=3). Normal lung tissues from C57BL/6 mice were used as controls. ** $p<0.01$. FIG. 9D provides qPCR analysis showing PDLIM2 re-induction by 5-aza-dC and MS-274 in mouse MAD109 lung cancer cells (n=3). * $p<0.05$.

Figure 10A:
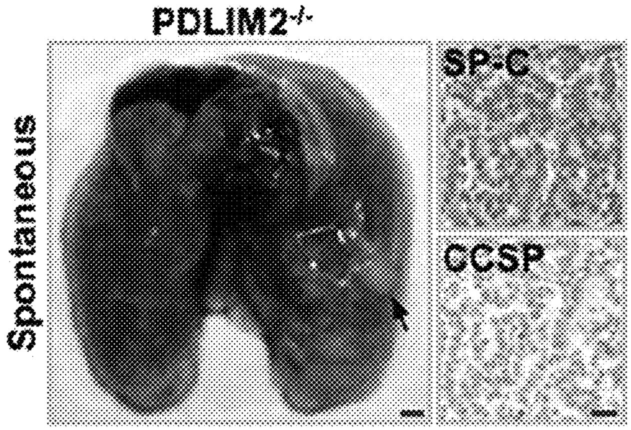
Figure 10B:
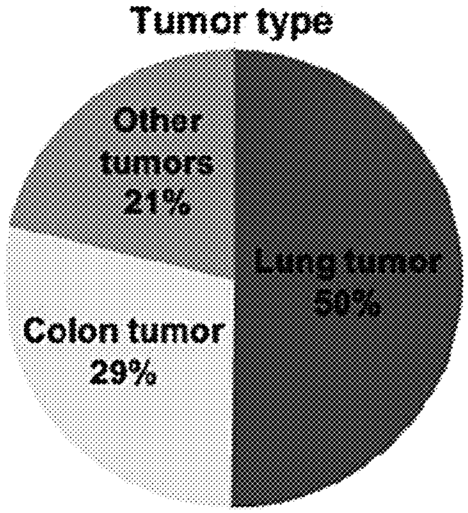
Figure 10C:
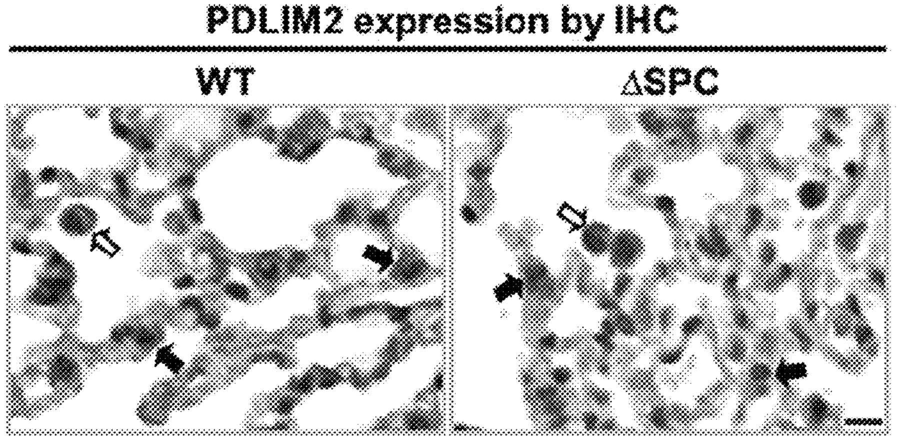
Figure 10D:
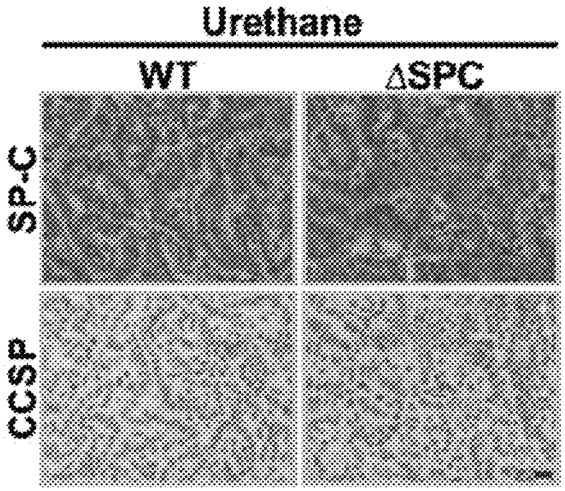
Figure 10E:
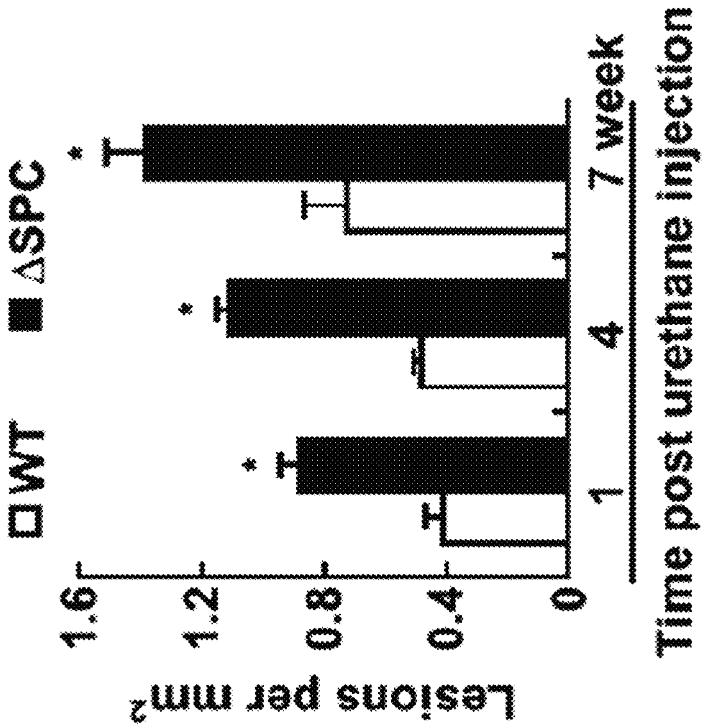
Figure 10F:
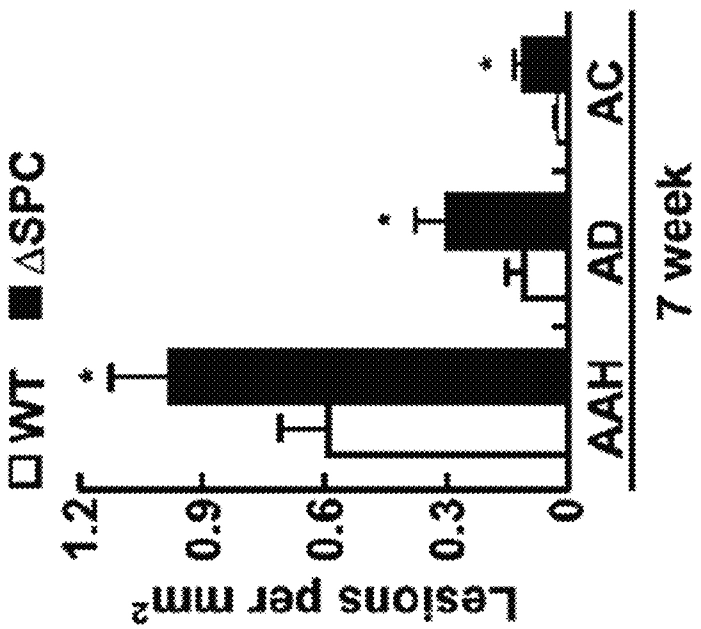

FIGS. 10A-10F provide that global or lung epithelial-specific deletion of PDLIM2 in mice led to increased lung cancer development. FIG. 10A provides representative of lung tissues and IHC staining of SP-C and CCSP in spontaneous lung tumors from PDLIM2-null ($PDLIM2^{-/-}$) mice. Scale bar, 1 mm for whole lung picture, 20 μm for IHC staining. FIG. 10B provides percentile of lung tumor among all tumors spontaneously developed in $PDLIM2^{-/-}$ mice. FIG. 10C provides representative IHC analysis of PDLIM2 in lung tissues from WT and ΔSPC mice treated with urethane. Lung epithelial and myeloid cells are indicated by black and white arrows, respectively. Scale bar, 10 μm. FIG. 10D provides representative IHC analysis of SP-C and CCSP in lung tumors from urethane-treated WT and ΔSPC. Scale bar, 20 μm. FIG. 10E provides H&E staining showing lesion numbers in WT and ΔSPC mice at the indicated time points post urethane treatment (n=4). * $p<0.05$. FIG. 10F provides H&E staining showing lesion numbers of atypical adenomatous hyperplasia (AAH), adenoma (AD) and adenocarcinoma (AC) in the lungs of WT and ΔSPC mice 7 weeks post urethane treatment (n=4). * $p<0.05$.

Figures 11A, 11B, 11C, 11D:
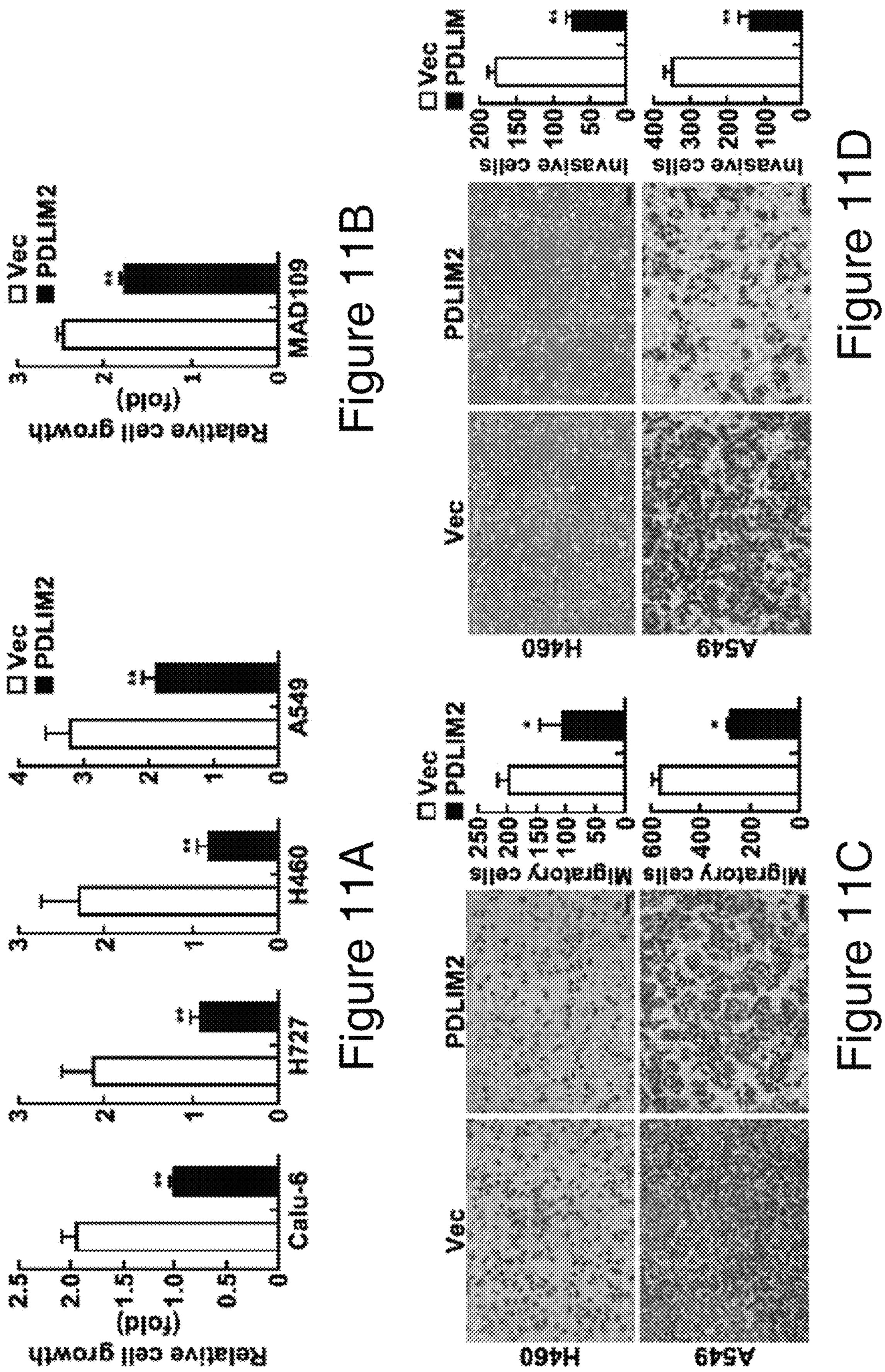
Figure 11F:
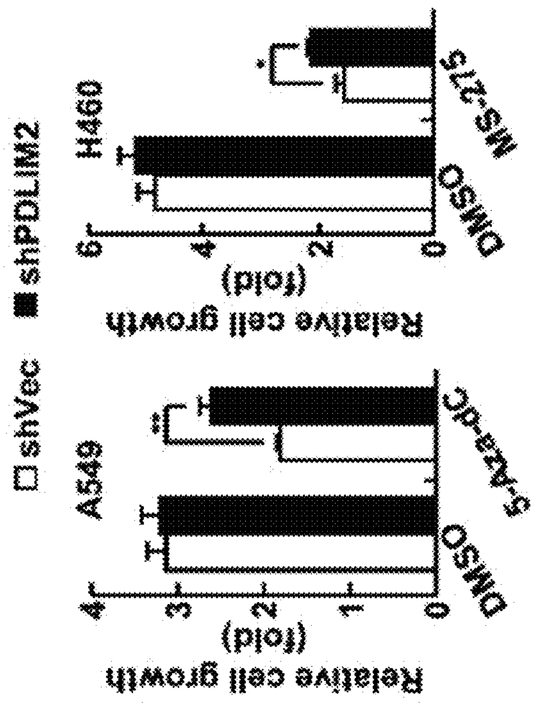
Figure 11E:
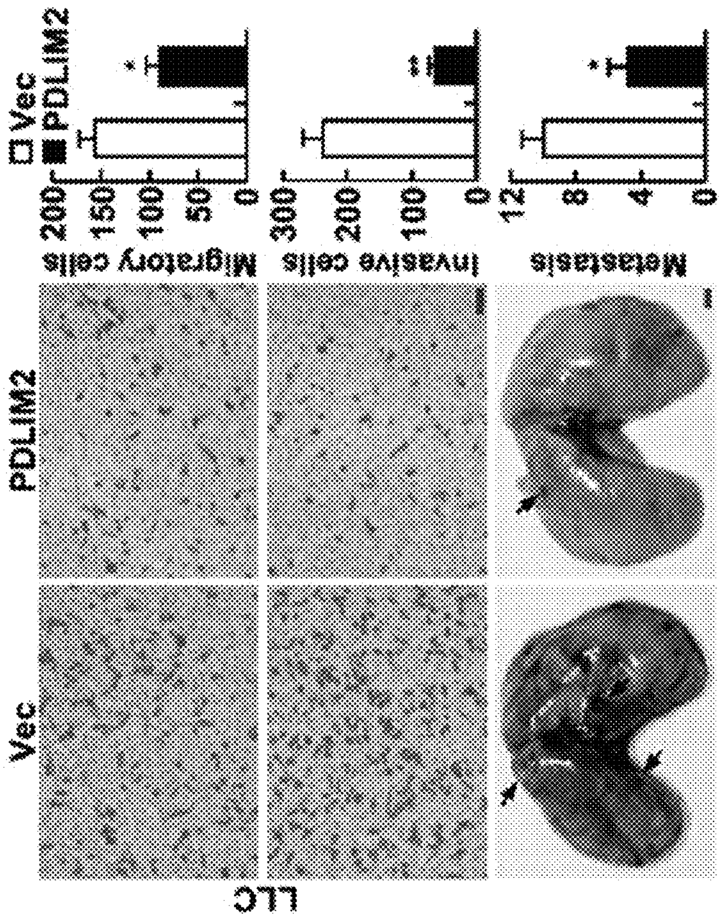

FIGS. 11A-11F provide that PDLIM2 reconstitution suppressed tumorigenicity of lung cancer cells both in vitro and in vivo. FIG. 11A provides cell growth assays showing decreased growth of the indicated human lung cancer lines by PDLIM2 reconstitution (n=3).  $p<0.01$. FIG. 11B provides cell growth assays showing decreased growth of the mouse lung cancer line MAD109 by PDLIM2 reconstitution (n=4).  $p<0.01$. FIG. 11C provides in vitro migration assays showing decreased migration of the indicated human lung cancer lines by PDLIM2 reconstitution (n=3). * $p<0.05$. Scale bar, 100 μm. FIG. 11D provides in vitro invasion assays showing decreased invasion of the indicated human lung cancer lines by PDLIM2 reconstitution (n=3). ** $p<0.01$. Scale bar, 100 μm. FIG. 11E provides in vitro migration and invasion assays (n=3, Scale bar, 100 μm) and in vivo metastasis assays (n=6, Scale bar, 1 mm) showing decreased migration, invasion and metastasis of the mouse lung cancer line LLC by PDLIM2 reconstitution. * $p<0.05$, ** $p<0.01$. FIG. 11F provides cell growth assays showing protection of human lung cancer cells from 5-aza-dC and MS275 by PDLIM2 knockdown (n=4). * $p<0.05$, ** $p<0.01$.

Figure 12A:
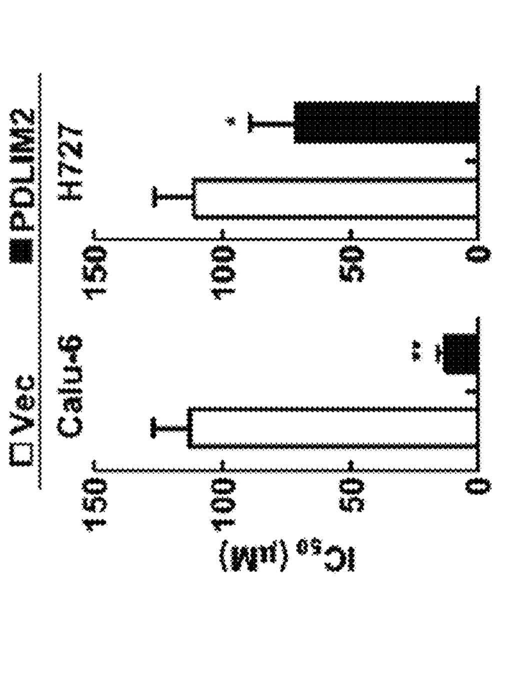
Figure 12B:
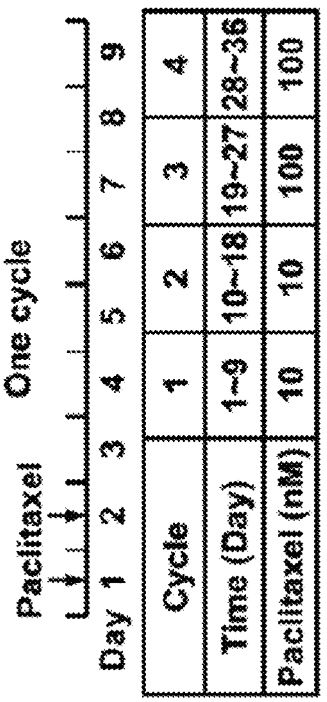
Figure 12C:
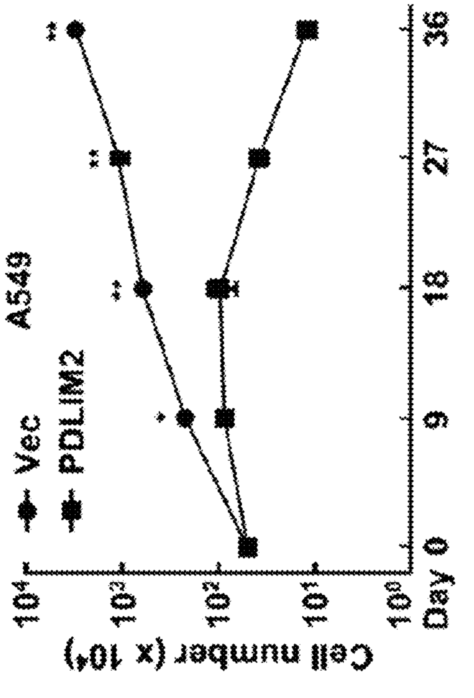
Figure 12D:
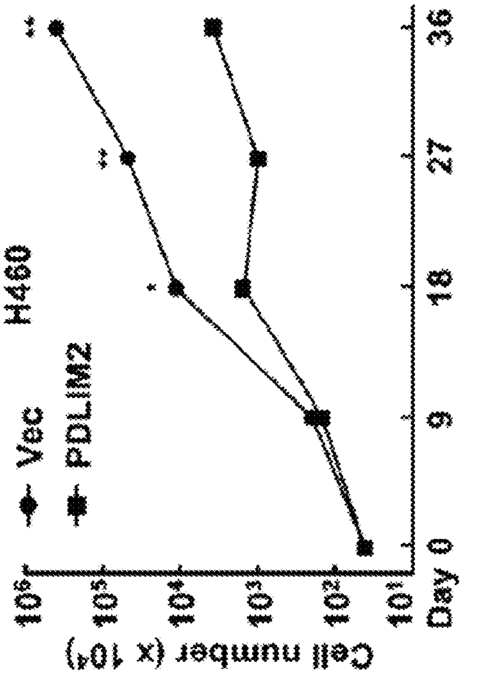

FIGS. 12A-12D provide that PDLIM2 reconstitution rendered lung cancer cells sensitive to chemotherapeutic drugs. FIG. 12A provides in vitro $IC_{50}$ assay showing increased carboplatin sensitivity of the indicated human lung cancer cells by PDLIM2 reconstitution. FIG. 12B provides schedule of paclitaxel treatment of human lung cancer cells in vitro. FIG. 12C provides cell growth assays showing increased paclitaxel sensitivity of the human lung cancer cells A549 by PDLIM2 reconstitution. FIG. 12D provides cell growth assays showing increased paclitaxel sensitivity of the human lung cancer cells H460 by PDLIM2 reconstitution. In FIGS. 12A, 12C, and 12D, * $p<0.05$, ** $p<0.01$.

Figure 13A:
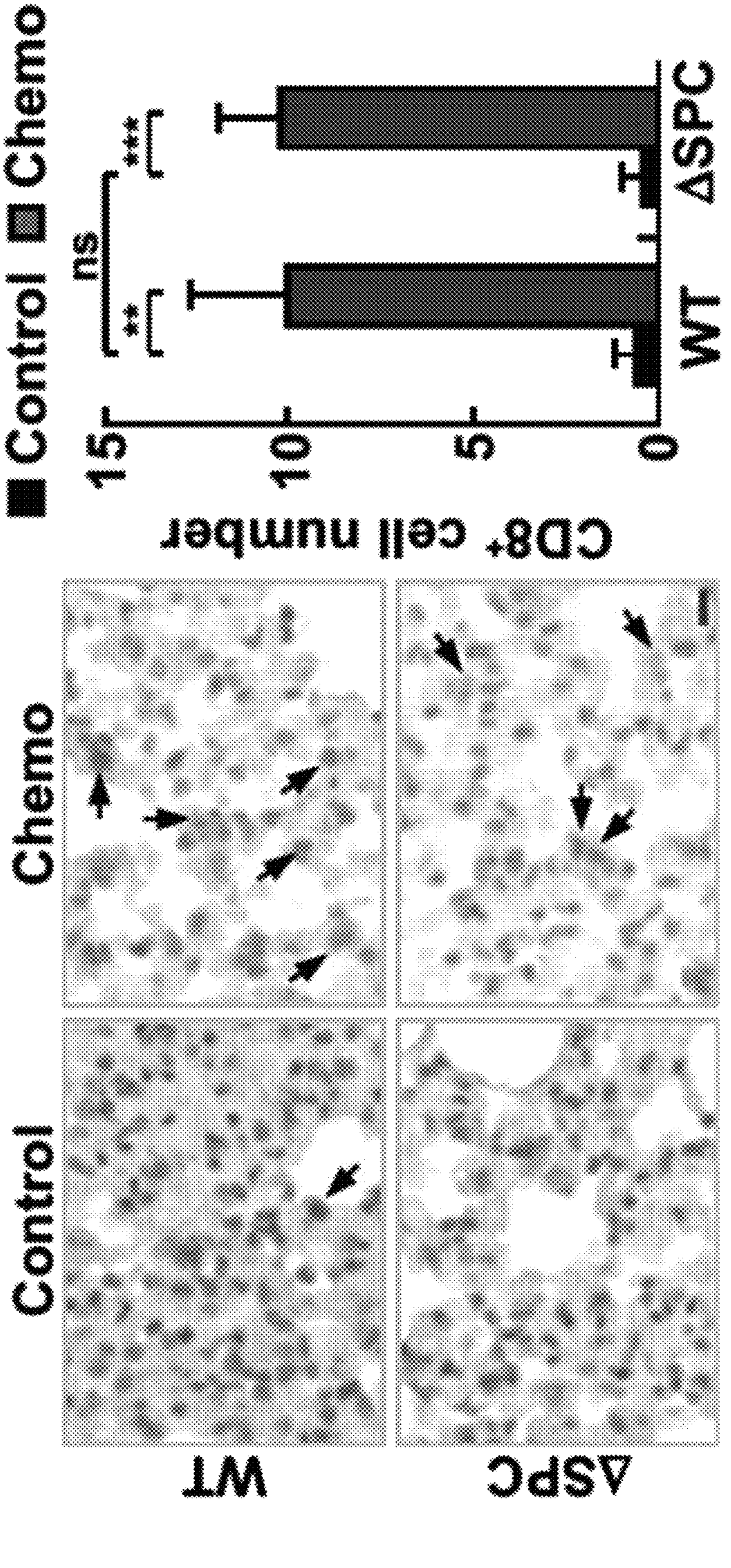
Figure 13B:
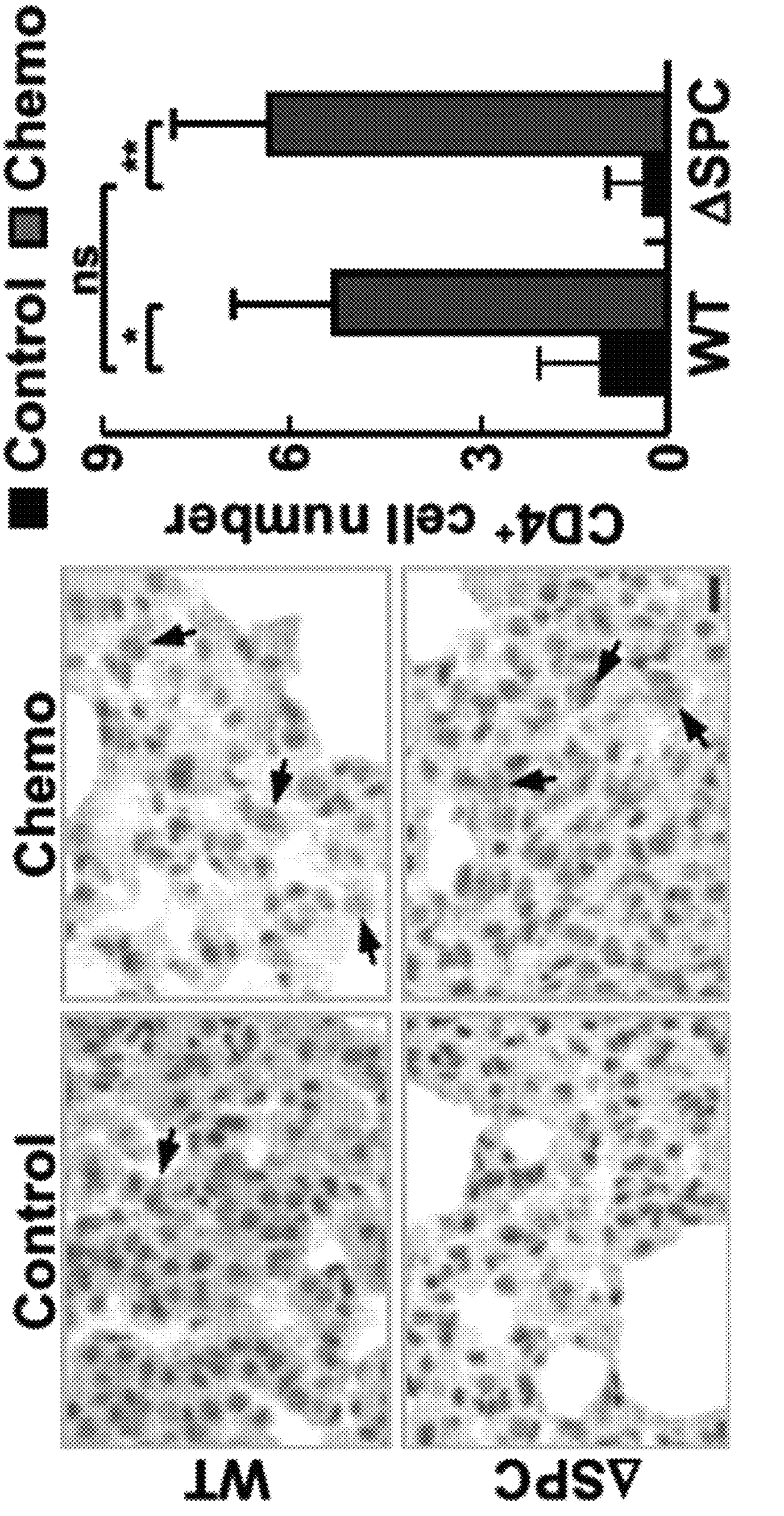
Figure 13C:
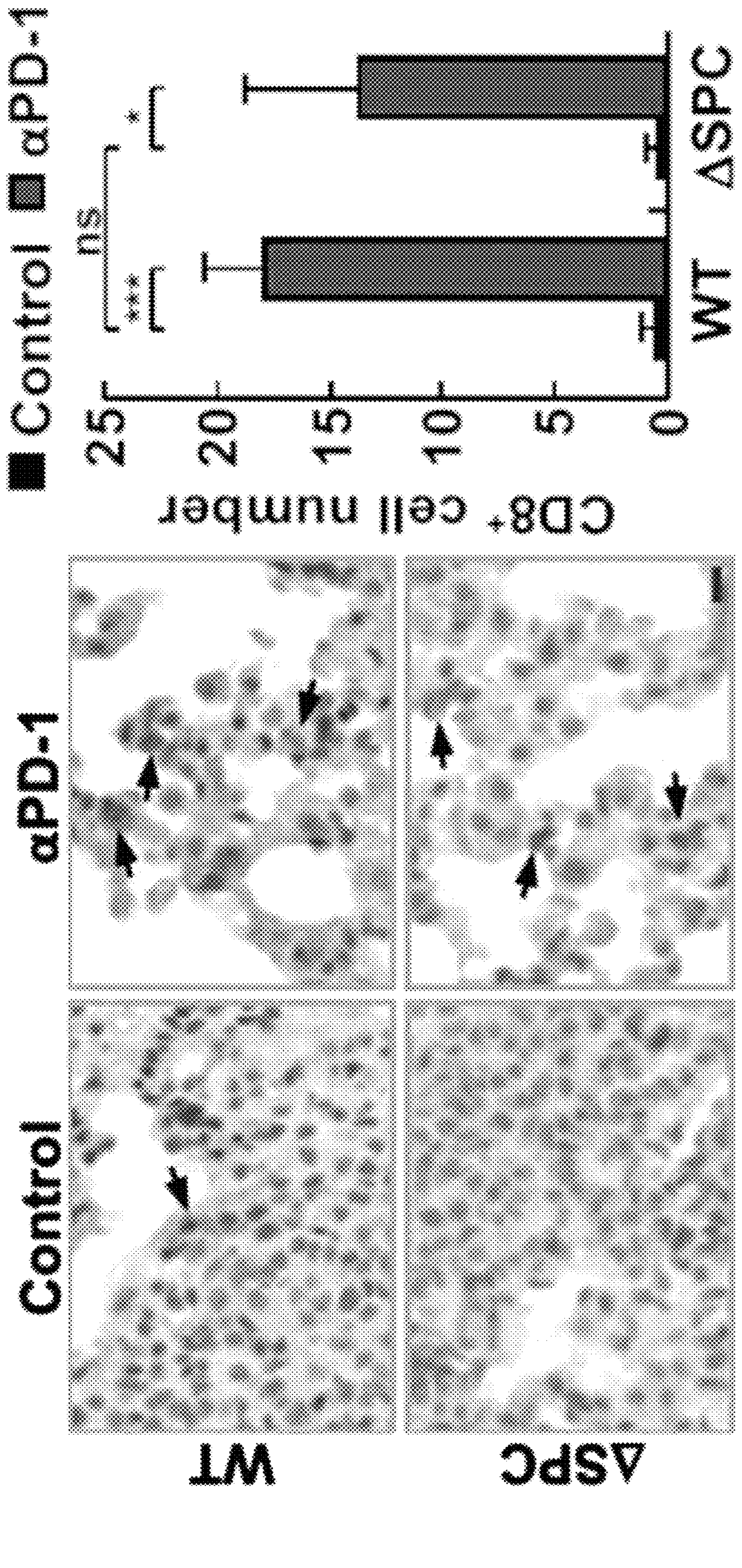
Figure 13D:
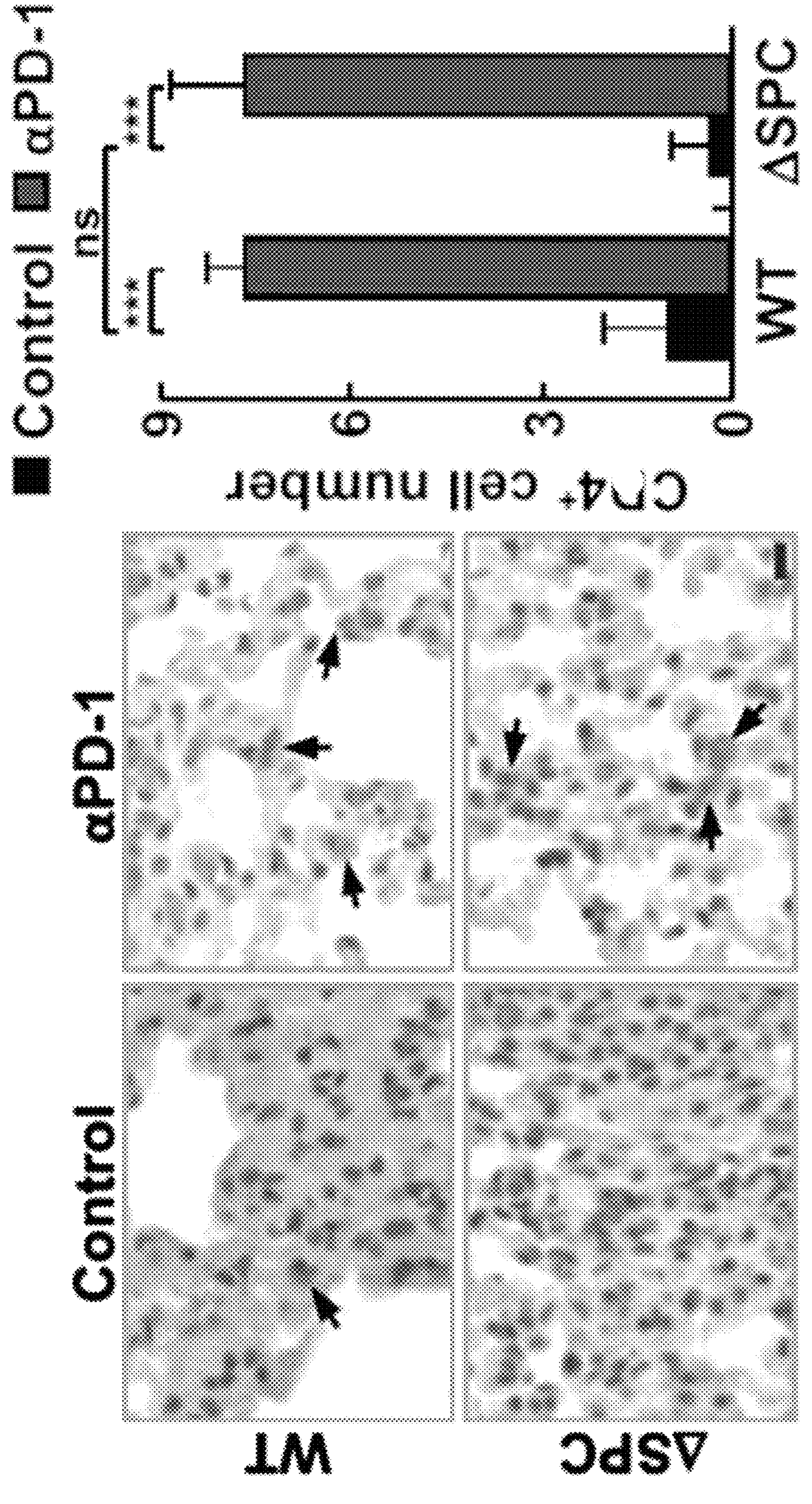

FIGS. 13A-13D provide that PDLIM2 selective deletion had no effect on the numbers of basal or treatment-induced tumor infiltration of lymphocytes. FIG. 13A provides representatives of CD8 IHC staining of lung tumors from urethane-treated WT and ΔSPC mice with or without carboplatin and paclitaxel combination (chemo) treatment (n=3).  $p<0.01$, * $p<0.001$. Scale bar, 10 μm. FIG. 13B provides representatives of CD4 IHC staining of lung tumors from urethane-treated ΔSPC mice and WT mice with or without chemo-treatment (n=3). * $p<0.05$, ** $p<0.01$. Scale bar, 10 μm. FIG. 13C provides representatives of CD8 IHC staining of lung tumors from urethane-treated ΔSPC mice and WT mice with or without anti-PD-1 treatment (n=3). * $p<0.05$, * $p<0.001$. Scale bar, 10 μm. FIG. 13D provides representatives of CD4 IHC staining of lung tumors from urethane-treated WT and ΔSPC mice with or without anti-PD-1 treatment (n=3). * $p<0.001$. Scale bar, 10 μm.

Figures 14B, 14C:
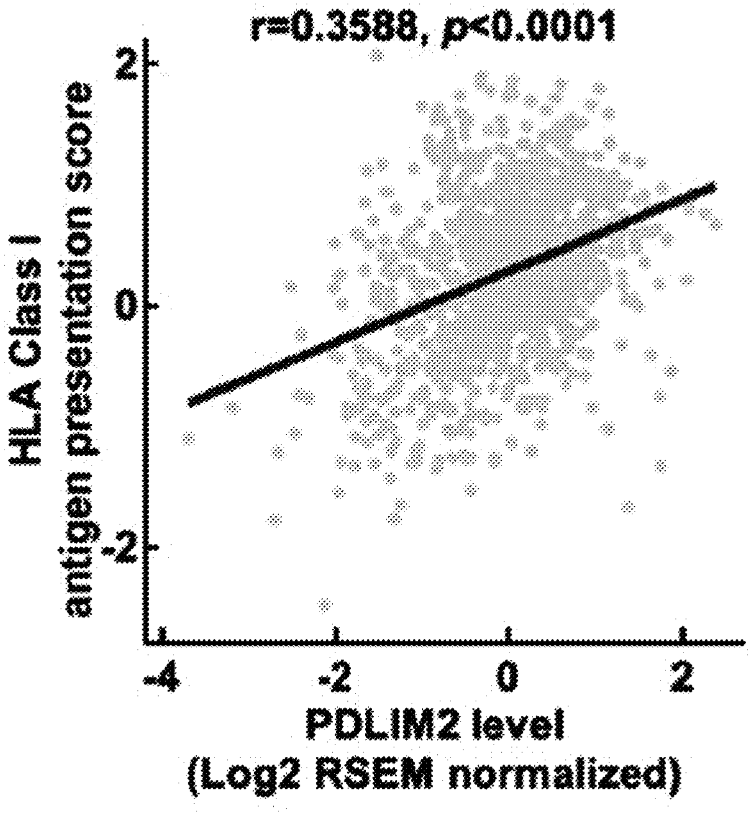

FIGS. 14A-14C provide that PDLIM2 expression in lung cancer was positively associated with T cell activation. FIG. 14A provides TCGA data showing positive association between PDLIM2 and T-cell activation-related genes in lung cancer. Only those genes with $r>0.3$ are listed. FIG. 14B provides TCGA data showing positive association of PDLIM2 expression with HLA class I antigen presentation-related genes in lung cancer (red, $r>0.3$). FIG. 14C provides TCGA data showing positive association between PDLIM2 expression and HLA class I antigen presentation-related genes in lung cancer.

Figure 15:
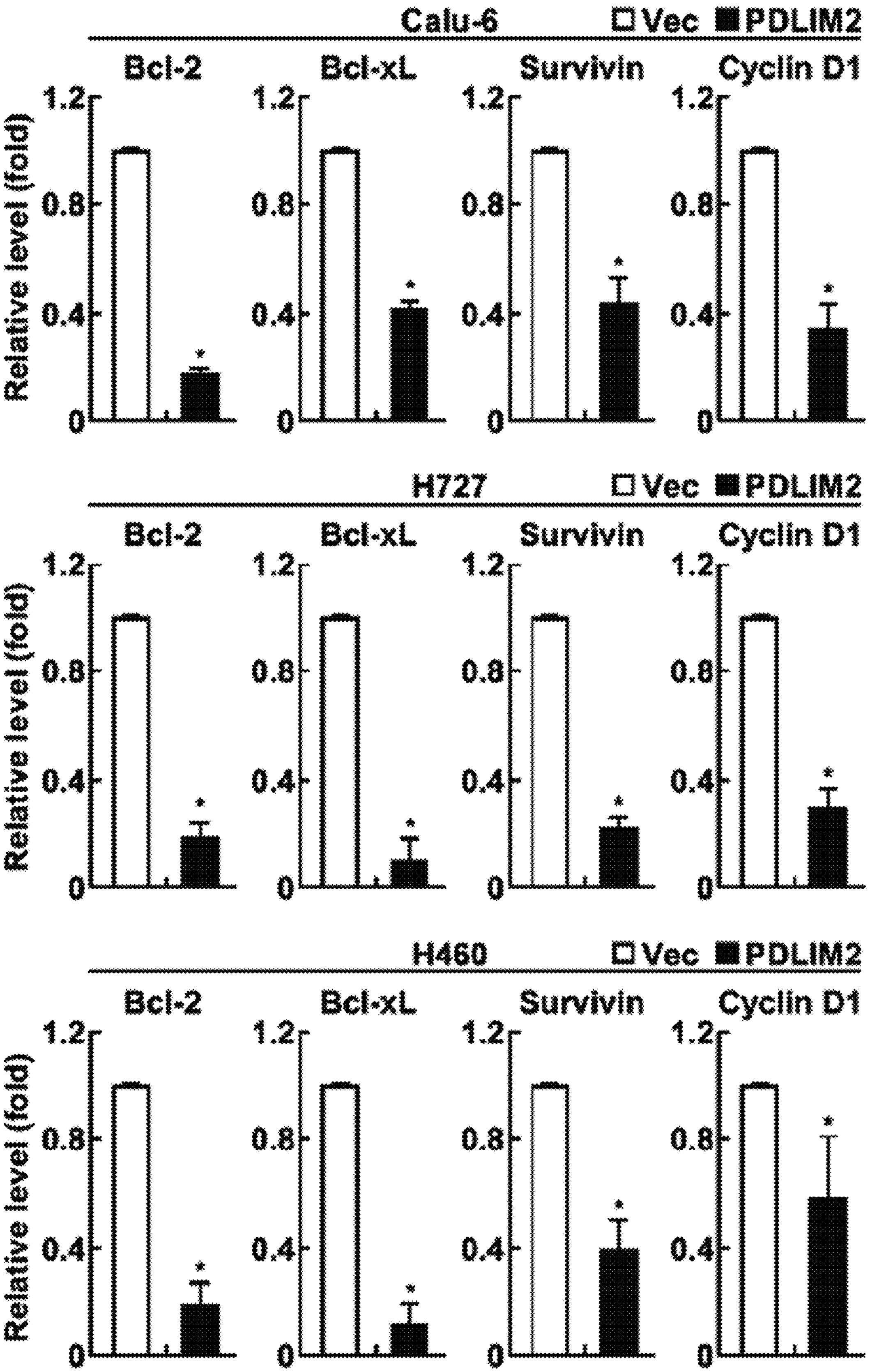

FIG. 15 provides PDLIM2 repressed expression of cell survival and proliferation genes in lung cancer. qPCR analysis showing decreased expression of Bcl-2, Bcl-xL, Survivin and Cyclin D1 in the indicated human lung cancer cell lines by PDLIM2 reconstitution (n=3). * $p<0.05$.

Figure 16A:
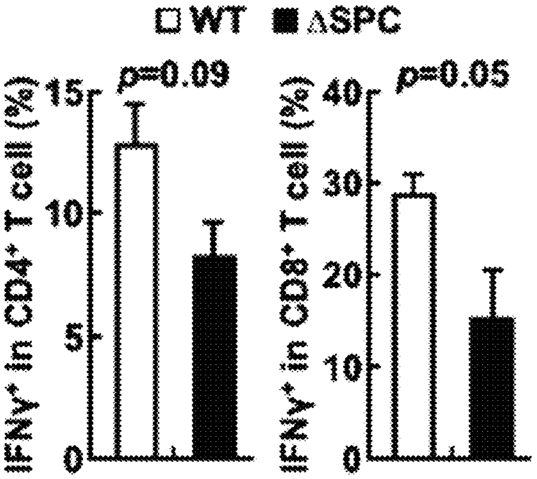
Figure 16B:
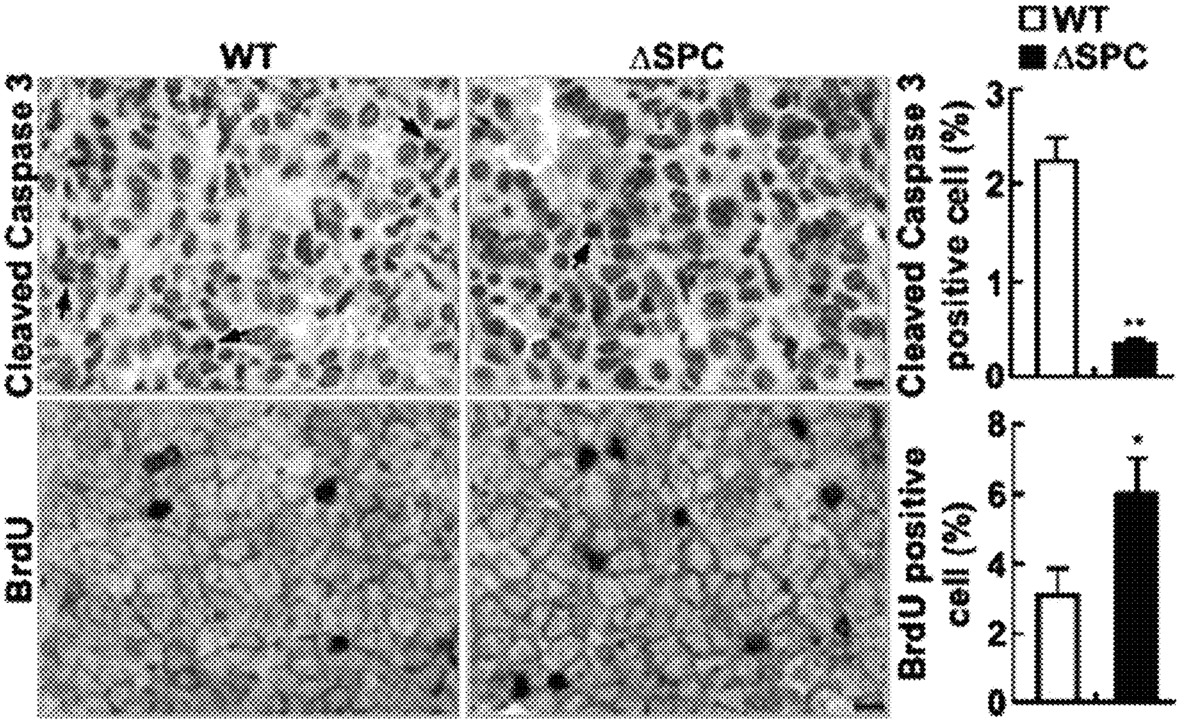
Figure 16C:
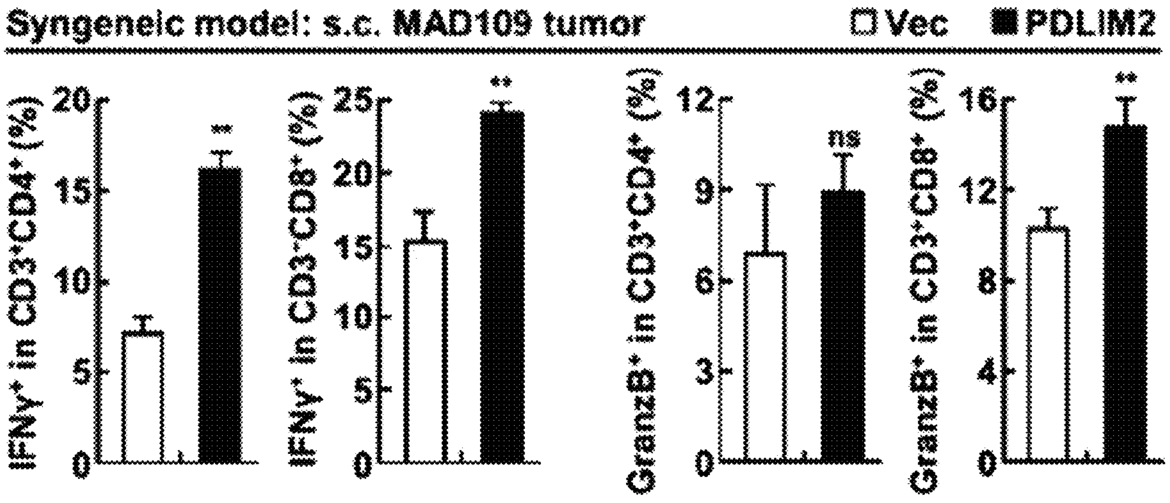
Figure 16D:
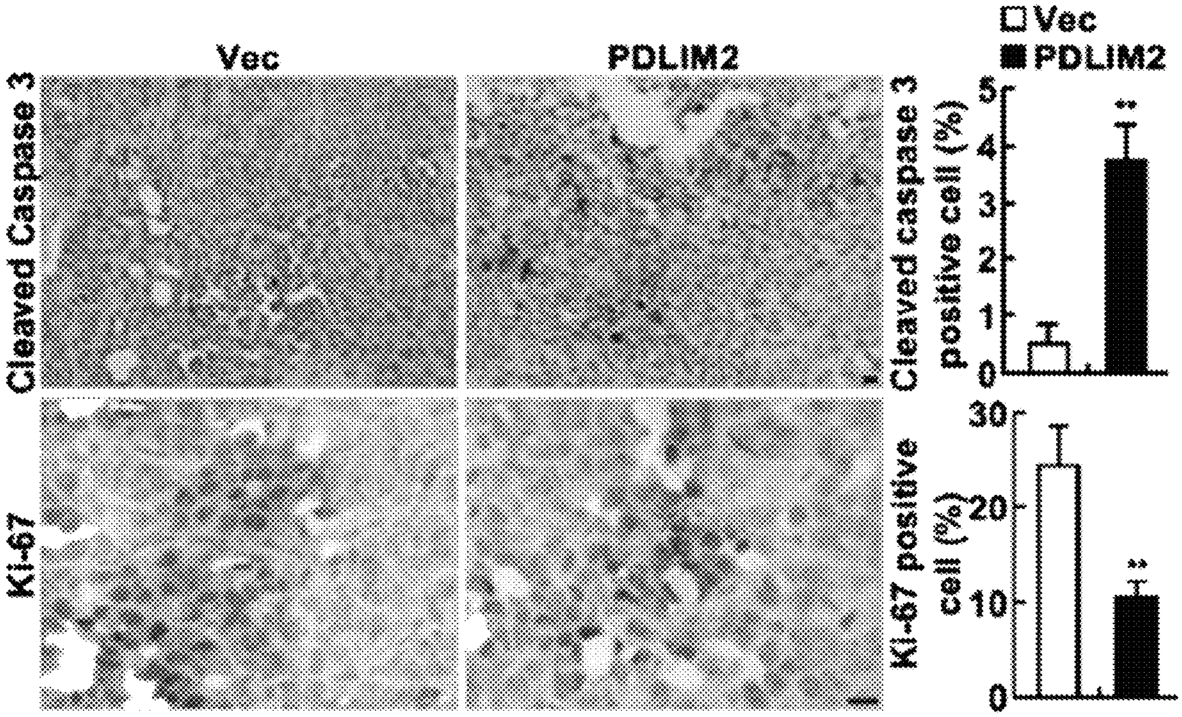

FIGS. 16A-16D provide that PDLIM2 suppressed T-cell activation in lung cancer. FIG. 16A provides FACS analysis showing decreased lung T-cell activation in ΔSPC mice treated with urethane (n=4). FIG. 16B provides IHC staining showing decreased apoptosis and increased proliferation of lung cancer cells in ΔSPC mice (urethane model) (n≥3). * $p<0.05$; ** $p<0.01$. Scale bar, 10 μm. FIG. 16C provides FACS analysis showing increased activation of TILs by PDLIM2 reconstitution in MAD109 syngeneic model (n=3). * $p<0.05$; ** $p<0.01$. FIG. 16D provides IHC staining showing increased apoptosis and decreased proliferation of lung cancer cells by PDLIM2 reconstitution in MAD109 syngeneic model (n=3). * $p<0.05$; ** $p<0.01$. Scale bar, 10 μm.

Figure 17B:
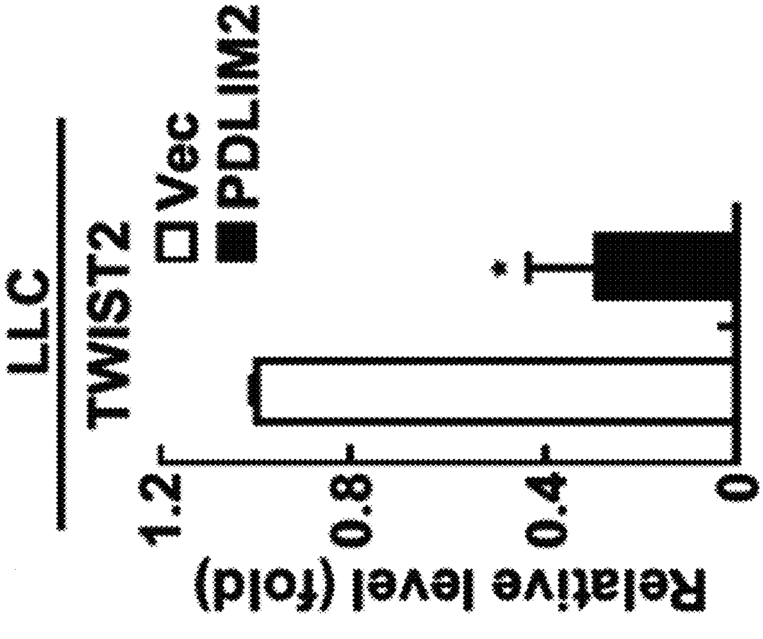
Figure 17A:
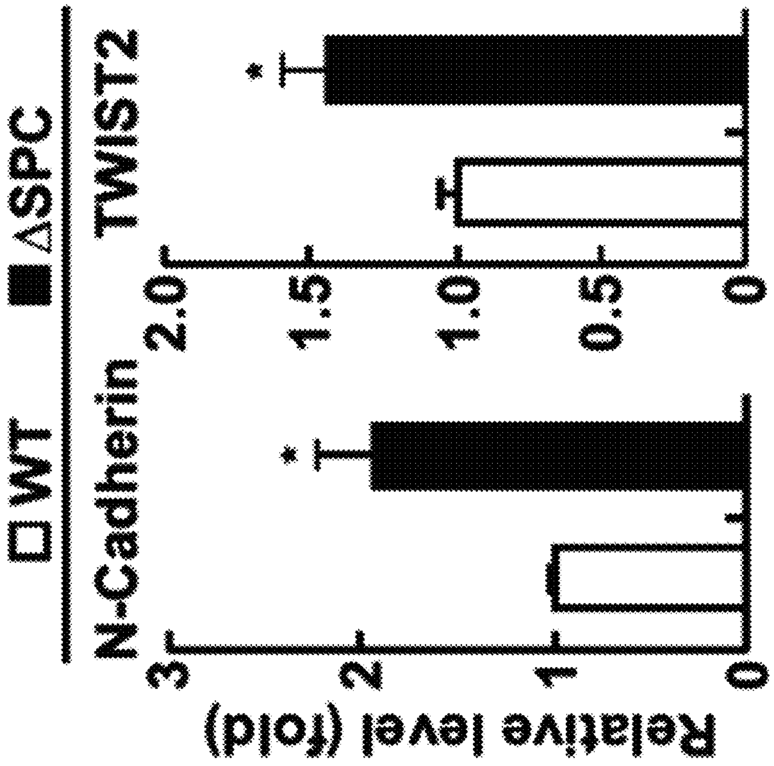
Figure 17C:
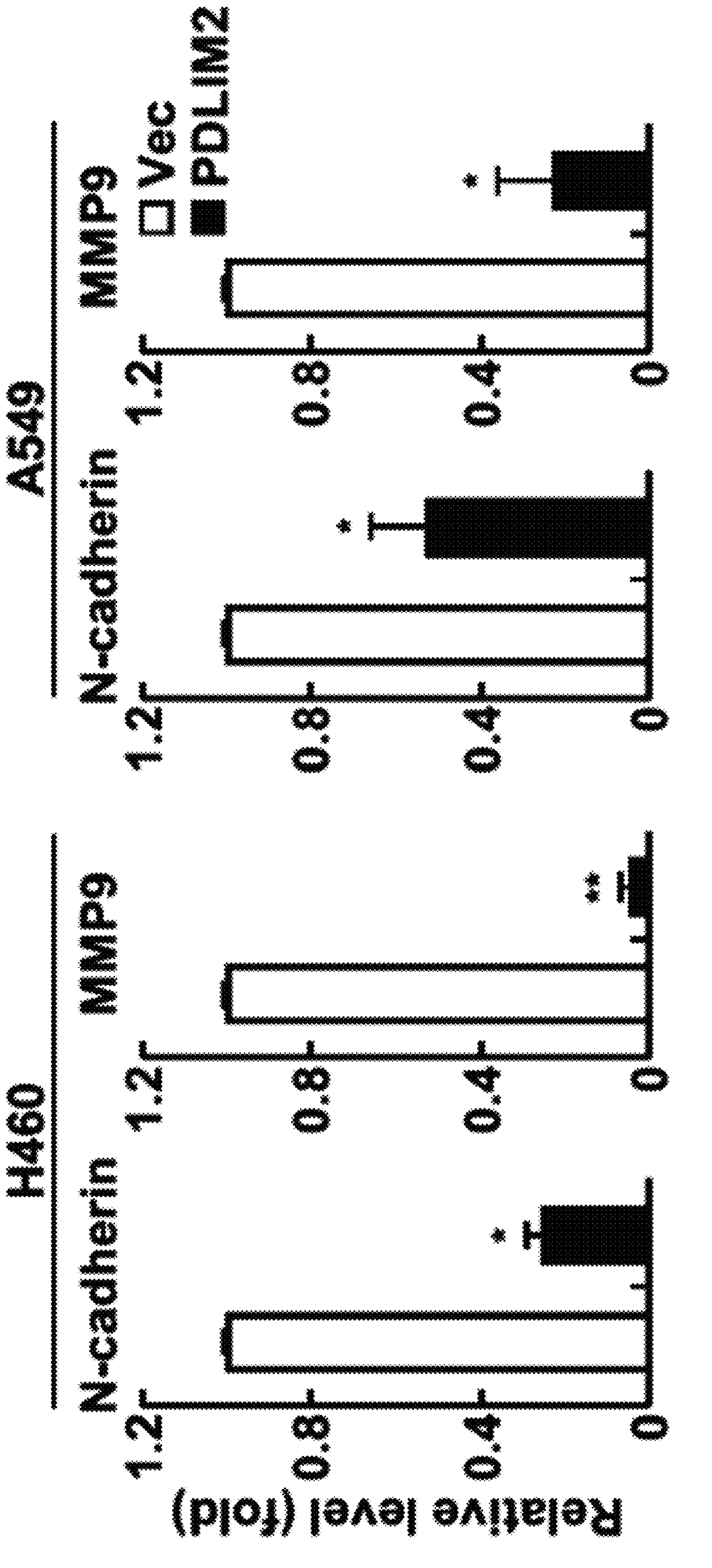

FIGS. 17A-17C provide that PDLIM2 repressed expression of cell migration and invasion-related genes in lung cancer. FIG. 17A provides qPCR analysis showing increased N-Cadherin and TWIST2 expression in lung tumor cells from ΔSPC mice treated with urethane (n=4). * $p<0.05$. FIG. 17B provides qPCR analysis showing decreased TWIST2 expression in LLC mouse lung cancer cells reconstituted with PDLIM2 (n=3). * $p<0.05$. FIG. 17C provides qPCR analysis showing decreased N-Cadherin and MMP9 expression in the indicated human lung cancer cells reconstituted with PDLIM2 (n=3). * $p<0.05$, ** $p<0.01$.

Figure 18A:
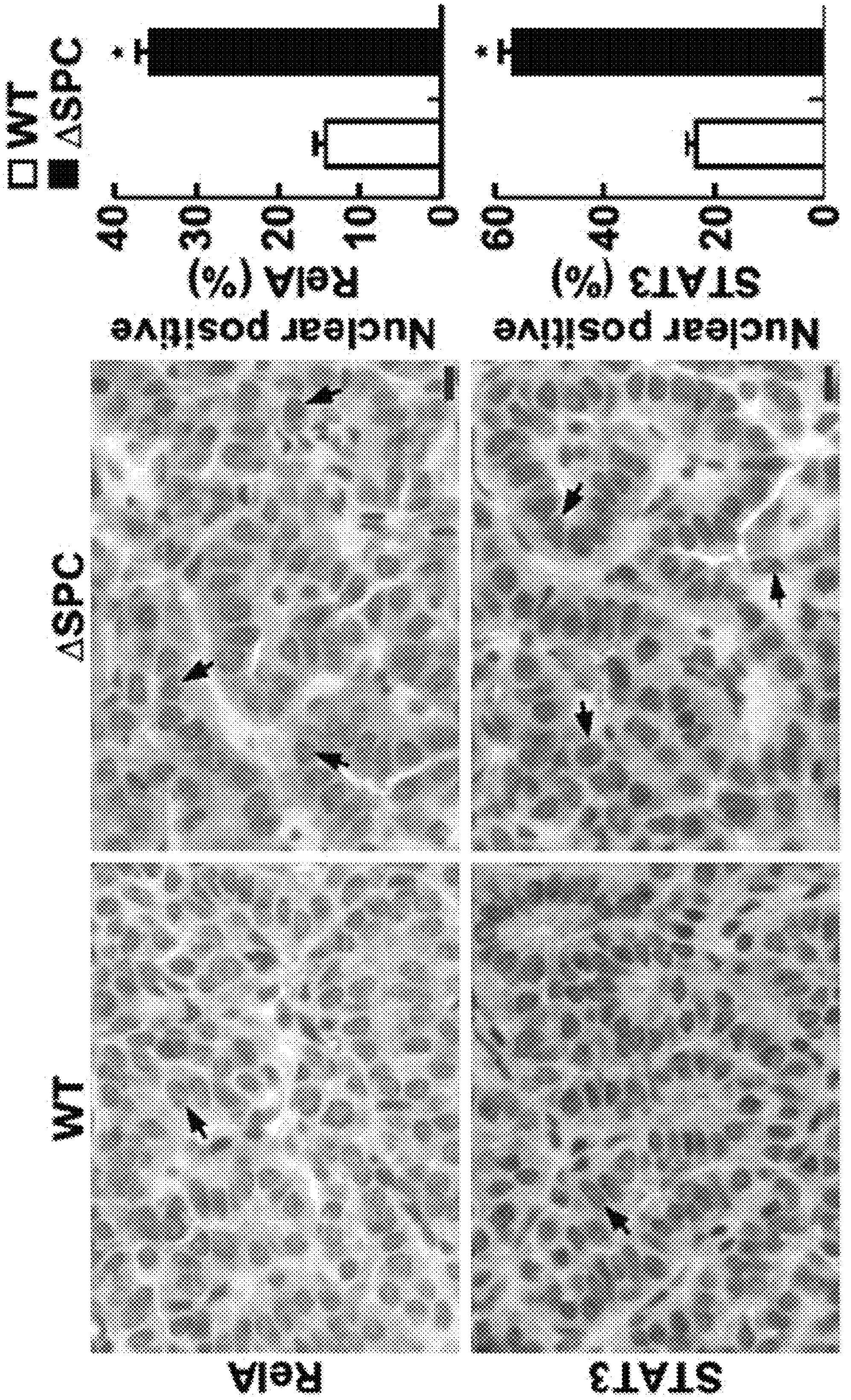
Figure 18B:
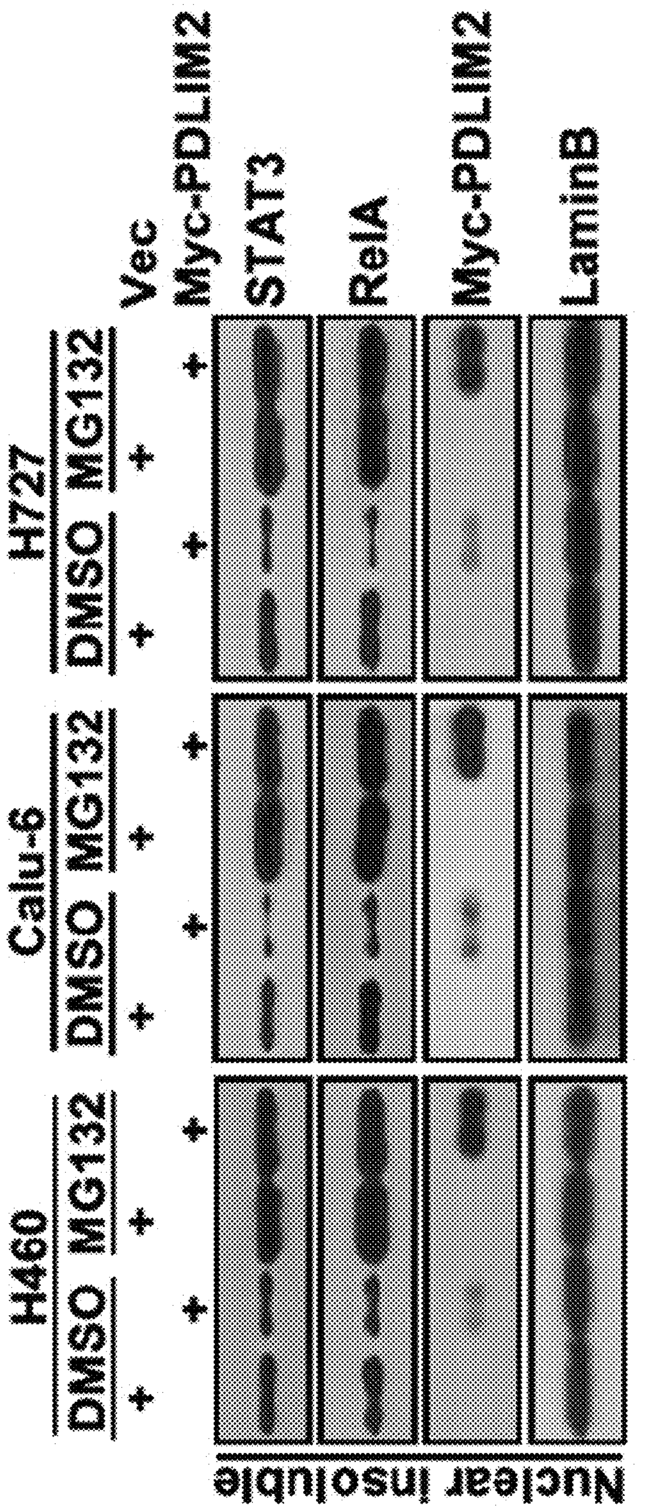

FIGS. 18A-18B provide that PDLIM2 decreased nuclear RelA and STAT3 in lung cancer cells. FIG. 18A provides IHC staining showing increased nuclear RelA and STAT3 in lung cancers cells by PDLIM2 deletion in urethane model (n≥3). * $p<0.05$. Scale bar, 10 μm. FIG. 18B provides nuclear fraction-IB assays showing increased proteasmal degradation and decreased expression of nuclear RelA and STAT3 in the indicated human lung cancer cells reconstituted with PDLIM2.

Figure 19A:
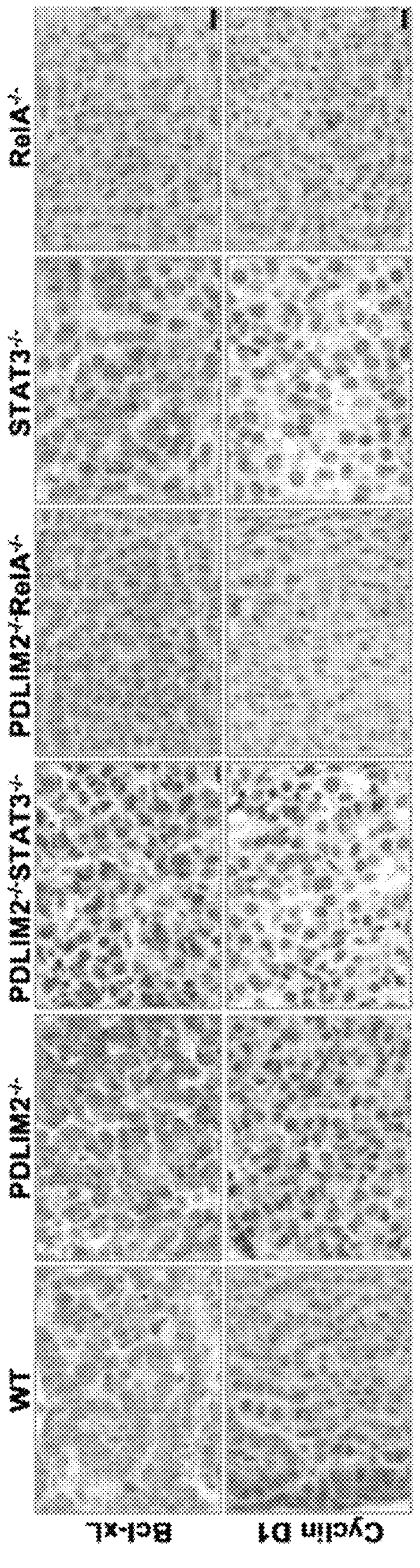
Figure 19B:
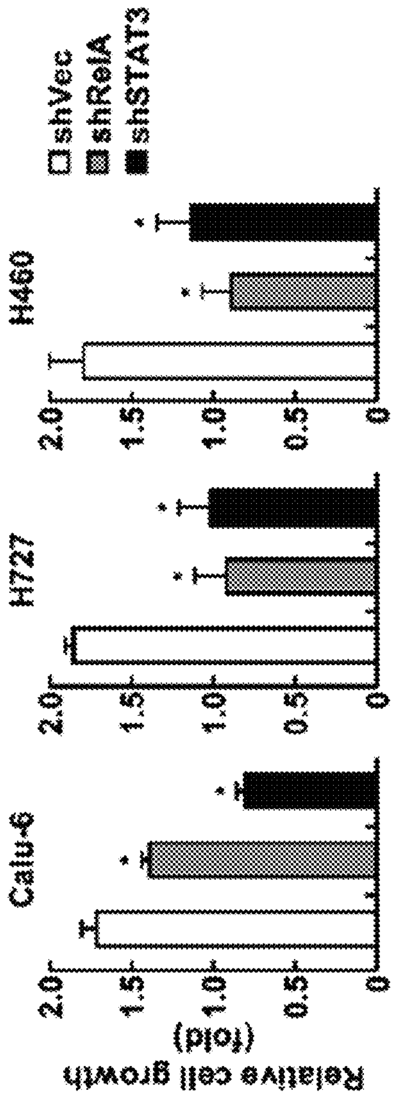
Figure 19C:
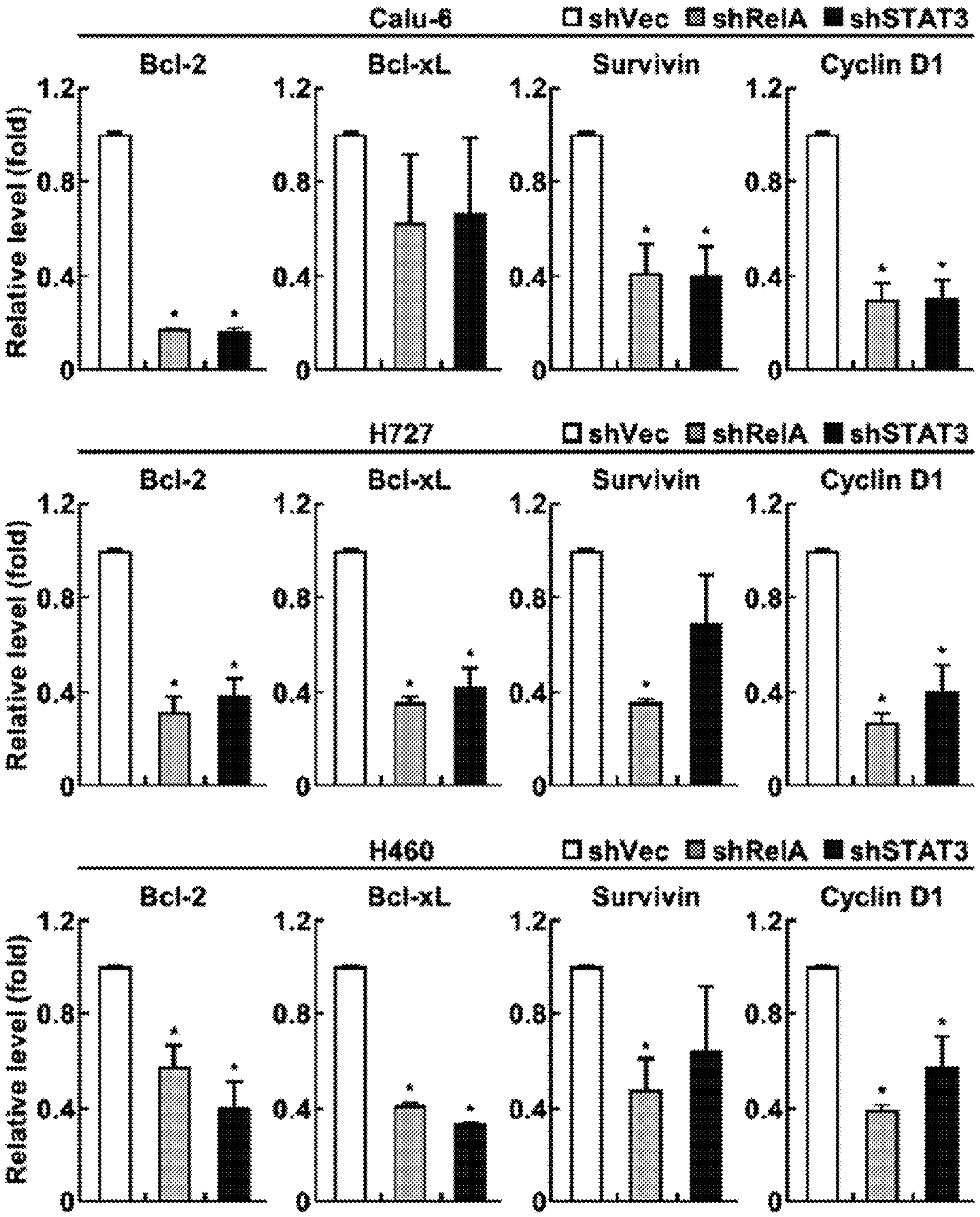

FIGS. 19A-19C provide that RelA and STAT3 were involved in the growth and growth-related gene expression of lung cancer. FIG. 19A provides IHC staining showing Bcl-xL and Cyclin D1 expression in lung tumors from the indicated mice (K-Ras$^{G12D}$ model). Scale bar, 10 μm. FIG. 19B provides cell growth assays showing decreased growth of the indicated human lung cancers by RelA or STAT3 knockdown (KD) (n=3). * $p<0.05$. FIG. 19C provides qPCR analysis showing decreased expression of the indicated growth-related genes in the indicated human lung cancer cells by RelA or STAT3 KD (n=3). * $p<0.05$.

Figure 20A:
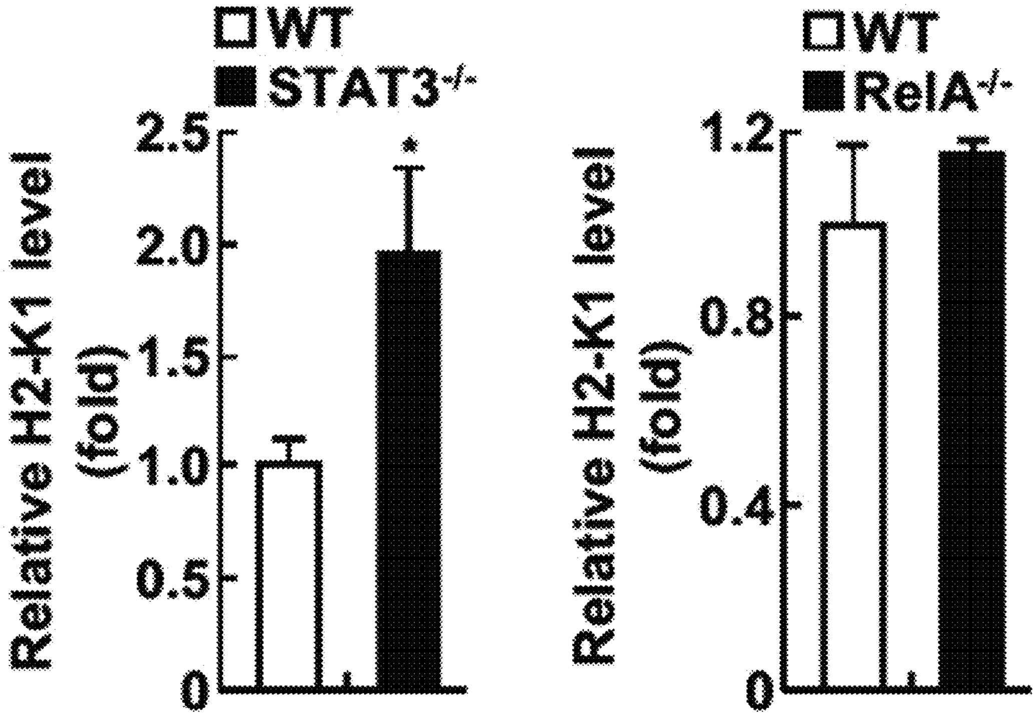
Figure 20B:
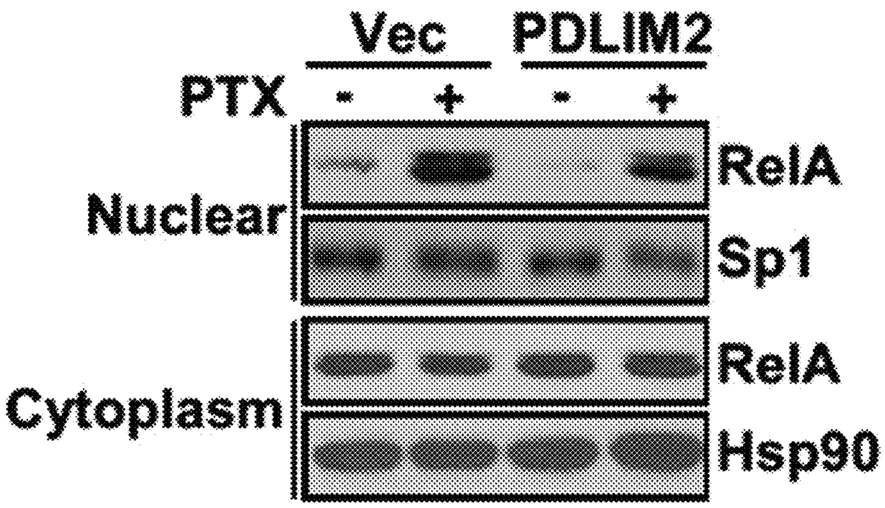
Figure 20C:
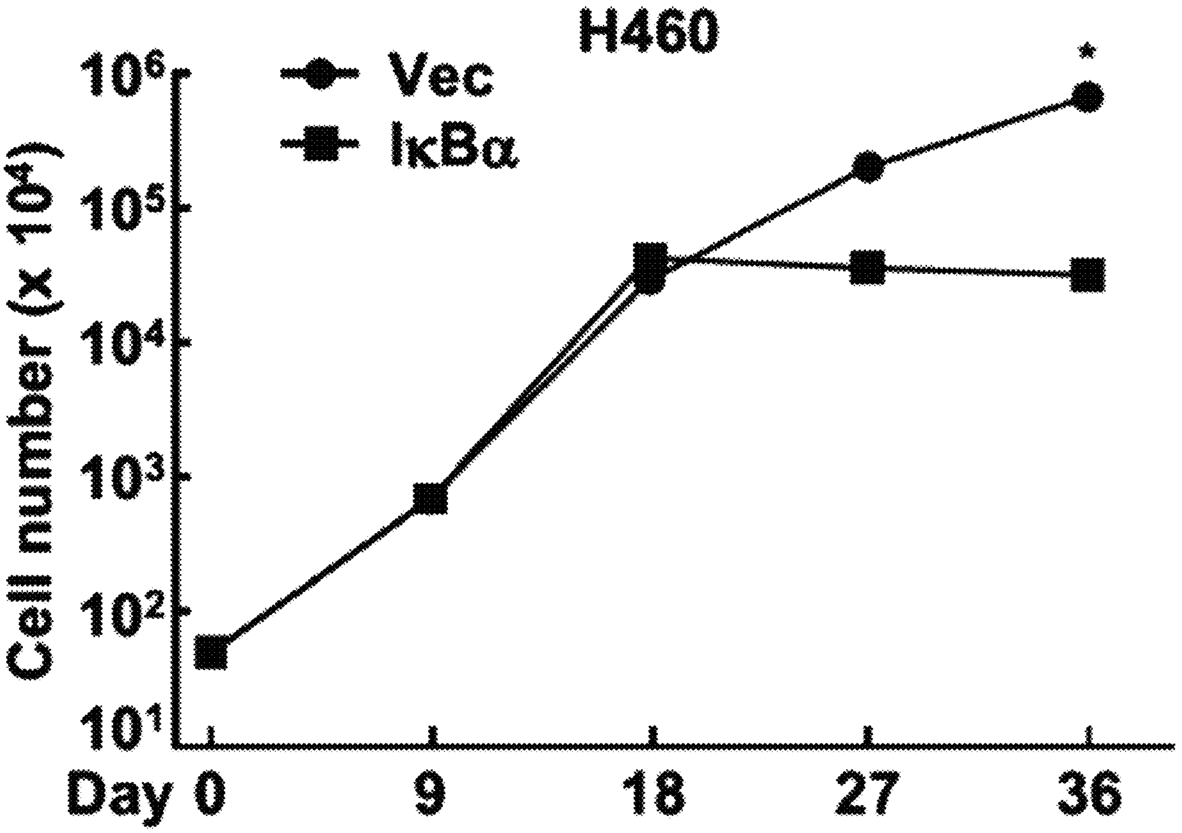

FIGS. 20A-20C provide that STAT3 repressed MHC-I expression in lung cancer cells and RelA activation in lung cancer cells is further induced by paclitaxel for the acquired paclitaxel resistance. FIG. 20A provides qPCR analysis showing increased H2-K1 expression in lung cancer cells by STAT3 deletion (n≥7) but not RelA deletion (n≥2) (urethane model). * $p<0.05$. FIG. 20B provides subcellular fraction-IB assays showing much lower paclitaxel induction of nuclear RelA in H460 human lung cancer cells reconstituted with PDLIM2. FIG. 20C provides cell growth assays showing increased paclitaxel sensitivity of H460 human lung cancers by stable IκBα expression. * $p<0.05$.

Figure 21B:
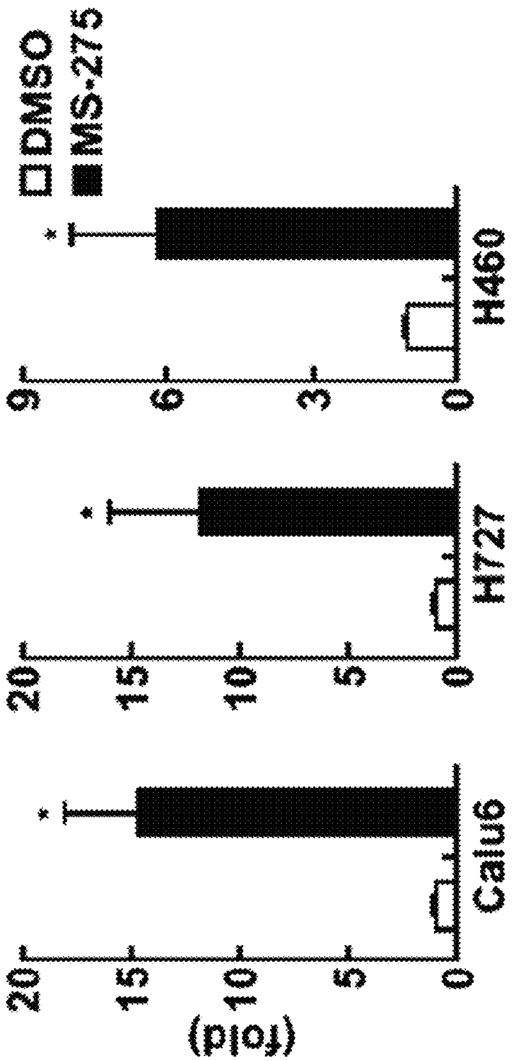
Figure 21A:
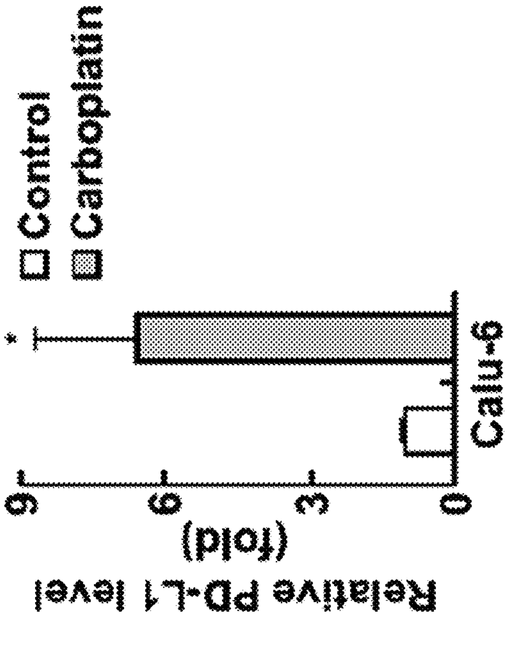
Figure 21C:
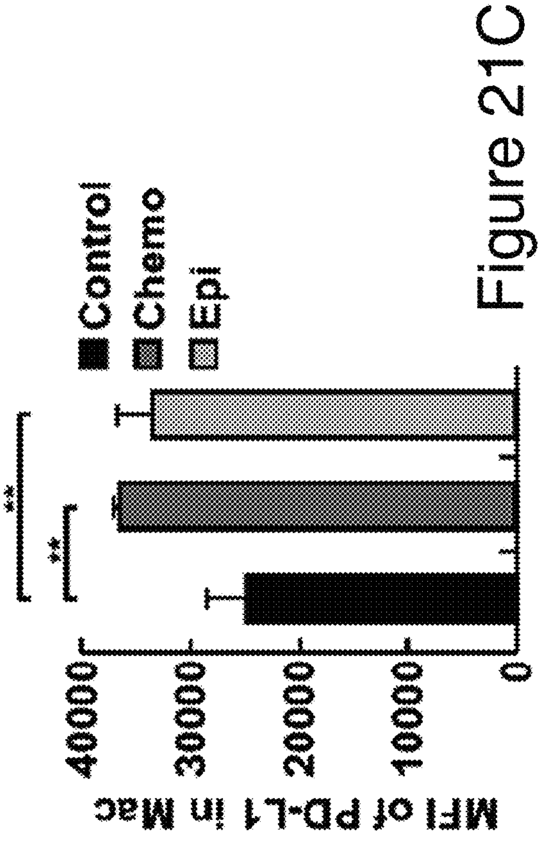

FIGS. 21A-21C provide that chemotherapeutic and epigenetic drugs induced PD-L1 expression in lung cancer cells. FIG. 21A provides qPCR showing PD-L1 induction in Calu-6 human lung cancer cells by carboplatin treatment (n=3). * $p<0.05$. FIG. 21B provides qPCR showing PD-L1 induction in the indicated human lung cancer cells by MS-275 treatment (n=3). * $p<0.05$. FIG. 21C provides FACS showing increased PD-L1 expression by chemo or epigenetic drugs in lung macrophages of mice with lung tumors (urethane model) (n≥4).

Figure 22A:
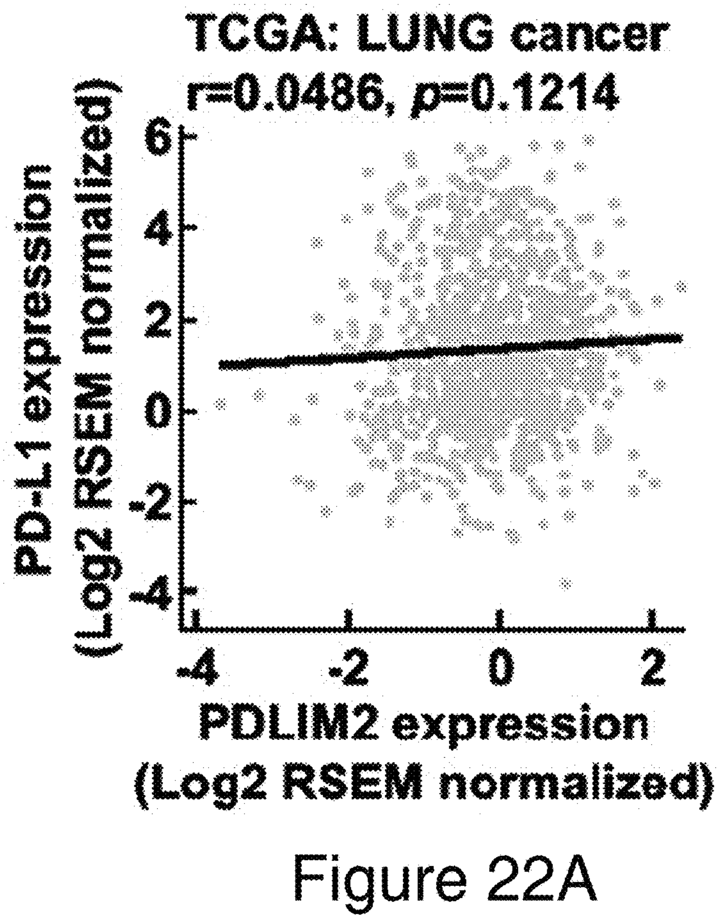
Figure 22B:
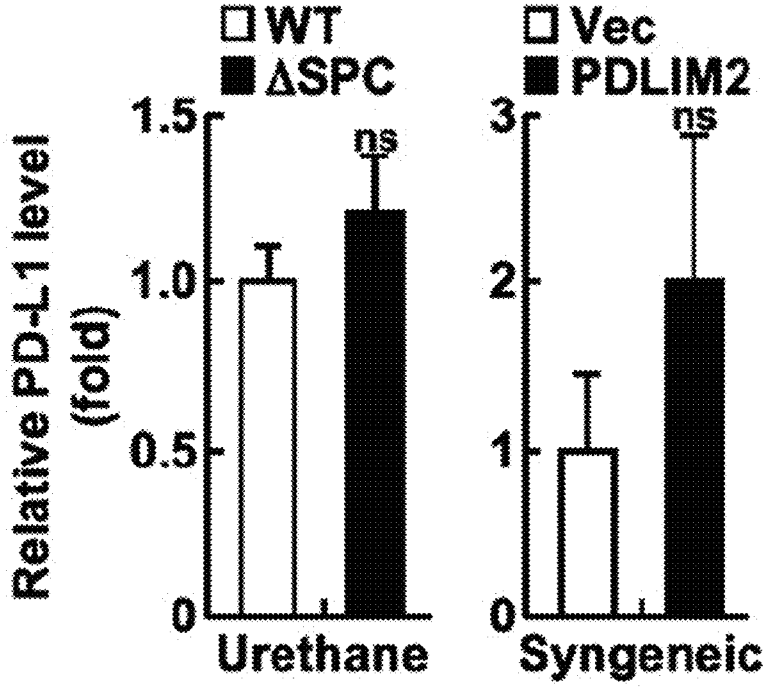
Figure 22C:
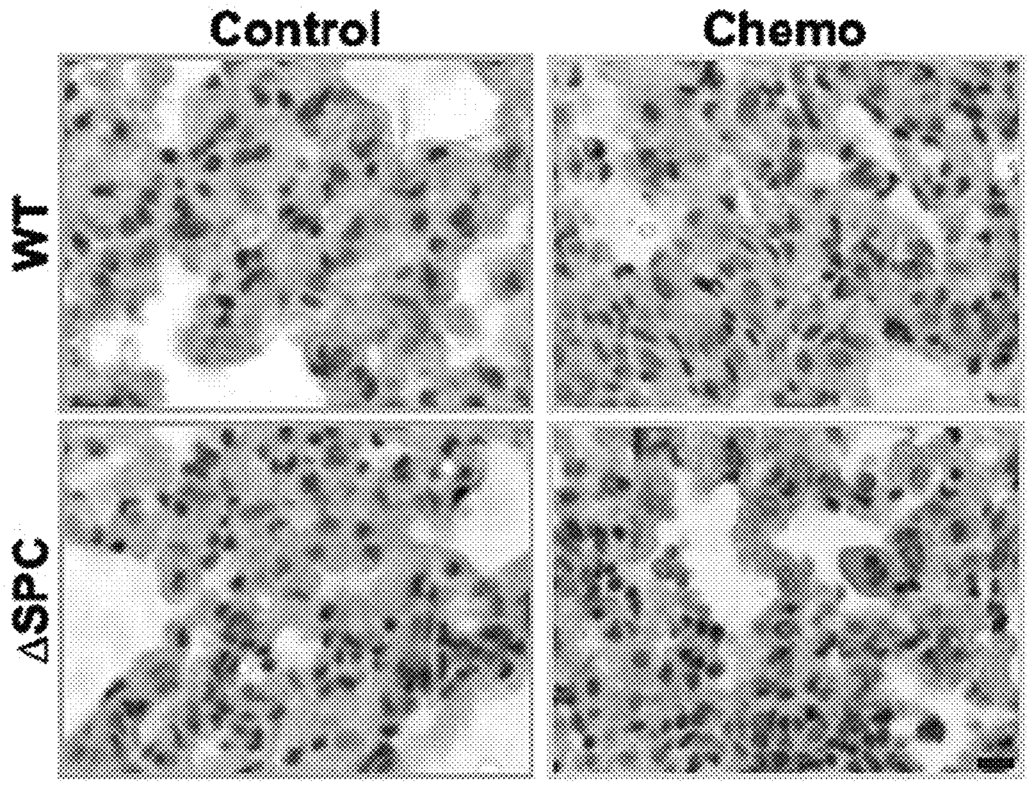
Figure 22D:
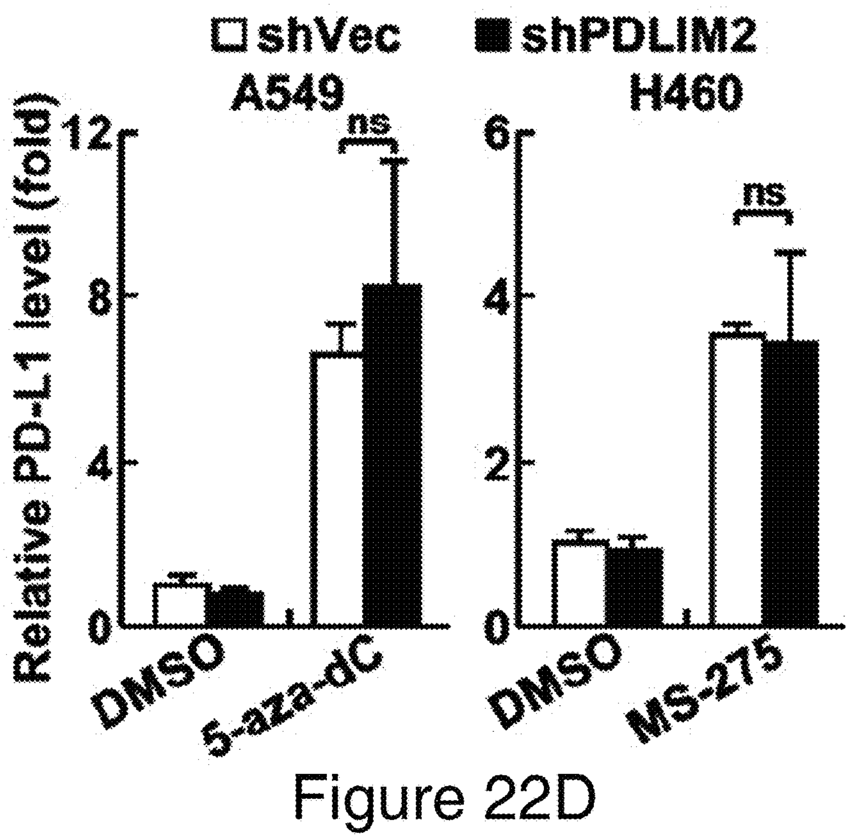

FIGS. 22A-22D provide that PD-L1 induction was PDLIM2-independent. FIG. 22A provides TCGA data showing no association between PDLIM2 and PD-L1 expression in human lung cancer. FIG. 22B provides qPCR showing no significant difference of PD-L1 expression in lung tumors by PDLIM2 deletion (urethane model) or by PDLIM2 reconstitution (MAD109 syngeneic mouse model). FIG. 22C provides IHC staining showing the similar PD-L1 increase in the lung tumors of WT or ΔSPC mice by chemotherapy (urethane model). Scale bar, 10 μm. FIG. 22D provides qPCR showing no significant effect of PDLIM2 knockdown on PD-L1 induction in lung tumor cells by epigenetic drugs (n=3). ns, no significant difference, Student's t test.

Figures 23A, 23B, 23C:
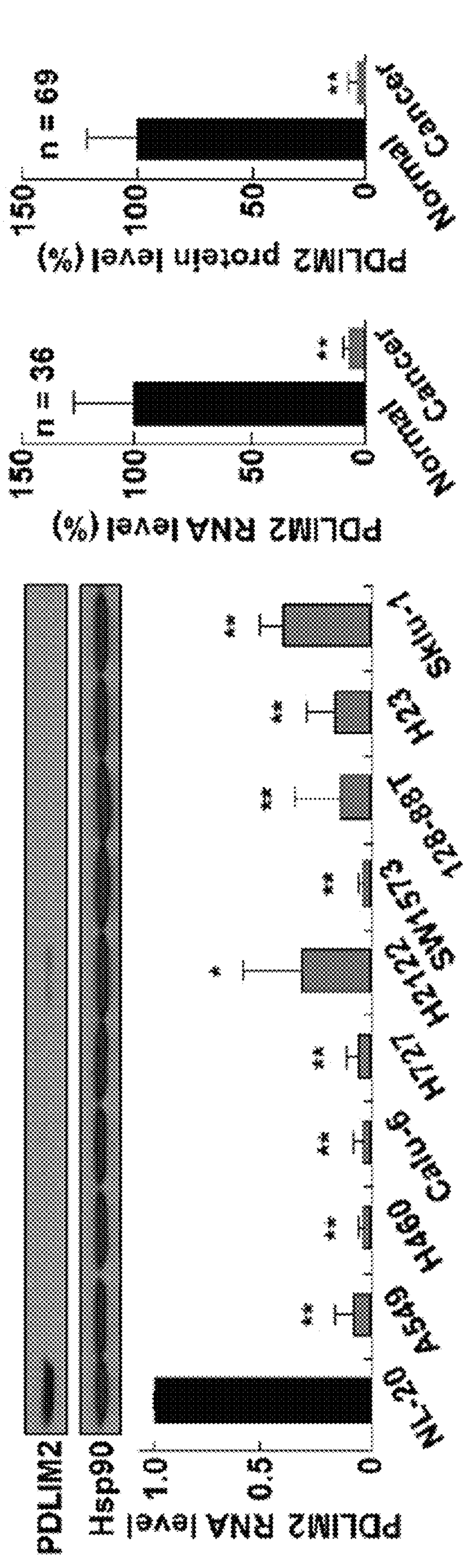
Figure 23D:
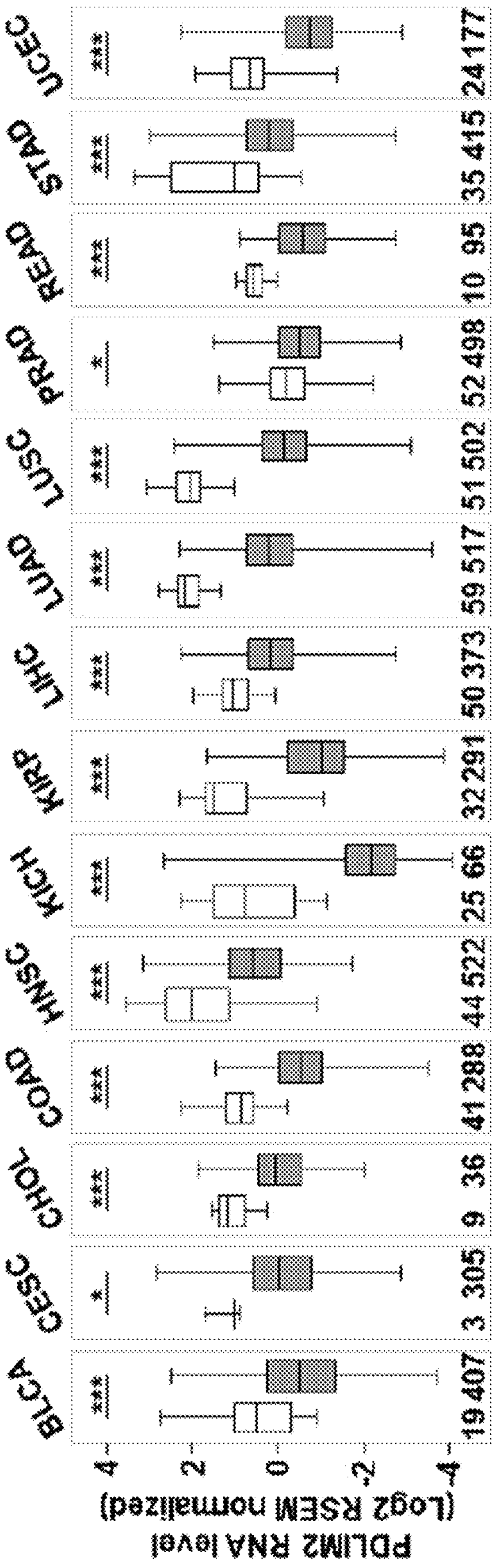

FIGS. 23A-23D provide that PDLIM2 was repressed in various human cancers including lung cancer. FIG. 23A provides quantitative RT-PCR (qPCR) and immunoblotting (IB) analysis to compare PDLIM2 expression in human lung cancer cell lines (n=3). NL20 is normal human lung epithelial cell line, whereas others are human lung cancer cell lines. FIG. 23B provides qPCR analysis to compare PDLIM2 RNA expression in human lung cancer tissues and in matched normal lung tissues from the same patients. FIG. 23C provides lung tumor tissue array assay to compare PDLIM2 protein expression in human lung cancer tissues and normal control tissues. FIG. 23D provides TCGA data showing significantly decreased PDLIM2 in various human cancers. For each cancer type, left white, normal control; right grey, tumor. *, $p<0.05$;  $p<0.01$; *, $p<0.001$, Student's t test.

Figure 24A:
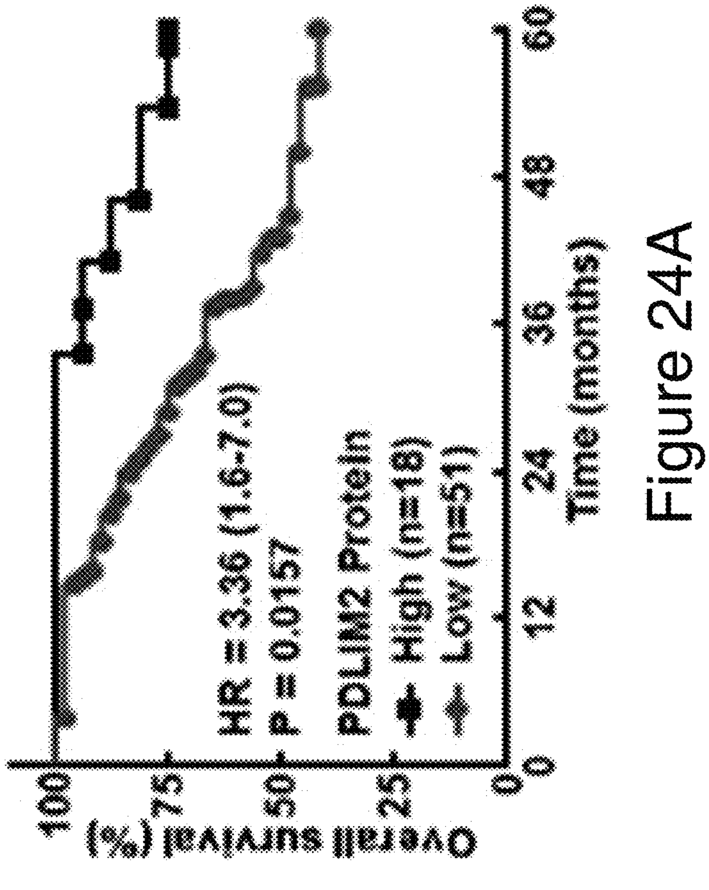
Figure 24B:
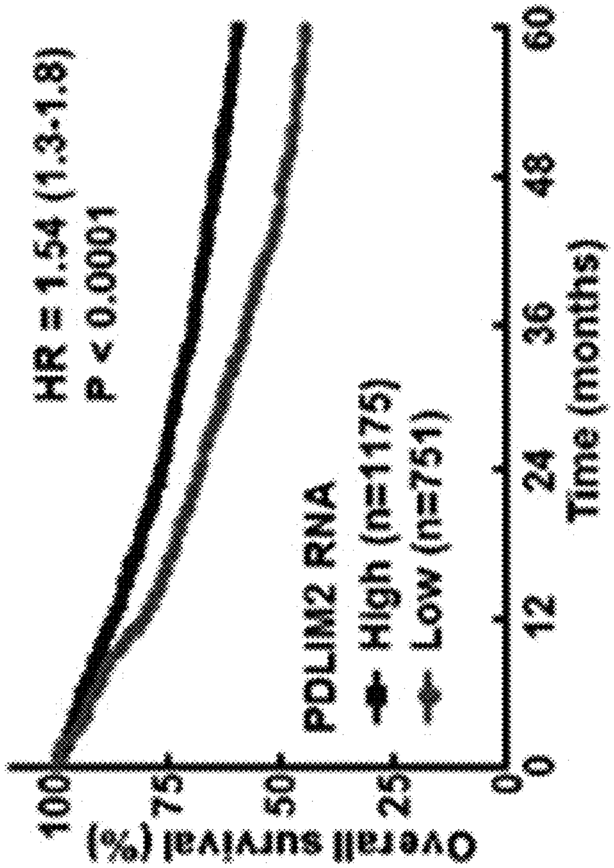
Figure 24C:
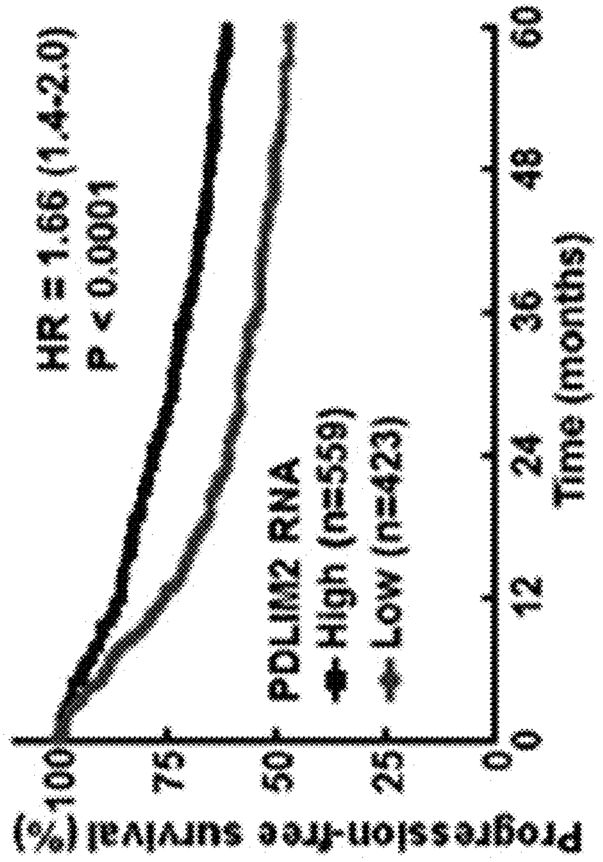
Figure 24D:
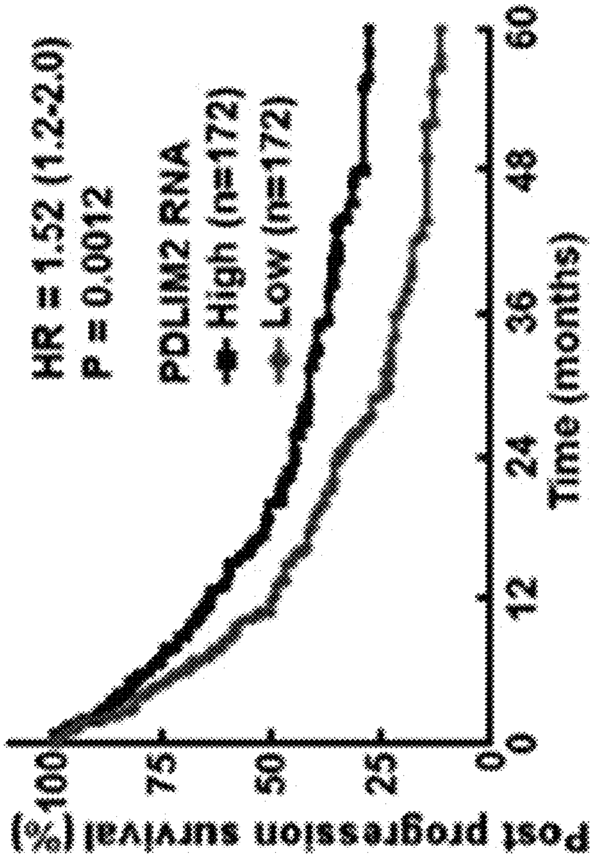

FIGS. 24A-24D provide that PDLIM2 repression in tumors was associated with poor patient survival. FIG. 24A provides Kaplan-Meier patient survival curve showing that lung tumor PDLIM2 protein low expression was associated with lung cancer patient poor overall survival. FIGS. 24B-24D provide Kaplan-Meier patient survival curve showing that lung tumor PDLIM2 RNA low expression was associated with lung cancer patient poor overall survival (FIG. 24B), progression-free survival (FIG. 24C), and post progression survival (FIG. 24D).

Figure 25A:
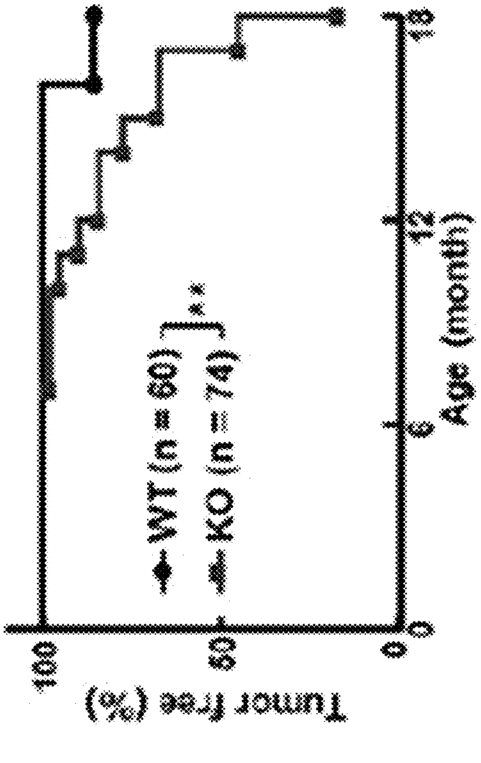
Figure 25B:
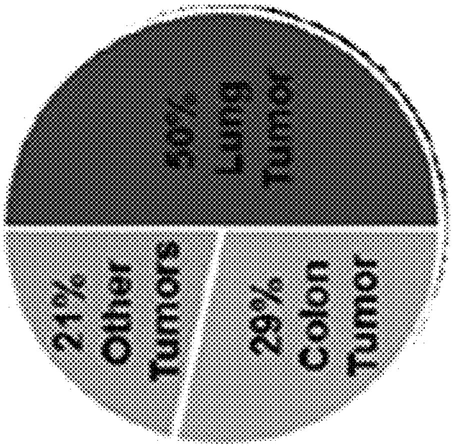
Figure 25C:
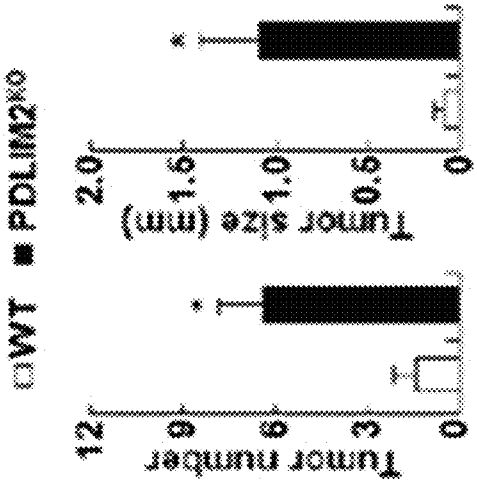
Figure 25D:
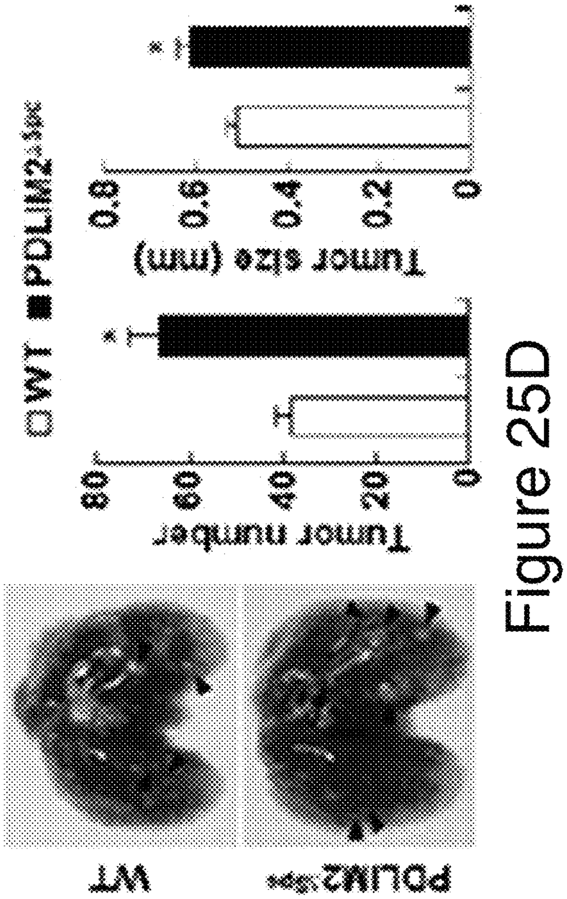

FIGS. 25A-25D provide that PDLIM2 genetic deletion increased not only spontaneous lung cancers, but also lung cancers induced by oncogenic K-Ras$^{G12D}$ mutant expression in the lung or chemical carcinogen urethane. FIG. 25A provides Kaplan-Meier tumor-free survival curve showing increased incidence of spontaneous tumors in PDLIM2$^{-/-}$ (KO) mice compared to PDLIM2$^{+/+}$ (WT) mice.  $p<0.01$, Log-rank (Mantel-Cox) test. FIG. 25B provides tumor types and their frequencies among total tumors in PDLIM2$^{-/-}$ mice. FIG. 25**C provides increased lung tumor numbers and sizes in PDLIM2$^{-/-}$ K-Ras$^{G12D}$ mice compared to PDLIM2$^{+/+}$(WT) K-RasG12D mice 8 weeks post K-Ras$^{G12D}$ induction. n≥5, * $p<0.05$, Student's t test. FIG. 25D provides increased lung tumor numbers and sizes in PDLIM2$^{\Delta Spc}$ mice compared to WT mice treated with chemical carcinogen urethane. In PDLIM2$^{\Delta Spc}$ mice, PDLIM2 was specifically deleted from Spc-expressing alveolar type II epithelial cells and bronchoalveolar stem cells, the cells-of-origin of lung cancer. n≥5, * $p<0.05$, Student's t test.

Figure 26A:
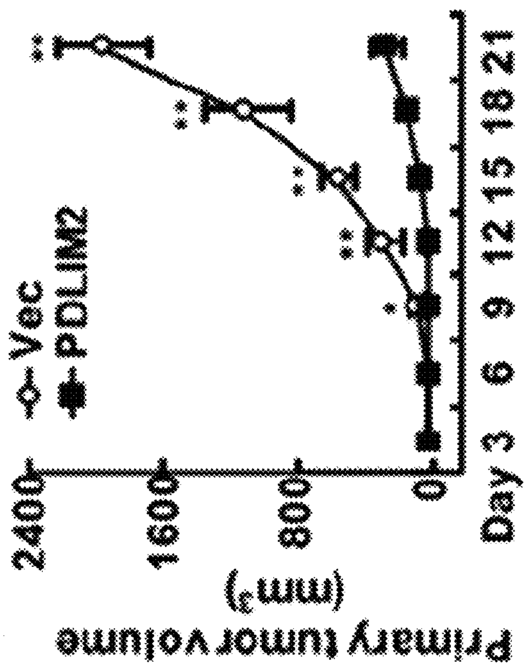
Figure 26B:
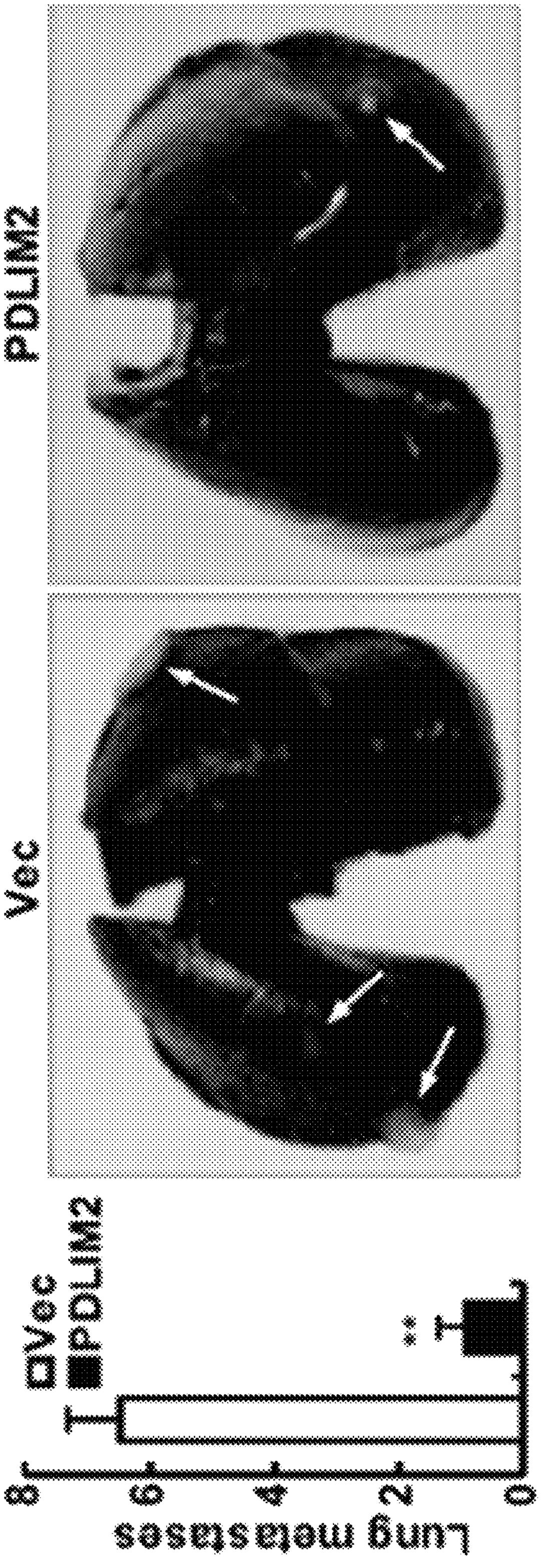
Figure 27A:
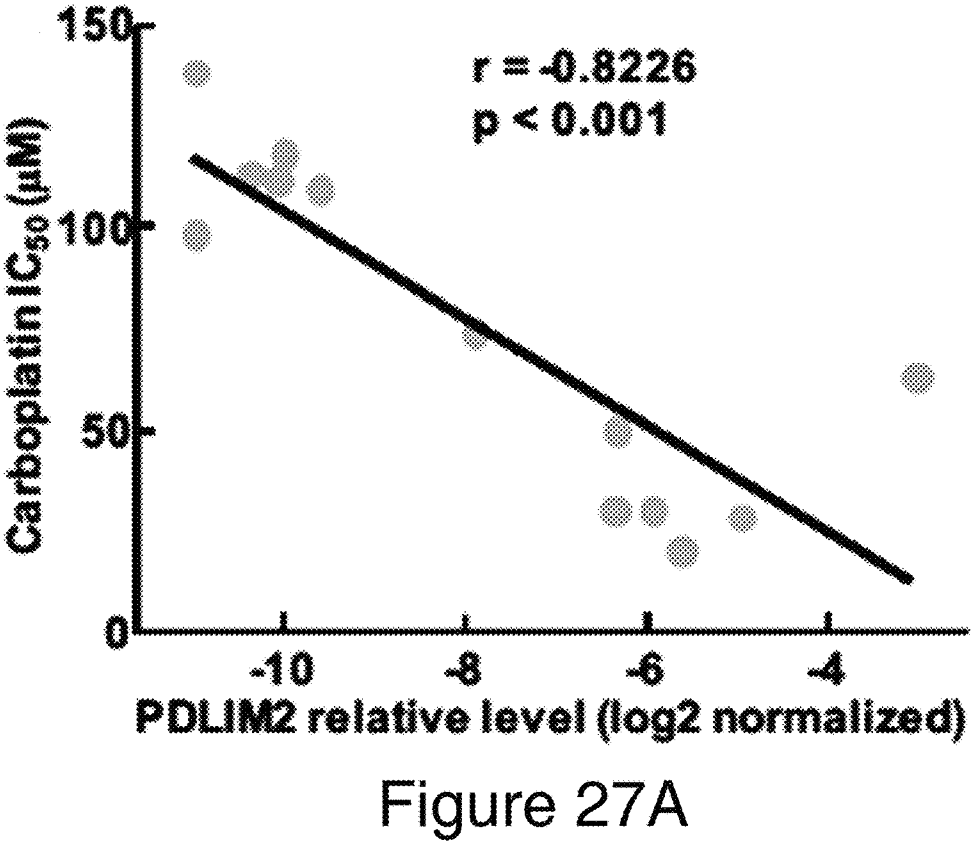
Figure 27B:
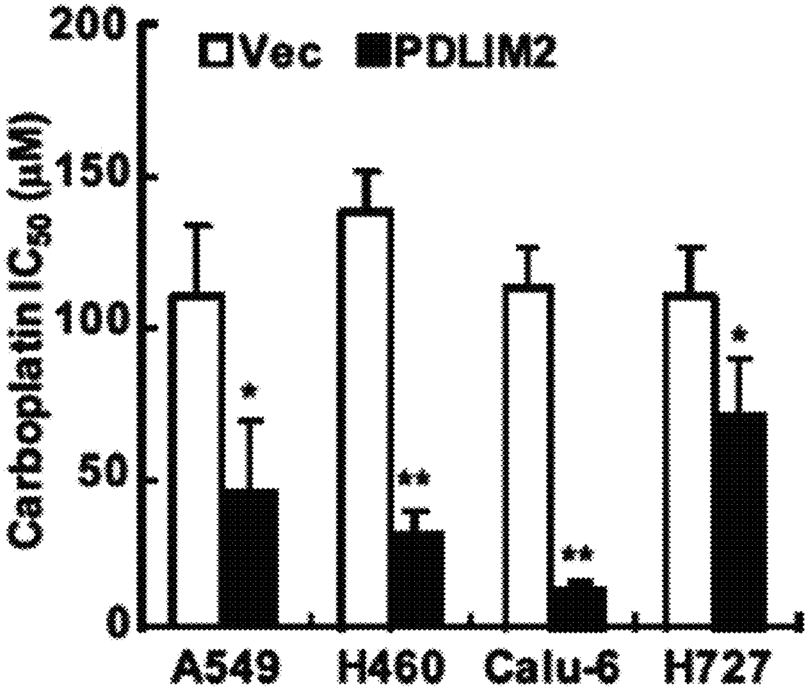
Figure 27C:
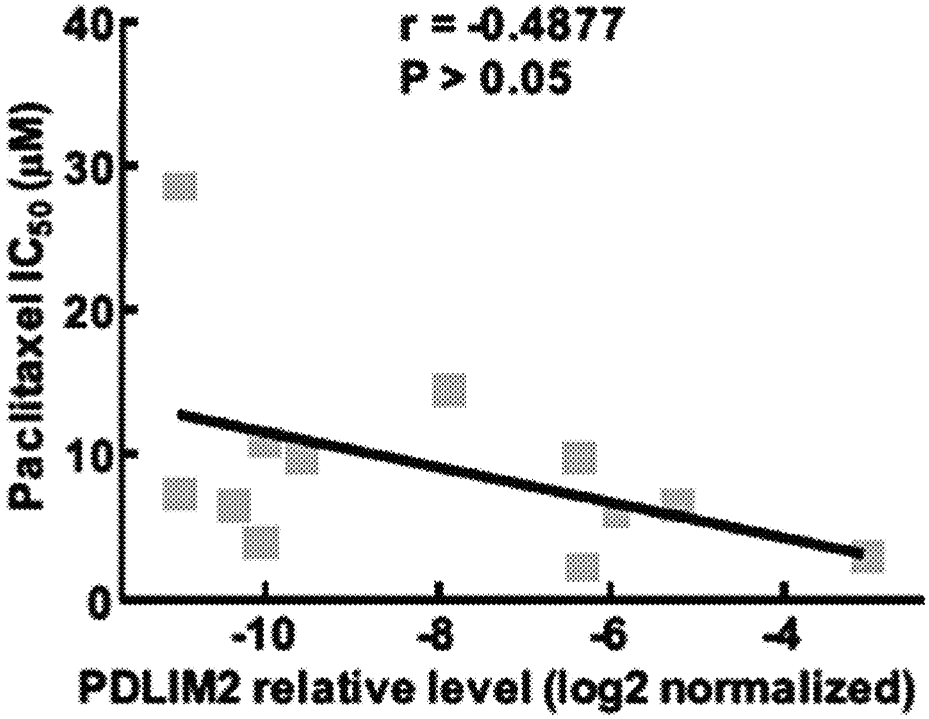
Figure 27D:
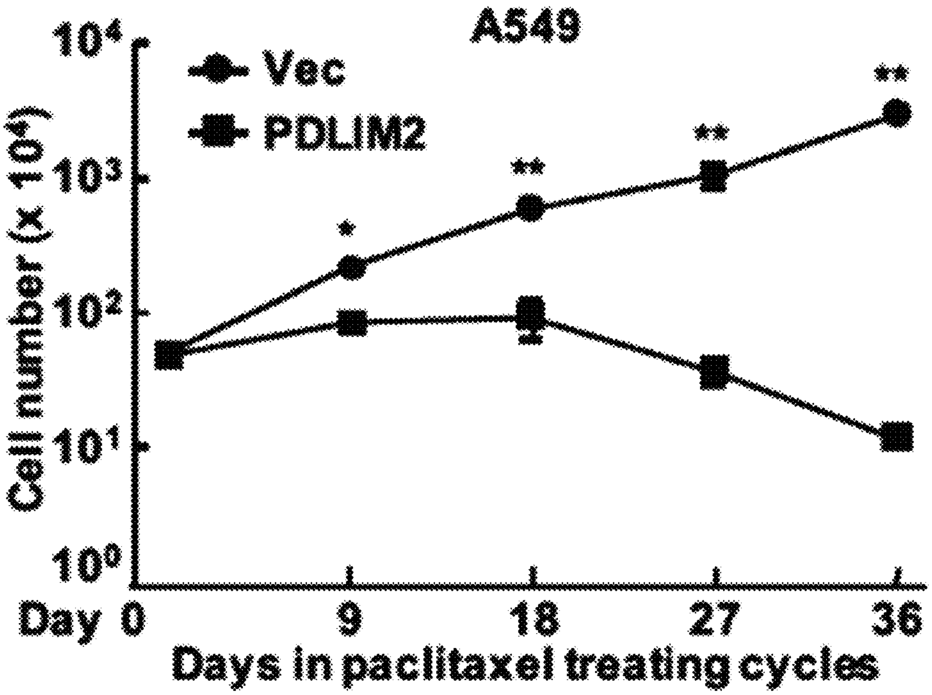
Figure 27E:
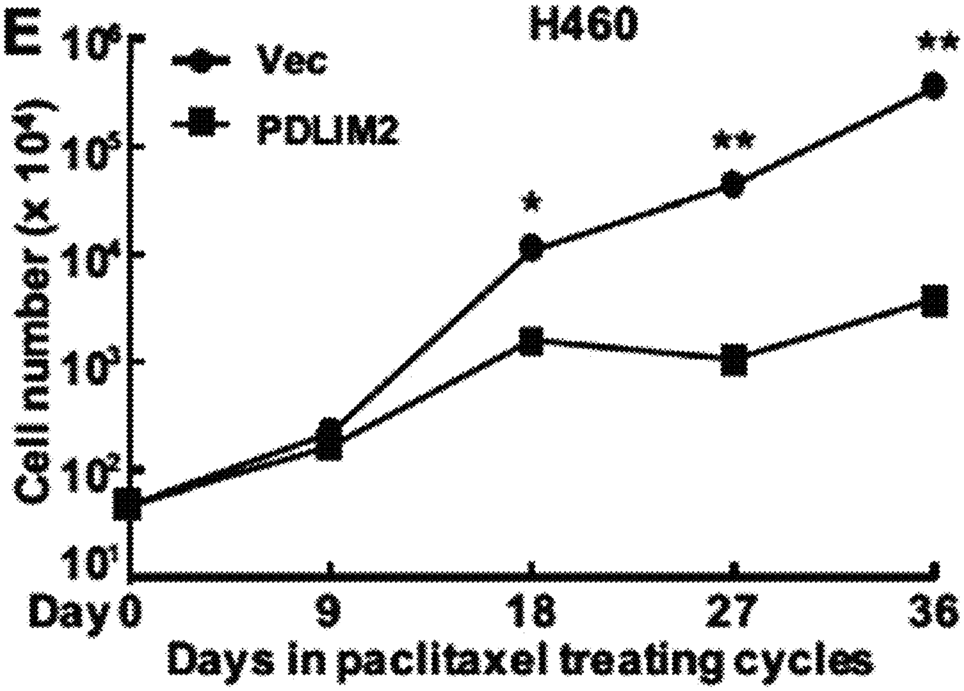

FIGS. 26A-26B provide that PDLIM2 re-expression suppressed both primary tumor growth and metastasis of lung cancer cells. Mouse lung cancer cell line MAD109 stably expressing PDLIM2 or an empty vector was inoculated subcutaneously in syngeneic Balb/c mice. FIG. 26A provides PDLIM2 reconstitution blocked primary tumor growth at the original inoculation sites. FIG. 26B provides PDLIM2 reconstitution inhibited tumor metastasis to lung. Representative of lung tissues with metastatic lung tumor cells (indicated by arrows) are shown. n=4, * $p<0.05$,  $p<0.01$, Student's t test FIGS. 27A-27F provide that PDLIM2 repression was associated with cancer chemotherapy resistance and its expression restoration sensitizes cancer cells to chemotherapy reagents treatment. FIG. 27A provides that PDLIM2 expression level was inversely associated with lung cancer cells' sensitivity to carboplatin. FIG. 27B provides that PDLIM2 ectopic expression increased lung cancer cell sensitivity to carboplatin. FIG. 27C provides that PDLIM2 expression level was not associated with lung cancer cells' sensitivity to paclitaxel. FIGS. 27D-27E provide that PDLIM2 ectopic expression increased lung cancer cell A549 (FIG. 27D) and H460 (FIG. 27E) acquired sensitivity to paclitaxel. FIG. 27**F provides that PDLIM2 deficient lung tumors of PDLIM2$^{\Delta Spc}$ mice were more resistant to carboplatin and paclitaxel treatment in the presently disclosed mouse model of lung cancer induced by chemical carcinogen urethane. n≥4, * $p<0.05$, Student's t test.

Figure 28A:
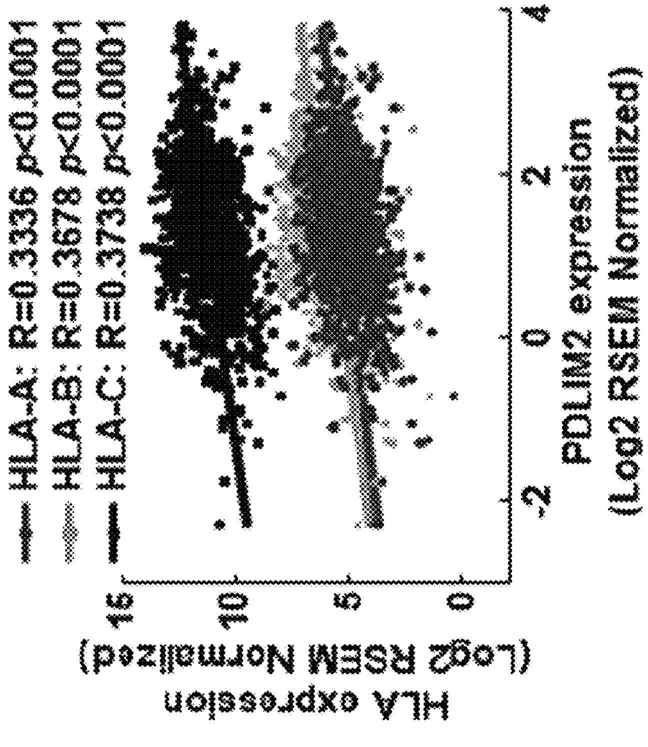
Figure 28B:
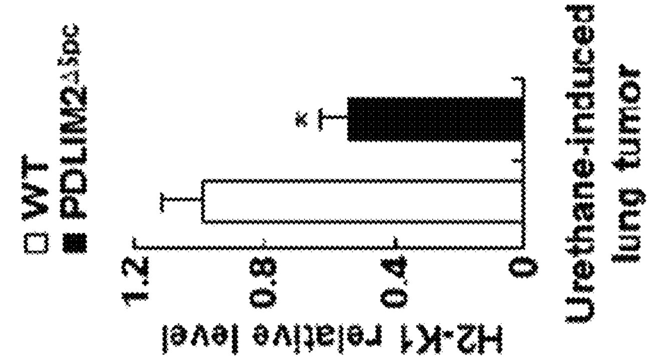
Figure 28C:
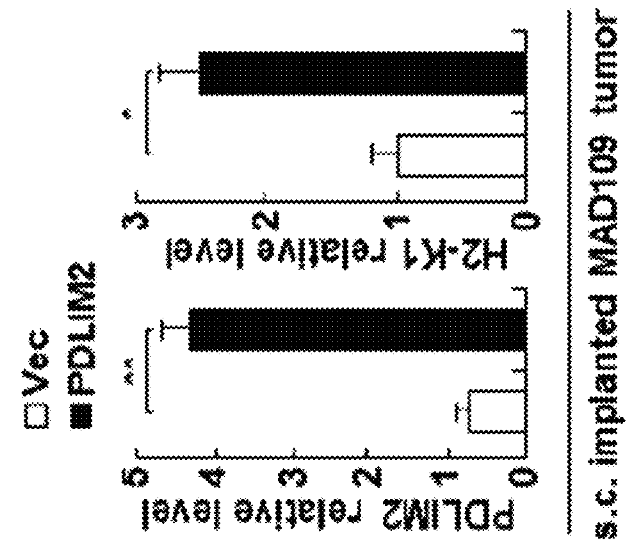
Figure 28D:
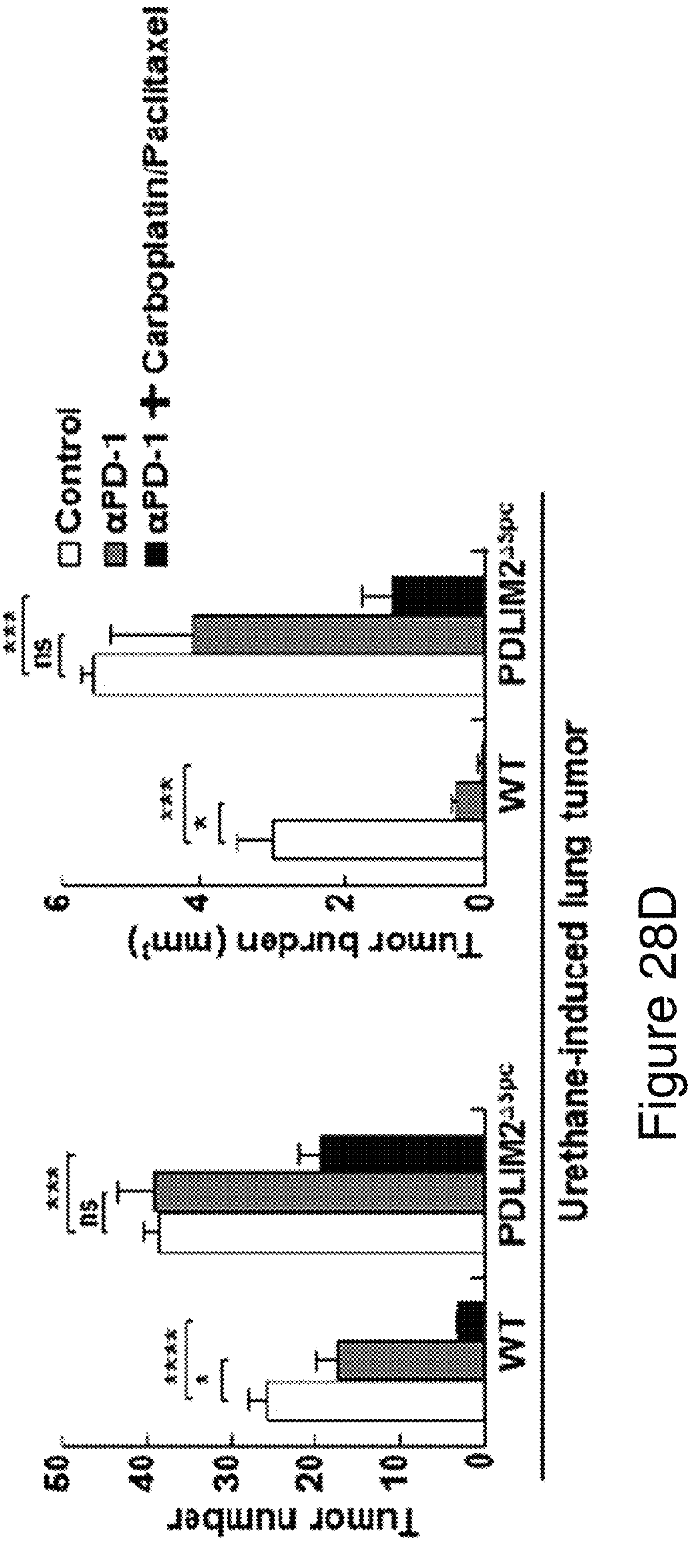

FIGS. 28A-28D provide that PDLIM2 level affected antigen presenting gene expression and cancer immunotherapy efficiency. FIG. 28A provides TCGA data showing PDLIM2 expression was positively associated with expression of antigen presenting genes in lung cancer. FIG. 28B provides qPCR showing decreased antigen presenting gene H2-K1 expression in PDLIM2 deficient lung tumors of PDLIM2ΔSpc mice. FIG. 28C provides qPCR showing increased H2-K1 expression in PDLIM2 reconstituted MAD109 lung tumor cells subcutaneously embedded in syngeneic Balb/c mice. FIG. 28D provides that PDLIM2 deficient lung tumors of PDLIM2ΔSpc mice were more resistant to PD-1 blockade treatment, and PD-1 blockade treatment combined with carboplatin/paclitaxel treatment in the presently disclosed mouse model of lung cancer induced by chemical carcinogen urethane. n≥3, * p<0.05, Student's t test.

Figures 29A, 29B, 29C:
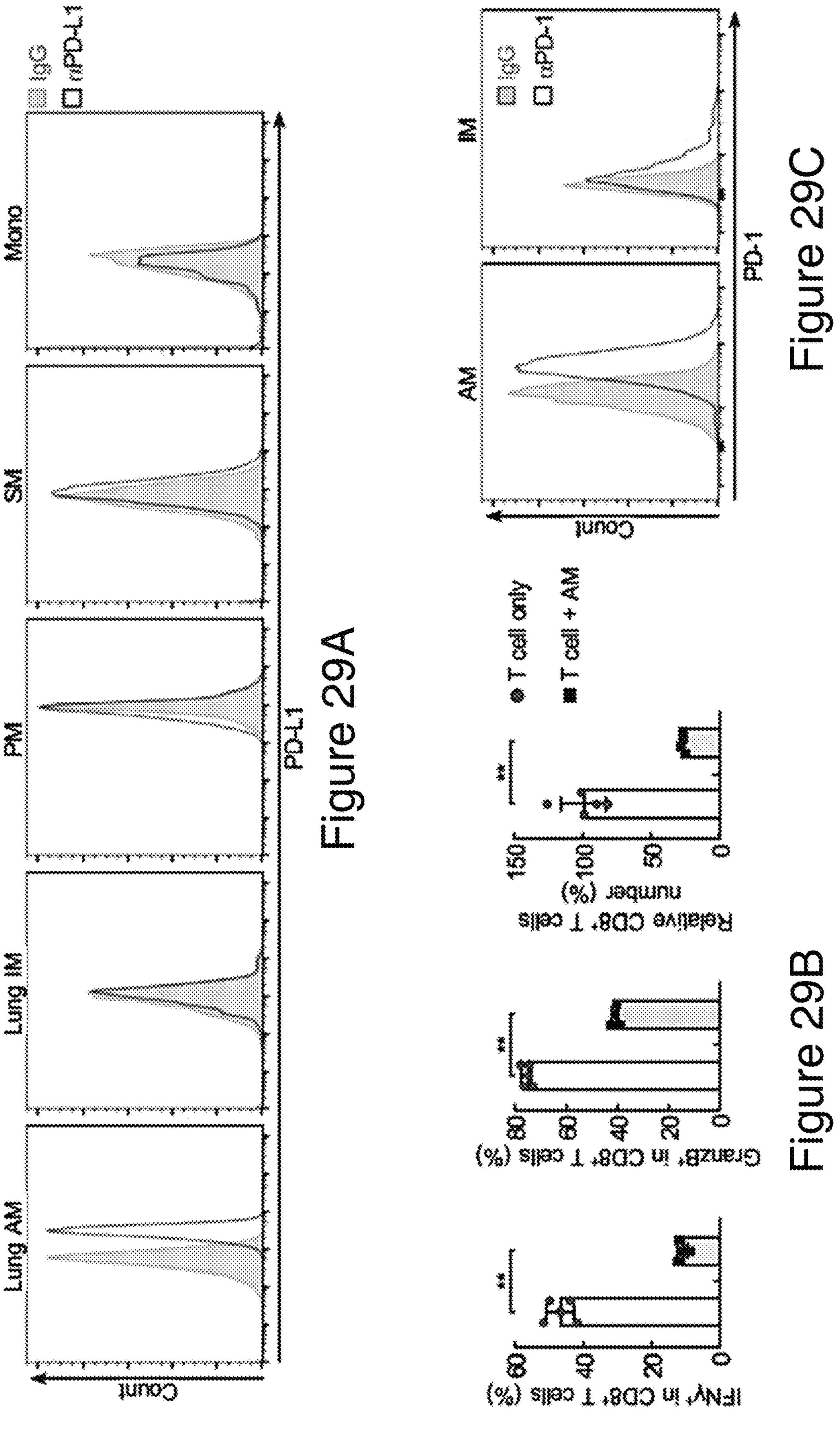
Figure 29D:
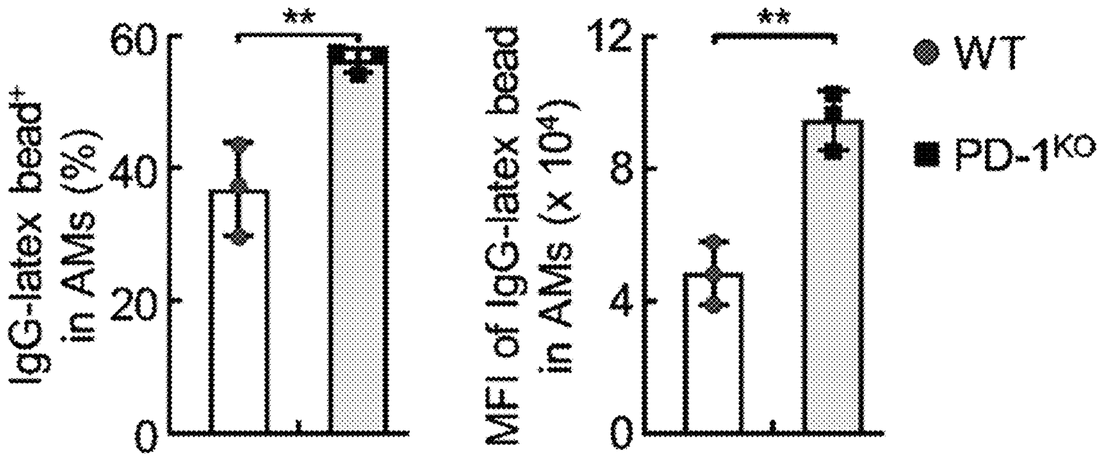
Figure 29E:
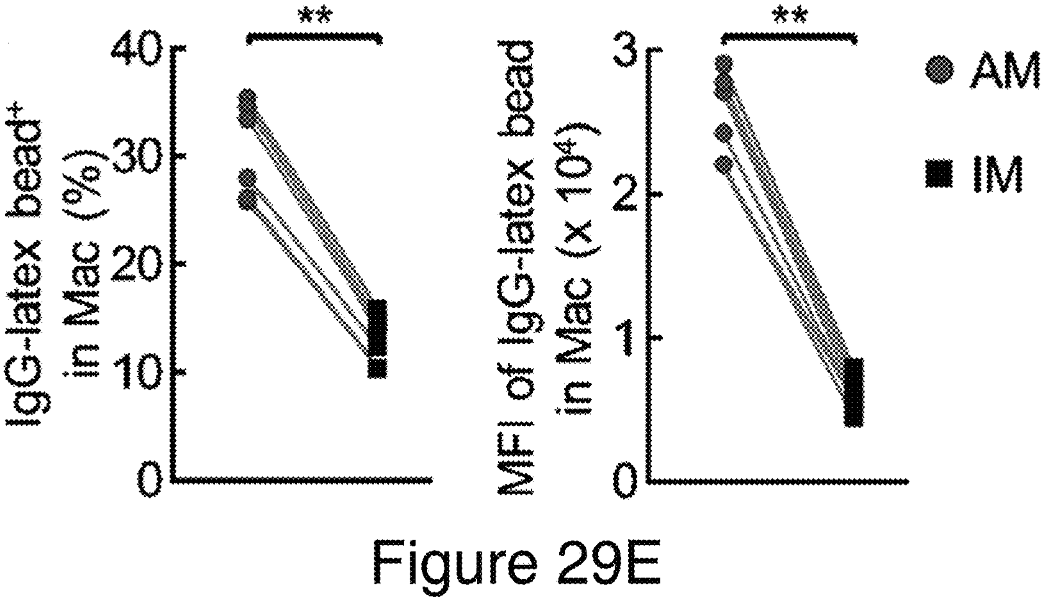
Figure 29F:
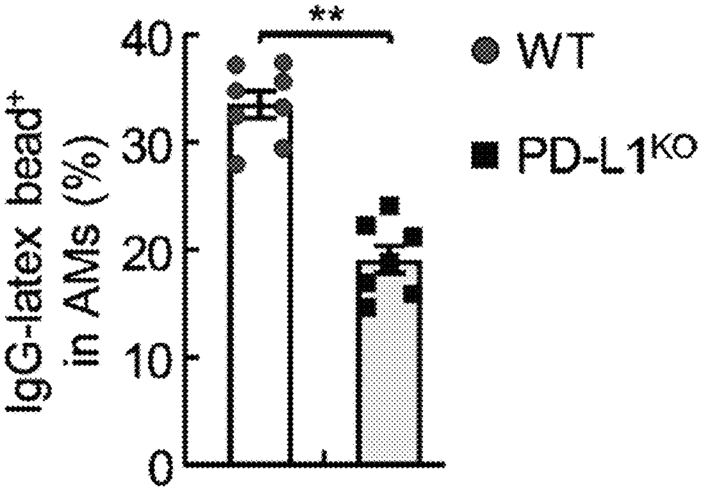
Figure 29H:
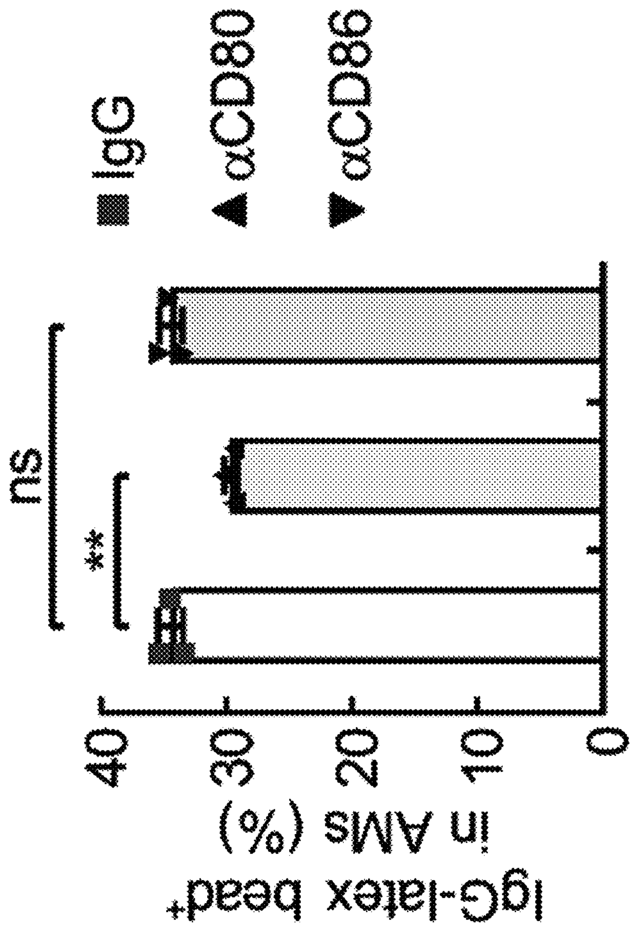
Figure 29G:
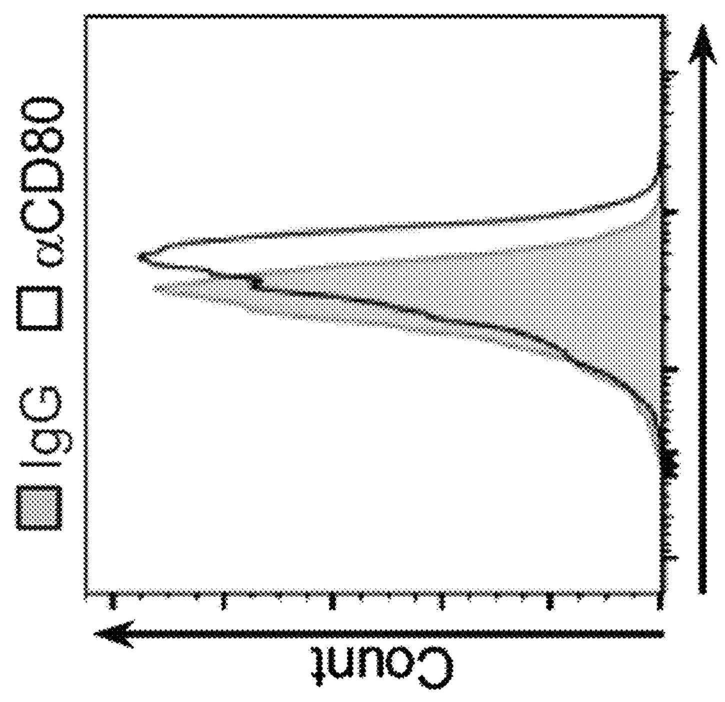
Figure 29J:
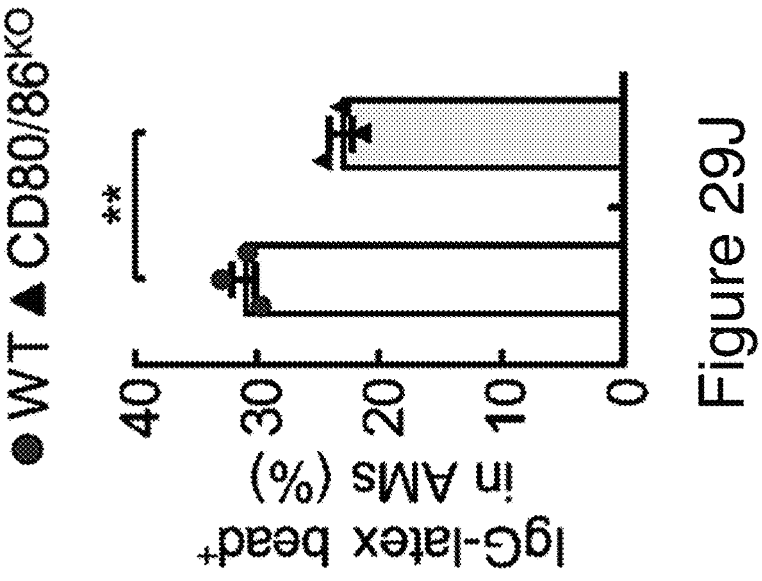
Figure 29I:
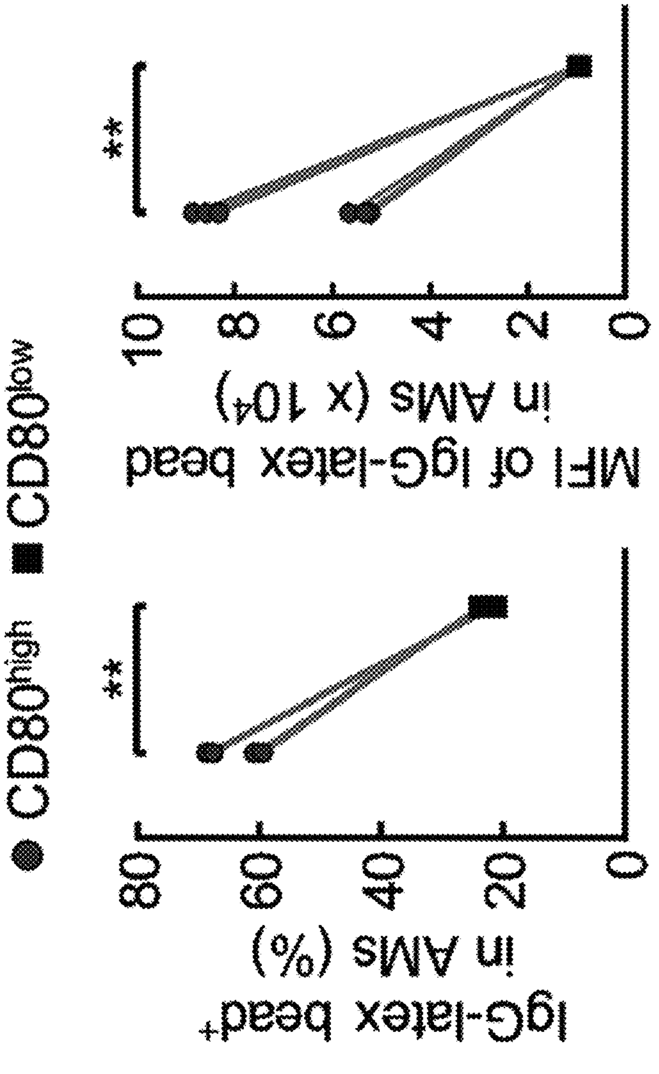

FIGS. 29A-29J provide selective expression of PD-L1 on AMs and its significance in AM phagocytosis and CTL suppression. FIG. 29A depicts FACS analysis showing specific expression of PD-L1 on AMs (n=3). AM: alveolar macrophage; IM: interstitial macrophage; PM: peritoneal macrophage; SM: splenic macrophage; Mono: lung monocyte. FIG. 29B depicts ex vivo co-culture assays showing AM repression of CD8+ T cells (n≥4). FIG. 29C depicts FACS analysis showing selective PD-1 expression on AMs (n=3). FIG. 29D depicts FACS analysis showing enhanced phagocytic ability of AMs by PD-1 deletion (n=3). FIG. 29E depicts FACS analysis showing superior phagocytic ability of AMs (n=6). FIG. 29F depicts FACS analysis showing decreased AM phagocytosis by PD-L1 deletion (n≥7). FIG. 29G depicts FACS analysis showing constitutive CD80 expression on AMs. FIG. 29H depicts FACS analysis showing decreased AM phagocytosis of AMs by CD80− but not CD86-blocking antibody (n=3). FIG. 29I depicts FACS analysis showing higher phagocytic ability of AMs expressing CD80 on the surface (n=6). FIG. 29J depicts FACS analysis showing decreased AM phagocytosis by CD80 and CD86 deletion (n=3). Student's t test was performed (two tailed, unpaired for FIGS. 29A, 29D, 29F, 29H, 29J and paired for FIGS. 29E and 29I and data represent means±SEM in (B, D-F, H-J). *P<0.05; **P<0.01; ns, not statistically significant.

Figure 30A:
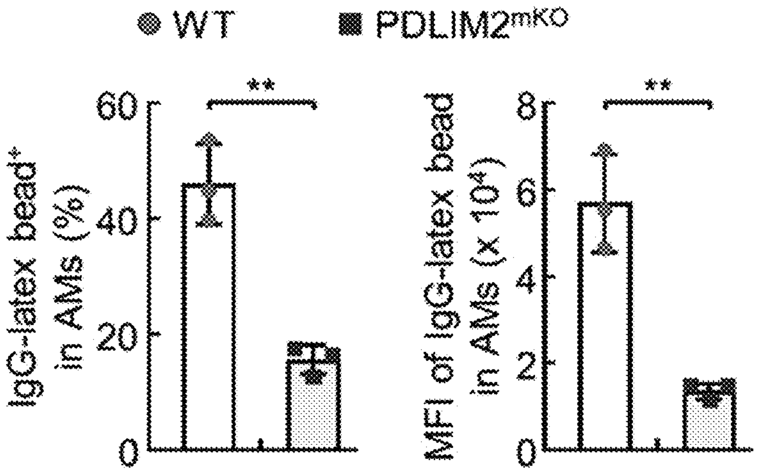
Figure 30B:
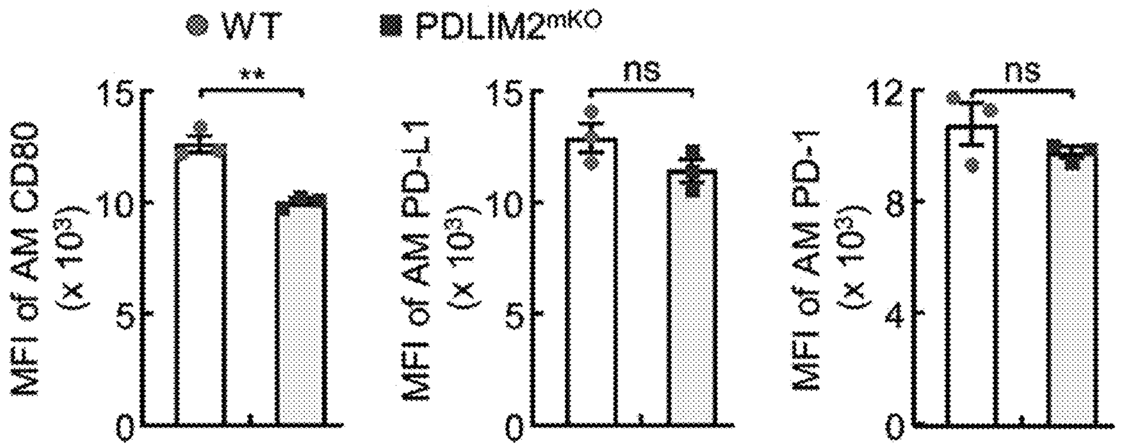
Figure 30C:
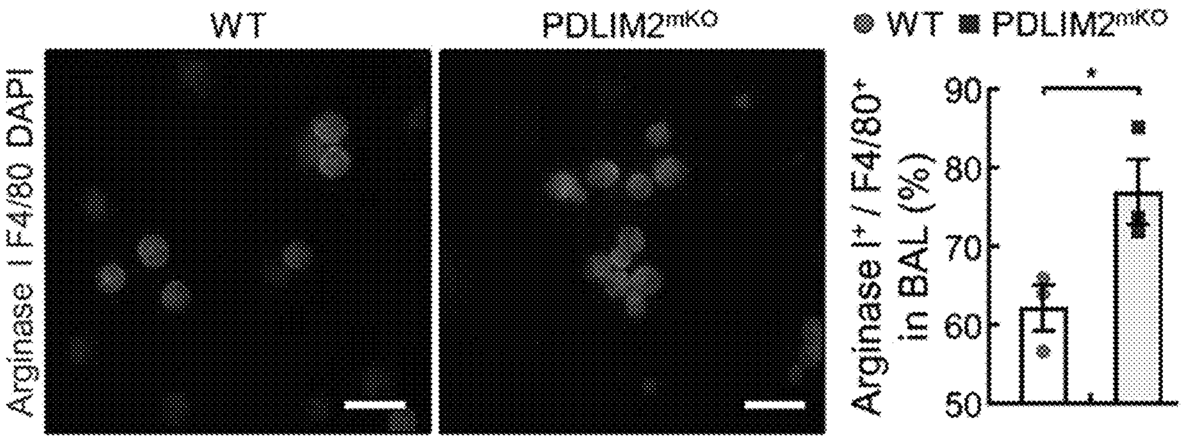
Figure 30D:
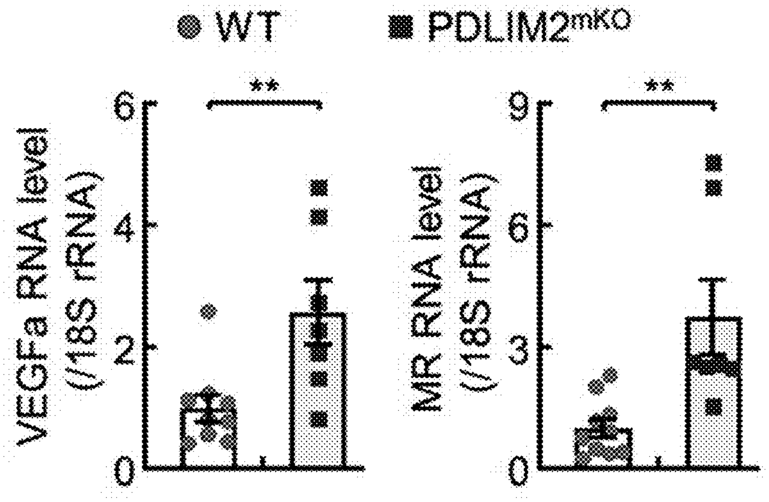
Figure 30E:
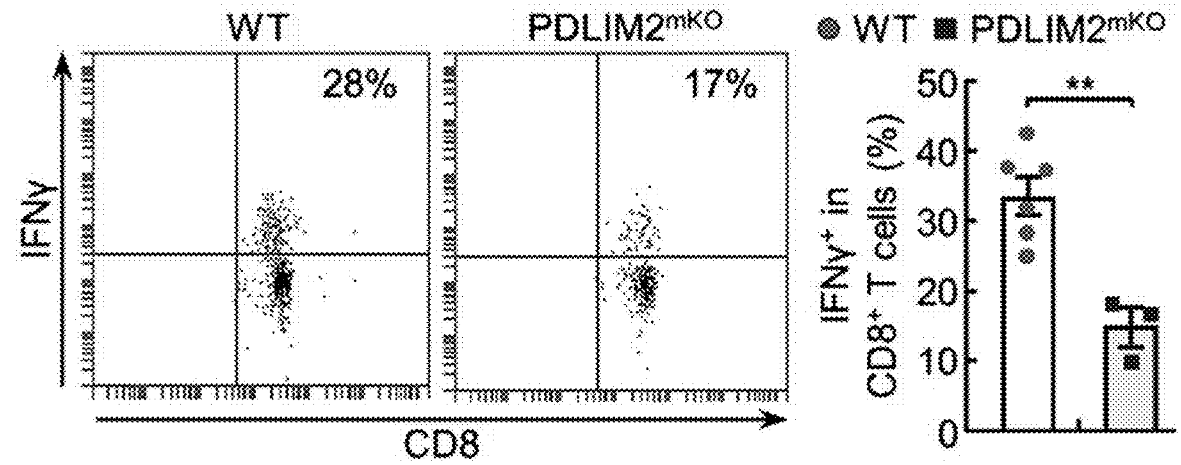
Figure 30F:
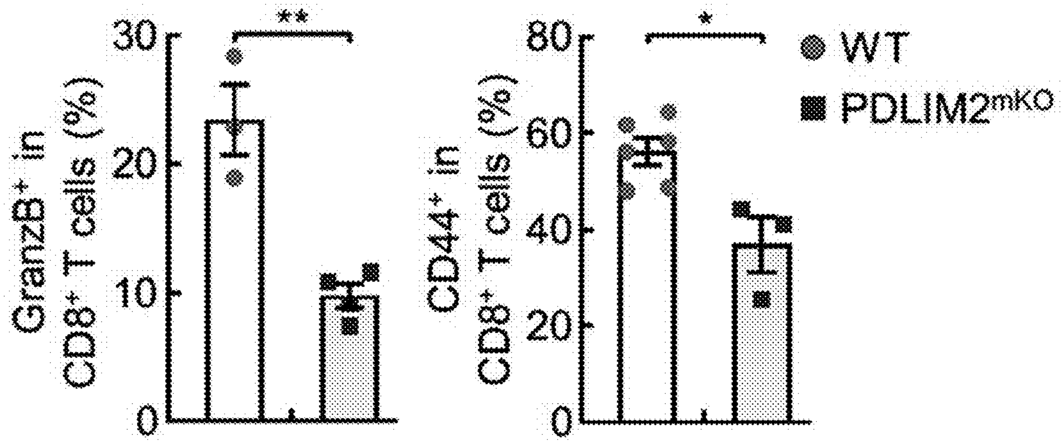

FIGS. 30A-30F provide the role of cell-intrinsic PDLIM2 in AM phagocytosis and restricting AM pro-tumorigenic activation and suppression of CTLs during lung tumorigenesis. FIG. 30A depicts FACS analysis showing defective phagocytic ability of AMs from urethane-treated PDLIM2mKO mice (n=3). FIG. 30B depicts FACS analysis showing decreased CD80 but stable PD-L1 and PD-1 expression on AMs from urethane-treated PDLIM2mKO mice (n=3). FIG. 30C depicts IF analysis showing increased Arginase-1 in AMs of urethane-treated PDLIM2mKO mice. Scale bar: 20 μm. FIG. 30D depicts qPCR showing increased VEGFa and mannose receptor (MR) expression in AMs of urethane-treated PDLIM2mKO mice (n≥7). FIG. 30E-30F depict FACS analysis showing decreased activation of lung CD8+ T cells in urethane-treated PDLIM2mKO mice (GranzB: Granzyme B) (n≥3). Student's t test was performed (two tailed, unpaired) and data represent means±SEM in (A-F). *P<0.05; **P<0.01; ns, not statistically significant.

Figure 31B:
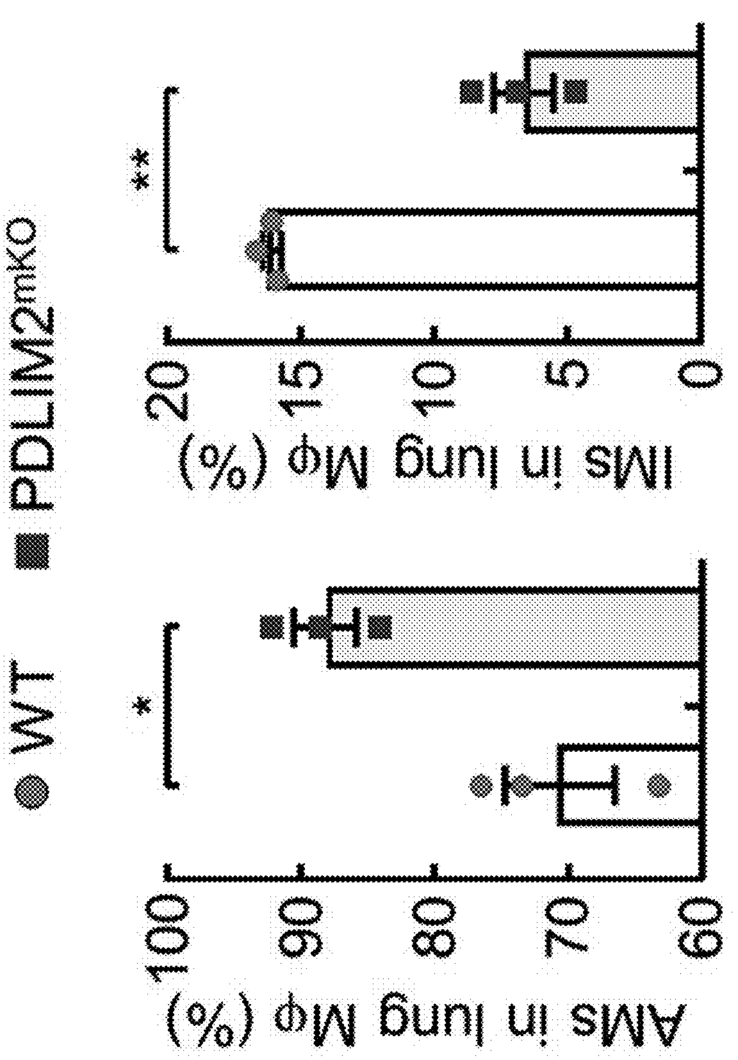
Figure 31A:
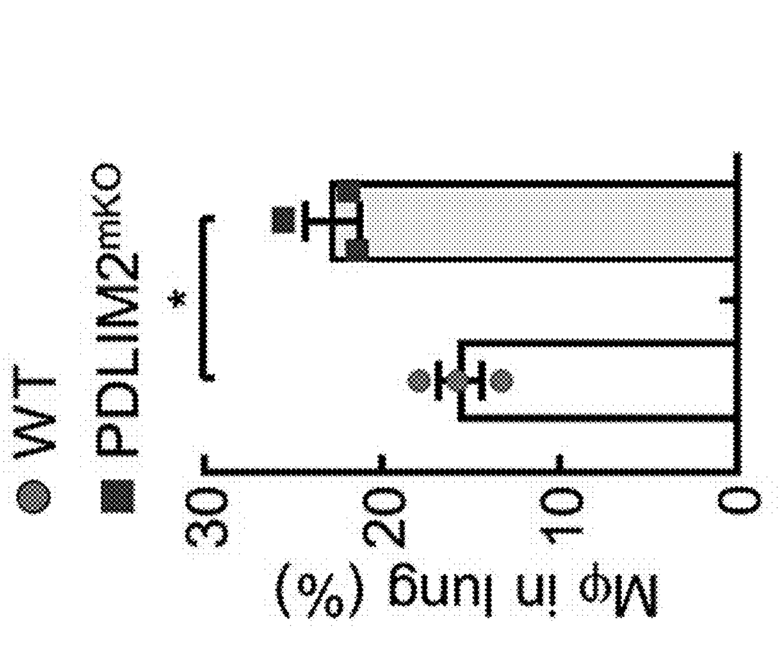
Figure 31C:
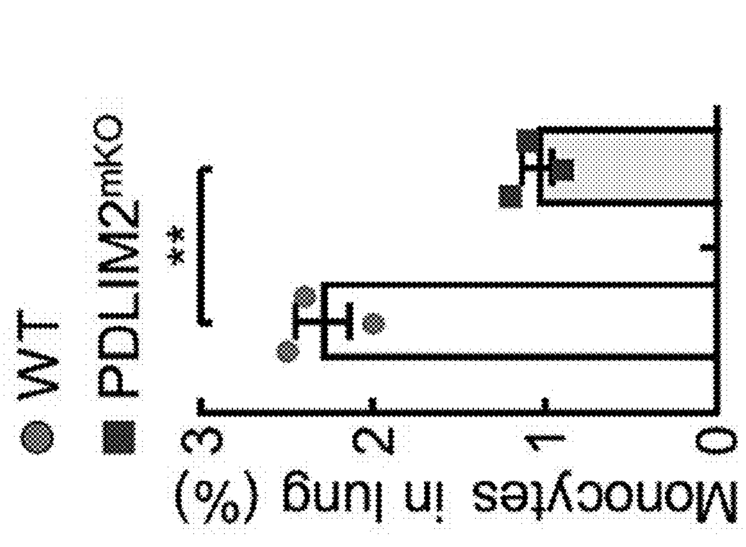
Figure 31D:
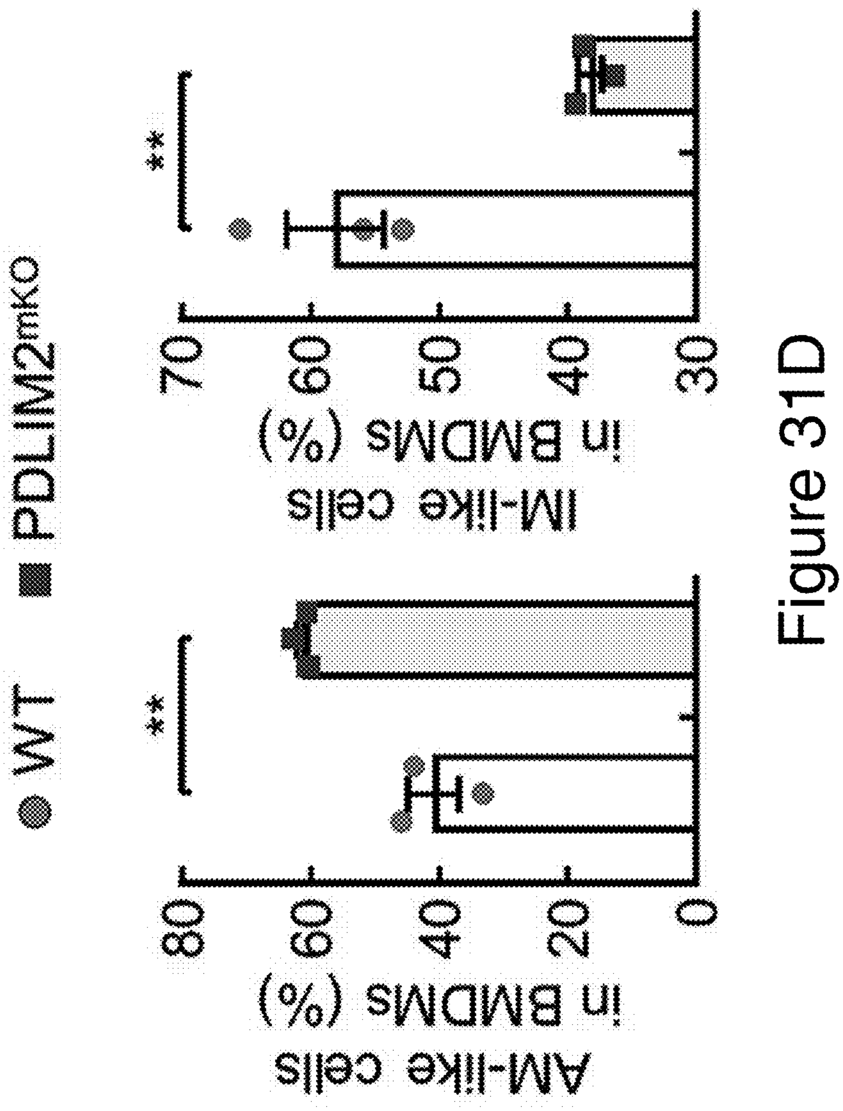
Figure 31F:
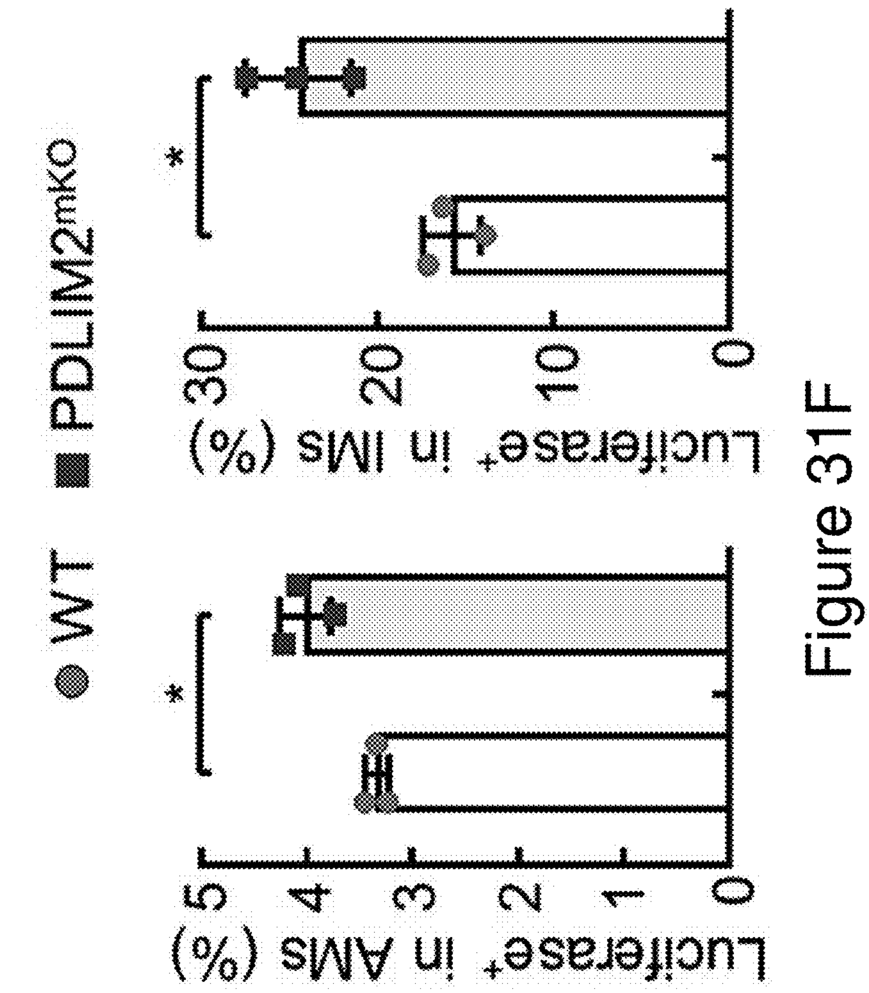
Figure 31E:
Figure 31G:
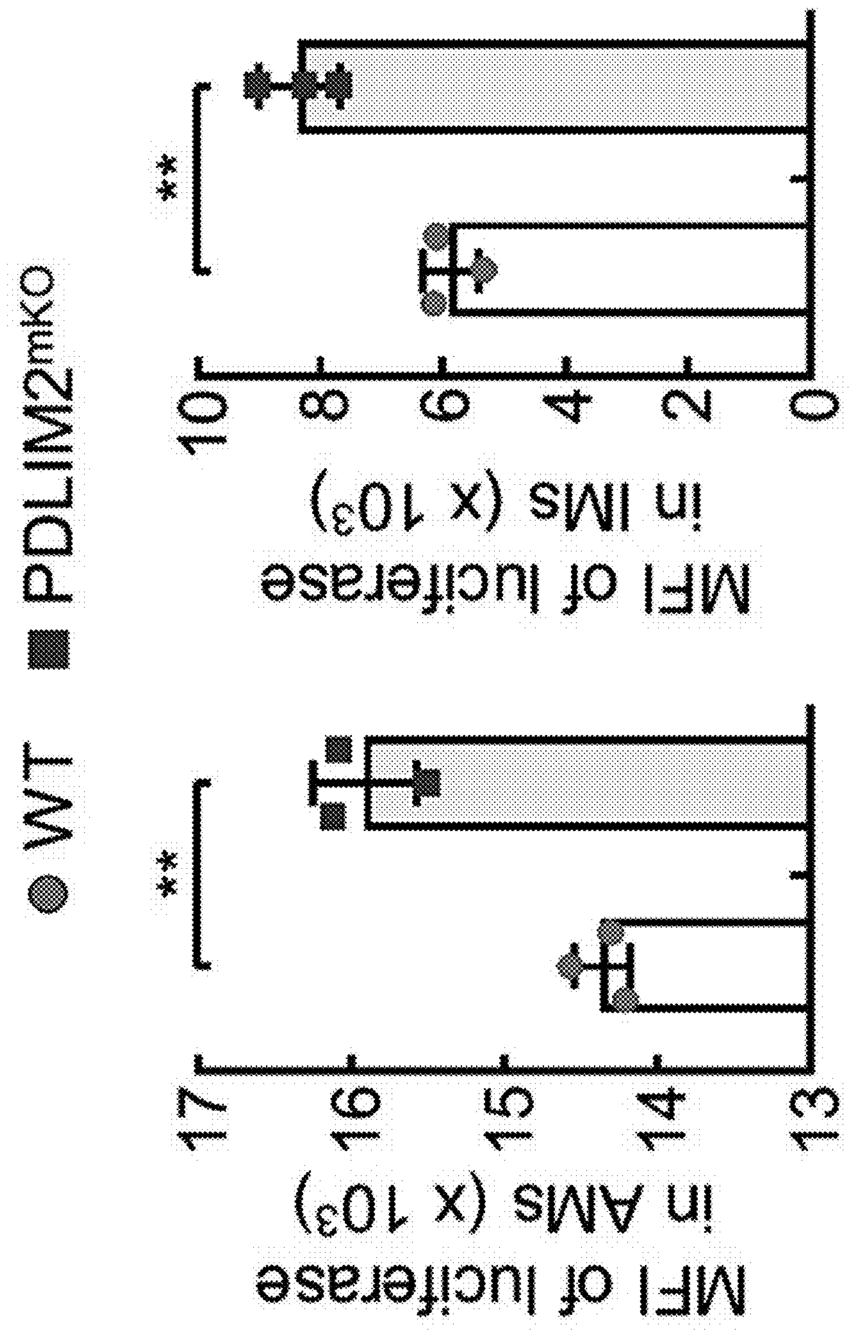

FIG. 31A-31G provide cell-intrinsic PDLIM2 restriction of BMDM lung recruitment and differentiation into IMs and AMs during lung tumorigenesis. FIG. 31A depicts FACS analysis showing increased lung macrophages (Mφ) in urethane-treated PDLIM2mKO mice (n=3). FIG. 31B depicts FACS analysis showing increased percentage of AMs but decreased percentage of IMs among total lung macrophages in urethane-treated PDLIM2mKO mice (n=3). FIG. 31C depicts FACS analysis showing decreased percentage of monocytes in total lung cells in urethane-treated PDLIM2mKO mice (n=3). FIG. 31D depicts FACS analysis showing increased percentage of AM-like cells but decreased percentage of IM-like cells among total macrophages differentiated from PDLIM2−/− BMDMs (n=3). FIG. 31E depicts FACS analysis showing increased lung recruitment of PDLIM2−/− monocyte-derived macrophage in tumorigenesis by urethane (n=3). FIGS. 31F-31G depict FACS analysis showing increased PDLIM2−/− AMs and IMs derived from bone marrow in urethane-treated WT mice lung (n=3). Student's t test was performed (two tailed, unpaired) and data represent means±SEM in (A-G). *P<0.05; **P<0.01.

Figure 32A:
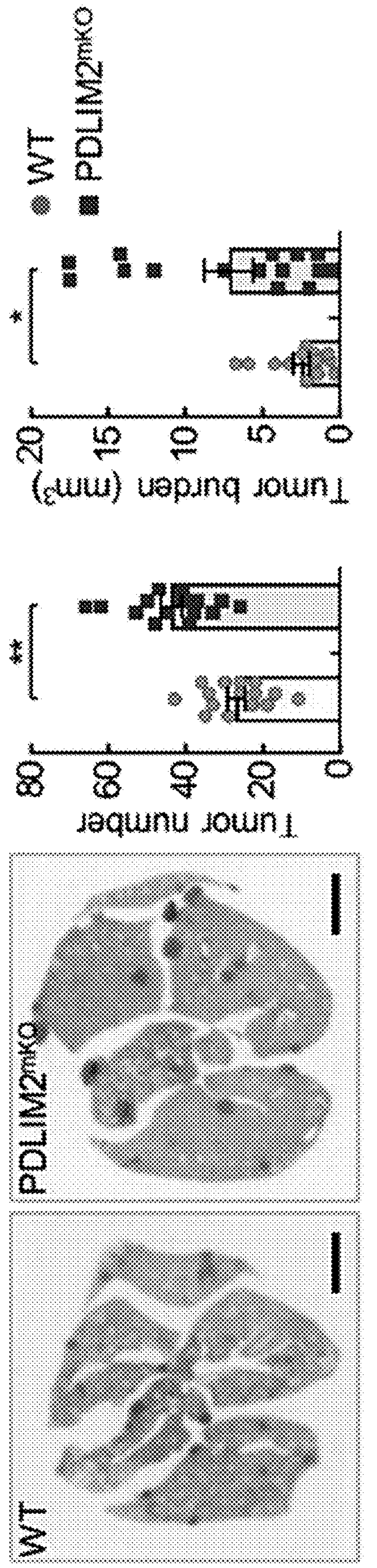
Figure 32B:
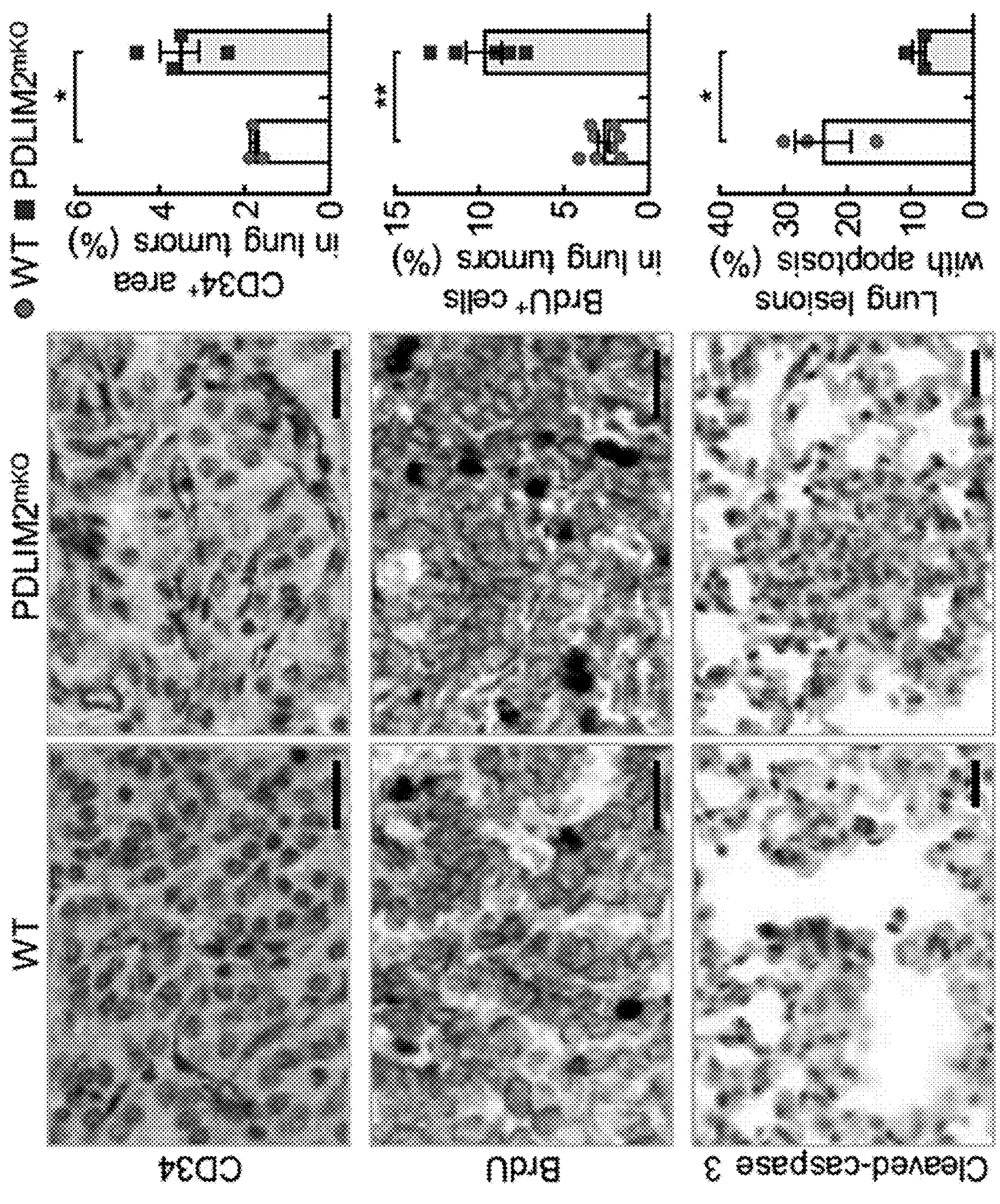
Figure 32C:
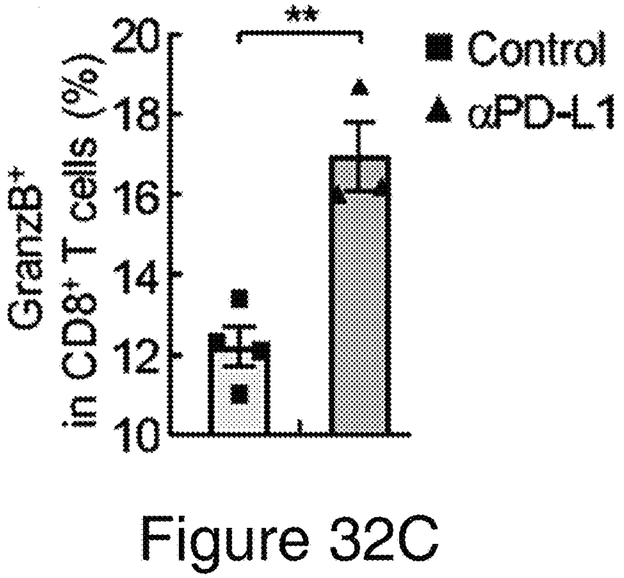
Figure 32D:
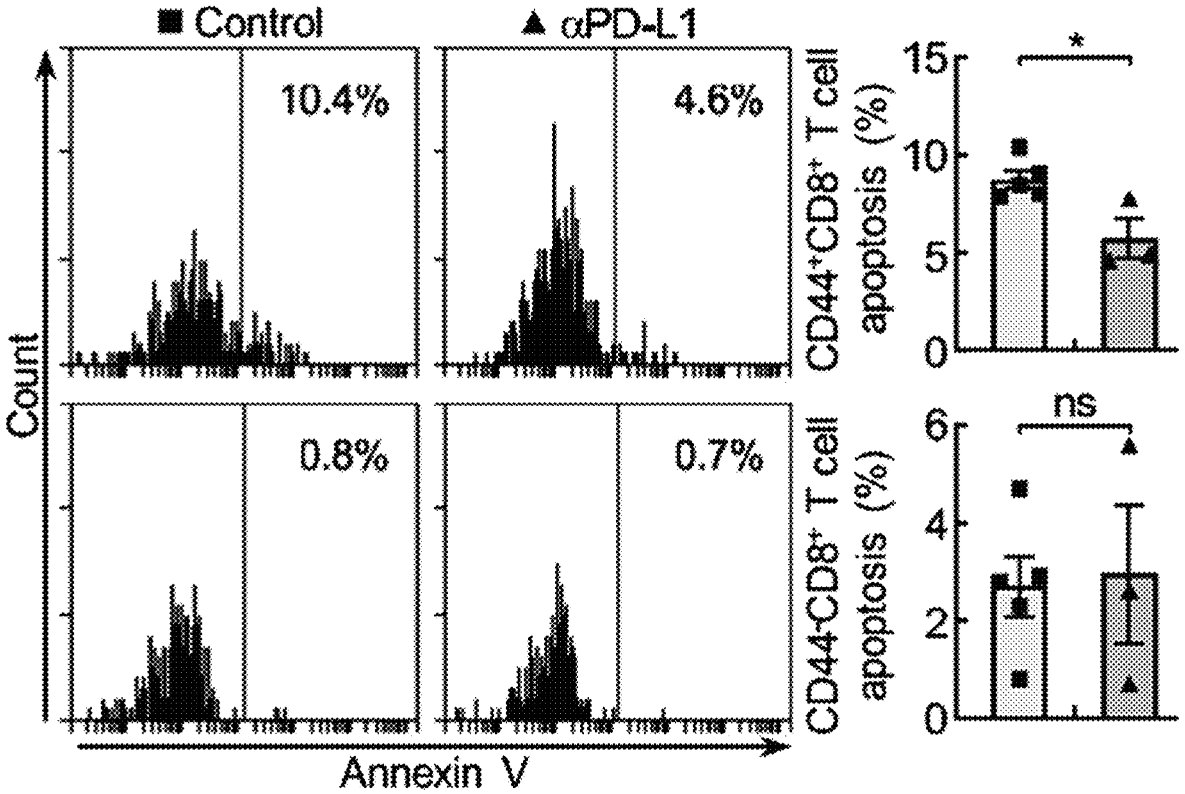
Figure 32E:
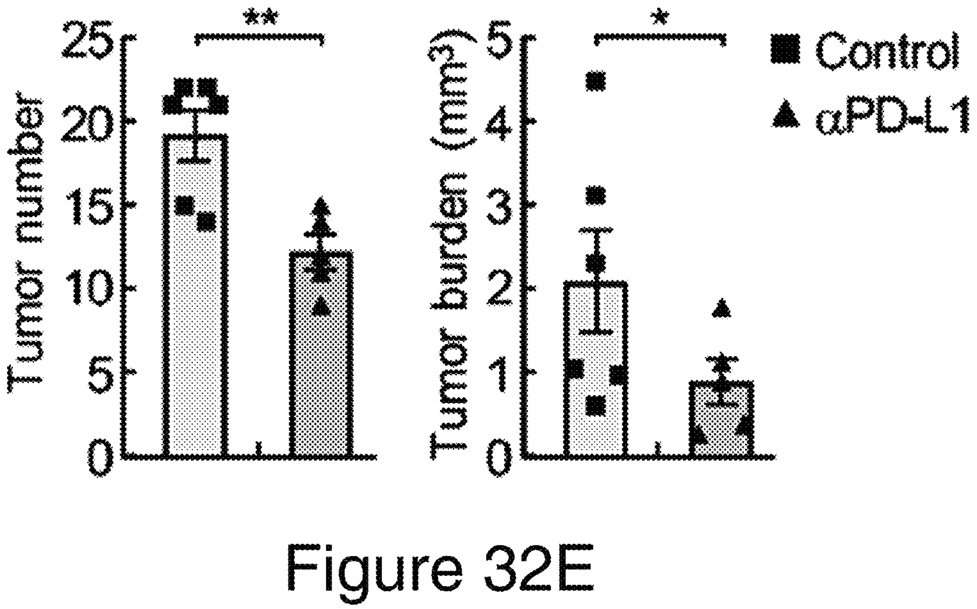

FIGS. 32A-32E illustrate PD-L1/PD-1 blockade suppression of increased lung tumorigenesis by myeloid PDLIM2 deletion. FIG. 32A depicts tumor examination and H&E staining showing both increased lung tumor numbers and tumor burden in urethane-treated PDLIM2mKO mice (n≥14). Scale bar: 2.5 mm. FIG. 32B depicts IHC staining showing increased tumor angiogenesis and tumor cell proliferation but decreased tumor cell apoptosis in urethane-treated PDLIM2mKO mice (n=3). Scale bar: 20 FIG. 32C depicts FACS analysis showing recovery of lung CD8+ T cell activation in urethane-treated PDLIM2mKO mice by PD-L1 antibody (GranzB: Granzyme B) (n≥3). FIG. 32D depicts FACS analysis showing inhibition of lung CD44+ CD8+ T cell apoptosis but no effect on the basal apoptosis of lung CD44−CD8+ T cells in urethane-treated PDLIM2mKO mice by PD-L1 antibody (n≥3). FIG. 32E depicts decreased tumor numbers and tumor burden in the lungs of urethane-treated PDLIM2mKO mice by PD-L1 antibody (n≥5). Student's t test was performed (two tailed, unpaired) and data represent means±SEM in (A-E). *P<0.05; **P<0.01.

Figure 33A:
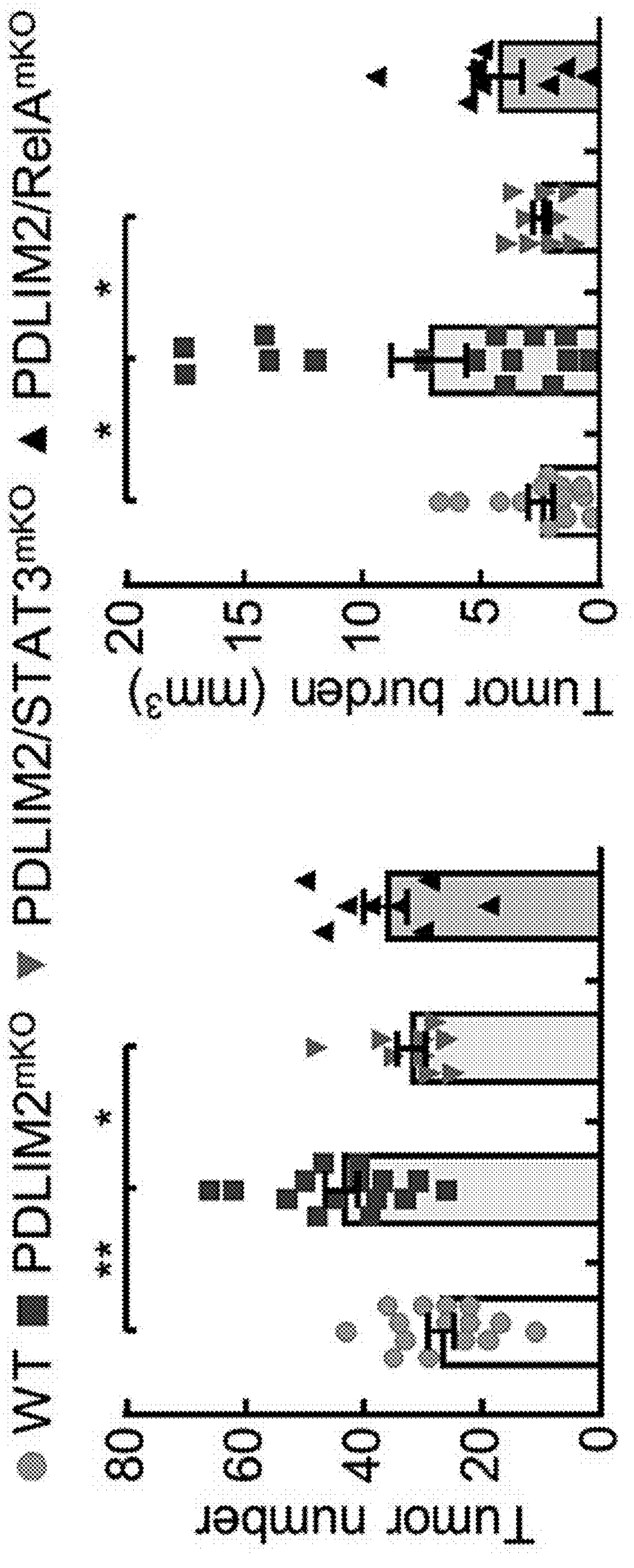
Figure 33B:
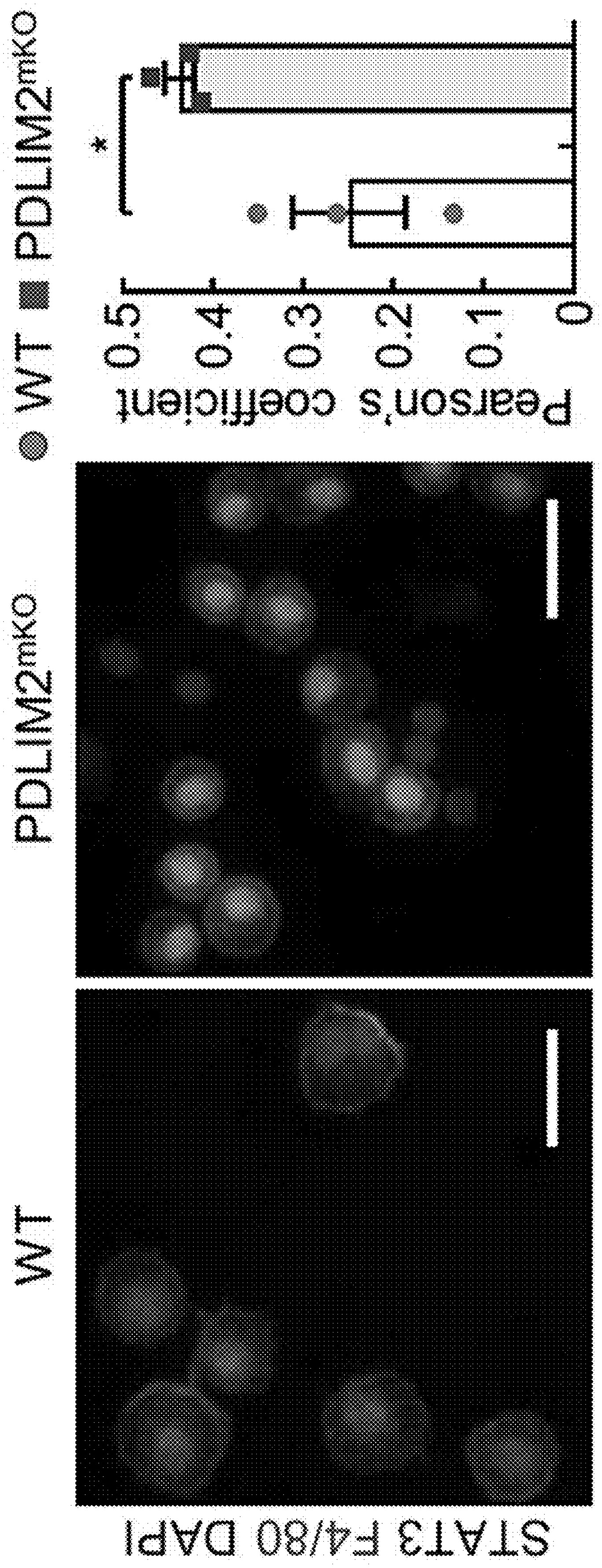
Figure 33C:
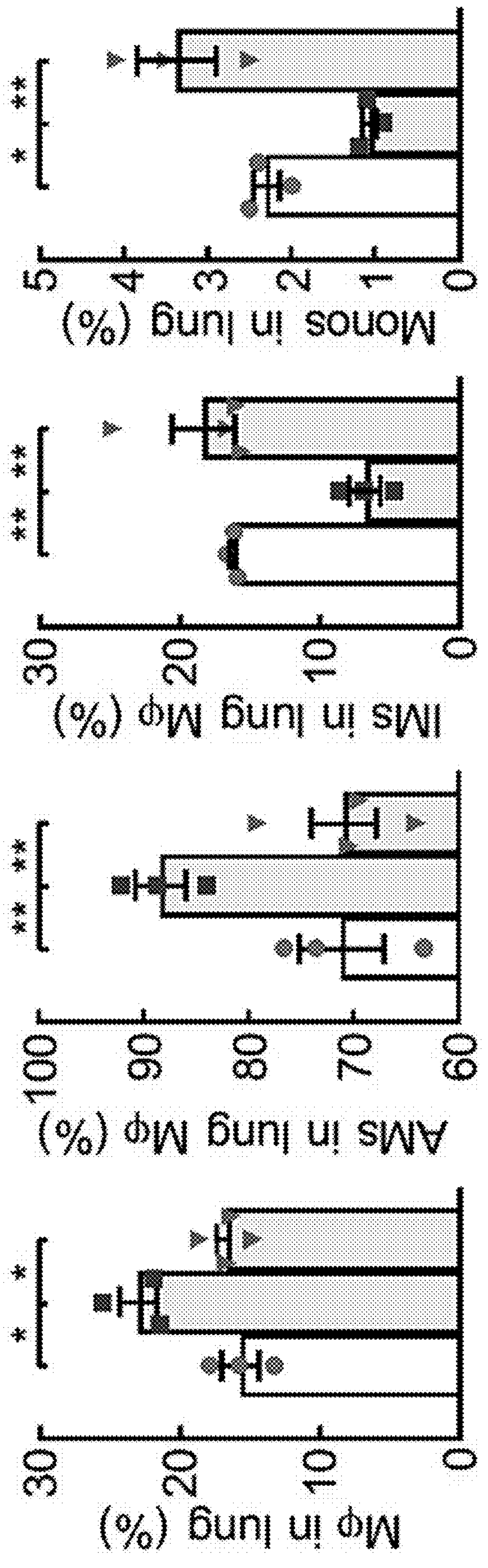
Figure 33E:
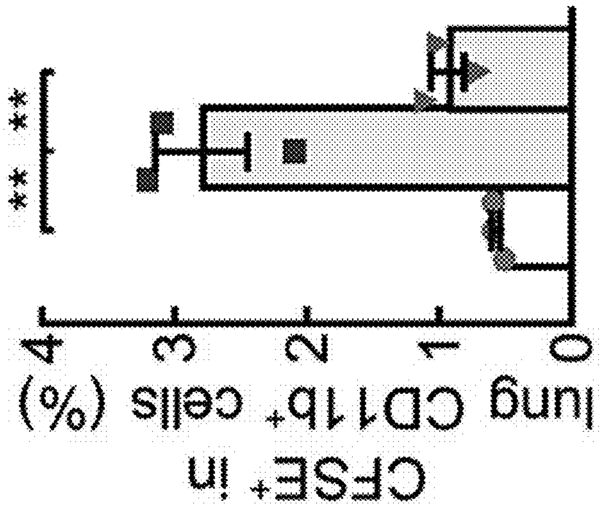
Figure 33D:
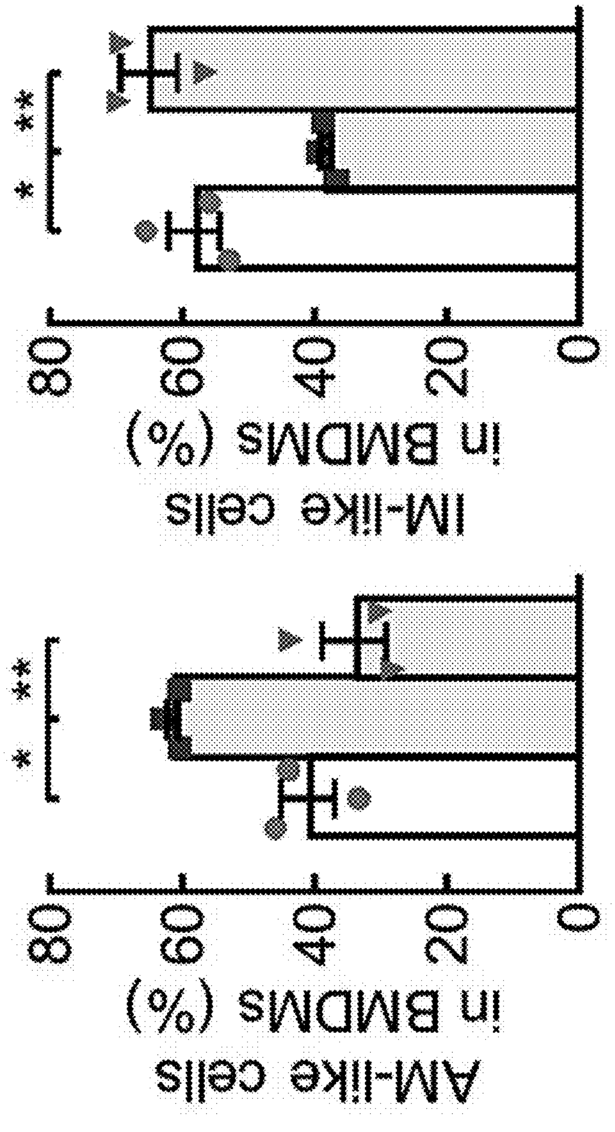
Figure 33G:
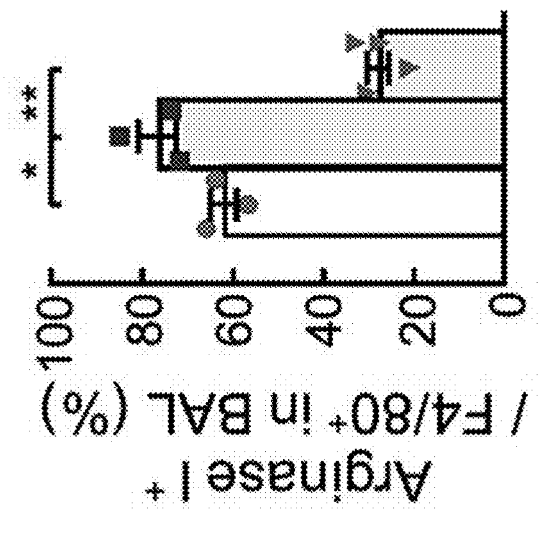
Figure 33F:
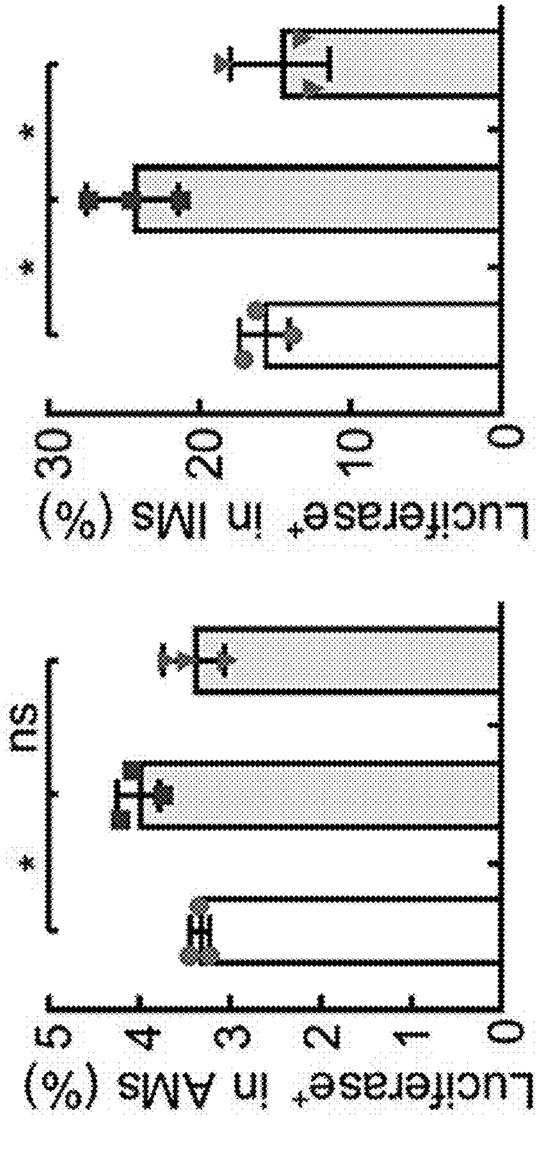
Figure 33H:
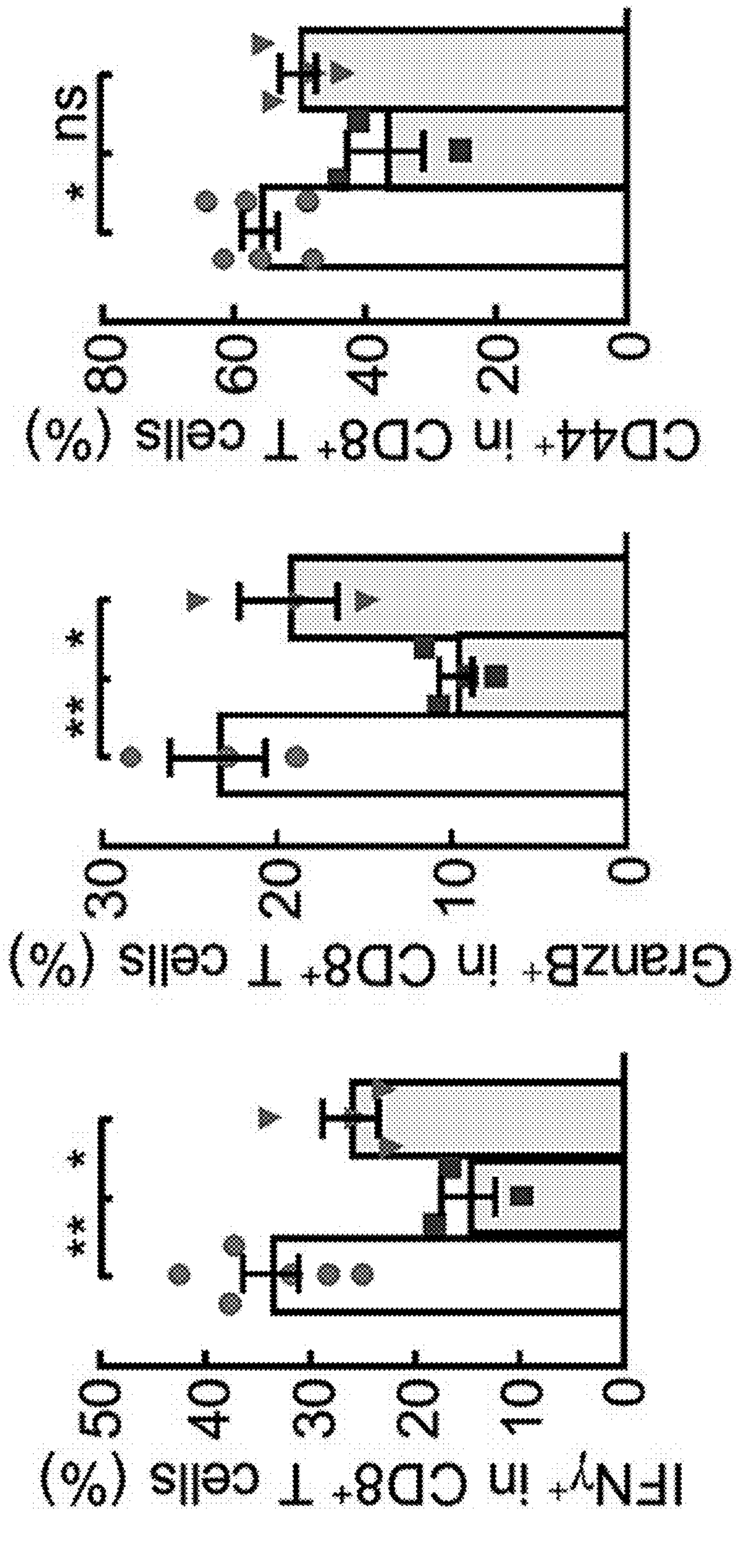
Figures 33I, 33J, 33K, 33L:
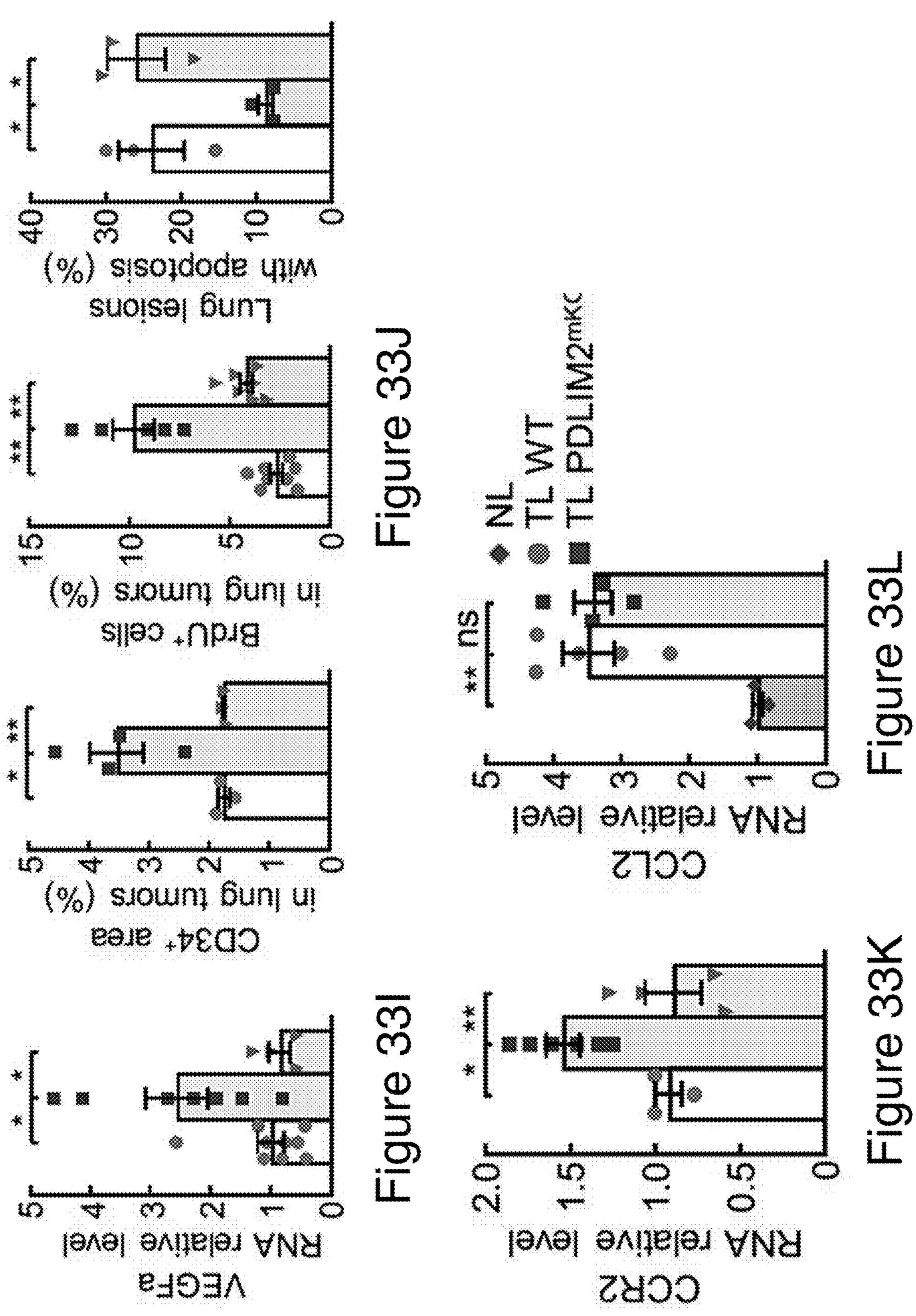

FIGS. 33A-33L show phenotype reversal in urethane-treated PDLIM2mKO mice by STAT3 co-deletion. FIG. 33A depicts tumor examination showing inhibition of the increased lung tumors in urethane-treated PDLIM2mKO mice by STAT3 but not RelA co-deletion (n≥8). FIG. 33B depicts IF analysis showing increased nuclear STAT3 in AMs in urethane-treated PDLIM2mKO mice. Scale bar: 20 μm. The colocalization of STAT3 and nucleus was analyzed by image J and represented with Pearson's correlation coefficient (n=3 mice, 3 images per mouse). FIG. 33C depicts FACS analysis showing that in urethane-treated PDLIM2mKO mice, STAT3 co-deletion inhibited the increase in lung macrophages, the increase of AM ratio and decrease of IM ratio in lung macrophages, and the decrease in lung monocytes (n≥3). ●: wild-type; ■: PDLIM2$^{mKO}$; ▼: PDLIM2/STAT3$^{mKO}$. FIGS. 33D-33F depict FACS showing that STAT3 co-deletion inhibited the increase of PDLIM2−/− BMDMs differentiating into AM-like cells (33D, n=3), the increase of PDLIM2−/− BMDM lung recruitment in tumorigenesis (33E, n=3), and the increase of PDLIM2−/−AMs and IMs derived from bone marrow in urethane-treated mice lungs (33F, n=3). FIG. 33G depicts IF analysis showing inhibition of the increased Arginase-1 in AMs in urethane-treated PDLIM2mKO mice by STAT3 co-deletion. FIG. 33H depicts FACS analysis showing that in urethane-treated PDLIM2mKO mice, STAT3 co-deletion inhibited the decrease of lung CD8+ T cell activation (n≥3). FIG. 33I depicts qPCR showing inhibition of the increased VEGFa expression in AMs in urethane-treated PDLIM2mKO mice by STAT3 co-deletion (n≥4). FIG. 33J depicts IHC assay showing reverse of the increased tumor angiogenesis and tumor cell proliferation and decreased tumor cell apoptosis in PDLIM2mKO mice by STAT3 co-deletion. FIG. 33K depicts qPCR showing inhibition of the increased CCR2 expression in PDLIM2−/− BMDMs by STAT3 co-deletion (n≥3). FIG. 33L depicts qPCR showing comparable CCL2 increase in lung tissues of urethane-treated WT and PDLIM2mKO mice (n≥3; NL: normal lung; TL: tumor-bearing lung). One way ANOVA/Tukey's test was performed in 33A, 33C-33L and Student's t test (two tailed, unpaired) was performed in 33B. Data represent means±SEM. *P<0.05; **P<0.01; ns, not statistically significant.

Figure 34A:
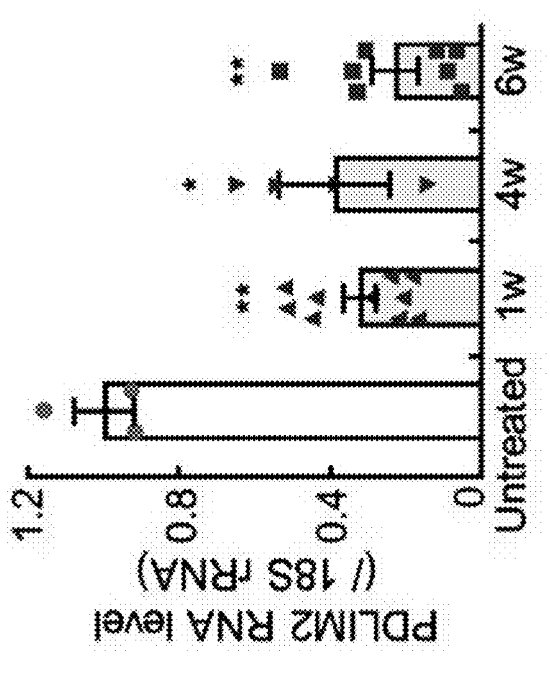
Figure 34B:
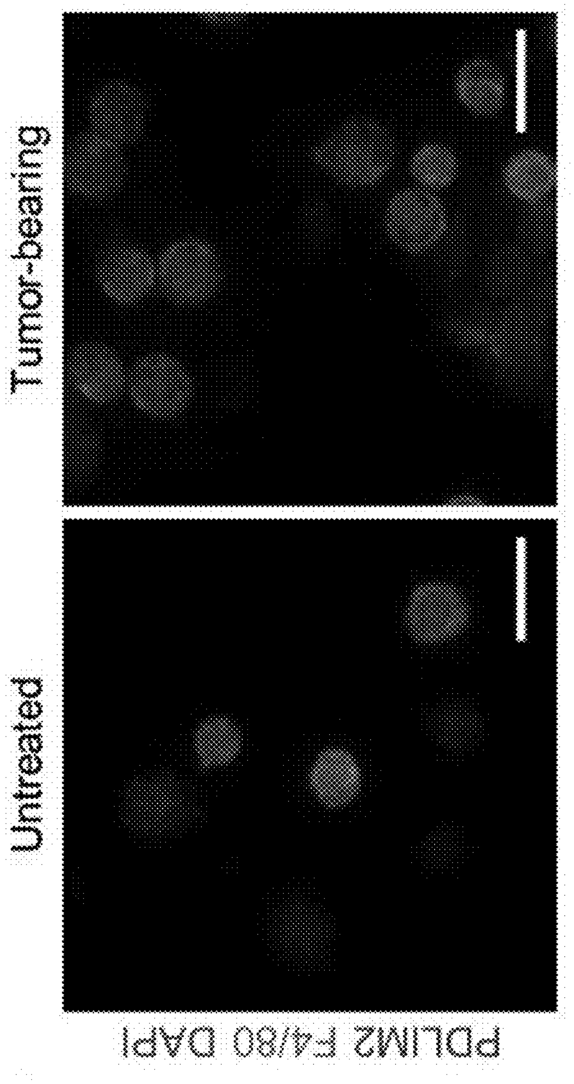
Figure 34C:
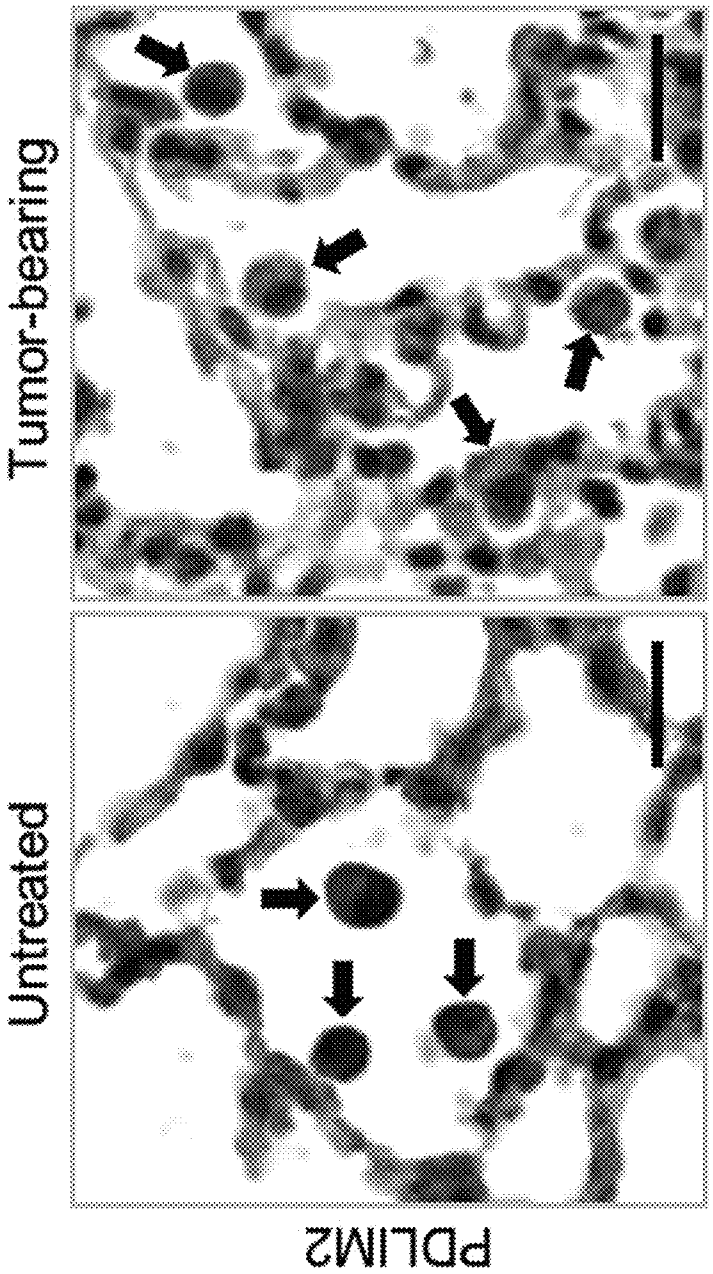
Figure 34D:
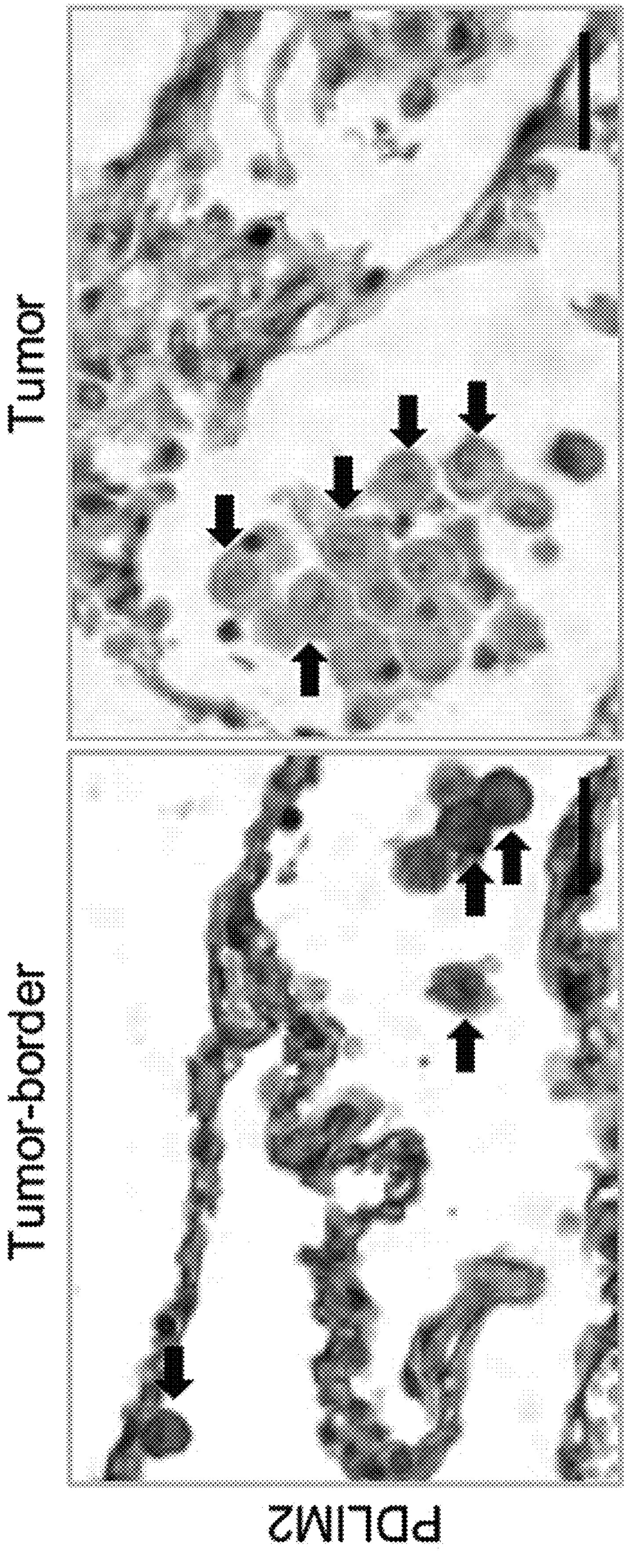
Figure 34E:
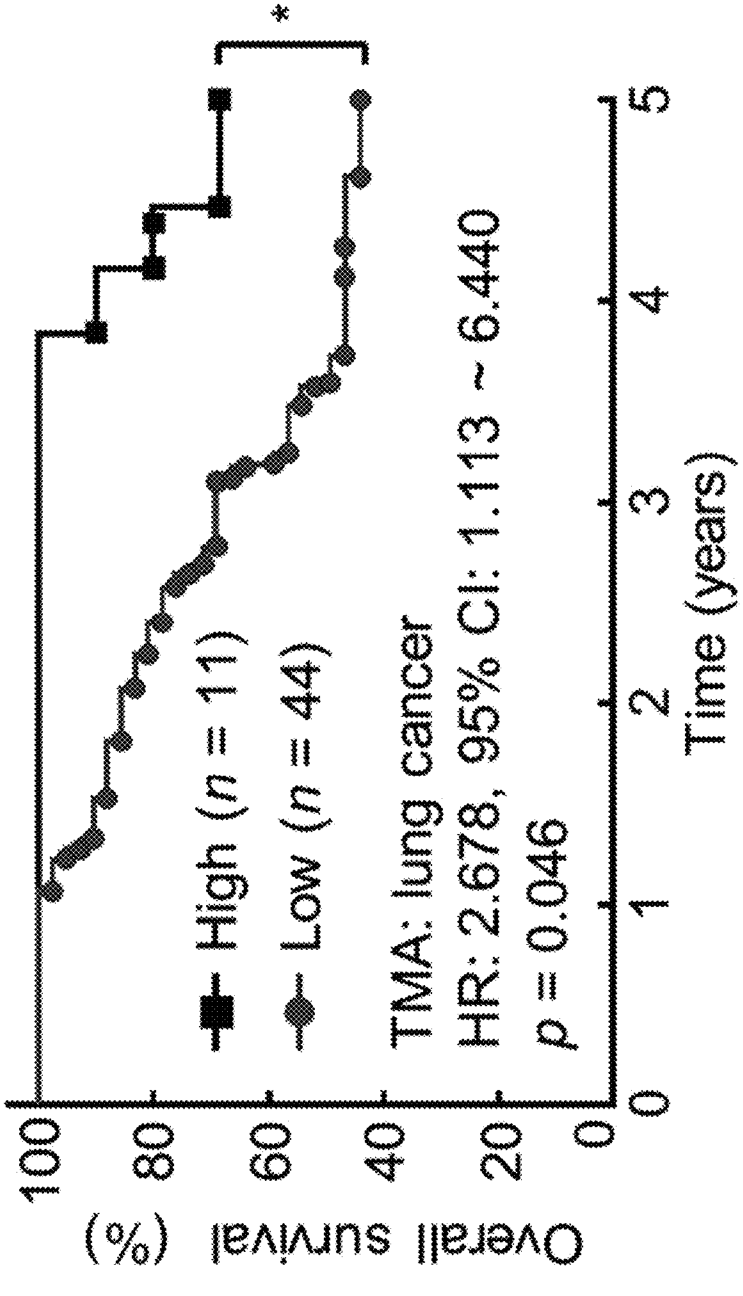

FIGS. 34A-34E show pathogenic and clinical relevance of PDLIM2 repression in AMs. FIG. 34A depicts qPCR showing decreased PDLIM2 expression in BAL cells during lung tumorigenesis (n≥3; 1 w, 4 w, 6 w: 1, 4, 6 weeks post urethane treatment, respectively). Student's t test was performed (two tailed, unpaired) and data represent means±SEM. *P<0.05; **P<0.01. FIGS. 34B and 34C depict IF (34B) and IHC analysis (34C) showing decreased PDLIM2 expression in AMs in urethane-treated mice. Arrows indicate AMs. Scale bar: 20 μm. FIG. 34D depicts IHC analysis showing decreased PDLIM2 in AMs around human lung cancer tissues compared to AMs in matched normal human lung tissues. Arrows indicate AMs. Scale bar: 20 μm. FIG. 34E depicts Kaplan-Meier survival curve showing the negative association between pulmonary myeloid PDLIM2 expression levels and lung cancer patient overall survival. P=0.046 by Gehan-Breslow-Wilcoxon test.

Figure 35F:
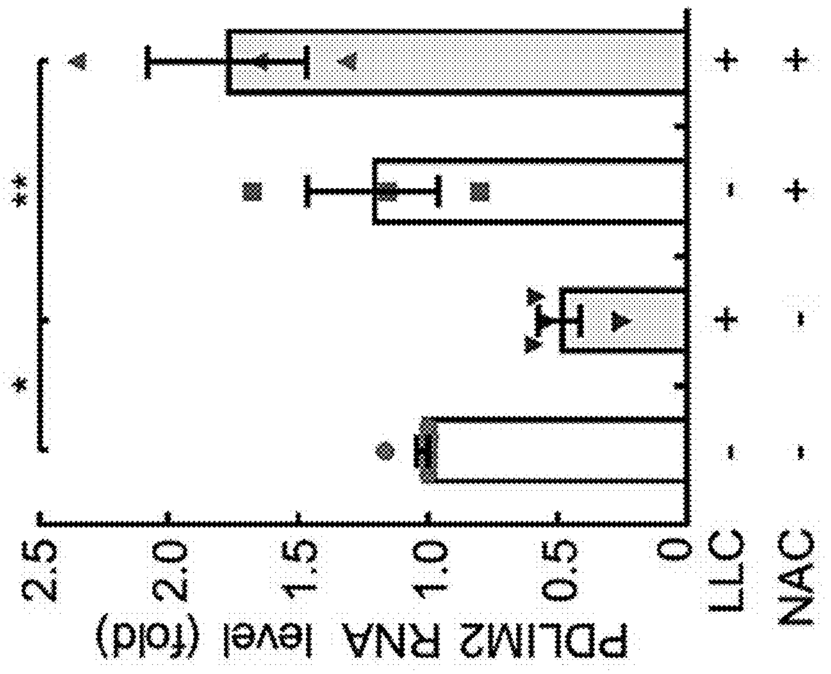
Figure 35E:
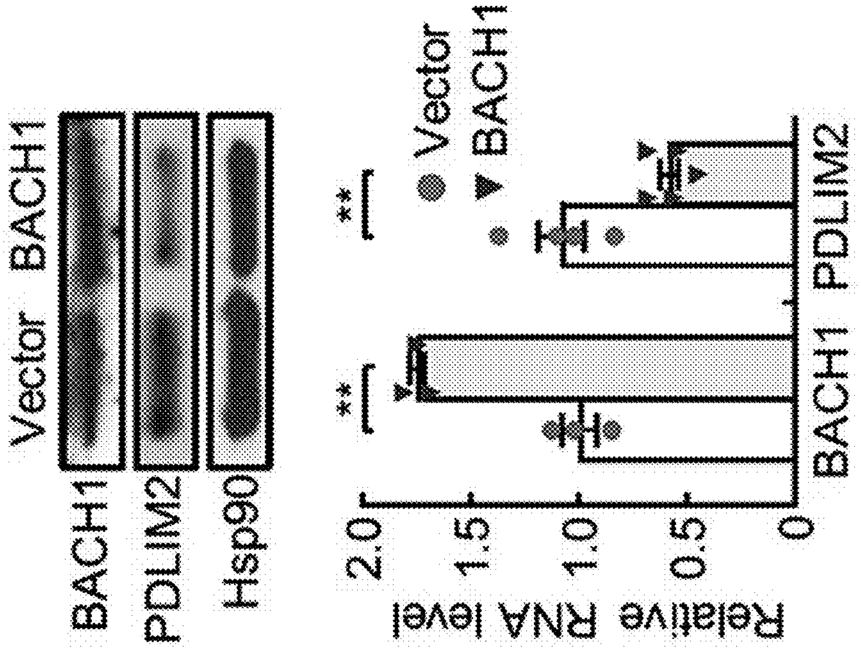
Figure 35G:
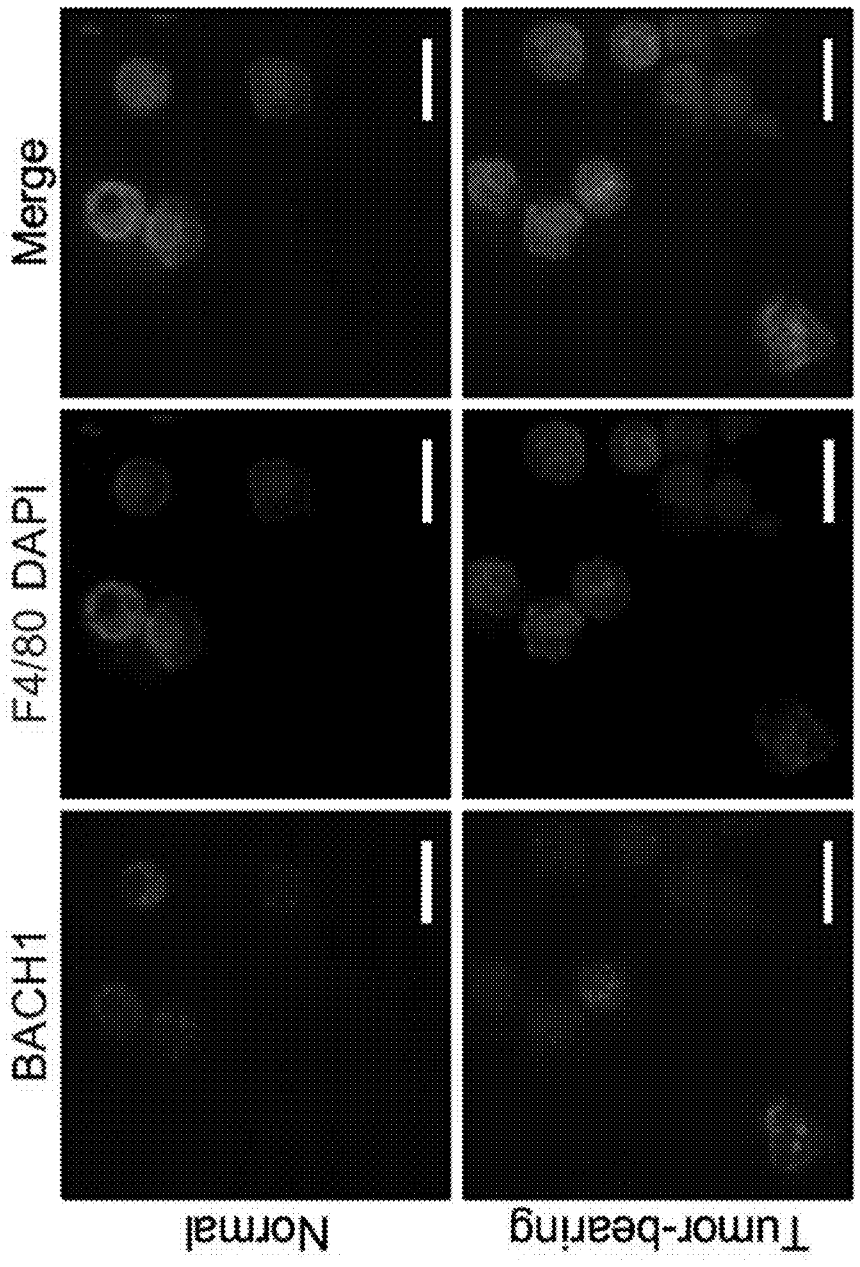
Figure 35I:
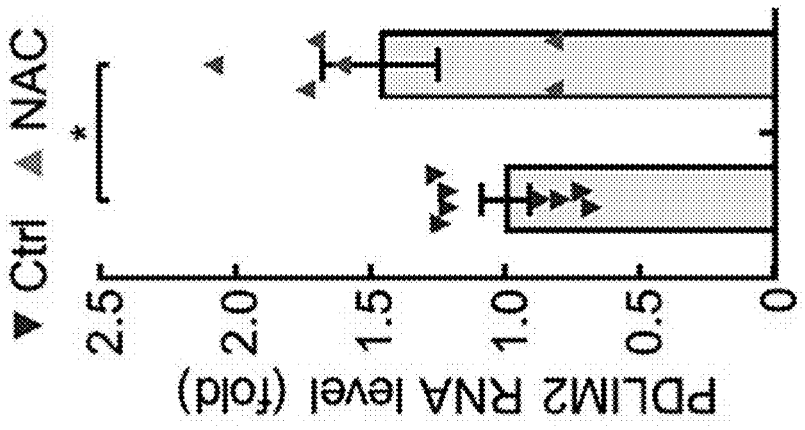
Figure 35H:
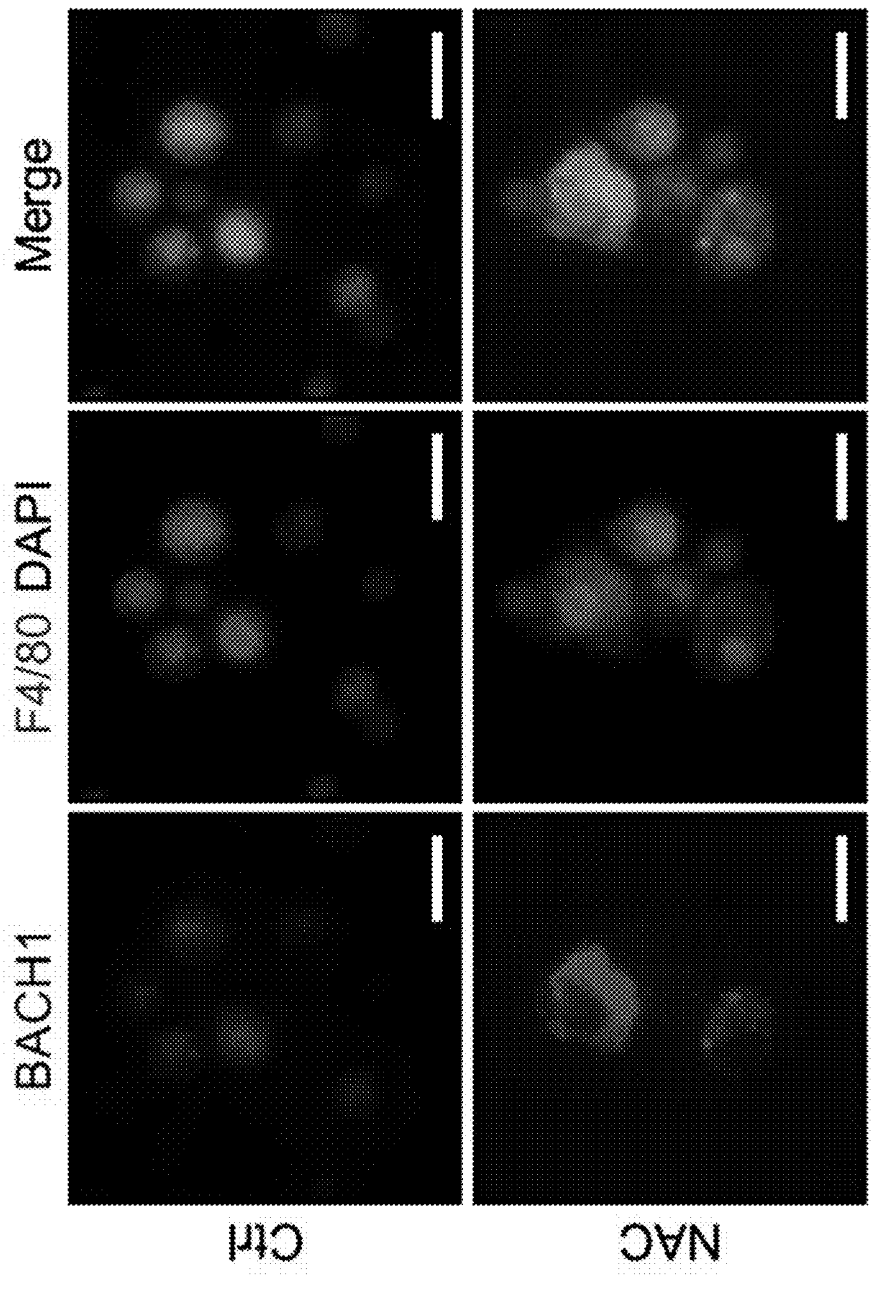
Figure 35J:
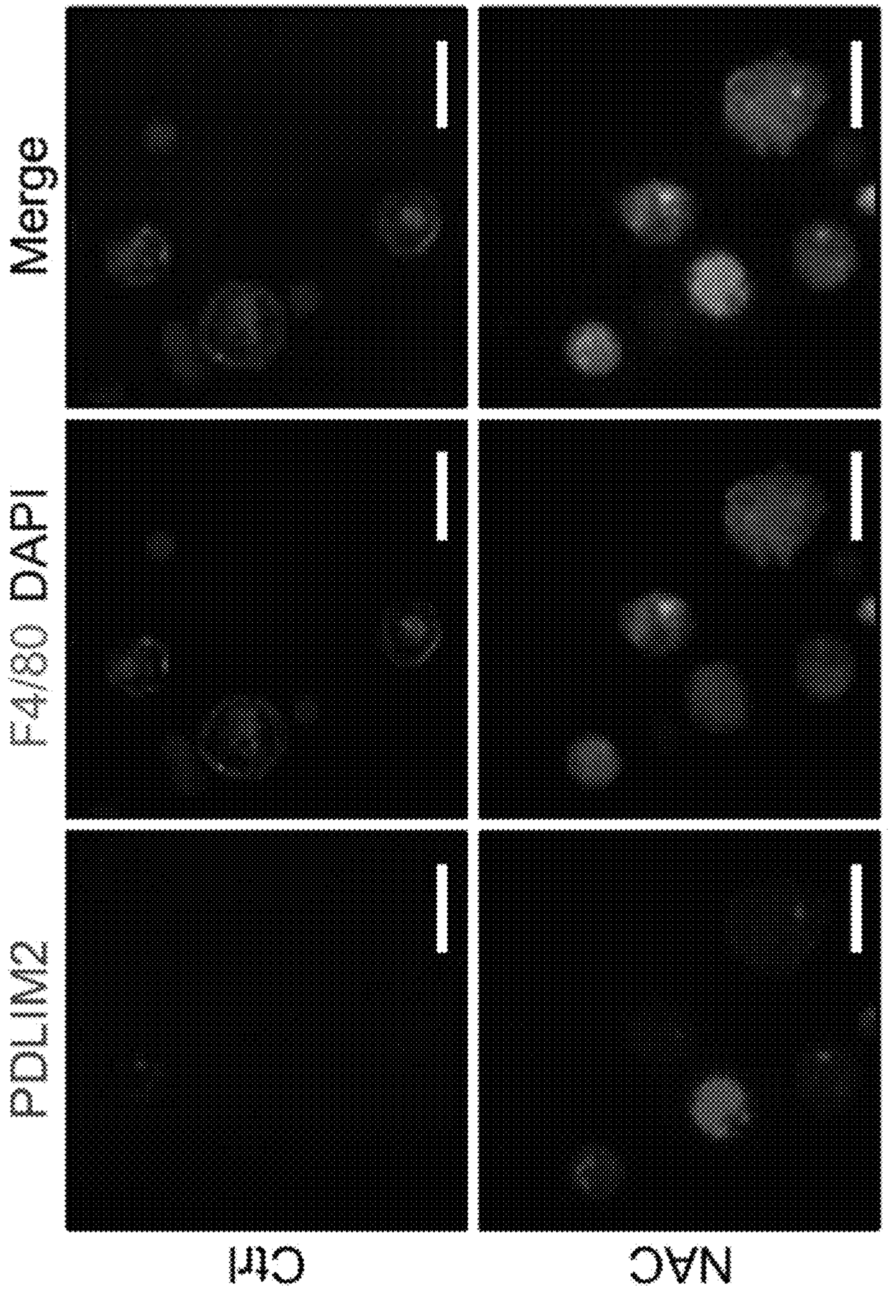

FIG. 35A-35J show PDLIM2 repression in AMs by ROS-activated BACH1. FIG. 35A depicts putative BACH1-binding site within the pdlim2 promoter. FIG. 35B depicts ChIP assays showing more BACH1 but less Pol II bound to the pdlim2 promoter in RAW264.7 mouse macrophages treated with 500 μM H2O2 for 4 hours (4 h, n=4). FIG. 35C depicts nuclear fraction D3 showing increased nuclear BACH1 in H2O2-treated RAW264.7 macrophages. FIG. 35D depicts qPCR showing decreased PDLIM2 in H2O2-treated RAW264.7 macrophages (normalized to β-actin, n=5). FIG. 35E depicts D3 and qPCR respectively showing decreased PDLIM2 in Raw264.7 macrophages transfected with BACH1 (n≥3). FIG. 35F depicts qPCR showing decreased PDLIM2 by LLC cell co-culture but recovery by NAC in RAW264.7 macrophages (n≥3). FIG. 35G depicts IF analysis showing increased nuclear translocation of BACH1 in AMs of mice with lung tumors. Scale bar: 20 μm. FIG. 35H depicts IF analysis showing inhibition of BACH1 nuclear translocation in the AMs of mice with lung tumors by in vivo NAC treatment. Scale bar: 20 μm. FIG. 35I depicts qPCR showing increased PDLIM2 in the AMs of mice with lung tumors by in vivo NAC treatment (n≥6). FIG. 35J depicts IF analysis showing PDLIM2 induction in the AMs of mice with lung tumors by in vivo NAC treatment (n≥3). Scale bar: 20 μm. Student's t test (two tailed, unpaired) was performed in 35B, 35D, 35E, 35I and one way ANOVA/Tukey's test was performed in 35F. Data represent means±SEM in (B, D-F, I). *P<0.05; **P<0.01.

Figure 36:
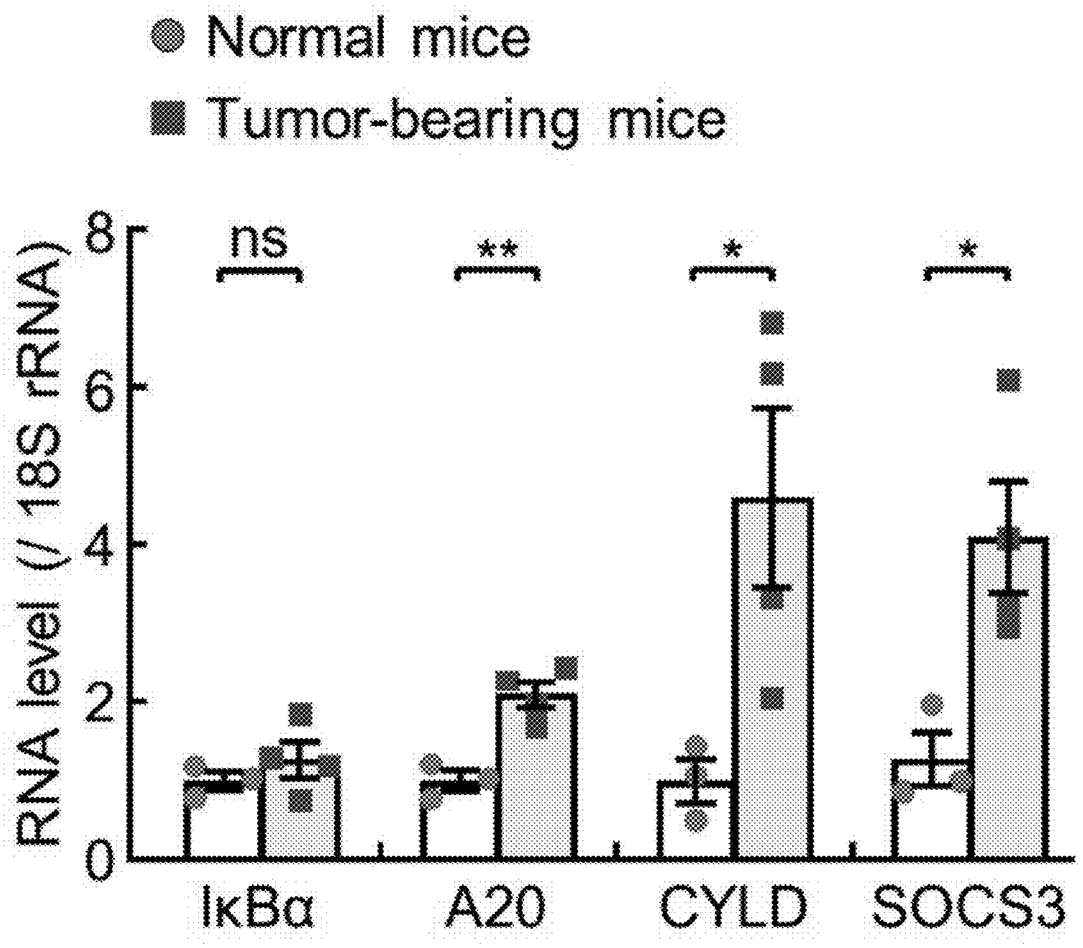

FIG. 36 shows increased expression of NF-KB and STAT3 inhibitors in lung macrophages in mice with lung cancers. qPCR analysis showing increased RNA expression of the indicated genes in the lung macrophages of tumor-bearing mice treated with urethane for 6 weeks, compared to untreated mice. Student's t test was performed (two tailed, unpaired) and data represent means±SEM (n≥3). *P<0.05; **P<0.01; ns, not statistically significant.

Figure 37A:
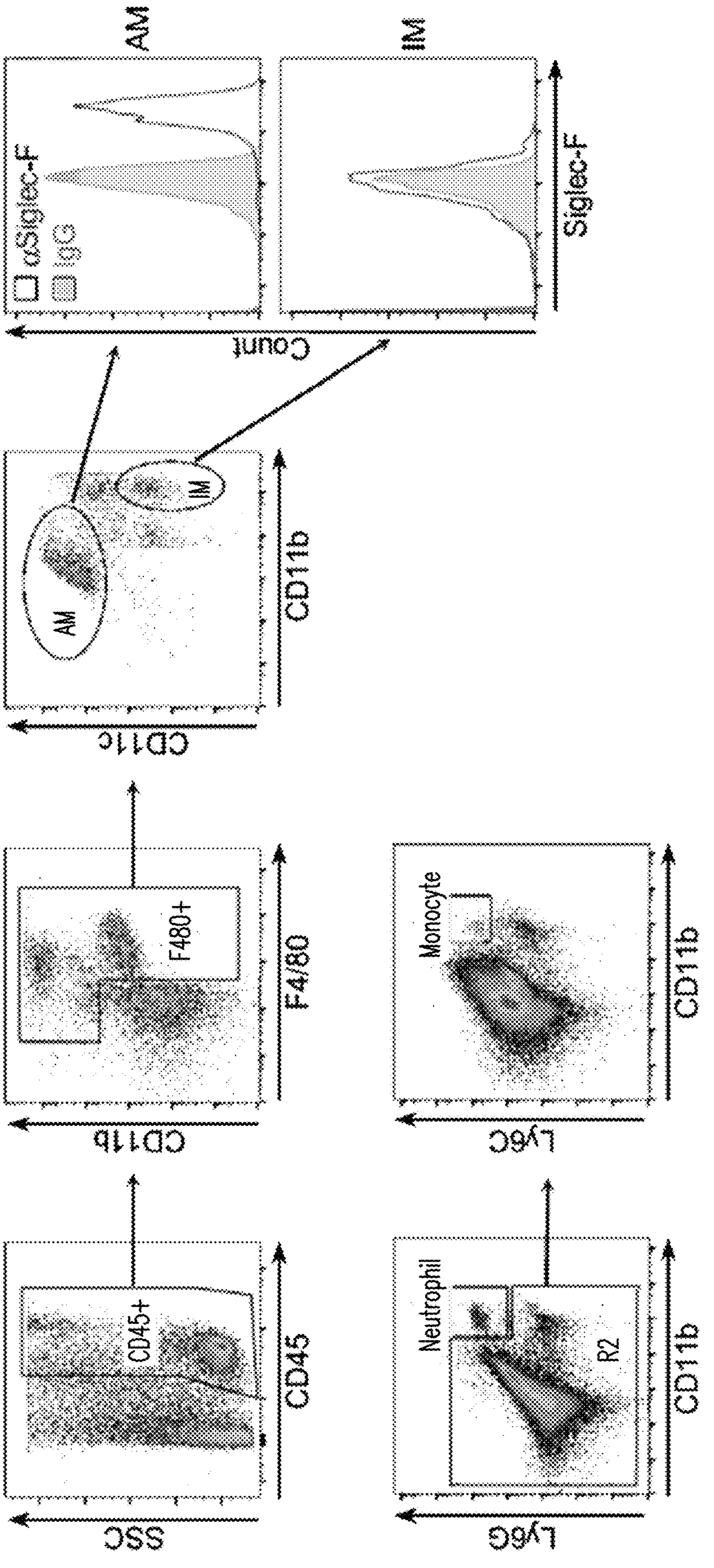
Figure 37B:
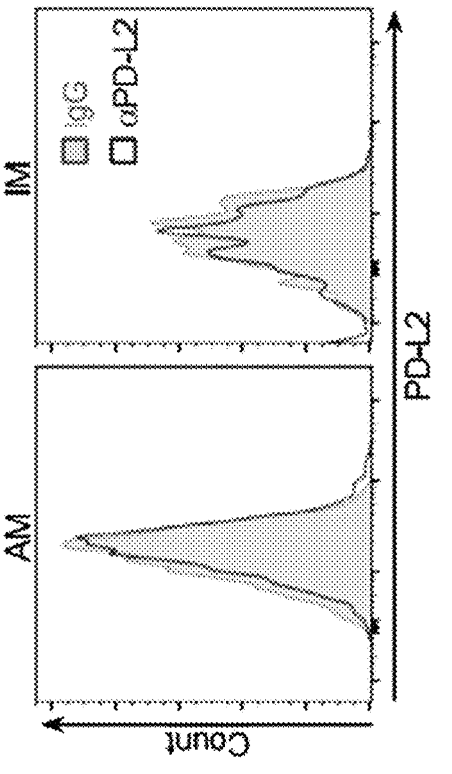
Figure 37C:
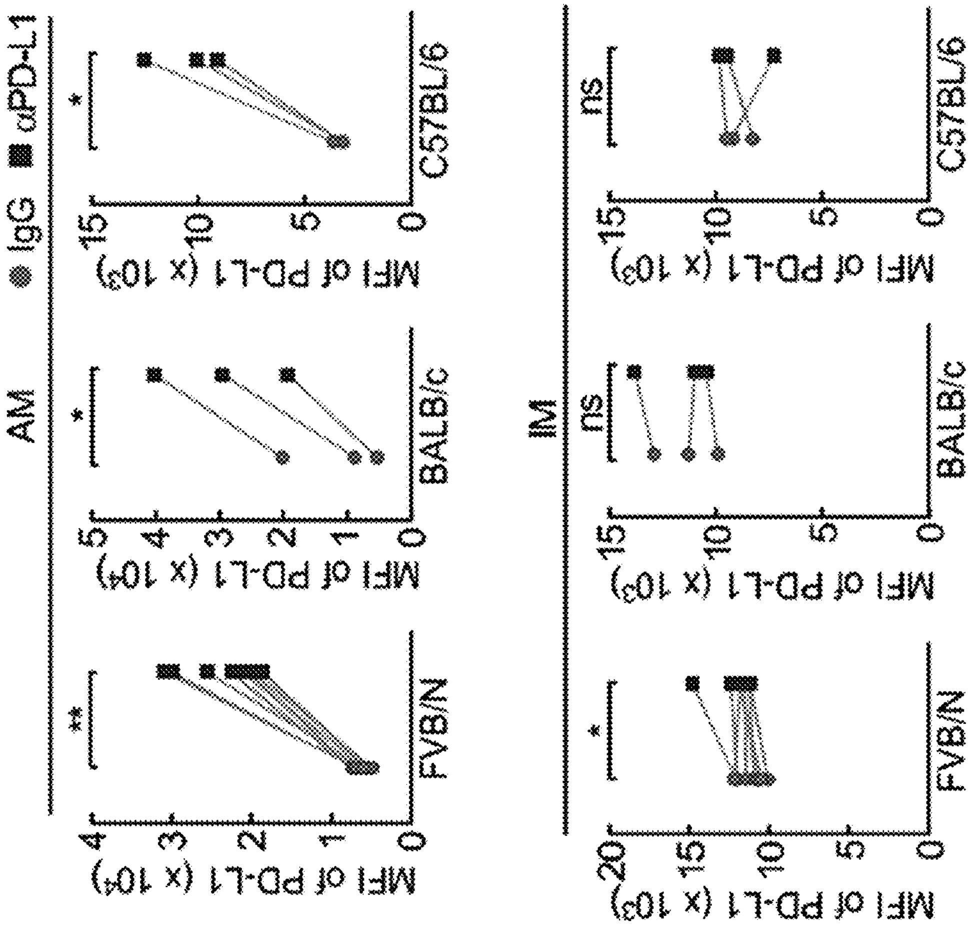
Figure 37D:
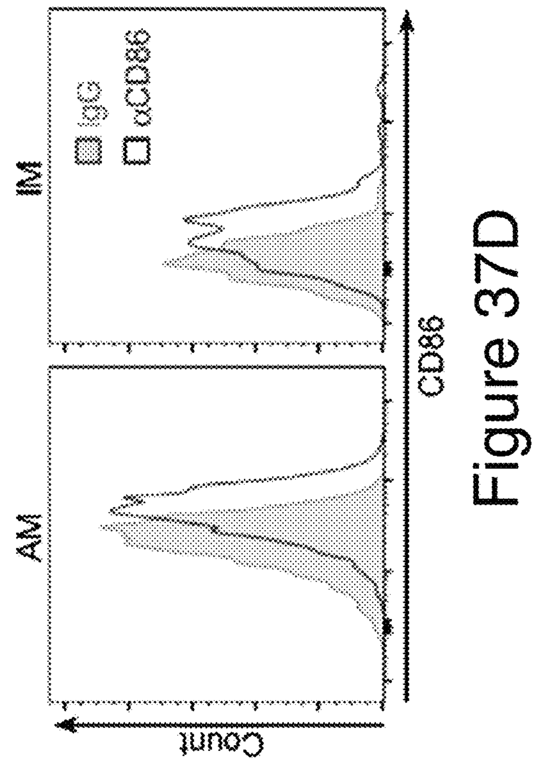

FIGS. 37A-37D show specific high expression of PD-L1 but not PD-L2 on lung AMs. FIG. 37A depicts gating strategy of AMs, IMs, neutrophils and monocytes in the lung tissues. FIG. 37B depicts FACS assays showing low PD-L2 expression on AMs and IMs. FIG. 37C depicts FACS assays showing specific AM expression of PD-L1 in different mouse strains (n≥3). Student's t test was performed (two tailed, paired). *P<0.05; **P<0.01; ns, not statistically significant. FIG. 37D depicts FACS assays showing CD86 expression on AMs and IMs.

Figure 38A:
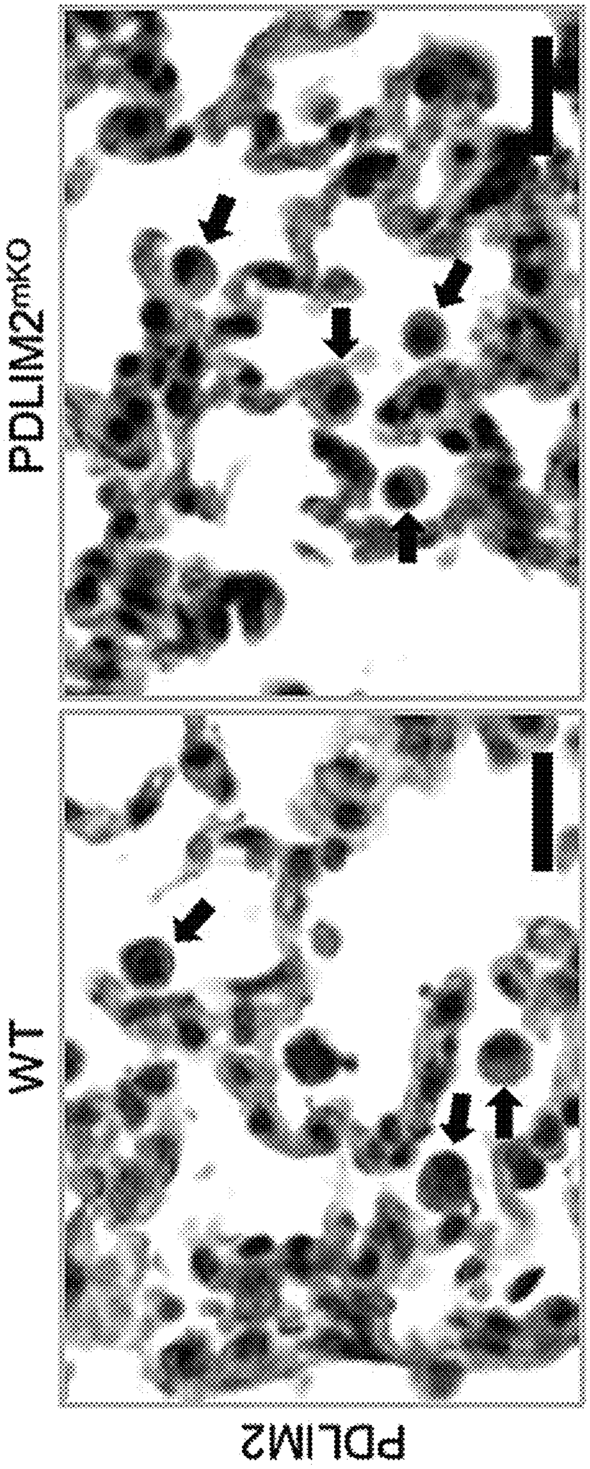
Figure 38B:
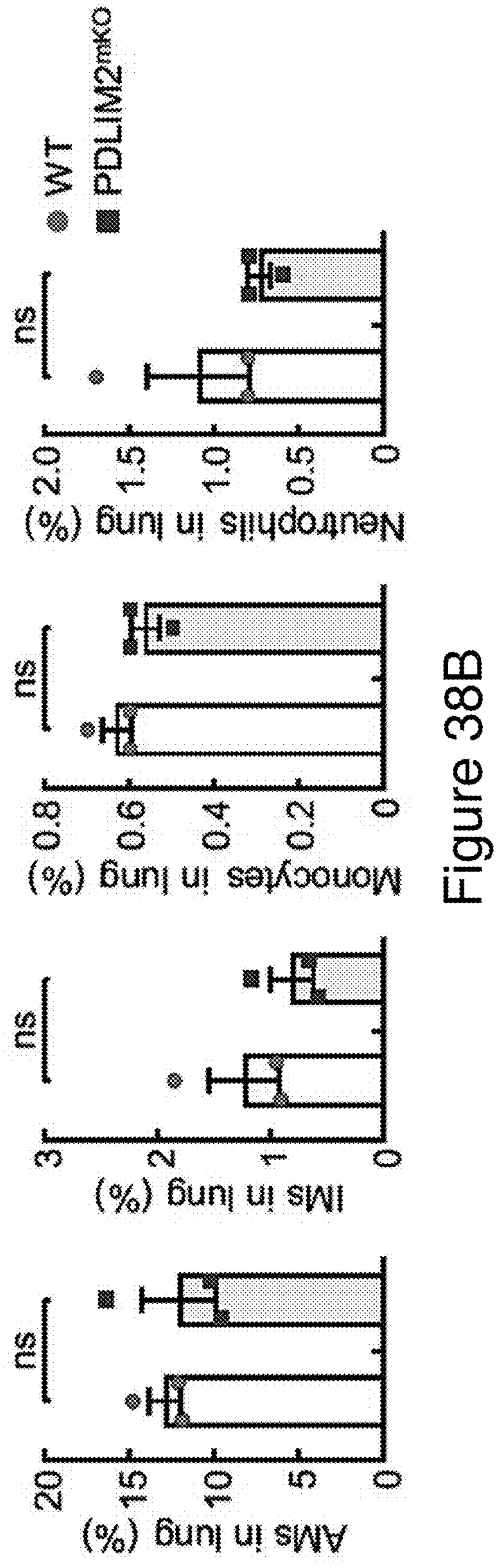
Figure 38D:
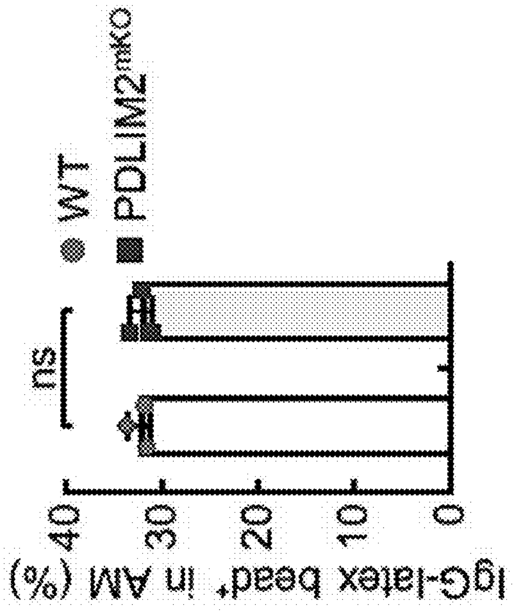
Figure 38C:
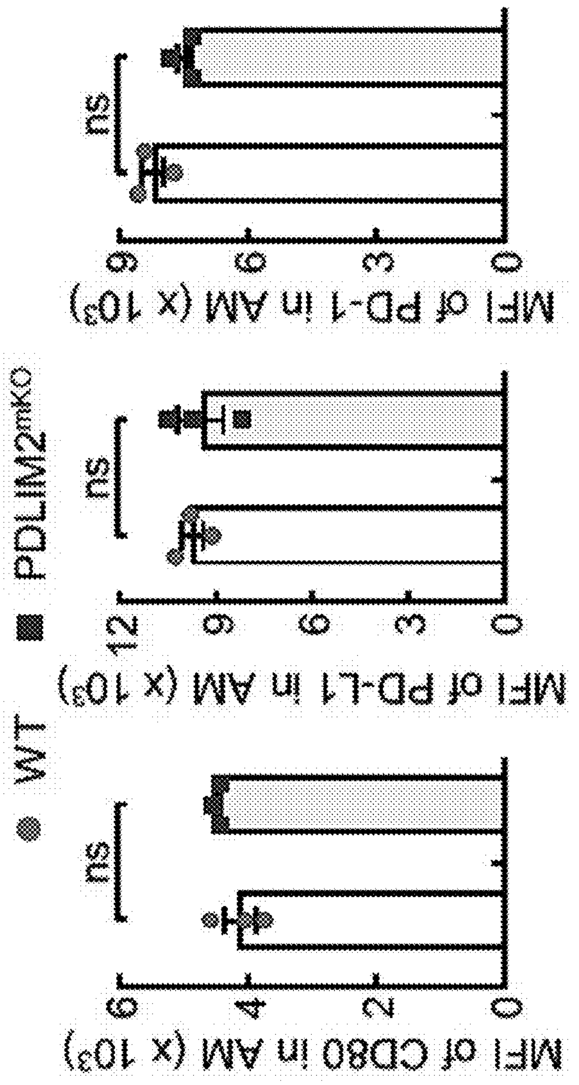

FIGS. 38A-38D show no obvious effect of myeloid PDLIM2 on myeloid cells under normal condition. FIG. 38A depicts IHC staining showing PDLIM2 selective deletion in myeloid cells of lung tissues from PDLIM2mKO mice. Arrows indicate myeloid cells. Scale bar: 20 μm. FIG. 38B depicts FACS assays showing no significant number difference in the lung AM, IM, monocyte and neutrophil populations between WT and PDLIM2mKO mice under normal condition (n=3). FIG. 38C depicts FACS assays showing that PDLIM2−/− AMs exhibited similar expressions of PD-L1, CD80 and PD-1 as wild type (WT) AMs (n=3). FIG. 38D depicts FACS assays showing that PDLIM2−/− AMs had a phagocytic ability similar to WT AMs (n=3). Student's t test was performed (two tailed, unpaired) and data represent means±SEM in (B-D). ns, not statistically significant.

Figure 39B:
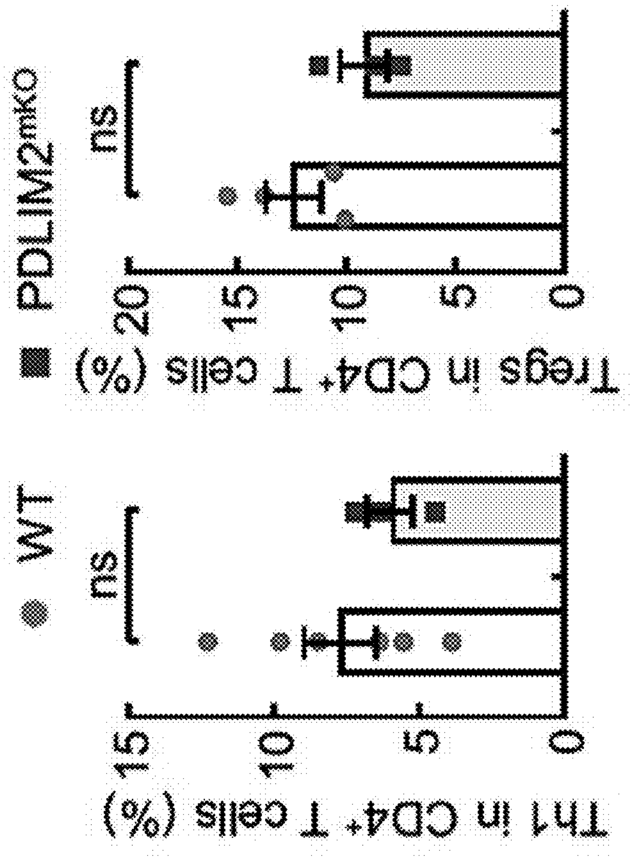
Figure 39A:
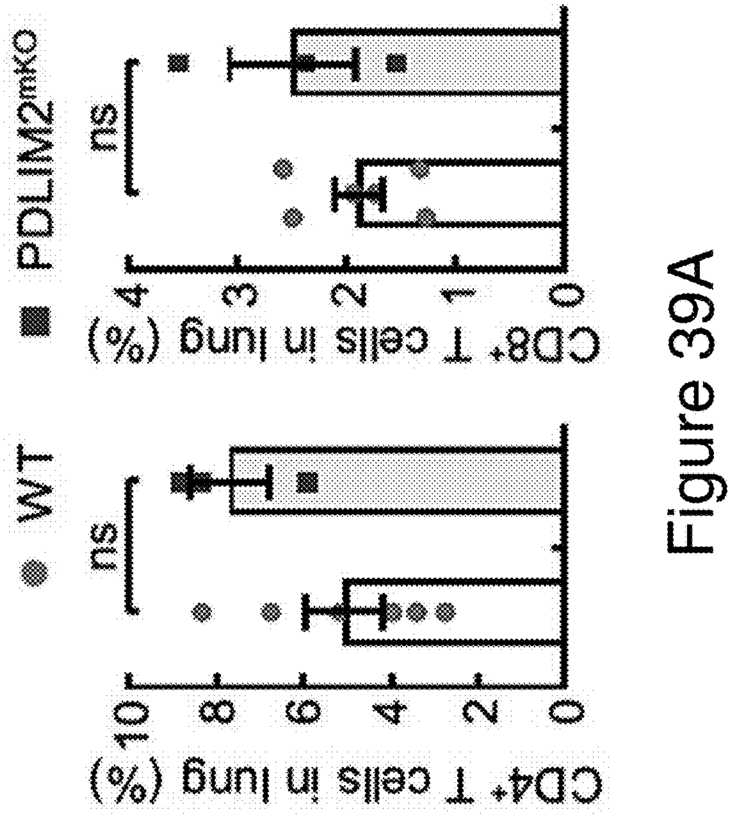

FIGS. 39A-39B show comparable lung CD4+ and CD8+ T cell total numbers, CD4+ T-cell activation and Treg cell differentiation in WT and PDLIM2mKO mice. FIG. 39A depicts FACS analysis showing comparable percentage of CD4+ T cells and CD8+ T cells in lung of WT and PDLIM2mKO mice treated with urethane (n≥3). FIG. 39B depicts FACS analysis showing comparable percentage of Th1 cells (CD4+IFNg+ cells) and Treg cells (CD4+CD25+ Foxp3+ cells) in CD4+ T cells in lung of WT and PDLIM2mKO mice treated with urethane (n≥3). Student's t test was performed and data represent means±SEM. ns, not statistically significant.

Figure 40A:
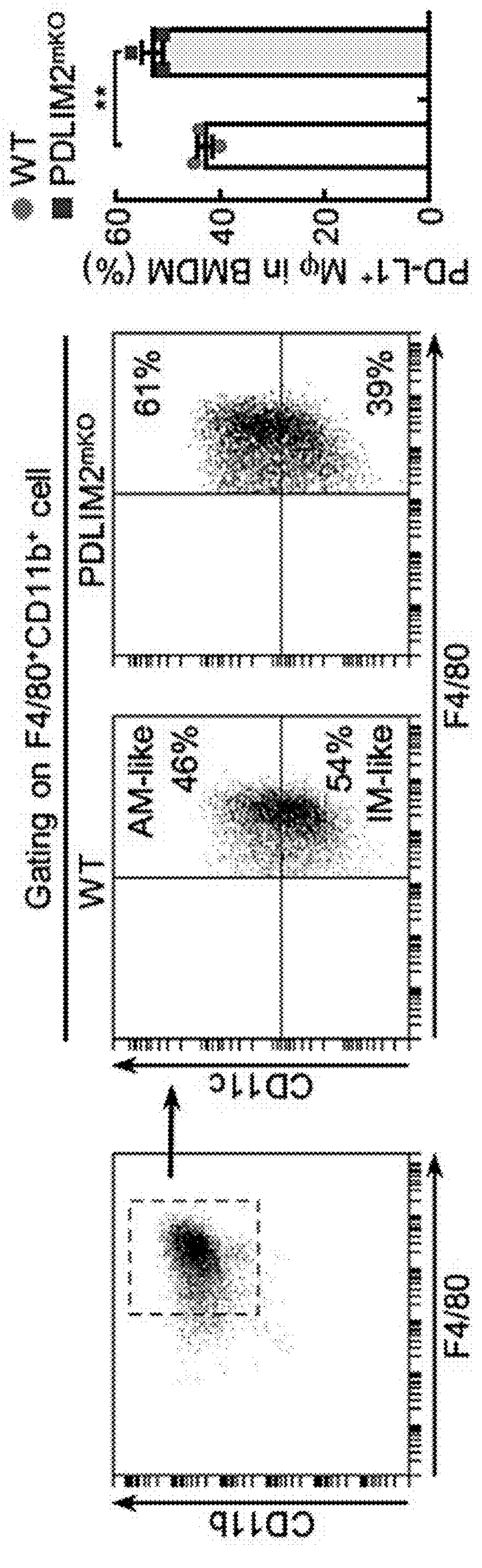
Figure 40C:
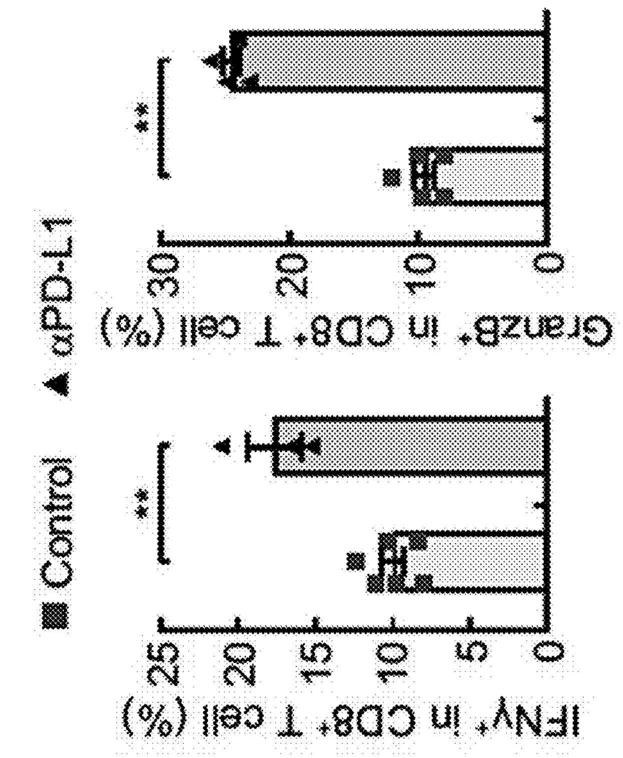
Figure 40B:
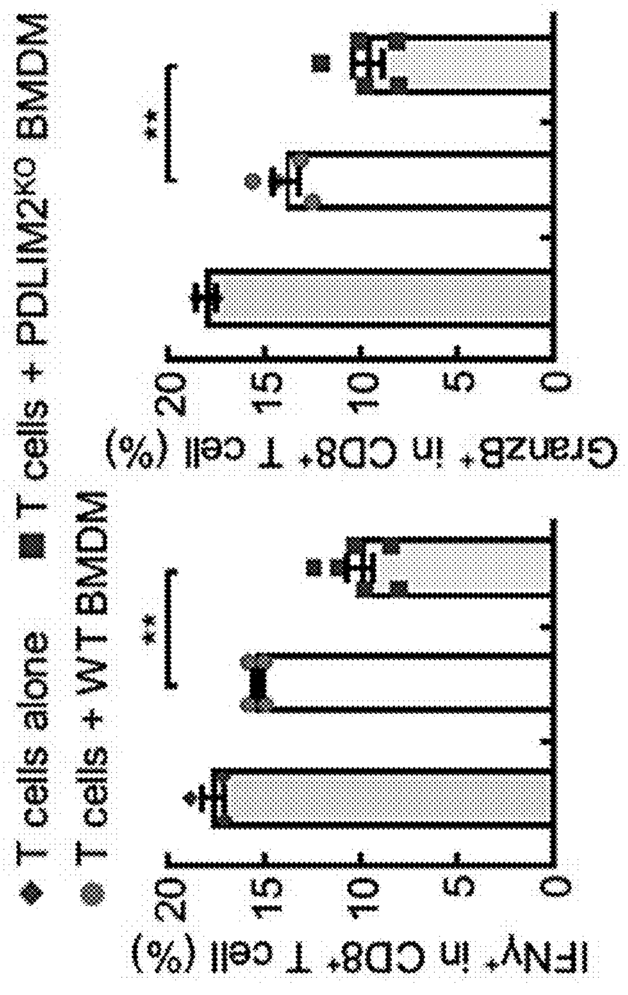

FIGS. 40A-40C show increased AM-like cell differentiation of BMDMs by PDLIM2 deletion. FIG. 40A depicts FACS assays showing increased differentiation of AM-like (CD11c+CD11b+F4/80+) BMDMs and increased PD-L1+ BMDMs from bone marrow of PDLIM2mKO mice (n=3). FIG. 40B depicts FACS assays showing increased BMDM suppression of CD8 T cell activation by PDLIM2 deletion (n≥2). FIG. 40C depicts FACS assays showing increased activation of CD8 T cells co-cultured with PDLIM2KO BMDM by PD-L1 antibody (n≥3). Student's t test was performed (two tailed, unpaired) and data represent means±SEM. *P<0.05; **P<0.01.

Figure 41:
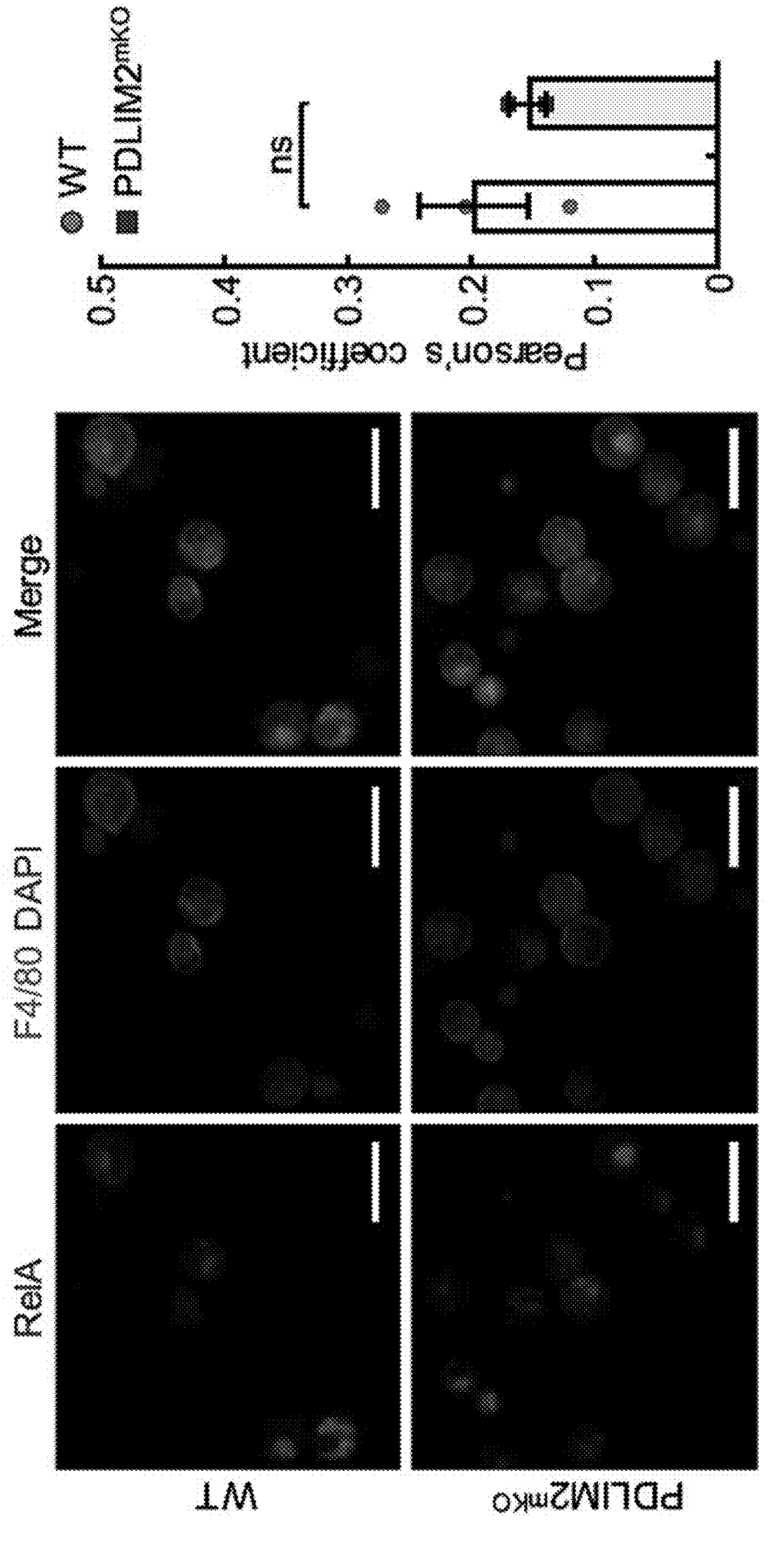

FIG. 41 shows that deletion of macrophage-intrinsic PDLIM2 has no significant effect on RelA activation in lung macrophages during lung tumorigenesis. IF co-staining of F4/80 (green) and RelA (red) in BAL cells showing no effect on nuclear expression of RelA in lung macrophages by PDLIM2 deletion during lung tumorigenesis. Scale bar: 20 μm. The colocalization of RelA and nucleus was analyzed by image J and represented by Pearson's correlation coefficient. Student's t test was performed (two tailed, unpaired) and data represent means±SEM (n≥3 mice, 3 images per mouse). ns, not statistically significant.

Figure 42B:
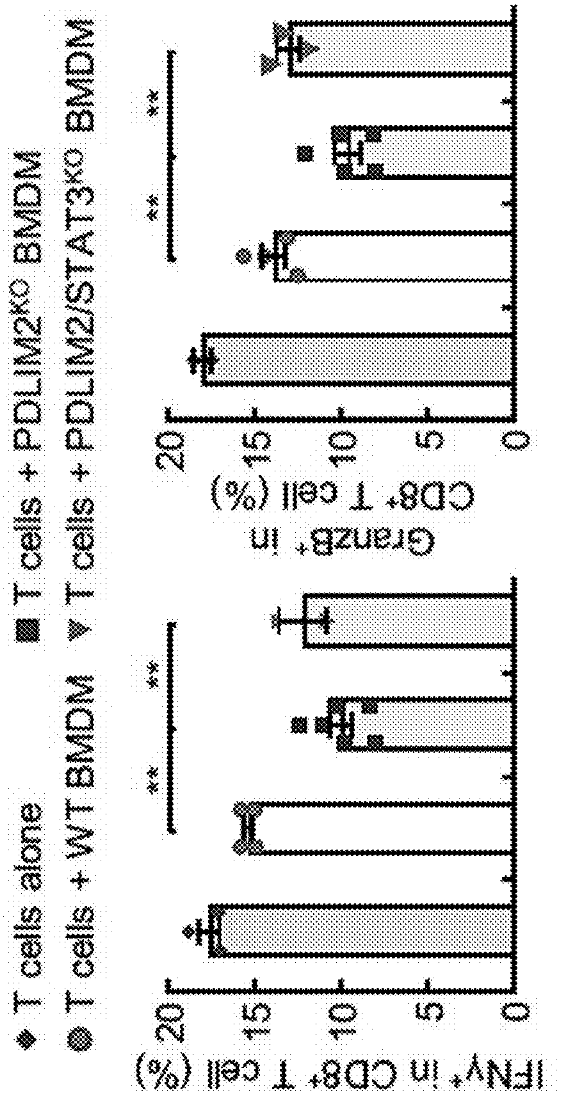
Figure 42A:
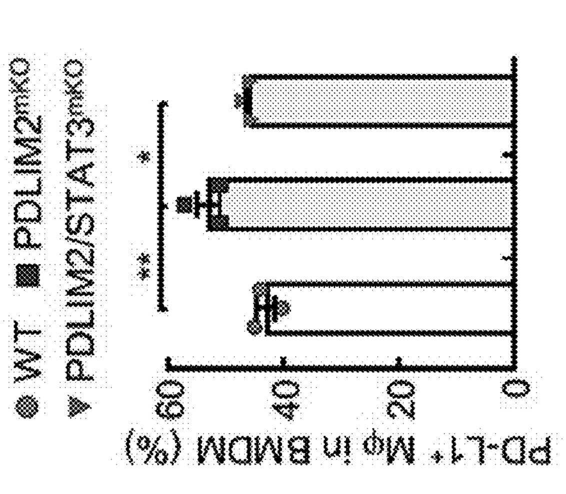

FIGS. 42A-42B show phenotype reversal in PDLIM2−/− myeloid cells by STAT3 co-deletion. FIG. 42A depicts FACS assays showing reversal of increased PD-L1+ cells in PDLIM2−/− BMDMs by STAT3 co-deletion (n=3). FIG. 42B depicts FACS assays showing reversal of increased PDLIM2−/− BMDMs suppression of CD8 T cell activation by STAT3 co-deletion (n≥2). Student's t test (two tailed, unpaired) was performed and data represent means±SEM. *P<0.05; **P<0.01.

Figure 43B:
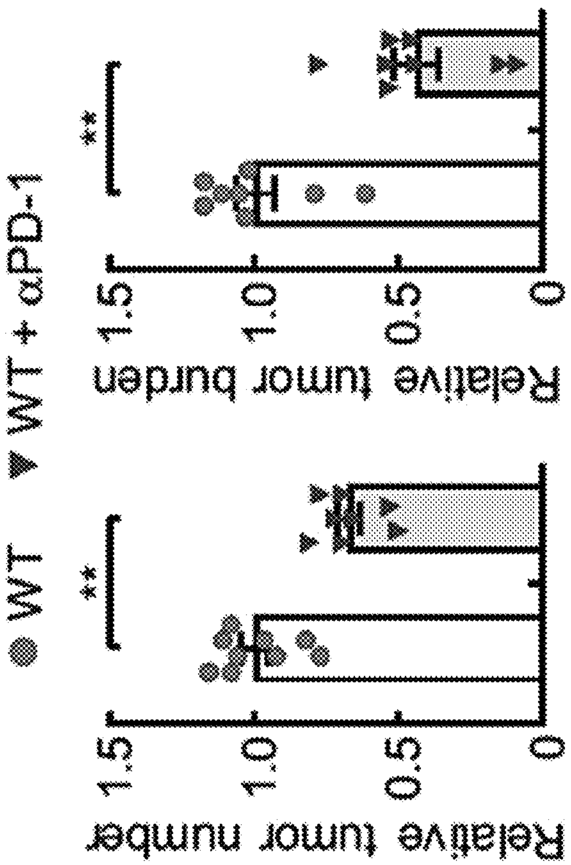
Figure 43A:
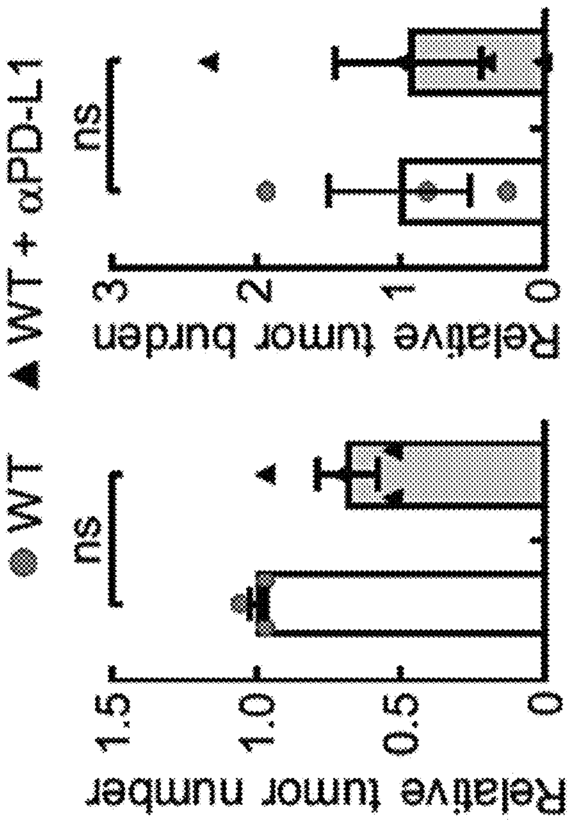

FIGS. 43A-43B show better efficacy of PD-1 antibody than PD-L1 antibody in lung cancer. FIG. 43A shows efficacy with PD-L1 antibody. FIG. 43B depicts efficacy with PD-1 antibody. Student's t test was performed (two tailed, unpaired) and data represent means±SEM in (n≥3). *P<0.05; **P<0.01; ns, not statistically significant.

Figure 44B:
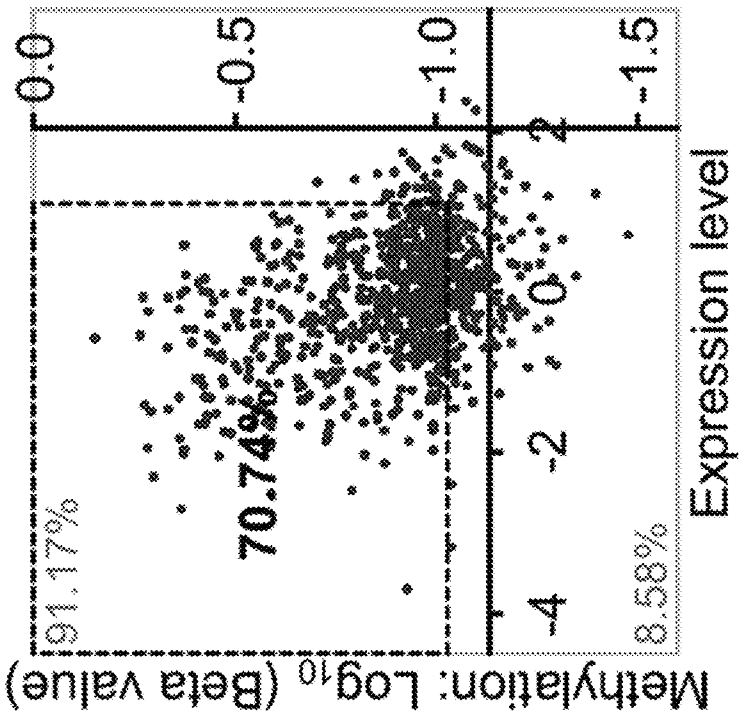
Figure 44A:
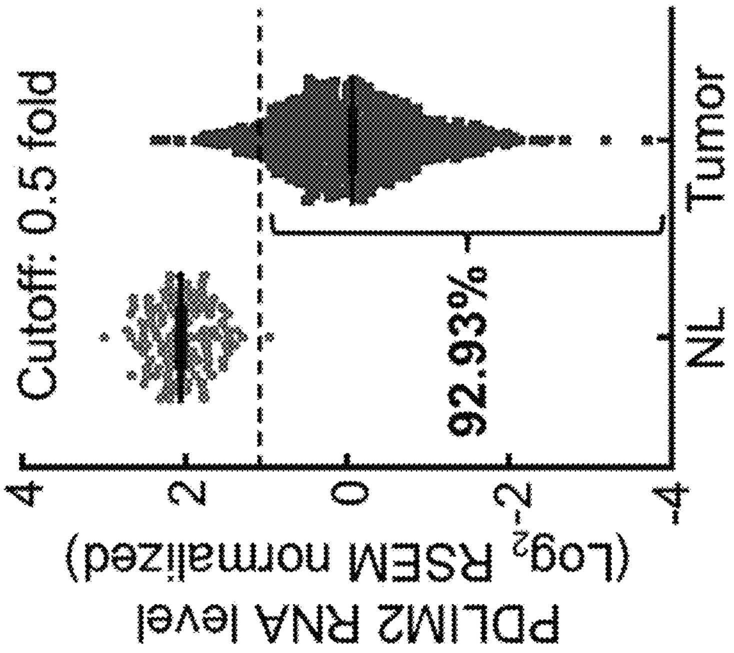
Figure 44C:
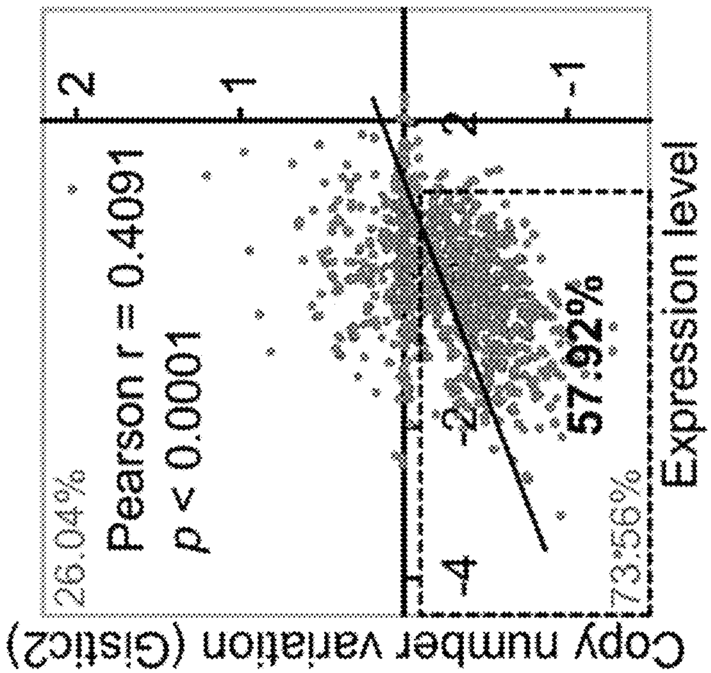
Figure 44D:
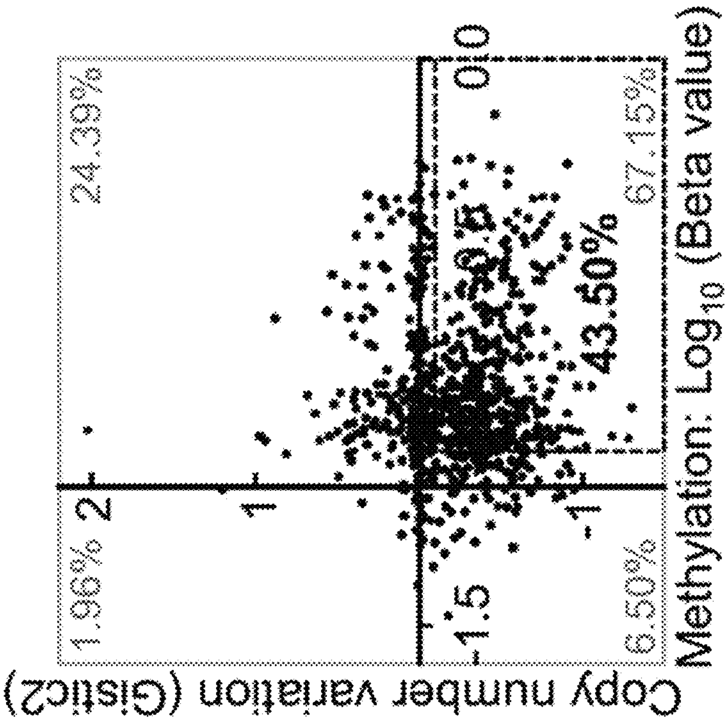
Figure 44E:
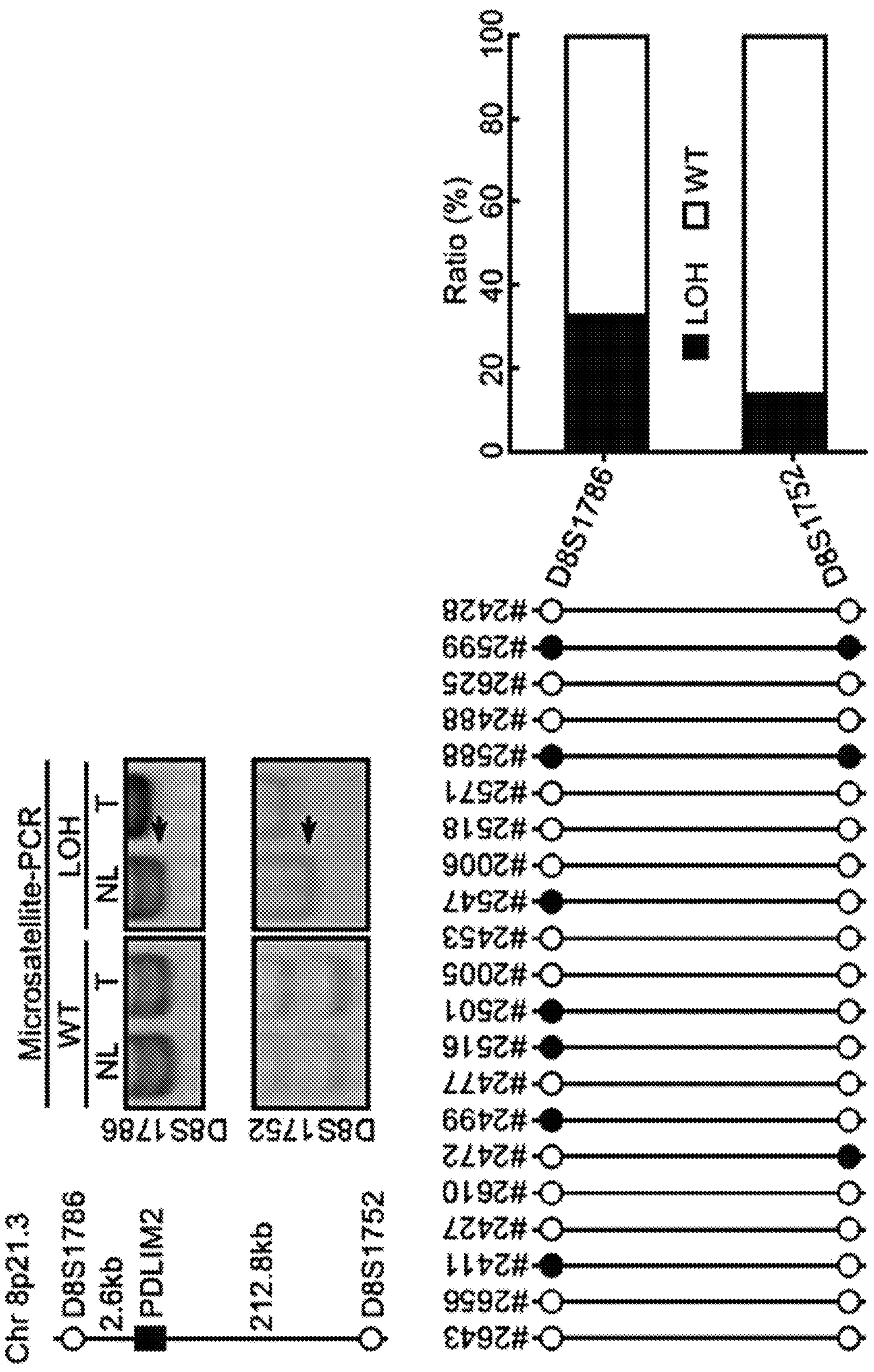
Figure 44F:
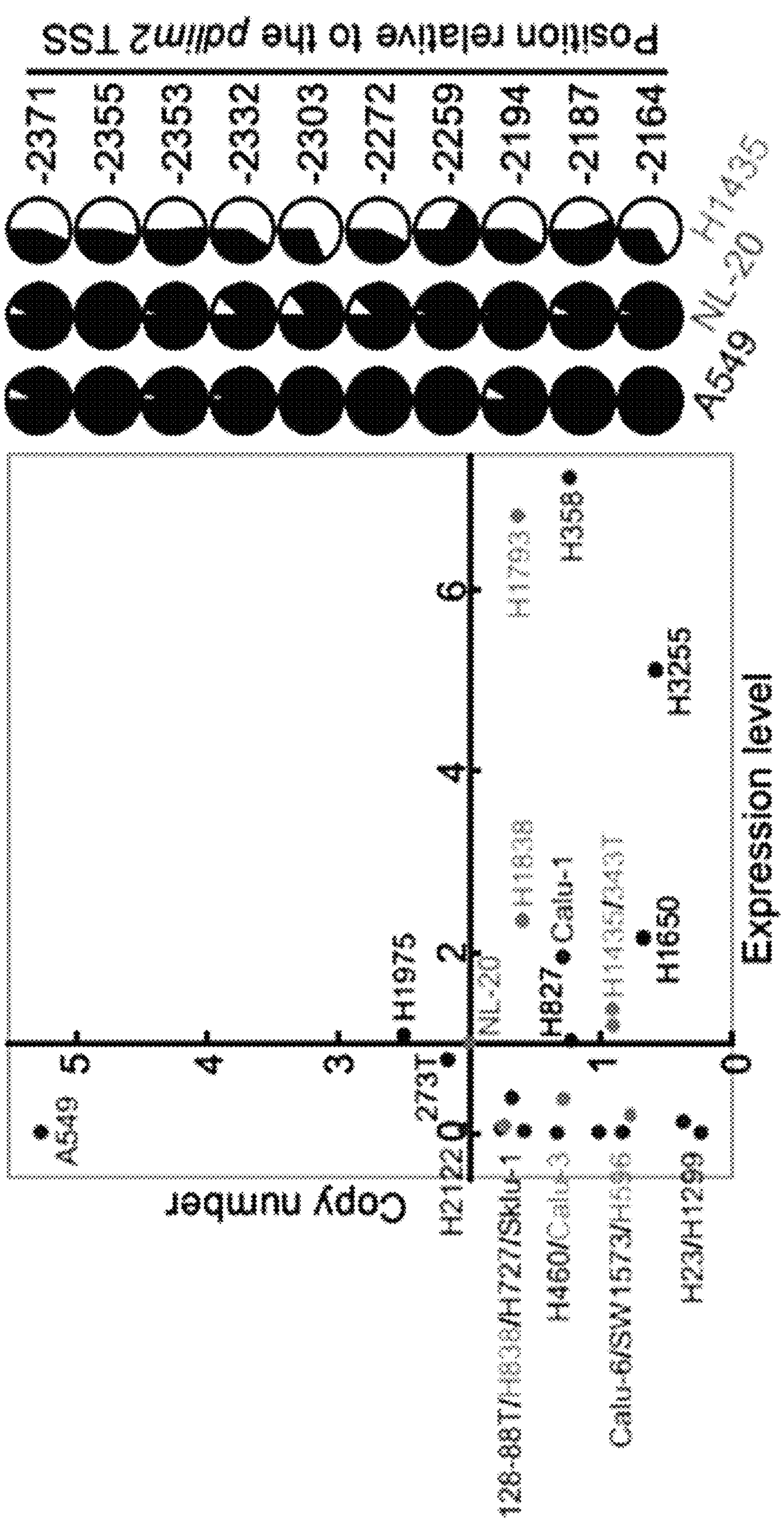

FIGS. 44A-44F show PDLIM2 repression in human lung cancers involves both epigenetic alteration and genetic deletion. FIG. 44A depicts TCGA data showing PDLIM2 repression in over 90% of lung cancers using 50% of the expression level in normal tissues as the cut-off. FIG. 44B depicts TCGA data showing pdlim2 promoter hypermethylation in over 70% of lung cancers using 125% of the methylation level in normal tissues as the cut-off. Dashed-box showing the percentage of the lung cancers with hypermethylated promoter and decreased RNA expression of PDLIM2. FIG. 44C depicts TCGA data showing positive associations between PDLIM2 expression and its gene copy numbers as well as PDLIM2 genetic deletion in about 58% of lung cancers using the copy number variation of −0.1 as the cut-off. Dashed-box showing the percentage of the lung cancers with genetic deletion and decreased RNA expression of PDLIM2. FIG. 44D depicts TCGA data showing simultaneous promoter hypermethylation and genomic deletion of PDLIM2 in about 44% of lung cancers. FIG. 44E depicts microsatellite-PCR showing pdlim2 loss in human lung cancers. FIG. 44F depicts qPCR showing pdlim2 loss in human lung cancer cell lines with known copy number of the pdlim2 gene and bisulfite genomic DNA sequencing showing the methylation status of the pdlim2 promoter in the normal human lung epithelial cell line NL-20 and lung cancer cell lines A549 and H1435 respectively with hyper- and hypo-methylated pdlim2 promoter. Each circle represents a CpG site. Ratio of the filled area represents the methylation percentile. The position of each CpG nucleotide relative to the pdlim2 transcription start site (TSS) (+1) is indicated at the right.

Figure 45A:
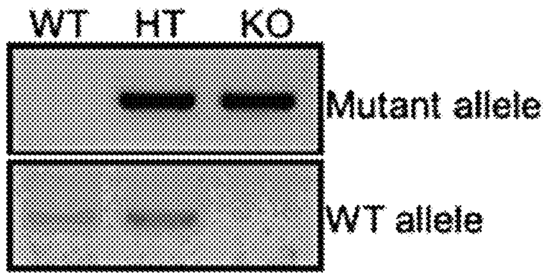
Figure 45B:
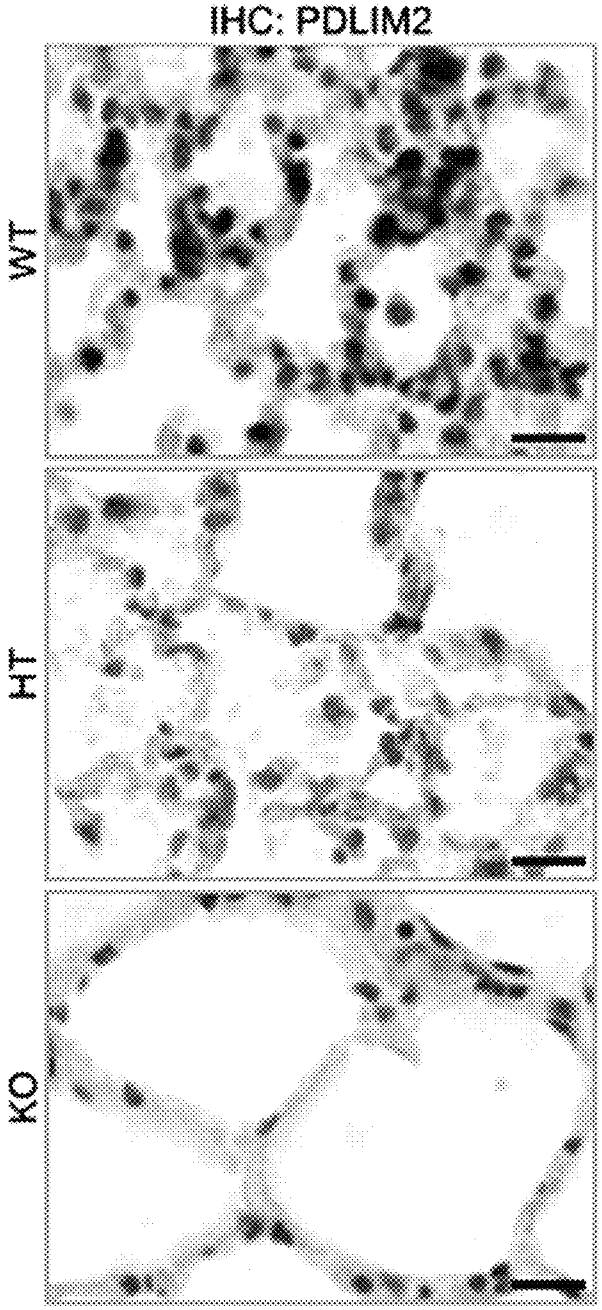
Figure 45C:
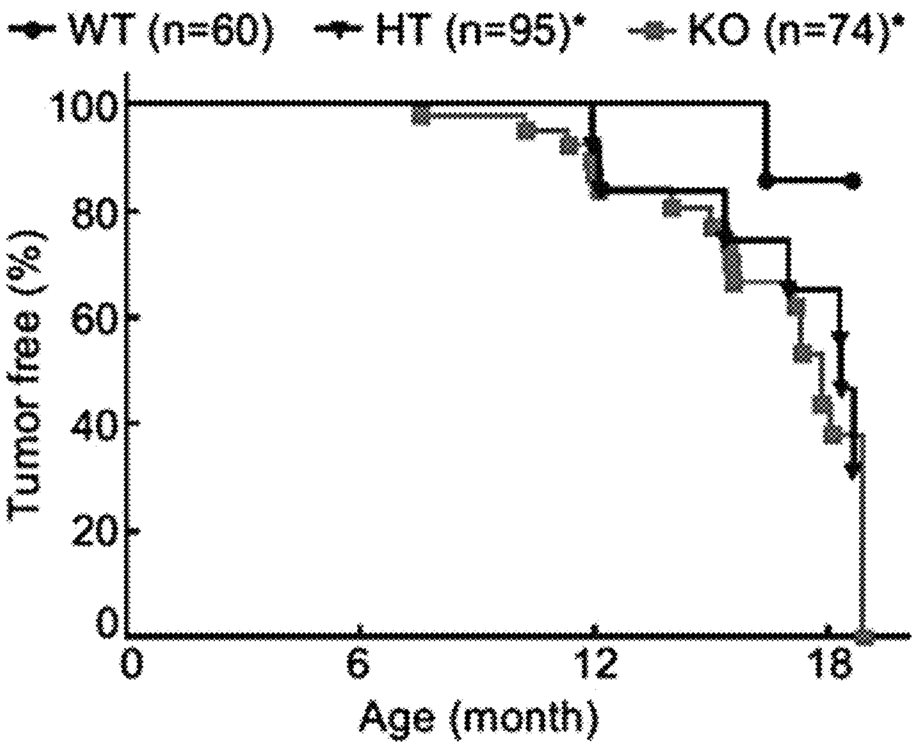
Figure 45D:
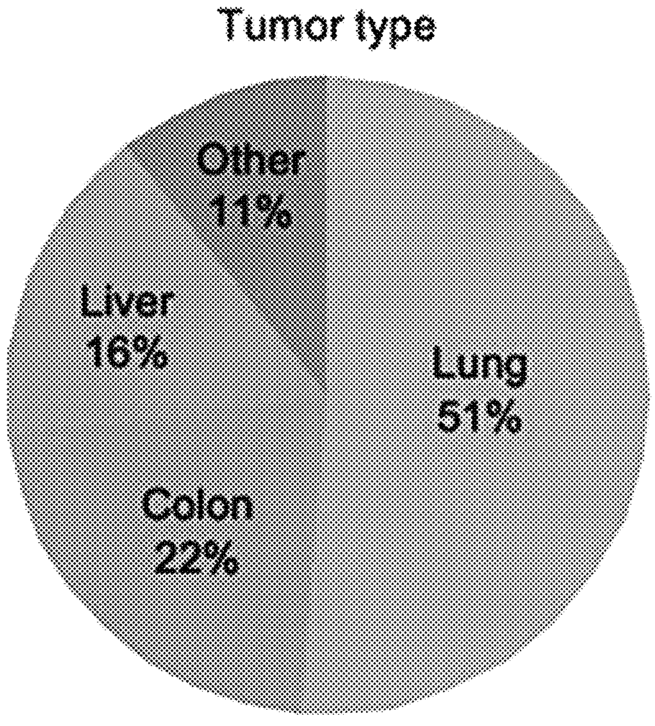
Figure 45E:
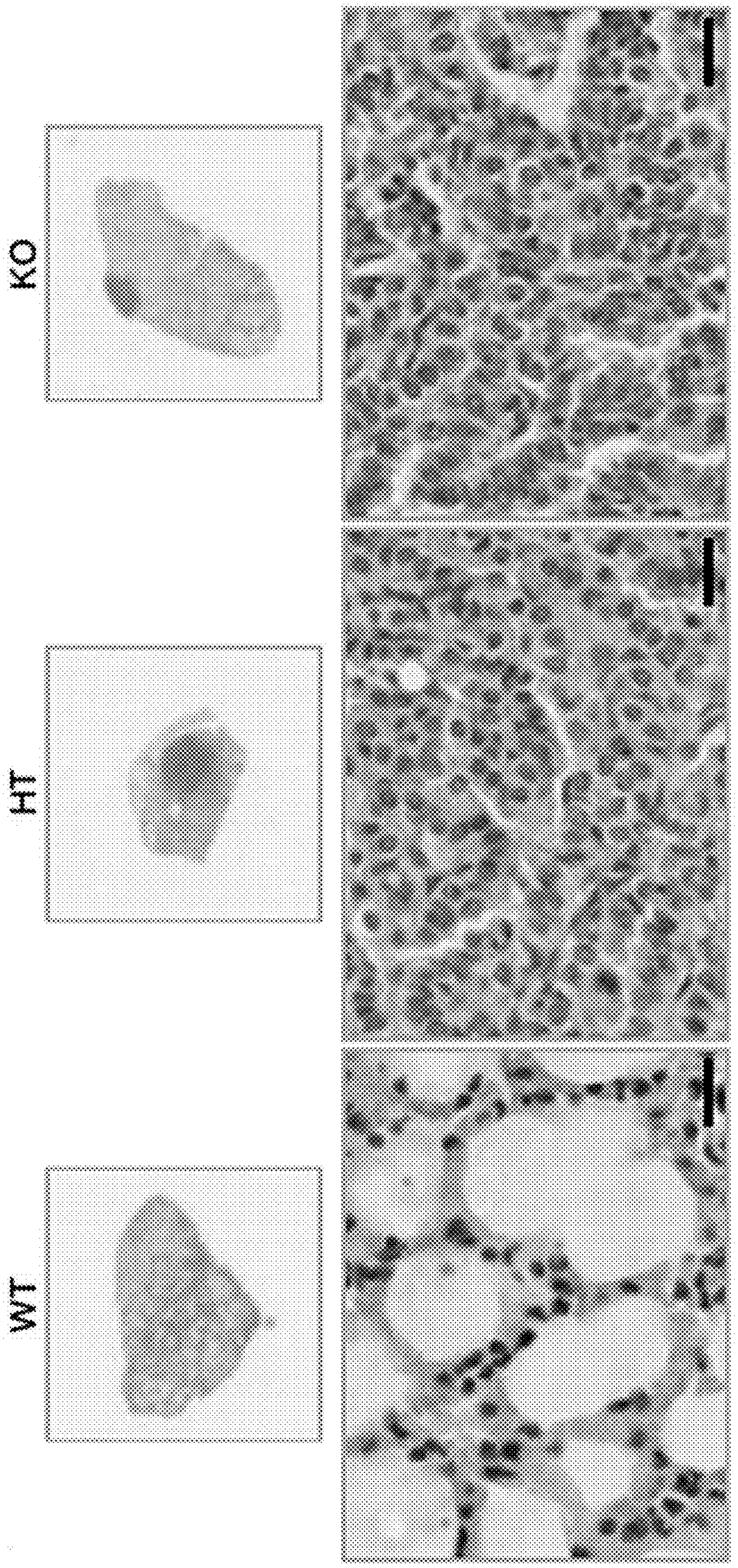

FIGS. 45A-45E show PDLIM2 heterozygous deletion in mice causes spontaneous tumors and lung cancer in particular. FIG. 45A depicts genomic DNA PCR assays showing PDLIM2 hetero- and homo-zygous deletion in PDLIM2+/− (HT) and PDLIM2−/− (KO) mice, respectively. Wild type (WT, PDLIM2+/+) mice were used as a control. FIG. 45B IHC assays showing decreased and complete loss of PDLIM2 protein expression in the lungs of PDLIM2+/− and PDLIM2−/− mice, respectively. Scale bar, 20 μm. FIG. 45C Kaplan-Meier tumor-free survival curve showing increased spontaneous tumors in PDLIM2−/− and PDLIM2+/− mice compared to WT mice. Gehan-Breslow-Wilcoxon test was performed. *p<0.05. FIG. 45D percentage of tumor types spontaneously developed in PDLIM2+/− mice showing a majority of lung tumors. FIG. 45E depicts H&E staining of the lung tissues and/or spontaneous lung tumors of PDLIM2+/+, PDLIM2+/− and PDLIM2−/− mice. Scale bar in FIGS. 45B and 45E, 20 μm.

Figure 46A:
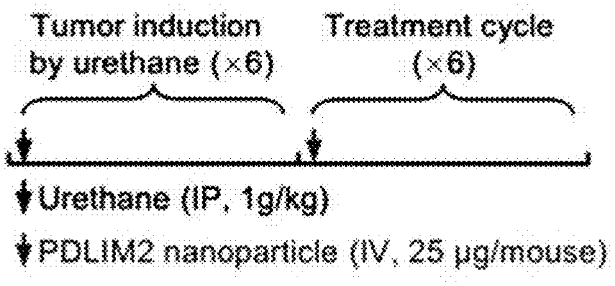
Figure 46B:
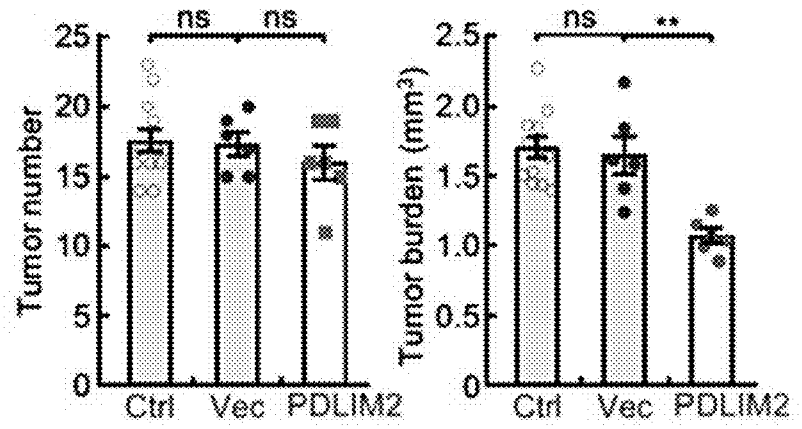
Figure 46C:
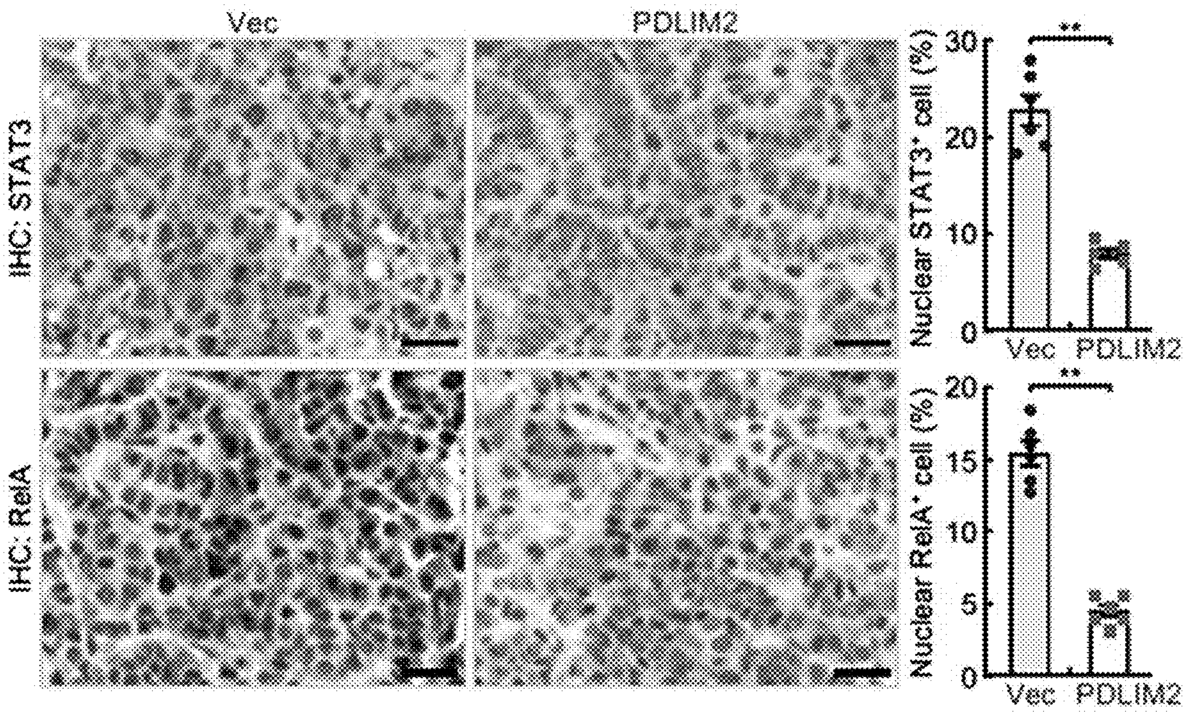
Figure 46D:
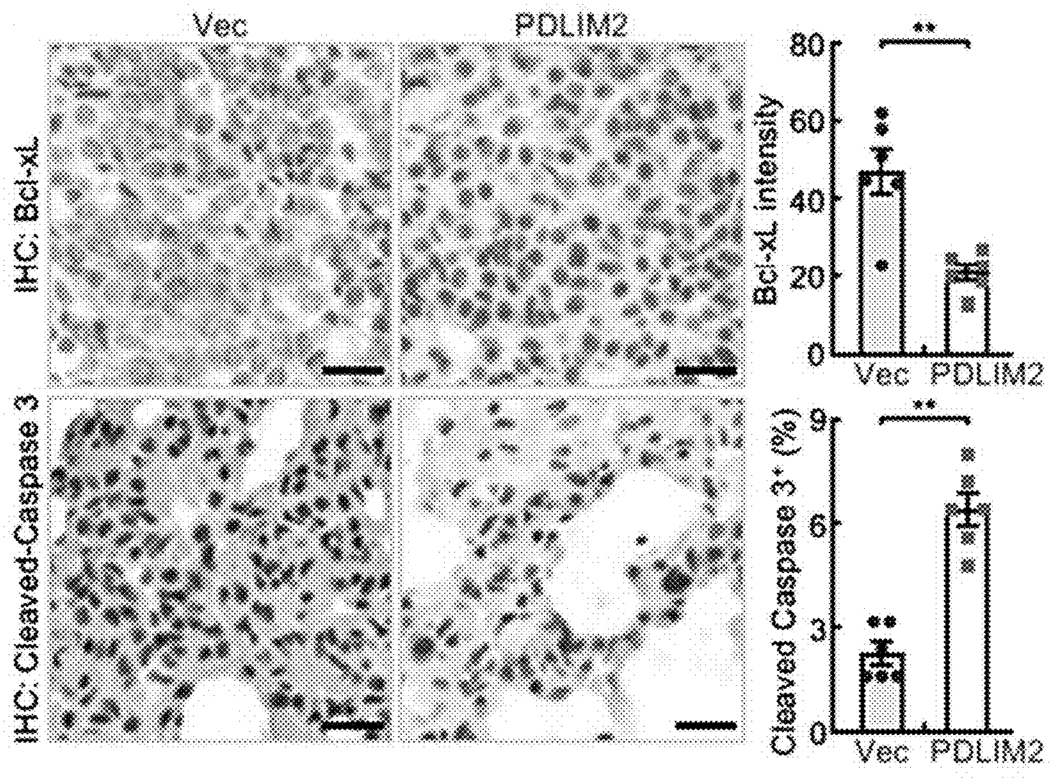
Figure 46E:
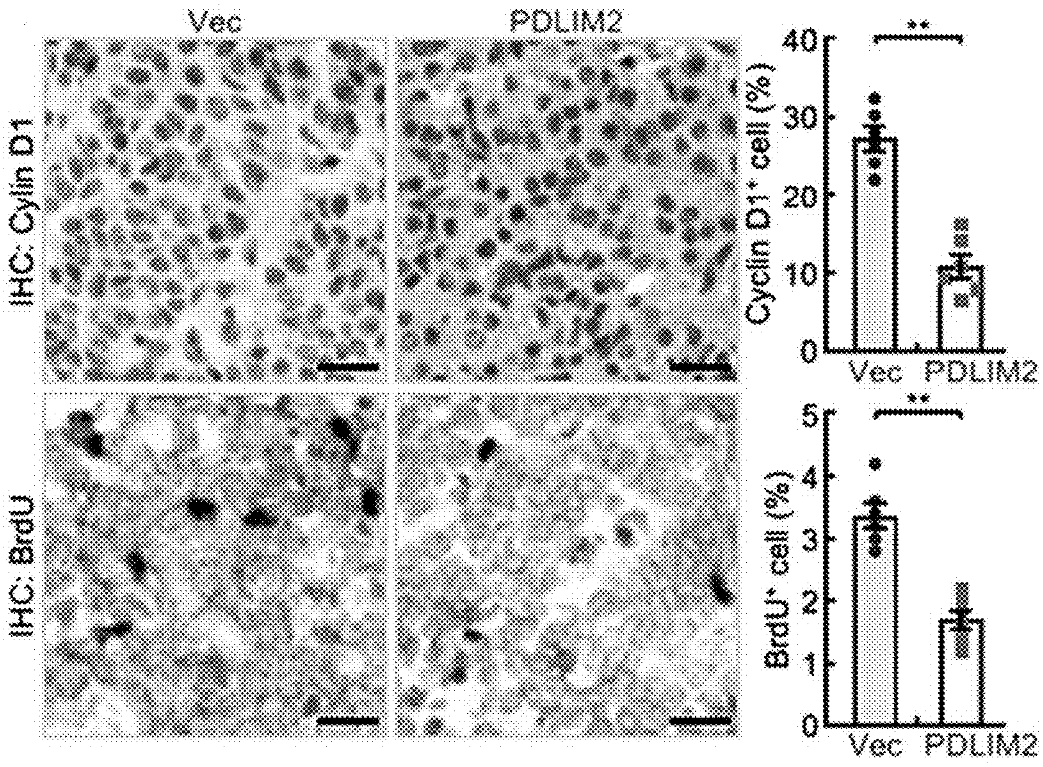

FIGS. 46A-46E show systemic administration of PDLIM2 plasmid nanoparticles with efficacy in mouse model of refractory lung cancer. FIG. 46A depicts schedule of lung cancer induction and treatment. FIG. 46B depicts urethane model showing efficacy of intravenous administration of PDLIM2 plasmid nanoparticles in refractory lung cancer. Nanoparticles with an empty plasmid that was employed to express PDLIM2 were used as a control (Vec). FIG. 46C depicts IHC staining showing decreased nuclear expression of STAT3 and RelA in lung tumors by PDLIM2 nanotherapy. FIG. 46D depicts IHC staining showing decreased Bcl-xL and increased apoptosis in lung tumors by PDLIM2 nanotherapy. FIG. 46E depicts IHC staining showing decreased Cyclin D1 and proliferation in lung tumors by PDLIM2 nanotherapy. Scale bar in FIGS. 46C and 46E, 20 μm. Student's t test was performed (two tailed, unpaired) and data represent means±SEM in FIGS. 46B and 46E. **p<0.01; ns, not statistically significant.

Figure 47A:
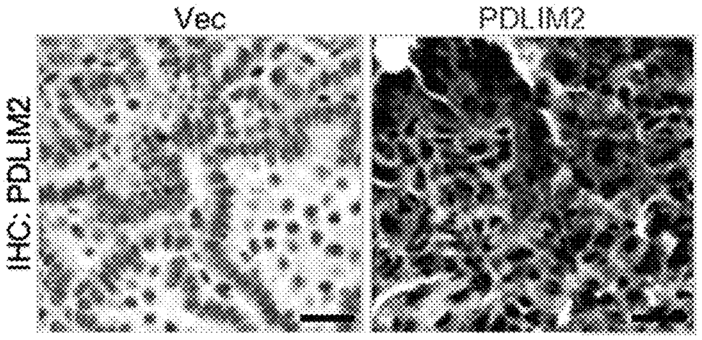
Figure 47B:
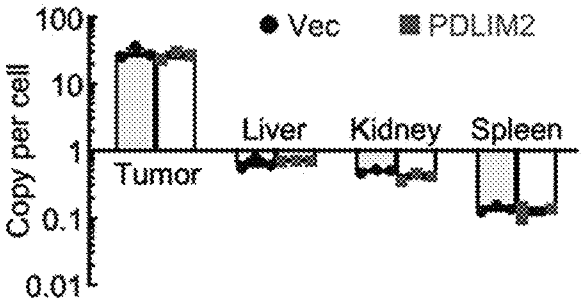
Figure 47C:
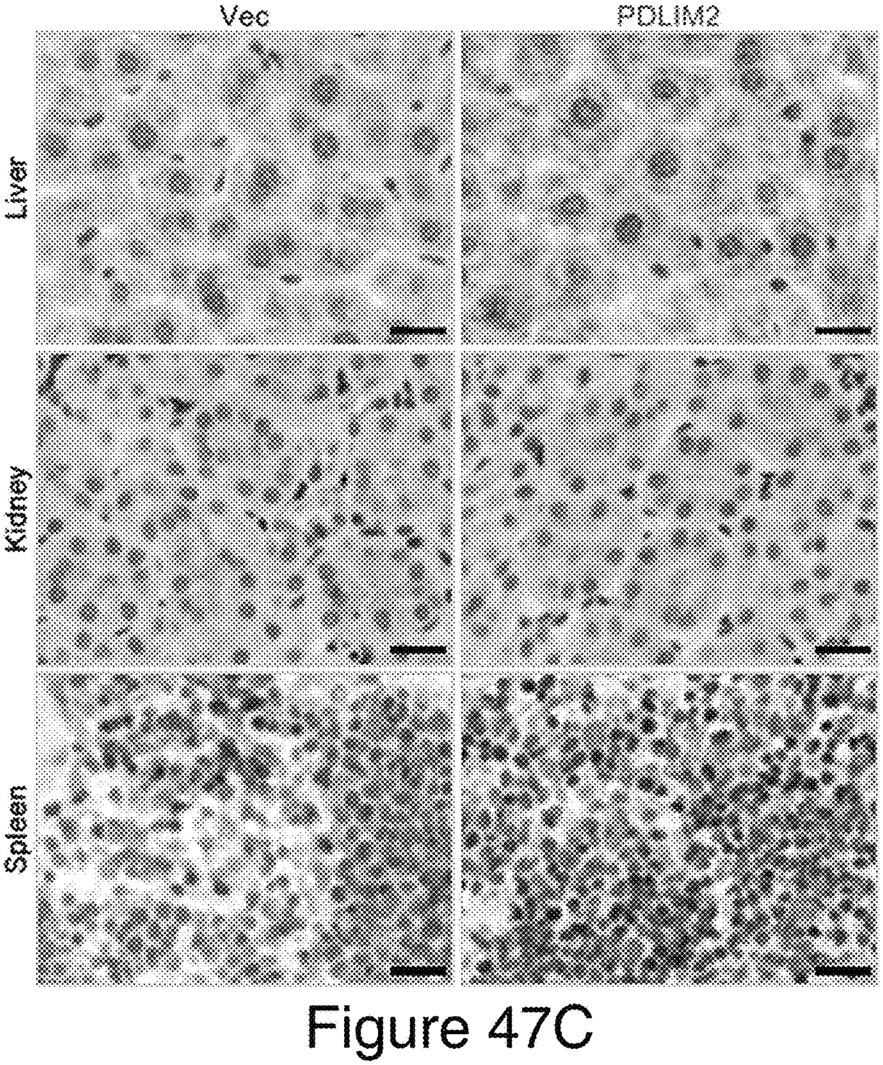
Figure 47D:
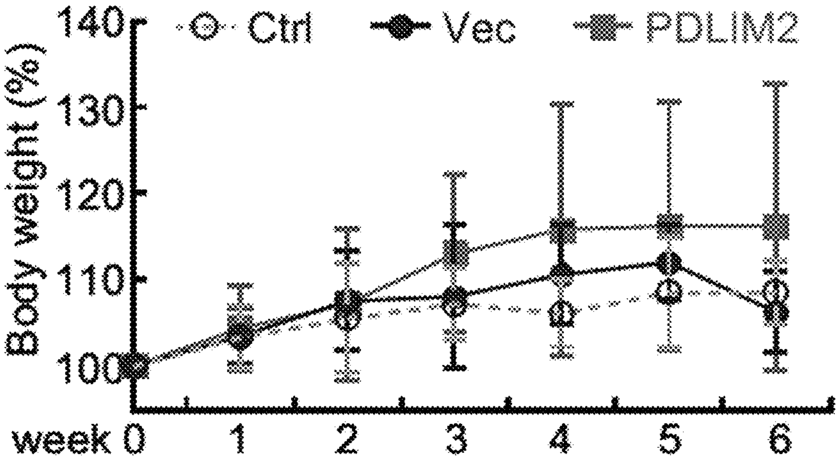
Figure 47E:
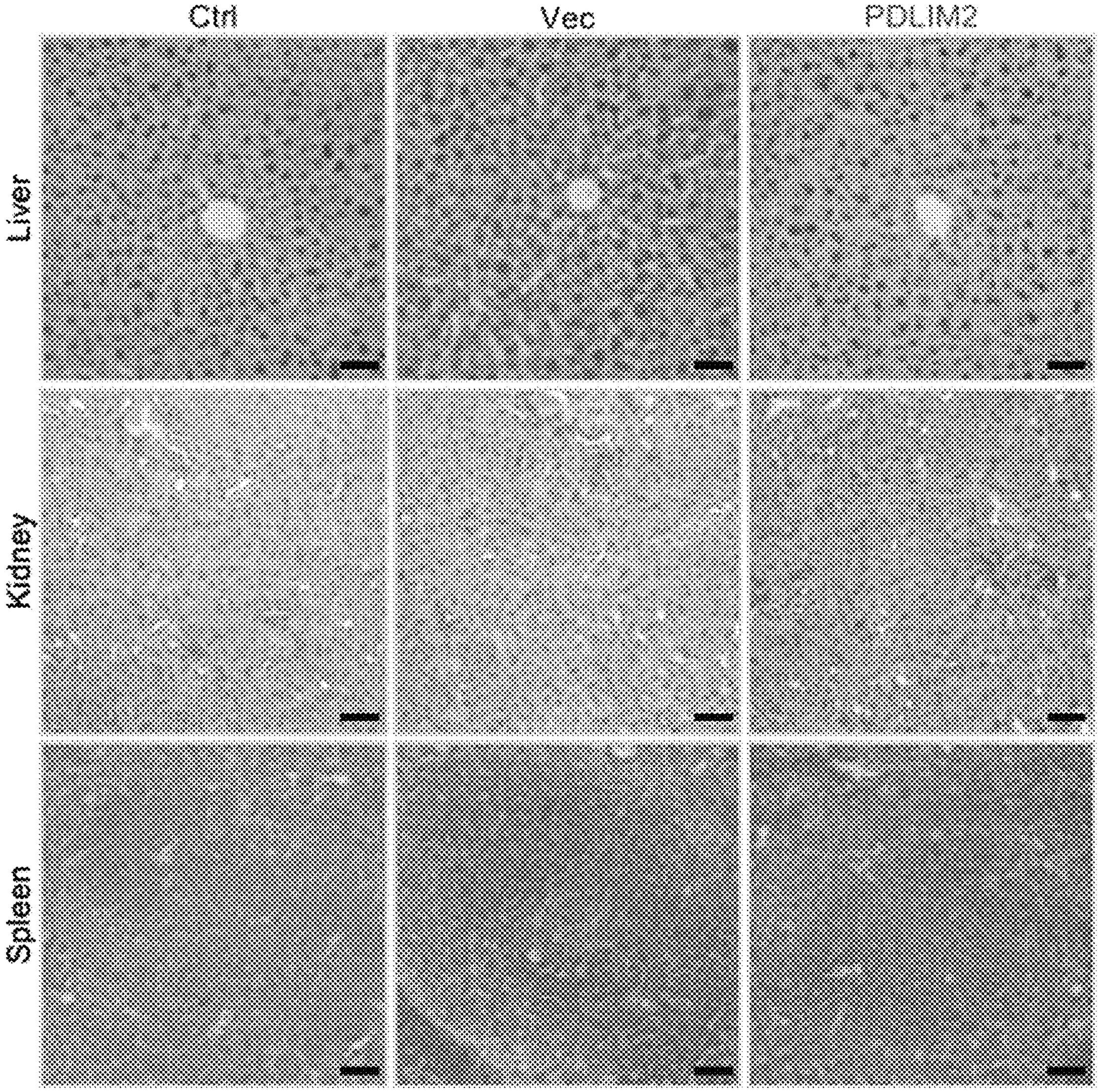

FIGS. 47A-47E show PDLIM2 nanotherapy with high tumor specificity and low toxicity. FIG. 47A depicts IHC staining showing high PDLIM2 re-expression in lung tumors after PDLIM2 nanotherapy. FIG. 47B depicts PCR assays showing lung tumor-specific delivery of plasmids by nanoparticles. FIG. 47C depicts IHC staining showing comparable expressions of PDLIM2 in the indicated tissues of mice treated with PDLIM2 expression plasmid or empty plasmid nanoparticles. FIG. 47D shows no significant changes in animal body weight by PDLIM2 nanotherapy. FIG. 47E depicts H&E staining showing no noticeable changes in major organs by PDLIM2 nanotherapy. Scale bar in FIGS. 47A and 47C, 20 μm; in FIG. 47E, 50 μm.

Figure 48A:
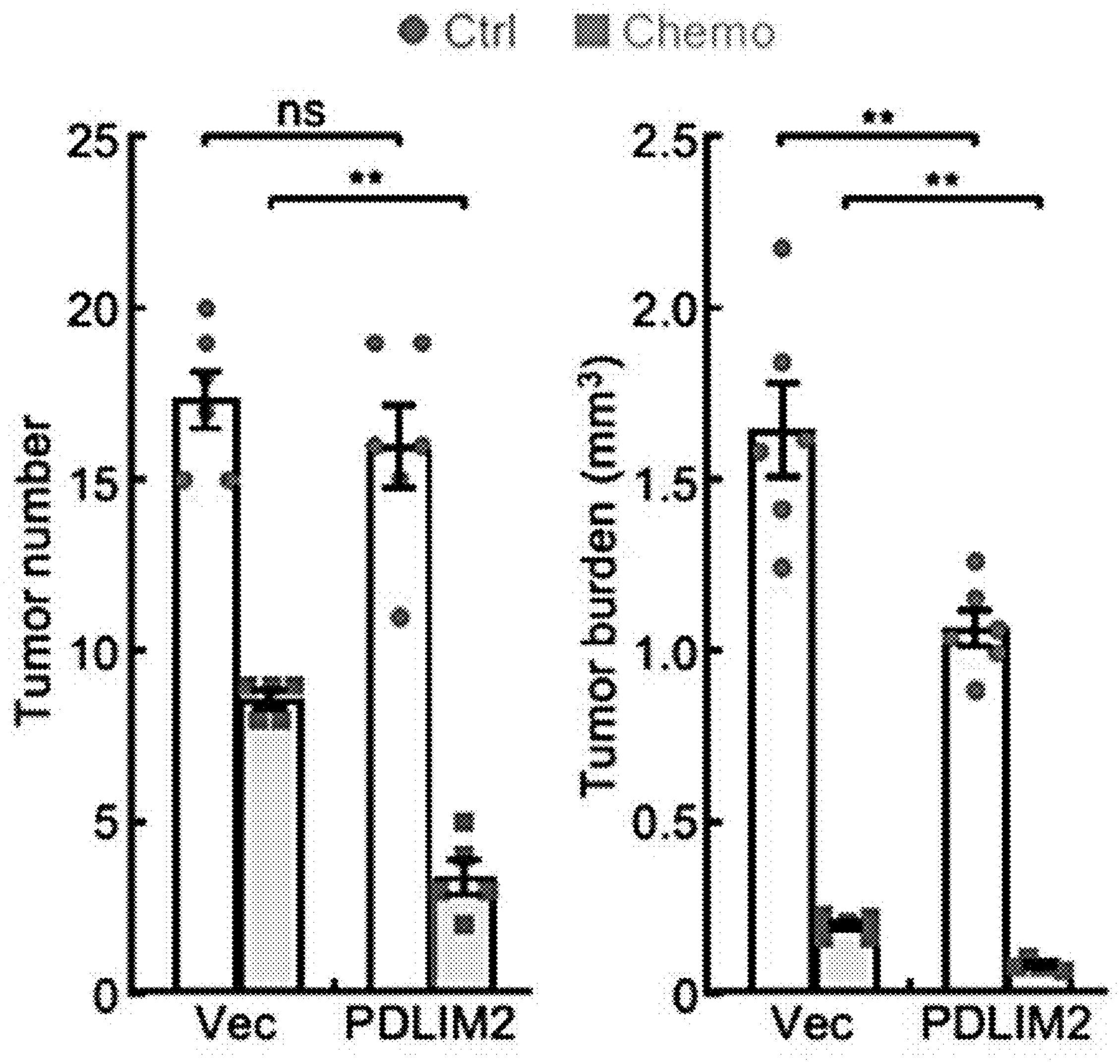
Figure 48B:
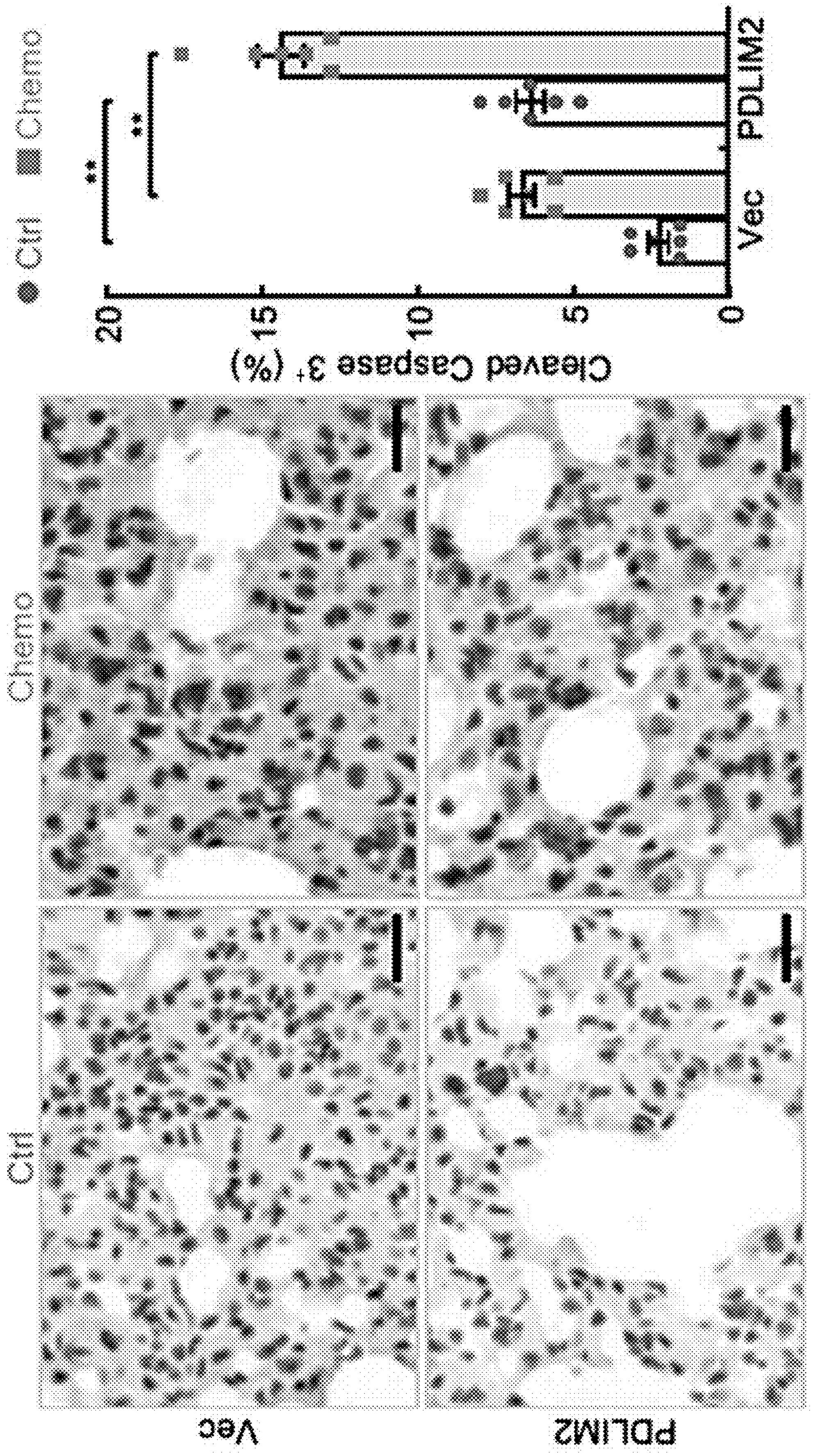
Figure 48C:
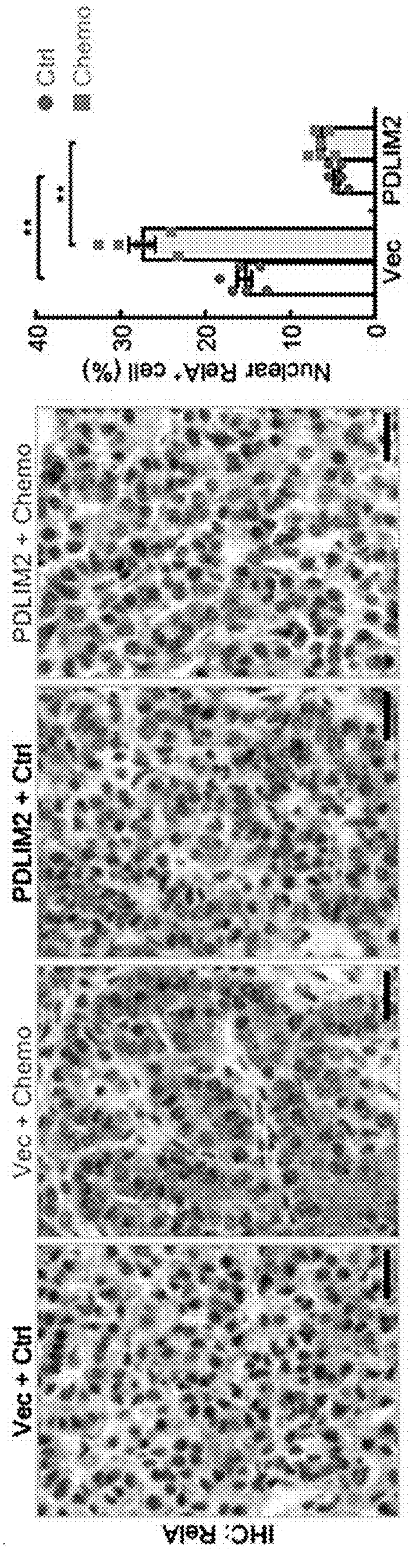
Figure 48D:
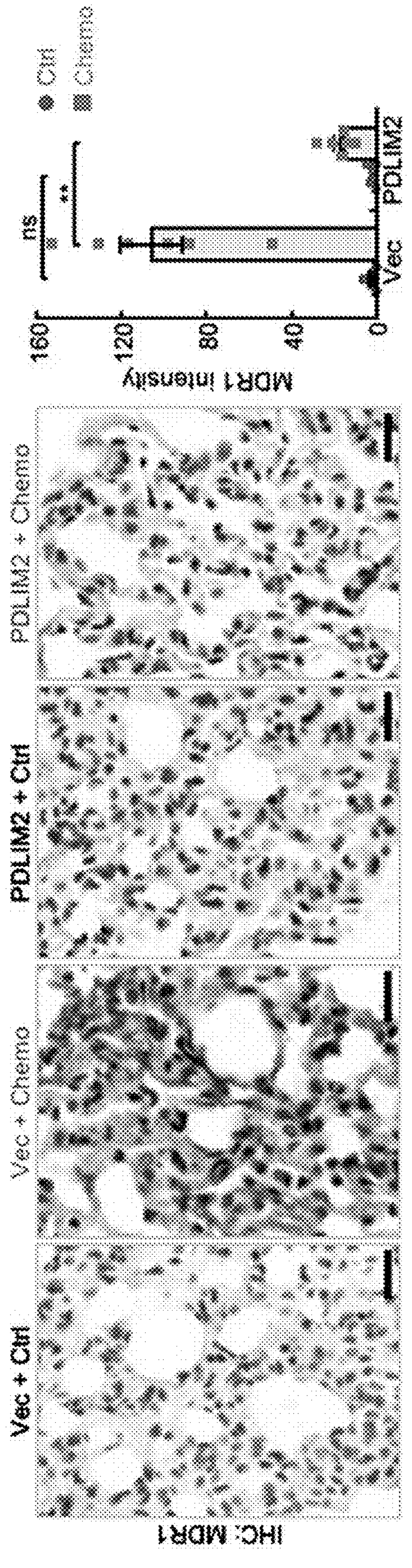

FIGS. 48A-48D show PDLIM2 nanotherapy renders lung cancers much more vulnerable to chemotherapy. FIG. 48A depicts urethane model showing high synergy of PDLIM2 nanotherapy and chemotherapy in lung cancer treatment. FIG. 48B depicts IHC staining showing increased lung cancer cell apoptosis by the combination of PDLIM2 nanotherapy and chemotherapy. FIG. 48C depicts IHC staining showing RelA activation by chemotherapy and blockage of chemo activation of RelA by PDLIM2 nanotherapy. FIG. 48D depicts IHC staining showing strong MDR1 induction by chemotherapy and blockage of MDR1 induction by PDLIM2 nanotherapy. Scale bar in FIG. 48B-48C, 20 Student's t test was performed (two tailed, unpaired) and data represent means±SEM. **p<0.01; ns, not statistically significant.

Figure 49A:
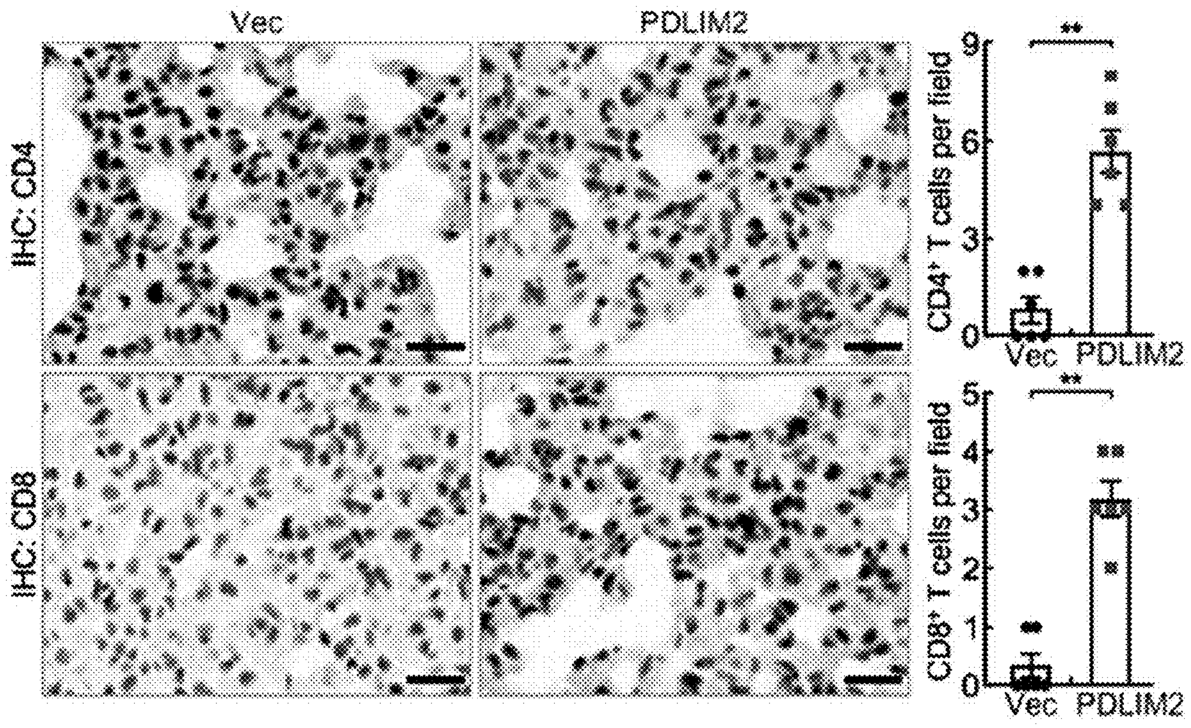
Figure 49B:
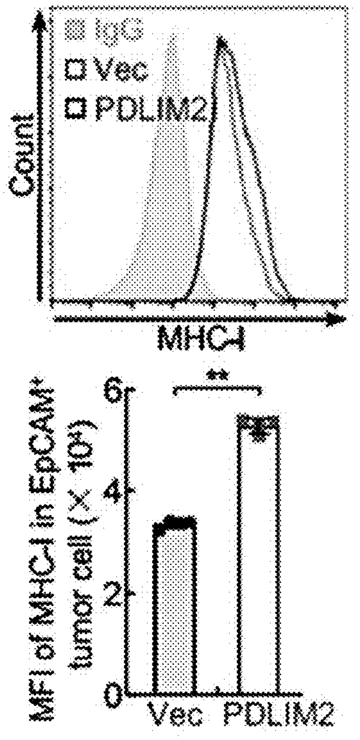
Figure 49C:
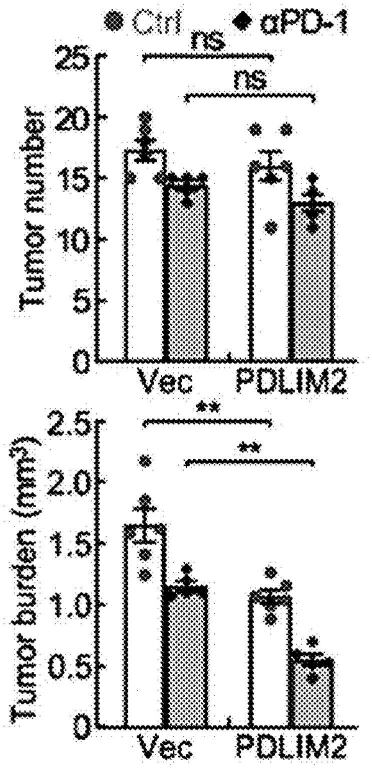
Figure 49D:
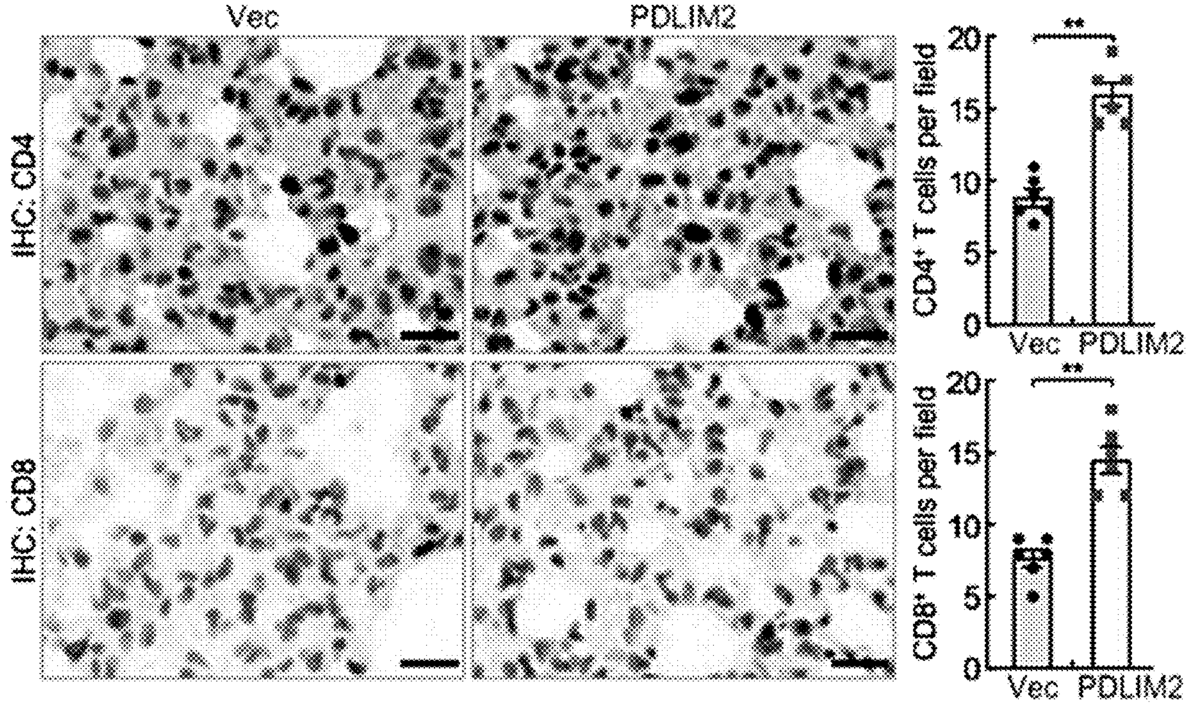
Figure 49E:
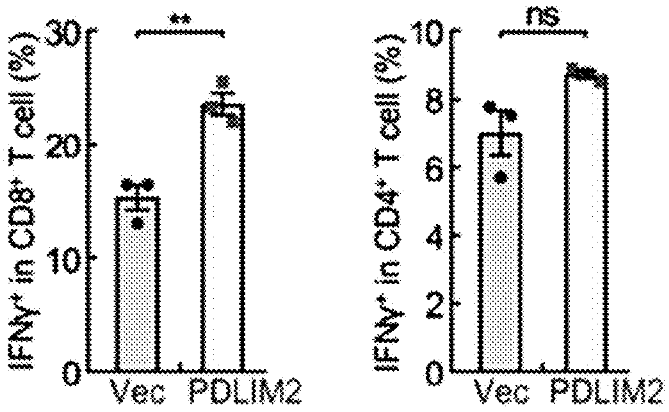
Figure 49F:
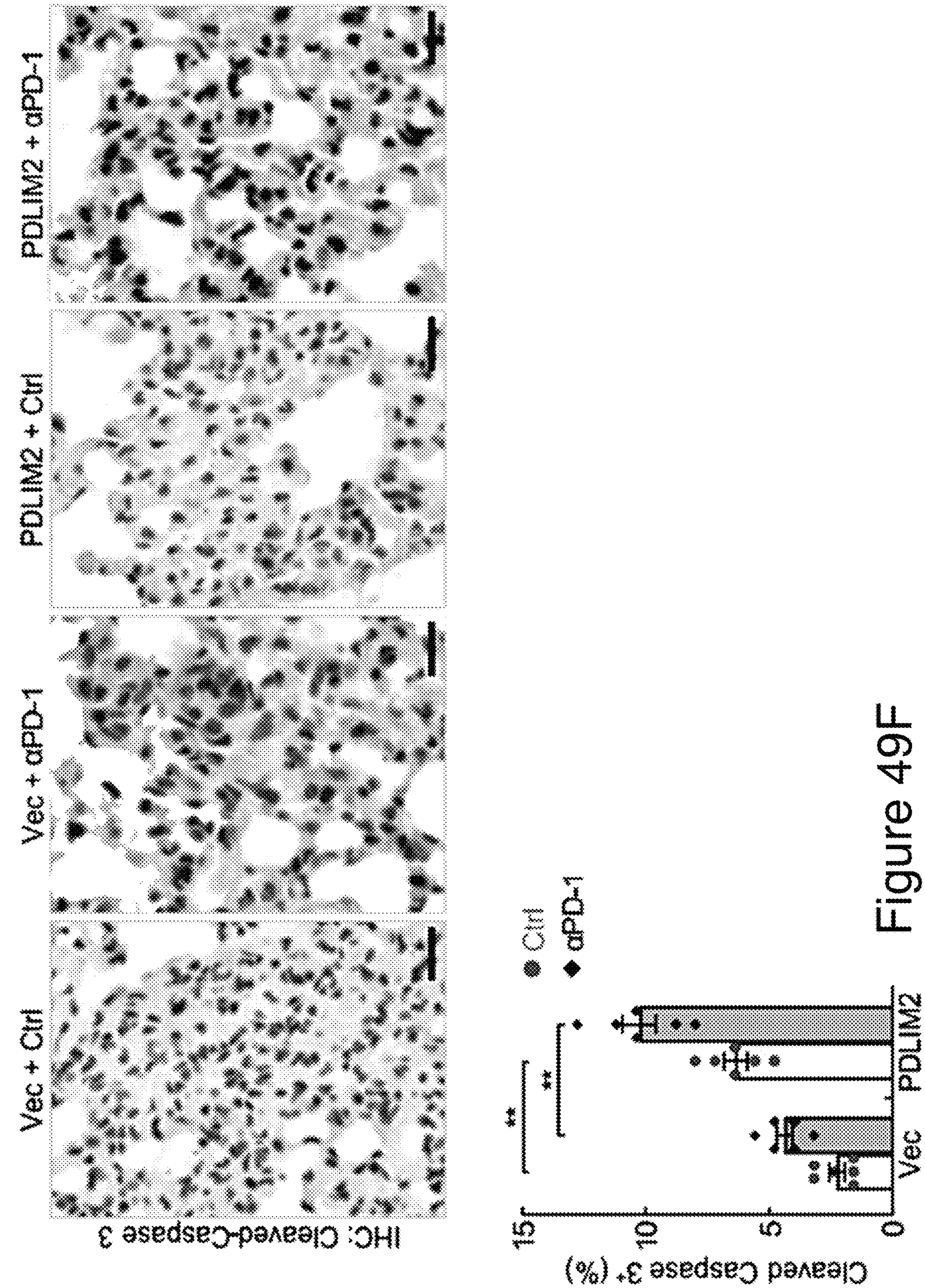

FIGS. 49A-49F show that PDLIM2 nanotherapy increases the efficacy of PD-1 blockade immunotherapy in refractory lung cancer. FIG. 49A depicts IHC staining showing an increase in TILs in lung tumors by PDLIM2 nanotherapy. FIG. 49B depicts FACS showing an increase in MHC-I in lung tumors by PDLIM2 nanotherapy. FIG. 49C depicts urethane model showing moderate synergy of PDLIM2 nanotherapy and PD-1 immunotherapy in lung cancer treatment. FIG. 49D depicts IHC staining showing increased TILs by the combination of PDLIM2 nanotherapy and immunotherapy. FIG. 49E depicts FACS showing increased activation of CD8+ T cells by the combination of PDLIM2 nanotherapy and immunotherapy. FIG. 49F depicts IHC staining showing increased tumor cell apoptosis by the combination of PDLIM2 nanotherapy and immunotherapy. Scale bar in FIGS. 49A, 49D and 49F, 20 μm. Student's t test was performed (two tailed, unpaired) and data represent means±SEM. **p<0.01; ns, not statistically significant.

Figure 50A:
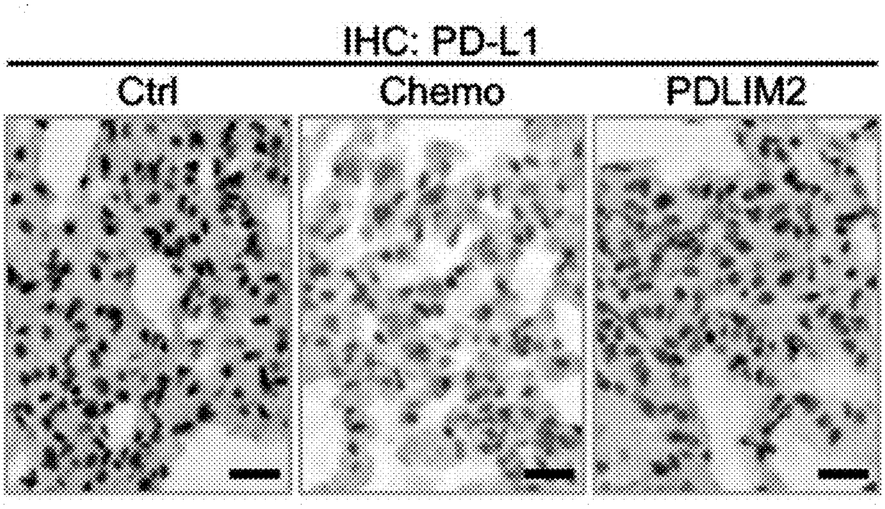
Figure 50B:
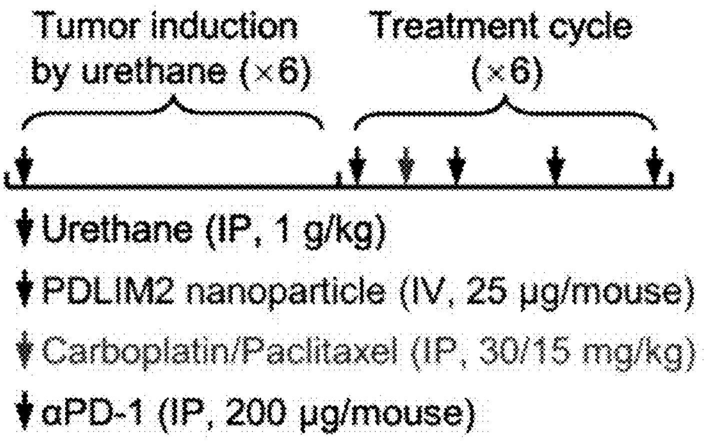
Figure 50C:
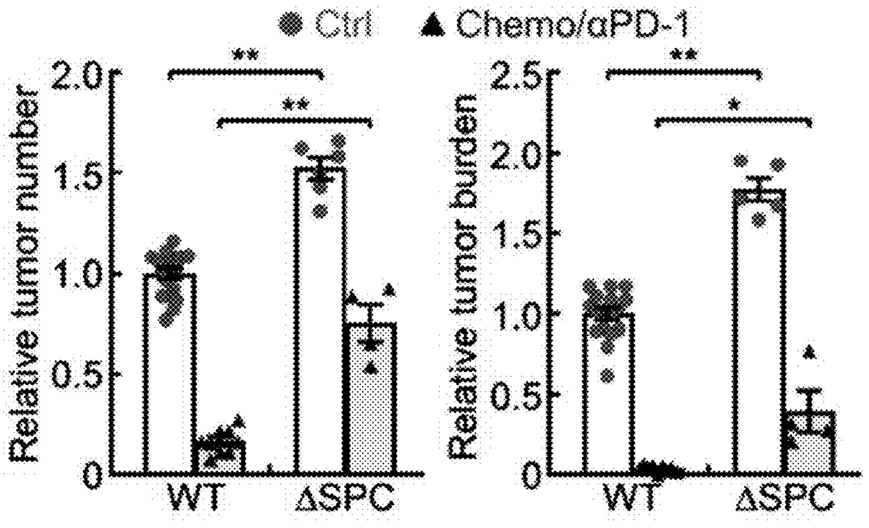
Figure 50D:
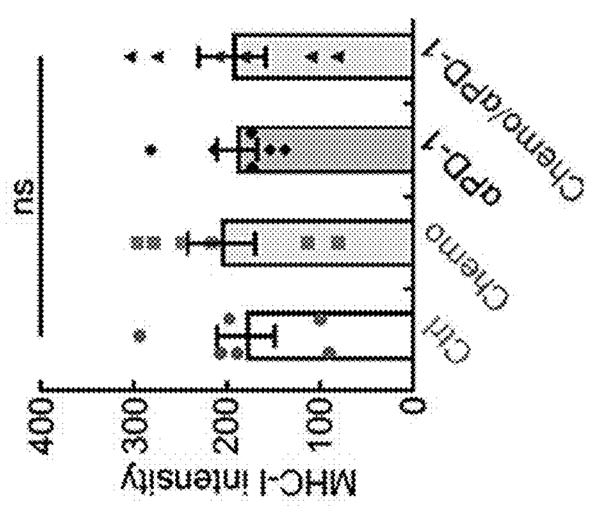
Figure 50E:
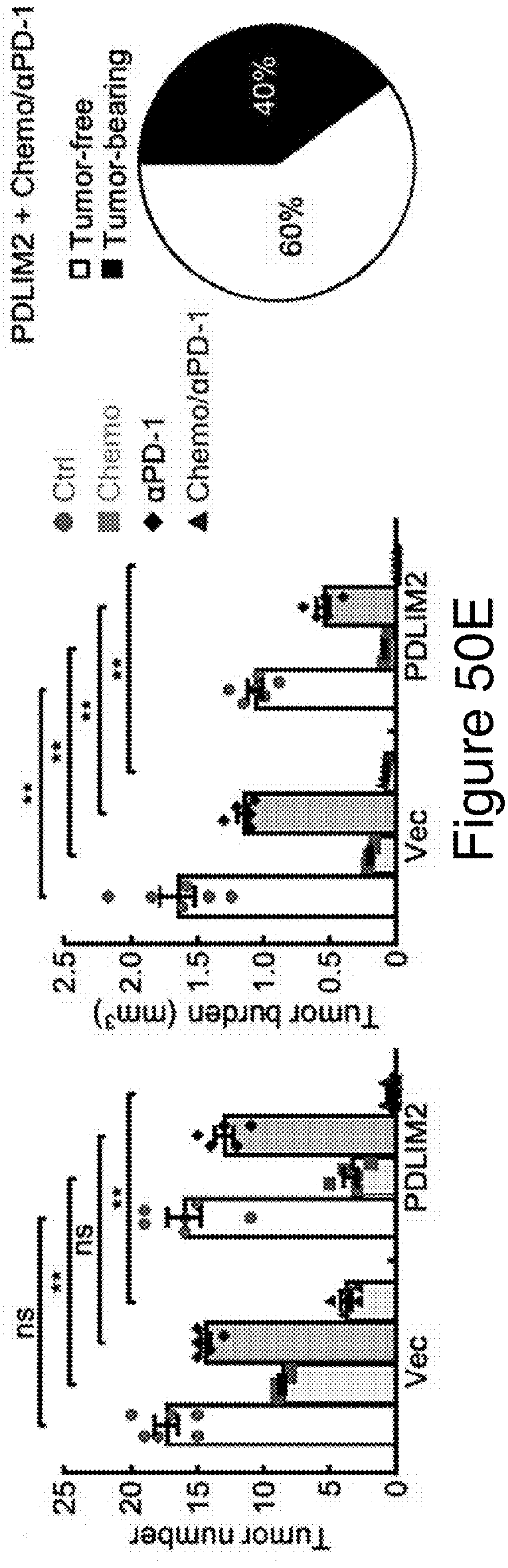
Figure 50F:
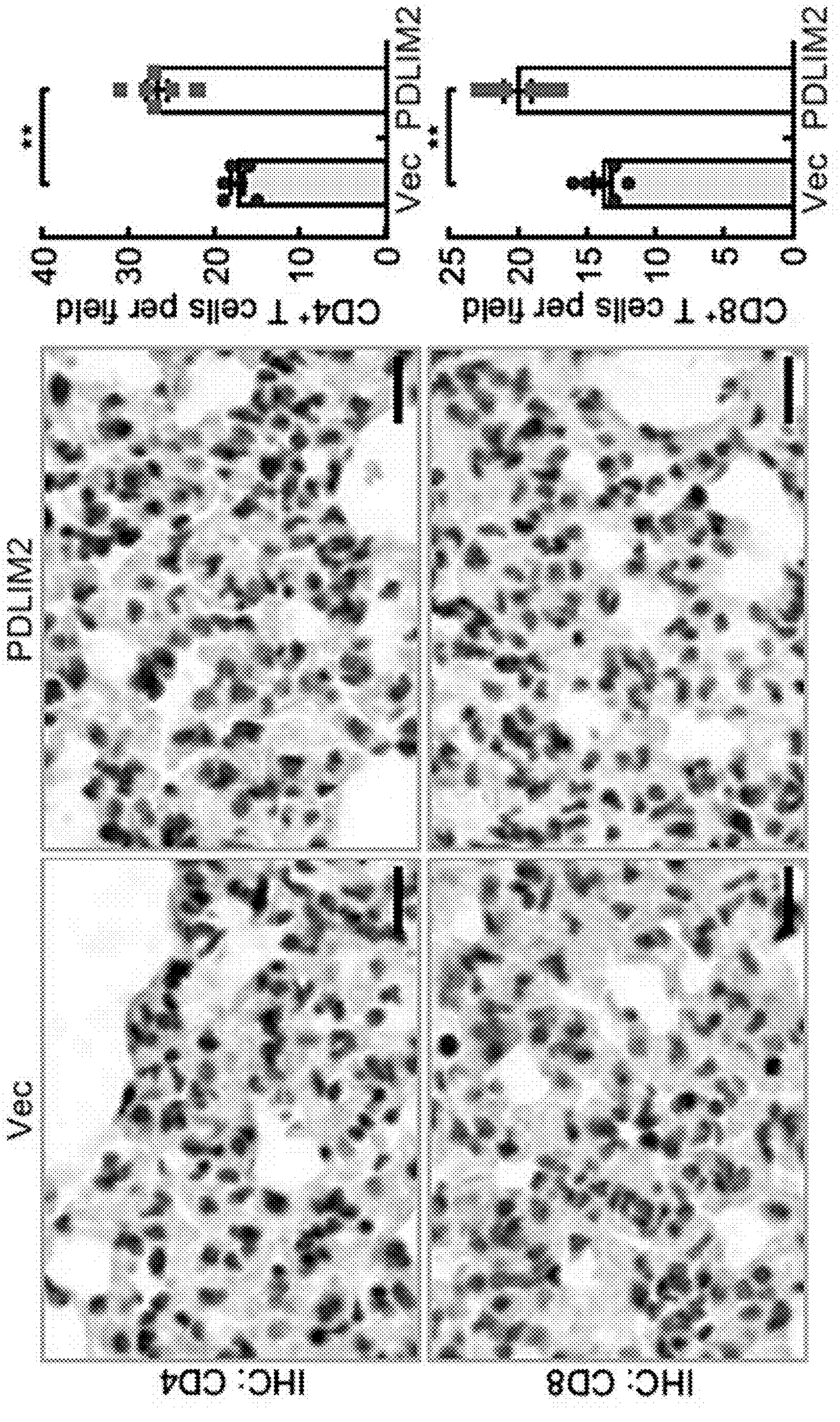
Figure 50G:
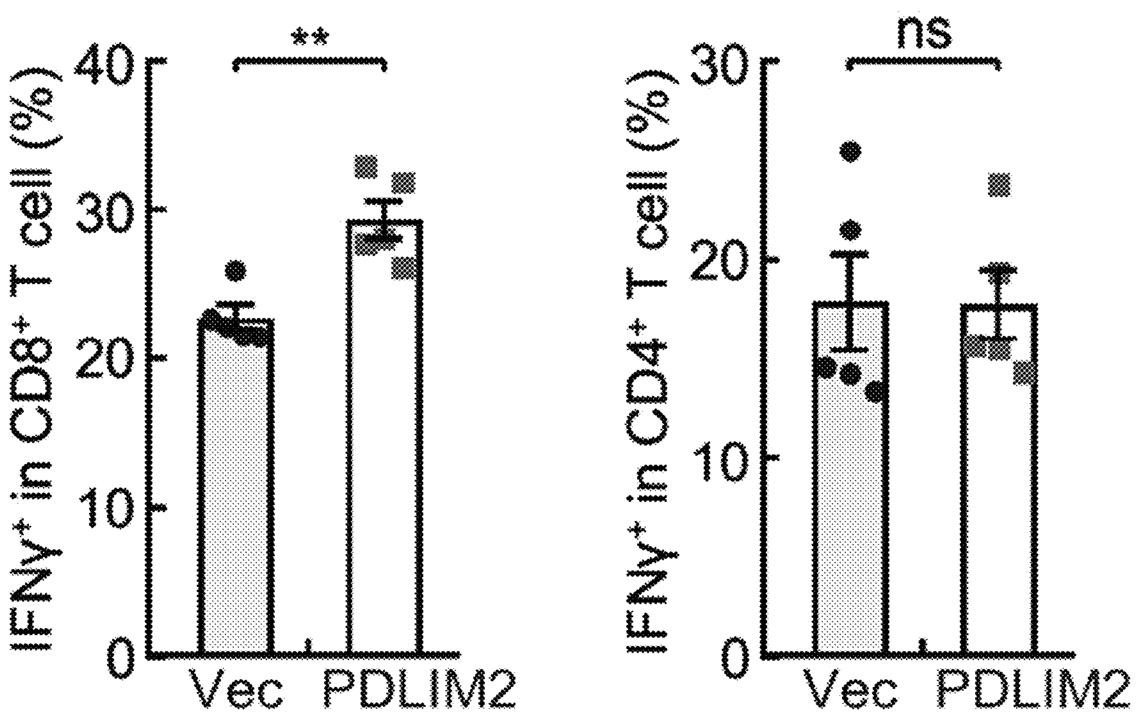
Figure 50H:
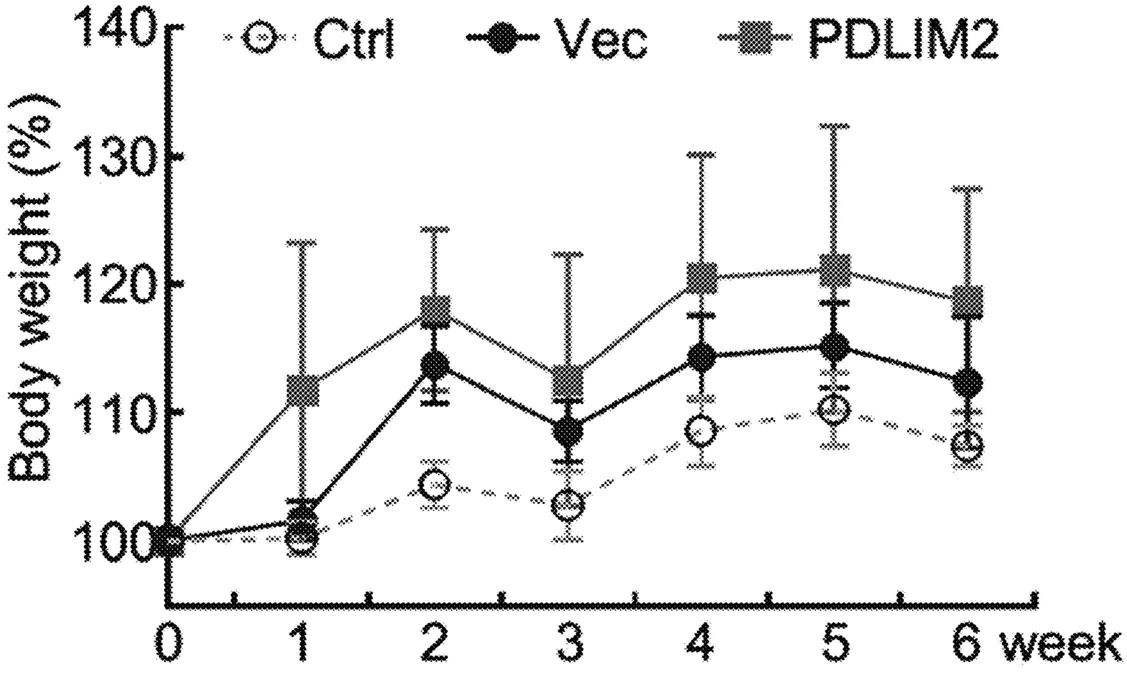

FIGS. 50A-50H show that the combination treatment of PDLIM2 nanotherapy and chemotherapy and immunotherapy induces complete remission of all lung cancers in most animals. FIG. 50A depicts IHC staining PD-L1 induction by chemotherapy but not PDLIM2 nanotherapy. FIG. 50B depicts schedule of lung cancer induction and treatment. FIG. 50C depicts urethane model showing high resistance of lung cancer to the chemo and αPD-1 combination therapy in lung epithelial PDLIM2 specific deletion mice (DSPC). FIG. 50D depicts IHC staining showing no MHC-I induction by chemotherapy, PD-1 immunotherapy and their combination. FIG. 50E depicts tumor examination showing complete remission of all lung tumors in 60% of mice by the combination of three therapies (n≥5). FIG. 50F depicts IHC staining showing increased TILs by PDLIM2 nanotherapy in mice treated with anti-PD-1 and chemotherapeutic drugs (n=6). FIG. 50G depicts FACS analysis showing increased lung CD8+ T-cell activation by PDLIM2 nanotherapy in mice treated with anti-PD-1 and chemotherapeutic drugs (n=5). FIG. 50H shows no significant effect of PDLIM2 nanotherapy on the body weight of mice treated with anti-PD-1 and chemotherapeutic drugs (n=5). Scale bar in FIGS. 50A and 50F, 20 μm. Student's t test was performed (two tailed, unpaired) and data represent means±SEM in (C-G). *p<0.05; **p<0.01; ns, not statistically significant.

Figure 51:
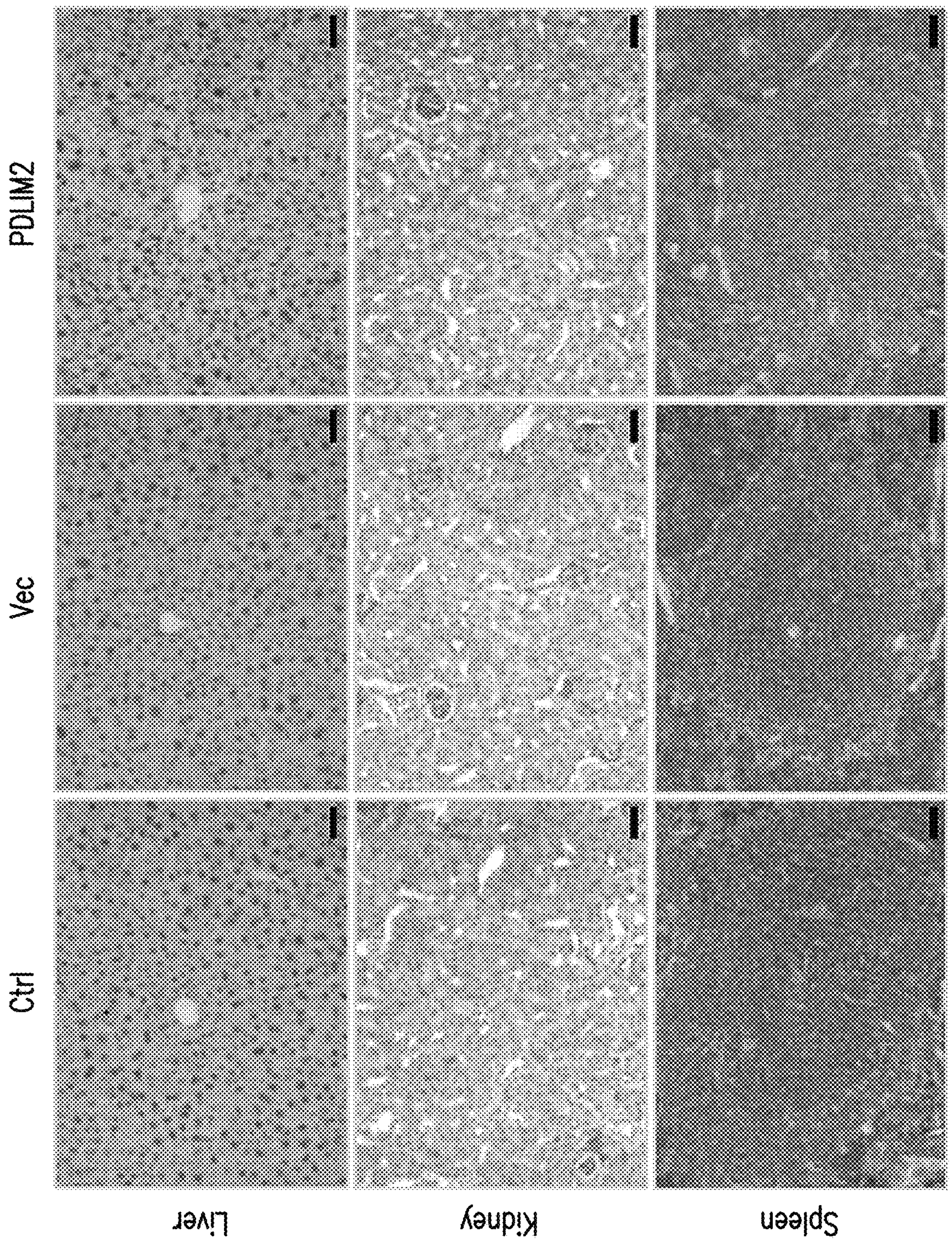

FIG. 51 shows no difference in toxicity in several organs by PDLIM2 nanotherapy. H&E staining showing comparable toxicity in liver, kidney and spleen between Vec and PDLIM2 group in the context of combination therapy (n=3). Scale bar: 50 μm.

Figure 52:
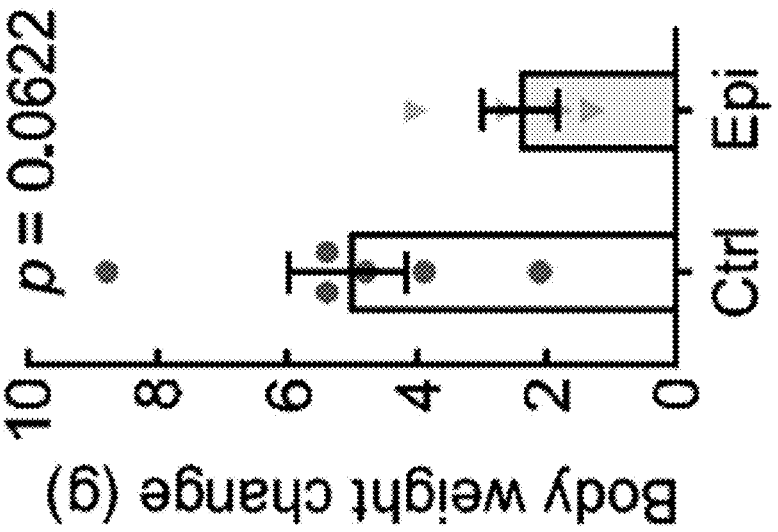

FIG. 52 shows that epigenetic drug causes body weight loss in mice with lung cancer. Mice lung tumor were induced by i.p. urethane (1 g/kg) for 6 weeks, and then treated with 1 mg/kg of 5-aza-dC and MS-275 twice per week for 6 weeks. Body weight change between first treatment and sacrifice endpoint was showed.

Figure 53:
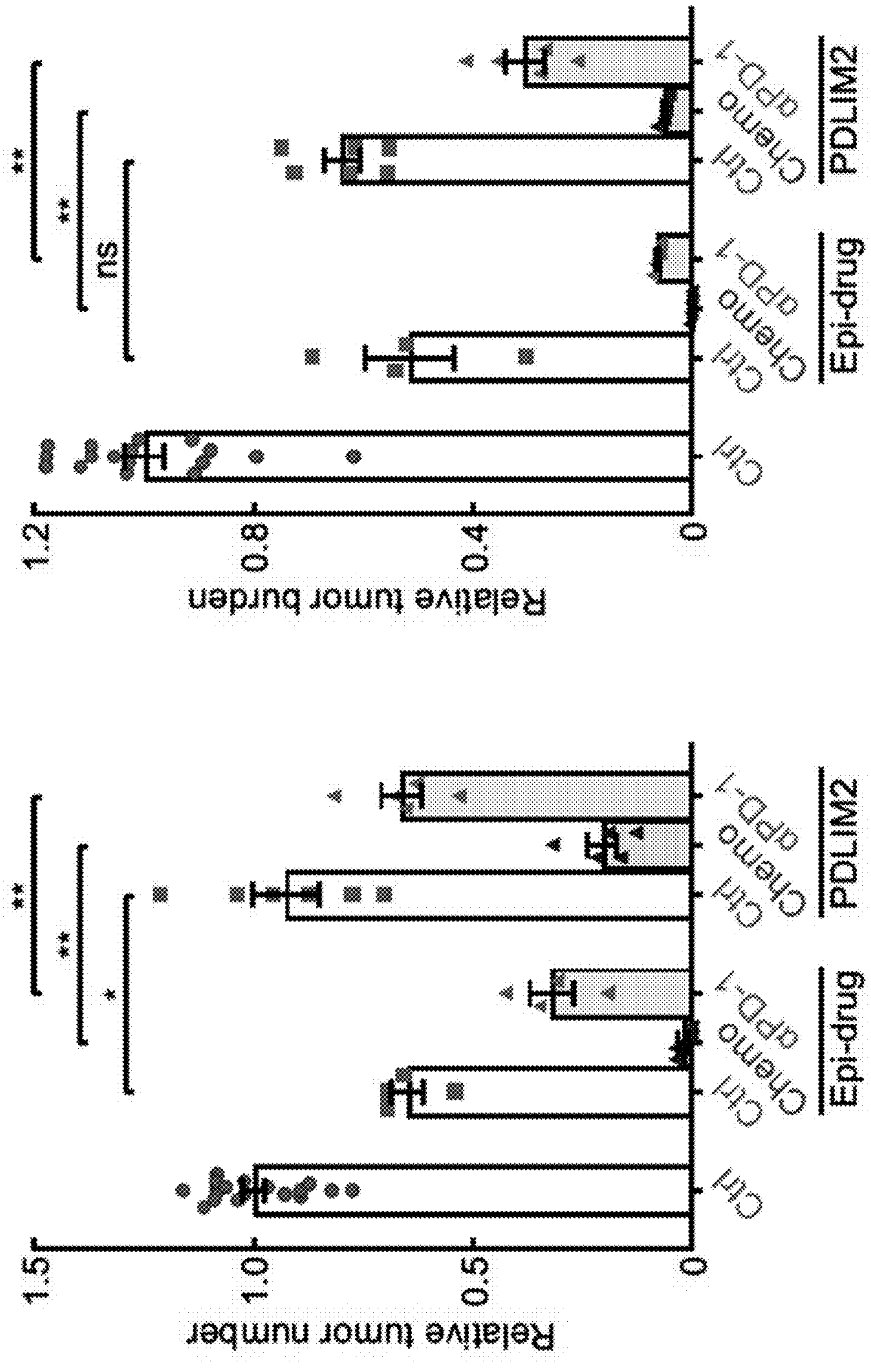

FIG. 53 shows that epigenetic drug shows better efficacy in lung cancer treatment. Mice lung tumor were induced by i.p. urethane (1 g/kg) for 6 weeks, and then treated with 5-aza-dC and MS-275 (i.p., 1 mg/kg each, twice per week), carboplatin and paclitaxel (i.p., 30 mg/kg and 15 mg/kg, respectively, once per week), anti-PD-1 antibody (i.p., 200 μg/mouse, three times per week), PDLIM2 plasmid (i.v., 25 μg/mouse, once per week), and their combinations. 6 weeks later, mice were sacrificed for tumor examination.

5. DETAILED DESCRIPTION

The present disclosure provides PDLIM2-based anti-cancer treatments, and use of PDLIM2 as a biomarker for the diagnosis, prognosis, and anti-cancer treatment selection of a cancer. Non-limiting embodiments of the present disclosure are described by the present specification and Examples.

For purpose of clarity and not by way of limitation, the detailed description is divided into the following subsections:

5.1 Definitions;
5.2 Methods of treatment;
5.3 Biomarkers;
5.4 Drug screening methods; and
5.5 Kits.

5.1 Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one."

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of", and "consisting essentially of," the embodiments or elements presented herein, whether explicitly set forth or not.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

An "effective amount" of a substance as that term is used herein is that amount sufficient to effect beneficial or desired results, including clinical results, and, as such, an "effective amount" depends upon the context in which it is being applied. An effective amount can be administered in one or more administrations.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount can vary according to factors such as the disease state, age, sex, and weight of the subject, and the populations of cells administered. In certain embodiments, the provided methods involve administering the cells and/or compositions at effective amounts, e.g., therapeutically effective amounts.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more sign or symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a subject diagnosed with cancer.

As used herein, the term "targeted drug therapy" refers to a cancer treatment that uses drugs to target specific genes and proteins involved in the growth and survival of cancer cells. Non-limiting examples of target drug therapy include, without limitation, inhibitors of the epidermal growth factor receptor (EGFR) (e.g., osimertinib, erlotinib, afatinib, gefitinib), inhibitors of RET fusion (e.g., selpercatinib), or drugs targeting MET Exon 14 skipping (e.g., capmatinib).

A "biological sample" or "sample," as used interchangeably herein, refers to a sample of biological material obtained from a subject, including a biological fluid and/or body fluid, e.g., blood, plasma, serum, stool, urine, lymphatic fluid, ascites, ductal lavage, nipple aspirate, saliva, bronchoalveolar lavage, tears and cerebrospinal fluid. In certain non-limiting embodiments, the presence of one or more biomarkers of the present disclosure is determined in one or more samples obtained from a subject, e.g., plasma samples. In certain embodiments, the sample contains nucleic acids, e.g., DNA, that are released into vascular system, present in circulation, e.g., blood or plasma, present in body fluid, e.g., plasma, serum, urine or pleural effusion or is extracellular, e.g., outside of (not located within) any cell, bound or unbound to the cell surface.

As used herein, the terms "guide RNA" and "gRNA" refer to any nucleic acid that promotes the specific association (or "targeting") of an RNA-guided nuclease such as a Cas9 to a target sequence such as a genomic or episomal sequence in a cell.

As used herein, a good prognosis predicts survival of a subject within a predetermined time period from surgical removal of tumor or from diagnosis of a cancer, and a poor prognosis predicts non-survival of a subject having a cancer within the predetermined time period. The predetermined time period can be 2, 3, 4, or 5 years.

5.2 Methods of Treatment

The presently disclosure provides methods of treating a subject having cancer, including increasing the expression of PDLIM2 in the subject. In certain embodiments, increasing the expression of PDLIM2 restores PDLIM2 function in the subject.

In certain embodiments, the expression of PDLIM2 includes the level of PDLIM2 mRNA and/or the level of PDLIM2 protein.

In certain embodiments, the expression of PDLIM2 is increased in a tumor cell of the subject. In certain embodiments, the expression of PDLIM2 is increased in a non-tumor cell of the subject. Non-tumor cells can promote tumor angiogenesis, proliferation, invasion, or metastasis, or mediate cancer therapeutic resistance. Non-limiting examples of non-tumor cells include vascular endothelial cells, pericytes, adipocytes, fibroblasts, and bone-marrow mesenchymal stromal cells, immune cells. In certain embodiments, the non-tumor cells are immune cells. In certain embodiments, the immune cells are selected from monocytes, macrophages, T cells, effector lymphocytes, regulatory T cells, dendritic cells, natural killer cells, myeloid-derived suppressor cells, neutrophils, mast cells, eosinophils, B cells, and combinations thereof. In certain embodiments, non-tumor cells comprise tumor-associated cells. In certain embodiments, tumor-associated cells exist in the tumor microenvironment, along with the tumor cells. Non-limiting examples of tumor-associated cells include vascular endothelial cells, pericytes, adipocytes, fibroblasts, and bone-marrow mesenchymal stromal cells, immune cells.

Methods disclosed herein can be used for treating any suitable cancers. Non-limiting examples of cancers encompassed by the disclosed subject matter include liver cancers, brain cancers, cervical cancers, colorectal cancers, breast cancers, endometrial carcinomas, gastric cancers, cancers of the head and neck, bladder cancers, lung cancers, ovarian cancers, biliary tree cancers, hepatocellular carcinomas, leukemia, lymphoma, myeloma, and sarcoma. In certain embodiments, methods disclosed herein can be used for treating a cancer selected from bladder urothelial carcinoma, cervical squamous cell carcinoma and endocervical adenocarcinoma, cholangiocarcinoma, colon adenocarcinoma, head and neck squamous cell carcinoma, kidney chromophobe, kidney renal papillary cell carcinoma, liver hepatocellular carcinoma, lung adenocarcinoma, lung squamous cell carcinoma, prostate adenocarcinoma, rectum adenocarcinoma, stomach adenocarcinoma, and uterine corpus endometrial carcinoma. In certain embodiments, methods disclosed herein can be used for treating a lung cancer. In certain embodiments, the lung cancer is selected from small cell lung carcinoma, lung adenocarcinoma, lung squamous cell carcinoma, and lung large cell carcinoma.

In certain embodiments, the subject is a human subject. In certain embodiments, the subject is a non-human subject, such as, but not limited to, a non-primate, a dog, a cat, a horse, a rabbit, a mice, a rat, a guinea pig, a fowl, a cow, a goat, or a sheep.

5.2.1 Agents for Increasing PDLIM2 Expression

In certain embodiments, methods disclosed herein include administering an agent to the subject to increase the expression of PDLIM2. Any agents known in the art that can increase the expression of PDLIM2 can be used with the presently disclosed methods. In certain embodiments, an agent for increasing PDLIM2 expression can modulate a PDLIM2 gene property. For example, without any limitation, an agent for increasing PDLIM2 expression can improve stability, reduce degradation, increase transcription efficiency, increase translation efficiency, or any combination thereof, of a PDLIM2 gene.

In certain embodiments, the agent for use with the presently disclosed methods is an epigenetic modulating agent. In certain embodiments, the epigenetic modulating agent is selected from histone deacetylase inhibitors, histone methyltransferase inhibitors, histone demethylases inhibitors, histone acetyltransferase inhibitors, DNA methyltransferase inhibitors, sirtuin inhibitors and modulators, bromodomain inhibitors, and any combination thereof. Non-limiting exemplary epigenetic modulating agents for use in the presently disclosed methods are disclosed in Prachayasittikul et al., Expert Opin Drug Discov. 2017 April; 12(4):345-362, the contents of which are incorporated by reference herein in its entirety. In certain embodiments, the DNA methyltransferase inhibitors are selected from 5-aza-cytidine (azacitidine), 5-azadeoxycitidine (5-aza-dC or decitabine), SGI-110, procainamide, epigallocatechin 3-gallate (EGCG), RG108, hydralazine, derivatives thereof, and combinations thereof.

In certain embodiments, the histone acetyltransferase inhibitors are selected from curcumin, garcinol, anacardic acid, derivatives thereof, and combinations thereof. In certain embodiments, the histone deacetylase inhibitors are selected from short chain fatty acids (e.g., sodium butyrate, phenylbutyrate, pivanex, and valproic acid), cyclic tetrapeptides (e.g., romidepsin), hydroxamic acids (e.g. vorinostat, belinostat, panobinostat, and dacinostat), benzamides (e.g. entinostat and mocetinostat), bicyclic depsipeptide (e.g. romidepsin). In certain embodiments, sirtuin inhibitors (SIRTi) and modulators are selected from β-naphthols (e.g.

sirtinol, splitomicin, salermide, and cambinol), indoles (e.g. EX-527 and oxyindole), ureas (e.g. suramin and tenovin), chalcone, 1,4-dihydropyridine, phenol derivatives (e.g., resveratrol, quercetin, piceatannol, SRT1720 and SRT2183), derivatives thereof, and combinations thereof. In certain embodiments, the histone demethylase inhibitors are selected from pargyline, phenelzine, tranylcypromine, derivatives thereof, and combinations thereof. In certain embodiments, histone methyltransferase inhibitors are selected from EPZ004777, EPZ-5676, 3-deazaneplanocin-A (DZNep), CPI-1205, GSK2816126, and EPZ6438, histone-lysine N-methyltransferase, H3 lysine-9 specific 3 (CHEMBL6032), histone-lysine N-methyltransferase MLL (CHEMBL1293299), RM65, TBBD (ellagic acid), EPZ015666 (GSK3235025), AMI-1 (arginine N-methyltransferase inhibitor-1), derivatives thereof, and combinations thereof. In certain embodiments, the bromodomain inhibitors are selected from RVX-208, OTX015, BMS-9861158, GSK525762, TEN-010, and CPI-0610, GS-5829, BAY1238097, ABBV-075, INCB054329, derivatives thereof, and combinations thereof.

In certain embodiments, the epigenetic modulating agent for use with the presently disclosed methods is selected from DNA methyltransferase inhibitors, histone deacetylase inhibitors, and any combinations thereof. In certain embodiments, the DNA methyltransferase inhibitor is 5-azadeoxycitidine (5-aza-dC). In certain embodiments, the histone deacetylase (HDAC) inhibitor is a HDAC1 inhibitor, a HDAC2 inhibitor, a HDAC3 inhibitor, an inhibitor of other HDACs, and/or a pan-HDAC inhibitor. In certain embodiments, the HDAC inhibitor increases H3K14 acetylation at the PDLIM2 gene promoter and PDLIM2 transcription. In certain embodiments, the HDAC inhibitor is entinostat (also known as MS-275, and SNDX-275). In certain embodiments, the HDAC inhibitor is Trichostatin A (TSA). In certain embodiments, the HDAC inhibitor is vorinostat. In certain embodiments, the HDAC inhibitor is panobinostat. In certain embodiments, the HDAC inhibitor is romidepsin. In certain embodiments, the HDAC inhibitor is belinostat.

In certain embodiments, the agent for use with the presently disclosed methods is an antioxidant. As used herein, an "antioxidant" is any molecule capable of slowing or preventing the oxidation of other molecules. For example, in certain embodiments, an antioxidant can react with oxygen-free radicals to thereby restore or increase the expression and/or activity of PDLIM2. In certain embodiments, the antioxidant is natural. In certain embodiments, the antioxidant is artificial. In certain embodiments, without limitation, the antioxidation is selected from hesperidin, quercitrin, rutin, tangeritin, flyoglycosides, kaempferol, catechins, resveratrol, selenium, lycopene, tocopherols (e.g., α-tocopherol), tocotrienols, α-carotene, β-carotene, β-cryptoxanthin, γ-tocopherol, lutein, a polyphenol (e.g., resveratrol), retinol, uric acid, lipoic acid, glutathione, melatonin, ubiquinol, luteolin, apigenin, tangeritin, quercetin, kaempferol, myricetin, fisetin, isorhamnetin, pachypodol, rhamnazin, hesperetin, naringenin, eriodictyol, homoeriodictyol, dihydroquercetin, dihydrokaempferol, genistein, daidzein, glycitein, catechins, gallocatechin (GC), catechin 3-gallate (Cg), gallocatechin 3-gallate (GCg), epicatechins or anthocyanidins, and combinations thereof. In certain embodiments, the antioxidant is metformin. In certain embodiments, the antioxidant is selected from N-acetyl cysteine, glutathione flavonoids, carotenoids, vitamin A, vitamin C, vitamin E, polyphenols, and combinations thereof.

In certain embodiments, the agent for use with the presently disclosed methods is an antioxidant enzyme. Non-limiting examples of antioxidant enzymes include free-radical scavenging enzymes, superoxide elimination enzymes, AKR1C, AKR1C2, AKR1C3, heme oxygenase-1 (HO-1), quinone reductase (i.e. NAD(P)H:quinone reductase, NQO1), superoxide dismutase, glutathione peroxidase, nuclear erythroid-2 related factor 2 (Nrf2), UDP-glucuronosyl transferase 2B7, or any combination thereof.

In certain embodiments, the agent for use with the presently disclosed methods is an agent that can increase the activity, expression, or binding of at least one transcription factor that binds to a PDLIM2 promoter, resulting in an increased expression of PDLIM2. In certain embodiments, the agent is selected from vitamin D, and derivatives thereof. In certain embodiments, the agent is a biologically active form of vitamin D. In certain embodiments, the biologically active form of vitamin D is 1α,25-dihydroxyvitamin D3, and derivatives thereof (Vanoirbeek et al., Oncogene. 2014; 33(15):1904-11). "1α,25-Dihydroxyvitamin $D_3$" refers to a molecule with a CAS number of 32222-06-3, a molecular formula of $C_{27}H_{44}O_3$, for example, see structure below:

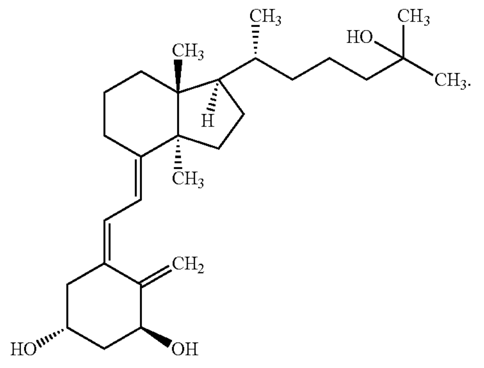

In certain embodiments, the agents disclosed herein can be administered to the subject by any suitable route known in the art, including, but not limited to, oral, parenteral, topical, intravenous, subcutaneous, intraperitoneal, intrapulmonary, intranasal, and/or intralesional, intra-arterial, or intrathecal. Parenteral infusions include intramuscular, intravenous, intraarterial, intraperitoneal, or subcutaneous administration.

In certain embodiments, the agents disclosed herein are included in pharmaceutical compositions to be administered to the subject. In certain embodiments, the pharmaceutical compositions further include a pharmaceutically acceptable carrier. Suitable pharmaceutically acceptable carriers that can be used with the presently disclosed subject matter have the characteristics of not interfering with the effectiveness of the biological activity of the active ingredients, e.g., epigenetic modulating agents, and that is not toxic to the subject to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers include gels, bioabsorbable matrix materials, implantation elements containing the inhibitor and/or any other suitable vehicle, delivery or dispensing mechanism or material. Such pharmaceutically acceptable carriers can be formulated by conventional methods and can be administered to the subject. In certain embodiments, the pharmaceutical acceptable carriers can include buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, the suitable pharmaceutically acceptable carriers can include one or more of water, saline, phosphate buffered saline, dextrose, glycerol, ethanol or combinations thereof.

In certain non-limiting embodiments, the pharmaceutical compositions of the present disclosure can be formulated using pharmaceutically acceptable carriers well known in the art that are suitable for oral administration. Such carriers can enable the pharmaceutical compositions to be formulated as tablets, pills, capsules, liquids, gels, syrups, slurries, suspensions and the like, for oral or nasal ingestion by a subject to be treated. In certain embodiments, the pharmaceutical composition is formulated as a capsule. In certain embodiments, the pharmaceutical composition can be a solid dosage form. In certain embodiments, the tablet can be an immediate release tablet. Alternatively or additionally, the tablet can be an extended or controlled release tablet. In certain embodiments, the solid dosage can include both an immediate release portion and an extended or controlled release portion.

In certain embodiments, the pharmaceutical compositions suitable for use in the presently disclosed subject matter can include compositions where the active ingredients, e.g., epigenetic modulating agents, are contained in an effective amount. The effective amount of an active ingredient can vary depending on the active ingredient, compositions used, the cancer and its severity, and the age, weight, etc., of the subject to be treated. In certain embodiments, a subject can receive an effective amount of the active ingredient in single or multiple administrations of one or more composition, which can depend on the dosage and frequency as required and tolerated by the subject.

In certain embodiments, the pharmaceutical compositions further include a second anti-cancer agent as disclosed in Section 5.2.3.

5.2.2 Genetic Engineering Methods for Increasing PDLIM2 Expression

In certain embodiments, methods disclosed herein employ a genetic engineering system to modulate (e.g., knock down or knock out) at least one negative regulator of the PDLIM2 gene, to increase the expression of PDLIM2, or a functional fragment thereof. Non-limiting examples of negative regulators of the PDLIM2 gene include KRAS, HDACs, DMNTs, and combinations thereof.

In certain embodiments, methods disclosed herein employ a genetic engineering system to modulate (e.g., knock in or deliver) the PDLIM2 gene, to increase the expression of PDLIM2, or a functional fragment thereof. In certain embodiments, the genetic engineering methods comprise removal of negative cis-acting elements, insertion and/or knock-in of positive cis-acting elements, deliver positive regulators, deliver inhibitors of negative regulators, or any combination thereof. In certain embodiments, the genetic engineering methods modulate a promoter and/or an enhancer of the PDLIM2 gene. For example, without any limitation, the genetic engineering system can demethylate a promoter and/or enhancer of the PDLIM2 gene by expressing a dCas9 fused with a demethylating enzyme. In further examples, the genetic engineering system can regulate the acetylation state of a promoter and/or enhancer of the PDLIM2 gene by expressing a dCas9 fused with a histone deacetylase. In certain embodiments, the genetic engineering system comprises a dCas9 fused and/or coupled with a transcription factor. In certain embodiments, the genetic engineering system comprises an epigenetic modulator of a PDLIM2 gene, a PDLIM2 promoter, a PDLIM2 enhancer, or a combination thereof. In certain embodiments, the genetic engineering system provides for a PDLIM2 gene with improved properties. For example, without any limitation, a PDLIM2 gene can show improved stability, reduced degradation, increased transcription efficiency, increased translation efficiency, or any combination thereof.

In certain embodiments, methods disclosed herein employ a genetic engineering system to modulate (e.g., knock down or knock out) at least one microRNA that targets PDLIM2 mRNA, to increase the expression of PDLIM2. In certain embodiments, the microRNA is selected from hsa-miR-421, hsa-miR-330-5p, hsa-miR-326, hsa-miR-222, hsa-miR-224, hsa-miR-214, hsa-miR-132, hsa-miR-212, hsa-miR-942-5p, hsa-miR-30b-3p, hsa-miR-579-3p, hsa-miR-664b-3p, hsa-miR-627-3p, hsa-miR-149-3p, hsa-miR-221-3p, hsa-miR-222-3p, hsa-miR-326, hsa-miR-330-5p, hsa-miR-146a-3p, hsa-miR-650, hsa-miR-661, hsa-miR-134-5p, hsa-miR-345-3p, hsa-miR-324-3p, hsa-miR-296-5p, hsa-miR-873-5p, hsa-miR-550a-3-5p, hsa-miR-550a-5p, hsa-miR-939-3p, hsa-miR-519d-5p, hsa-miR-129-1-3p, hsa-miR-588, hsa-miR-147a, hsa-miR-129-2-3p, hsa-miR-613, hsa-miR-146a-3p, hsa-miR-660-3p, hsa-miR-3158-5p, hsa-miR-4524a-3p, hsa-miR-1827, hsa-miR-1285-3p, hsa-miR-1972, hsa-miR-1305, hsa-miR-3192-5p, hsa-miR-3187-5p, hsa-miR-3140-5p, hsa-miR-1299, hsa-miR-3136-3p, and combinations thereof.

Non-limiting examples of the genetic engineering system that can be used with the presently disclosed methods include CRISPR/Cas systems, zinc-finger nuclease (ZFN) systems, transcription activator-like effector nuclease (TALEN) systems, or the use of interfering RNAs.

A clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), and trans-activating crRNA (tracrRNA, binds to crRNA and forms an active complex with Cas9). gRNAs can be unimolecular (including a single RNA molecule, and referred to alternatively as chimeric) or modular (including more than one, and typically two, separate RNA molecules, such as a crRNA and a tracrRNA, which are usually associated with one another, for instance by duplexing).

CRISPR/Cas9 strategies can employ a vector to transfect the mammalian cell. The guide RNA (gRNA) can be designed for each application as this is the sequence that Cas9 uses to identify and directly bind to the target DNA in a cell. Multiple crRNAs and the tracrRNA can be packaged together to form a single-guide RNA (sgRNA). The sgRNA can be joined together with the Cas9 gene and made into a vector in order to be transfected into cells.

In certain embodiments, the gRNAs are administered to the cell in a single vector and the Cas9 molecule is administered to the cell in a second vector. In certain embodiments, the gRNAs and the Cas9 molecule are administered to the cell in a single vector. Alternatively, each of the gRNAs and Cas9 molecule can be administered by separate vectors. In certain embodiments, the CRISPR/Cas9 system can be delivered to the cell as a ribonucleoprotein complex (RNP) that includes a Cas9 protein complexed with one or more gRNAs, e.g., delivered by electroporation (see, e.g., DeWitt et al., Methods 121-122:9-15 (2017) for additional methods of delivering RNPs to a cell). In certain embodiments, administering the CRISPR/Cas9 system to the cell results in the knock out or knock down of at least one negative regulator of the PDLIM2 gene, and thus increasing the expression of PDLIM2. In certain embodiments, administering the CRISPR/Cas9 system to the cell results in knock in at least one copy of a PDLIM2 gene, and thus increasing the expression of PDLIM2. In certain embodiments, administering the CRISPR/Cas9 system to the cell results in an epigenetic or genetic modification of the PDLIM2 promoter/enhancer region, and thus increasing the expression of PDLIM2.

In certain embodiments, the genetic engineering system is a ZFN system. The ZFN can act as restriction enzyme, which is generated by combining a zinc finger DNA-binding domain with a DNA-cleavage domain. A zinc finger domain can be engineered to target specific DNA sequences which allows the zinc-finger nuclease to target desired sequences within genomes. The DNA-binding domains of individual ZFNs typically contain a plurality of individual zinc finger repeats and can each recognize a plurality of base pairs. A common method to generate a new zinc-finger domain is to combine smaller zinc-finger "modules" of known specificity. A common cleavage domain in ZFNs is the non-specific cleavage domain from the type IIs restriction endonuclease FokI. ZFN modulates the expression of proteins by producing double-strand breaks (DSBs) in the target DNA sequence, which will, in the absence of a homologous template, be repaired by non-homologous end-joining (NHEJ). Such repair can result in deletion or insertion of base-pairs, producing frame-shift and preventing the production of the harmful protein (Durai et al., *Nucleic Acids Res.;* 33 (18): 5978-90 (2005)). Multiple pairs of ZFNs can also be used to completely remove entire large segments of genomic sequence (Lee et al., *Genome Res.;* 20 (1): 81-9 (2010)).

In certain embodiments, the genetic engineering system is a TALEN system. TALENs are restriction enzymes that can be engineered to cut specific sequences of DNA. TALEN systems operate on a similar principle as ZFNs. TALENs are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome (Boch et al., *Nature Biotechnology;* 29(2):135-6 (2011)).

In certain embodiments, at least one microRNA that targets PDLIM2 mRNA ("PDLIM2 microRNA") can be knocked down using oligonucleotides that have complementary sequences to the microRNA. Non-limiting examples of such oligonucleotides include small interference RNA (siRNA), and short hairpin RNA (shRNA). In certain embodiments, such oligonucleotides can be homologous to at least a portion of a PDLIM2 microRNA sequence, wherein the homology of the portion relative to the PDLIM2 microRNA nucleic acid sequence is at least about 75 or at least about 80 or at least about 85 or at least about 90 or at least about 95 or at least about 98 percent. In certain non-limiting embodiments, the complementary portion can constitute at least 10 nucleotides or at least 15 nucleotides or at least 20 nucleotides or at least 25 nucleotides or at least 30 nucleotides and the antisense nucleic acid, shRNA, mRNA or siRNA molecules can be up to 15 or up to 20 or up to 25 or up to 30 or up to 35 or up to 40 or up to 45 or up to 50 or up to 75 or up to 100 nucleotides in length. Antisense nucleic acid, shRNA, mRNA or siRNA molecules can include DNA or atypical or non-naturally occurring residues, for example, but not limited to, phosphorothioate residues.

In certain embodiments, methods disclosed herein employ a genetic engineering system to increase (e.g., knock-in or delivering) the expression of PDLIM2, or a functional fragment thereof. In certain embodiments, the genetic engineering system can remove negative cis-acting elements, insert and/or knock-in positive cis-acting elements, deliver positive regulators, deliver inhibitors of negative regulators, or any combination thereof.

Non-limiting examples of the genetic engineering system include viral vectors and non-viral vectors comprising a nucleic acid sequence encoding for PDLIM2 protein, or a functional fragment thereof.

The genetic engineering system disclosed herein can be delivered into the mammalian cell using a viral vector, e.g., retroviral vectors such as gamma-retroviral vectors, and lentiviral vectors. Combinations of viral vector and an appropriate packaging line can be suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles can be suitable too, e.g., particles pseudotyped with VSVG, RD114 or GALV envelope and any other known in the art. Methods of transduction can also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to modify the mammalian cell disclosed herein. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). In certain embodiments, the viral vectors are oncolytic viral vectors that target cancer cells and deliver the genetic engineering system to the cancer cells. Non-limiting examples of oncolytic viral vectors are disclosed in Lundstrom et al., Biologics. 2018; 12: 43-60, and the content of which is incorporated by reference herein in its entirety. In certain embodiments, the oncolytic viral vectors are selected from adenoviruses, HSV, alphaviruses, rhabdoviruses, Newcastle disease virus (NDV), vaccinia viruses (VVs), and combinations thereof.

Non-viral approaches can also be employed for genetic engineering of the mammalian cell disclosed herein. For example, a nucleic acid molecule can be introduced into the mammalian cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation and protoplast fusion. Liposomes can also be beneficial for delivery of nucleic acid molecules into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cells (or its descendants) are injected into a targeted tissue or are injected systemically.

In certain embodiments, non-viral approaches include nanotechnology-based approaches, which use non-viral vectors. The non-viral vectors can be made of a variety of materials, including inorganic nanoparticles, carbon nanotubes, liposomes, protein and peptide-based nanoparticles, as well as nanoscale polymeric materials. Riley et al., Nanomaterials (Basel). 2017 May; 7(5): 94 reviews nanotechnology-based methods for delivery of a nucleic acid molecule to a subject, the content of which is incorporated as reference in its entirely.

In certain embodiments, non-viral approaches include nanoparticles. As used herein, a "nanoparticle" refers to any particle having a diameter of less than 1000 nm, e.g., about 10 nm to about 200 nm. In certain embodiments, the nanoparticles can have a diameter of about 10 nm to about 90 nm, or about 20 nm to about 80 nm, or about 60 nm to about 120 nm, or about 70 nm to about 120 nm, or about 80 nm to about 120 nm, or about 90 nm to about 120 nm, or about 100 nm to about 120 nm, or about 60 nm to about 130 nm, or about 70 nm to about 130 nm, or about 80 nm to about 130 nm, or about 90 nm to about 130 nm, or about 100 nm to about 130 nm, or about 110 nm to about 130 nm, or about 60 nm to about 140 nm, or about 70 nm to about 140 nm, or about 80 nm to about 140 nm, or about 90 nm to about 140 nm, or about 100 nm to about 140 nm, or about 110 nm to about 140 nm, or about 60 nm to about 150 nm, or about 70 nm to about 150 nm, or about 80 nm to about 150 nm, or about 90 nm to about 150 nm, or about 100 nm to about 150 nm, or about 110 nm to about 150 nm, or about 120 nm to about 150 nm.

In certain embodiments, the nanoparticles can comprise a core. In certain embodiments, the core comprises a nucleic acid encoding for the PDLIM2 or a functional fragment thereof.

In certain embodiments, the nanoparticle can comprise one or more lipids. In certain embodiments, the lipids can be neutral, anionic or cationic at physiological pH. In certain embodiments, the lipids can be sterols. For example, in certain embodiments, the lipid nanoparticle can comprise cholesterol, phospholipids and sphingolipids. In certain embodiments, the nanoparticles comprise PEGylated derivatives of the neutral, anionic, and cationic lipids. The incorporation of PEGylated derivatives can improve the stability of the nanoparticles. Non-limiting examples of PEGylated lipids include distearoylphosphatidylethanlamine-polyethylene glycol (DSPE-PEG), stearyl-polyethylene glycol and cholesteryl-polyethylene glycol. In certain embodiments, the nanoparticle can comprise substituted or unsubstituted fatty acids. Non-limiting examples of saturated fatty acids include caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, and combinations thereof. Non-limiting examples of unsaturated fatty acids include hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, oleic acid, eicosenoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, palmitoleic acid, vaccenic acid, gadoleic acid, erucic acid, and combinations thereof.

In certain embodiments, the nanoparticles can comprise polymers. In certain embodiments, the polymer can be amphiphilic, hydrophilic, or hydrophobic. In certain embodiments, the polymer can be biocompatible, e.g., the polymer does not induce an adverse and/or inflammatory response when administered to a subject. For example, without limitation, a polymer can be selected from polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers. In certain embodiments, the polymer can contain PEG.

In certain embodiments, the nanoparticles can comprise cationic polymers. In certain embodiments, the cationic polymers can be branched or linear. Cationic polymers are able to condense and protect negatively charged molecules such as DNA or RNA. In certain embodiments, without limitation, the cationic polymers can be polyethylenimines, poly-histidyl polymers, chitosan, poly(amino ester glycol urethane), polylysines, amino cyclodextrin derivatives. In certain embodiments, the nanoparticle comprises linear polyethylenimine. Additional information on nanoparticles comprising linear polyethylenimine can be found in International Patent Application Nos. PCT/IB2008/002339 and PCT/IB2008/055256, the content of which is incorporated in their entirety.

In certain embodiments, the nanoparticle can show organ tropism and can have an organ-specific distribution. For example, without limitation, the nanoparticle can deliver the nucleic acid to hepatic cells, lung cells, tumor cells, or immune cells. In certain embodiments, the nanoparticle can be conjugated to a ligand. In certain embodiments, the ligand can be mannose. In certain embodiments, the nanoparticle can show cell tropism by binding of the ligand to a specific molecule on the cell. In certain embodiments, the cell can be a cancer cell. In certain embodiments, the cell can be a myeloid cell. For example, without any limitation, the nanoparticle can be conjugated to mannose and can bind to a cell expressing a mannose-receptor (e.g., macrophages, dendritic cells) In certain embodiments, the nanoparticles can be biodegradable or non-biodegradable. In certain embodiment, the nanoparticle can be comprised in a pharmaceutical composition. Details on the pharmaceutical compositions contemplated by the present disclosure can be found in Section 5.2.1.

In certain embodiments, the presently disclosed subject matter comprises compositions comprising a PDLIM2 gene, or a functional fragment thereof, disclosed herein. In certain embodiments, the PDLIM2 gene, or a functional fragment thereof, is operably linked to a promoter. The presently disclosed subject matter provides nucleic acid compositions comprising a polynucleotide encoding a PDLIM2 polypeptide disclosed herein. In certain embodiments, the nucleic acid composition comprises a promoter that is operably linked to the sequence encoding the PDLIM2 polypeptide. In certain embodiments, the nucleic acid composition further comprises a second promoter that is operably linked to the antigen-recognizing receptor. In certain embodiments, the promoter is endogenous or exogenous. In certain embodiments, the exogenous promoter is selected from the group consisting of an elongation factor (EF)-1 promoter, a CMV promoter, a SV40 promoter, a PGK promoter, a long terminal repeat (LTR) promoter and a metallothionein promoter. In certain embodiments, the promoter is an inducible promoter. In certain embodiments, the inducible promoter is selected from the group consisting of a NFAT transcriptional response element (TRE) promoter, a CD69 promoter, a CD25 promoter, an IL-2 promoter, an IL-12 promoter, a p40 promoter, and a Bcl-xL promoter. In certain embodiments, the promoter can direct the expression in specific cell types.

In certain embodiments, the genetic engineering system is administered to the subject in vivo, and thus increase the expression of PDLIM2. In certain embodiments, the genetic engineering system is administered to a non-tumor cell (e.g., an immune cell) from the subject ex vivo, and thus increase the expression of PDLIM2 in the cell. The genetically modified cell is then administered back to the subject.

5.2.3 Second Anti-Cancer Treatments

In certain embodiments, methods disclosed herein further include administering a second anti-cancer treatment to the subject. Non-limiting exemplary anti-cancer treatments include, chemotherapy, radiation therapy, targeted drug therapy, immunotherapy, immunomodulatory agents, cytokines, monoclonal and polyclonal antibodies, and any combinations thereof.

In certain embodiments, the agent or genetic engineering system increasing the expression of PDLIM2, or functional fragments thereof, can be used in combination with one or more second anti-cancer treatments. Non-limiting examples of second anti-cancer treatments include chemotherapeutic treatments, radiotherapeutic treatments, anti-angiogenic treatments, apoptosis-inducing treatments, anti-cancer antibodies, anti-cyclin-dependent kinase agents, and/or treatments which promote the activity of the immune system including but not limited to cytokines such as but not limited to interleukin 2, interferon, anti-CTLA4 antibody, anti-PD-1 antibody, and/or anti-PD-L1 antibody. For example, but not by way of limitation, an agent or a genetic engineering system increasing the expression of PDLIM2 can be used in combination with anti-PD-1 antibodies. In certain embodiments, the agent or a genetic engineering system and the one or more anti-cancer treatments are administered to a subject as part of a treatment regimen or plan. In certain embodiments, the agent or a genetic engineering system and one or more anti-cancer treatments are not physically combined prior to administration. In certain embodiments, the agent or a genetic engineering system and one or more anti-cancer treatments are not administered over the same time frame.

In certain embodiments, the second anti-cancer treatment is chemotherapy, which include administering a chemotherapeutic agent to the subject. Any suitable chemotherapeutic agents known in the art can be used with the presently disclosed methods. Non-limiting examples of chemotherapeutic agents that can be used with the presently disclosed methods include acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; analogues and derivative thereof; and combinations thereof.

In certain embodiments, the chemotherapeutic agent used with the presently disclosed methods is selected from cisplatin, carboplatin, docetaxel, gemcitabine, paclitaxel, paclitaxel, vinorelbine, pemetrexed, analogs and derivatives thereof, and combinations thereof.

In certain embodiments, the second anti-cancer treatment is an immunotherapy (also known as immuno-oncology) that uses components of the immune system. Non-limiting examples of immunotherapies include immune checkpoint inhibitors, adoptive T cell transfer, therapeutic antibodies, cancer vaccines, cytokines, Bacillus Calmette-Guërin (BCG), and any combinations thereof.

In certain embodiments, the second anti-cancer treatment includes administering an immune checkpoint inhibitor to the subject. In certain embodiments, the immune checkpoint inhibitor is selected from anti-PD1 antibodies, anti-PD-L1 antibodies, anti-CTLA-4 antibodies, and any combinations thereof. Non-limiting examples of anti-PD1 antibodies include pembrolizumab (Keytruda), nivolumab (Opdivo), cemiplimab (Libtayo), and combinations thereof. Non-limiting examples of anti-PD-L1 antibodies include atezolizumab (Tecentriq), avelumab (Bavencio), durvalumab (Imfinzi), and combinations thereof. Non-limiting examples of anti-CTLA-4 antibodies include ipilimumab (Yervoy).

In certain embodiments, the immune checkpoint inhibitor is directed against one more immune checkpoint modulators. For example, without limitation, immune checkpoint inhibitors can target AMHRII, B7-H3, B7-H4, BTLA, BTNL2, Butyrophilin family, CD27, CD28, CD30, CD40, CD40L, CD47, CD48, CD70, CD80, CD86, CD155, CD160, CD226, CD244, CEACAM6, CLDN6, CCR2, CTLA4, CXCR4, GD2, GGG (guanylyl cyclase G), GIRT, GIRT ligand, HHLA2, HVEM, ICOS, ICOS ligand, IFN, IL1, IL1 R, IL1 RAP, IL6, IL6R, IL7, IL7R, IL12, IL12R, IL15, IL15R, LAG 3, LIGHT, LIF, MUC16, NKG2A family, 0X40, 0X40 ligand, PD1, PDL1, PDL2, Resokine, SEMA4D, Siglec family, SIRPalpha, STING, TGFbeta family, TIGIT, TIM3, TMIGD2, TNFRSFm VISTA, 4-1BB and 4-1BB ligand.

In certain embodiments, the second anti-cancer treatment is a combination of chemotherapy and immunotherapy (e.g., immune checkpoint inhibitor therapy). In certain embodiments, the chemotherapy and/or immunotherapy can be administered simultaneously together with any agent for increasing PDLIM2 expression described herein. In certain embodiments, the chemotherapy can be administered together with the immunotherapy. In certain embodiments, the chemotherapy and/or immunotherapy can be administered following the agent and/or genetic engineering system for increasing PDLIM2 expression administration.

5.3 Biomarkers

The present disclosure further provides methods for using PDLIM2 as a biomarker for determining and monitoring a subject's responsiveness to an anti-cancer treatment, providing a diagnosis and prognosis about a cancer in a subject, and selecting an effective anti-cancer treatment for a subject.

5.3.1 PDLIM2 Nucleic Acids and Proteins

PDLIM2 nucleic acids include DNA and RNA including at least a functional fragment or portion of a PDLIM2 gene, a PDLIM2 mRNA, or a PDLIM2 cDNA or a sequence complementary or homologous thereto (including but not limited to antisense or small interfering RNA). Said nucleic acid can be included of natural nucleotides and can optionally include nucleotide bases which are not naturally occurring. In certain non-limiting embodiments, a PDLIM2 nucleic acid is present in or obtained from a cell of a subject, which can be a cancer cell. In certain non-limiting embodiments, a PDLIM2 nucleic acid can be a modified PDLIM2 nucleic acid. For example, a modified PDLIM2 nucleic acid can show improved stability, transcription efficiency, translation efficiency, or any combination thereof. In certain other non-limiting embodiments, a PDLIM2 nucleic acid is a primer or probe which can be used to measure the level of PDLIM2 expression. As used herein, the term "functional fragment" or "portion" refers to any portion, part or fragment of a presently disclosed PDLIM2, which retains the biological activity of the PDLIM2 protein.

In certain non-limiting embodiments, a PDLIM2 nucleic acid can be detectably labeled, for example with a fluorescent, or radioactive, or colorimetric, or affinity label, using methods known in the art.

In certain non-limiting embodiments, a PDLIM2 nucleic acid is a human PDLIM2 nucleic acid molecule which has the nucleic acid sequence as set forth in GenBank/NCBI database accession no. NM_001368120.1, NM_021630.6, NM_176871.5, NM_198042.4, or a portion thereof. In certain embodiments, the portion can be, for example, at least 10, or at least 15, or at least 20, or at least 30, and up to 30, or up to 50, or up to 100, or up to 200; or between about 10 and 200 or between about 15 and 100 or between about 15 and 50, bases in length, or a nucleic acid which is at least about 90 percent or at least about 95 percent or at least about 98 percent homologous to the sequence set forth in NM_001368120.1, NM_021630.6, NM_176871.5, NM_198042.4, or a portion thereof. Homology as referred to herein can be determined using standard software, for example but not limited to BLAST or FASTA.

In certain non-limiting embodiments, a PDLIM2 nucleic acid is a cat, a chimpanzee, a mouse, or a dog PDLIM2 nucleic acid molecule which has the nucleic acid sequence as set forth in GenBank/NCBI accession nos. XM_006930645.4 (cat); XM_006930646.4 (cat); XM_019828438.2 (cat); XR_002155758.2 (cat); XM_001157480.6 (chimpanzee); XM_009454997.3 (chimpanzee); XM_016959208.2 (chimpanzee); XM_016959210.2 (chimpanzee); XM_016959209.1 (chimpanzee); NM_145978.2 (mouse); NM_001253736.1 (mouse); XM_006518781.3 (mouse); XM_006518782.3 (mouse); XM_006518783.3 (mouse); XM_014107531.1 (dog); XM_014107527.2 (dog); XM_014107528.2 (dog); XM_022409752.1 (dog); or a portion thereof, which portion can be, for example, at least 10, or at least 15, or at least 20, or at least 30, or between about 10 and 200 or between about 15 and 100 or between about 15 and 50, bases in length, or a nucleic acid which is at least about 90 percent or at least about 95 percent or at least about 98 percent homologous to the sequence set forth in XM_006930645.4; XM_006930646.4; XM_019828438.2; XR_002155758.2; XM_001157480.6; XM_009454997.3; XM_016959208.2; XM_016959210.2; XM_016959209.1; NM_145978.2; NM_001253736.1; XM_006518781.3; XM_006518782.3; XM_006518783.3; XM_014107531.1; XM_014107527.2; XM_014107528.2; XM_022409752.1, or a portion thereof.

A PDLIM2 protein is present in, produced by, or obtained from a cell of a subject, where the cell can be a tumor cell or a non-tumor cell. In certain non-limiting embodiments, a PDLIM2 protein can be a modified PDLIM2 protein. For example, without any limitation, a modified PDLIM2 protein can show improved stability. In certain non-limiting embodiment, a PDLIM2 protein is a human PDLIM2 protein molecule which has the amino acid sequence as set forth in GenBank/NCBI database accession no. NP_067643.3, NP_789847.1; NP_932159.1; or NP_001355049.1; or a variant thereof which is at least about 90 percent or at least about 95 percent or at least about 98 percent or at least about 99 percent homologous to the sequence set forth in NP_067643.3, NP_789847.1; NP_932159.1; or NP_001355049.1.

In certain non-limiting embodiments, a PDLIM2 protein is a cat, chimpanzee, mouse or dog PDLIM2 protein which has, respectively, the amino acid sequence as set forth in GenBank/NCBI accession nos. XP_006930707.1 (cat); XP_006930708.1 (cat); XP_019683997.1 (cat); NP_666090.1 (mouse); NP_001240665.1 (mouse); XP_006518844.1 (mouse); XP_006518845.1 (mouse); XP_006518846.1 (mouse); XP_001157480.1 (chimpanzee); XP_009453272.1 (chimpanzee); XP_016814698.1 (chimpanzee); XP_016814697.1 (chimpanzee); XP_016814699.1 (chimpanzee); XP_013963006.1 (dog); XP_013963002.1 (dog); XP_013963003.1 (dog); XP_022265460.1 (dog); or a variant thereof which is at least about 90 percent or at least about 95 percent or at least about 98 percent or at least about 99 percent homologous to the sequence set forth in XP_006930707.1 (cat); XP_006930708.1 (cat); XP_019683997.1 (cat); NP_666090.1 (mouse); NP_001240665.1 (mouse); XP_006518844.1 (mouse); XP_006518845.1 (mouse); XP_006518846.1 (mouse); XP_001157480.1 (chimpanzee); XP_009453272.1 (chimpanzee); XP_016814698.1 (chimpanzee); XP_016814697.1 (chimpanzee); XP_016814699.1 (chimpanzee); XP_013963006.1 (dog); XP_013963002.1 (dog); XP_013963003.1 (dog); XP_022265460.1 (dog).

5.3.2 Methods of Diagnosing and Determining Prognosis of Cancer

The present disclosure provides methods for diagnosing a cancer, the methods including determining the level of a PDLIM2 biomarker in a sample from a subject, comparing the level of the PDLIM2 biomarker to a reference level, and diagnosing the subject as having a risk of the cancer if the level of the PDLIM2 biomarker is lower than the reference level. In certain embodiments, the methods include diagnosing the subject as not having a risk of the cancer if the level of the PDLIM2 biomarker is higher than the reference level.

The present disclosure also provides methods for determining a prognosis of a cancer, the method includes determining the level of a PDLIM2 biomarker in a sample from a subject, comparing the level of the PDLIM2 biomarker to a reference level, and determining that the subject has a poor prognosis if the level of the PDLIM2 biomarker is lower than the reference level. In certain embodiments, the methods further include determining that the subject has a good prognosis if the level of the PDLIM2 biomarker is higher than the reference level.

In certain embodiments, the good prognosis indicates the survival of the subject within 1, 2, 3, 4, or 5 years. In certain embodiments, the poor prognosis indicates the non-survival of the subject within 1, 2, 3, 4, or 5 years.

In certain embodiments, the PDLIM2 biomarker is a PDLIM2 mRNA, a PDLIM2 protein, or a combination thereof.

In certain embodiments, the reference level is a predetermined level of the PDLIM2 biomarker. In certain embodiments, the reference level is the level of the PDLIM2 biomarker in a healthy individual free of the cancer or a population of healthy individuals free of the cancer. In certain embodiments, the reference level is the level of the PDLIM2 biomarker in the same subject at an earlier timepoint. In certain embodiments, the reference is the level of the PDLIM2 biomarker in non-tumor cells or non-tumor associated cells.

5.3.3 Methods of Predicting and Monitoring a Subject's Responsiveness to an Anti-Cancer Treatment The present disclosure provides methods for predicting a subject's responsiveness to an anti-cancer treatment, the method includes determining the level of a PDLIM2 biomarker in a sample from a subject, comparing the level of the PDLIM2 biomarker to a reference level, and predicting that the subject will be responsive to the anti-cancer treatment if the PDLIM2 biomarker is higher than the reference level. In certain embodiments, the methods further include predicting that the subject will not be responsive to the anti-cancer treatment if the PDLIM2 biomarker is lower than the reference level.

In certain embodiments, the methods further include treating the subject with the anti-cancer treatment if the subject is predicted to be responsive to the anti-cancer treatment. In certain embodiments, the method further includes treating the subject with a different anti-cancer treatment if the subject is predicted to be not responsive to the anti-cancer treatment. As such, the methods disclosed here can be used for selecting an effective anti-cancer treatment for the subject.

In certain embodiments, the methods further include increasing the expression of PDLIM2 if the subject is predicted to be not responsive to the anti-cancer treatment. In certain embodiments, the expression of PDLIM2 can be increased using the agents and/or the genetic engineering methods disclosed in Section 5.2.

In certain embodiments, the reference level is a predetermined level of the PDLIM2 biomarker. In certain embodiments, the reference level is the level of the PDLIM2 biomarker in a healthy individual free of cancer or a population of healthy individuals free of the cancer. In certain embodiments, the reference level is the level of the PDLIM2 biomarker in the same subject at an earlier timepoint. In certain embodiments, the reference is the level of the PDLIM2 biomarker in non-tumor cells or non-tumor associated cells.

The present disclosure further provides methods for monitoring a subject's responsiveness to an anti-cancer treatment, including determining the level of a PDLIM2 biomarker in a sample obtained from the subject before receiving the anti-cancer treatment, determining the level of the PDLIM2 biomarker in a sample obtained from the subject during or after receiving the anti-cancer treatment, comparing the levels of the biomarker in the samples, determining that the subject is responsive to the anti-cancer treatment if the level of the PDLIM2 biomarker increases during or after receiving the anti-cancer treatment. The methods further include determining that the subject is not responsive to the anti-cancer treatment if the level of the PDLIM2 biomarker decreases during or after receiving the anti-cancer treatment.

In certain embodiments, the PDLIM2 biomarker is a PDLIM2 mRNA, a PDLIM2 protein, or a combination thereof.

Non-limiting exemplary anti-cancer treatments that can be used with the presently disclosed methods include, chemotherapy, radiation therapy, targeted drug therapy, immunotherapy, immunomodulatory agents, hematopoietic growth factors, cytokines, monoclonal and polyclonal antibodies, and any combinations thereof.

In certain embodiments, the anti-cancer treatment is chemotherapy. Any suitable chemotherapy known in the art can be used with the presently disclosed methods. In certain embodiments, the chemotherapy includes administering to the subject a chemotherapeutic agent selected from cisplatin, carboplatin, docetaxel, gemcitabine, paclitaxel, paclitaxel, vinorelbine, pemetrexed, analogues and derivative thereof, and combinations thereof.

In certain embodiments, the anti-cancer treatment is an immunotherapy. Non-limiting examples of immunotherapies include immune checkpoint inhibitors, adoptive T cell transfer, therapeutic antibodies, cancer vaccines, cytokines, Bacillus Calmette-Guérin (BCG), and any combinations thereof.

In certain embodiments, the anti-cancer treatment includes administering an immune checkpoint inhibitor to the subject. Any suitable immune checkpoint inhibitors known in the art can be used with the presently disclosed methods. In certain embodiments, the immune checkpoint inhibitor is selected from anti-PD1 antibodies, anti-PD-L1 antibodies, anti-CTLA-4 antibodies, and any combinations thereof. Non-limiting examples of anti-PD1 antibodies include pembrolizumab (Keytruda®), nivolumab (Opdivo®), cemiplimab (Libtayo®), and combinations thereof. Non-limiting examples of anti-PD-L1 antibodies include atezolizumab (Tecentriq®), avelumab (Bavencio®), durvalumab (Imfinzi®), and combinations thereof. Non-limiting examples of anti-CTLA-4 antibodies include ipilimumab (Yervoy®).

5.3.4 Techniques for Measuring mRNA and Proteins

In certain embodiments, the presently disclosed methods include measuring the level of PDLIM2 mRNA, and/or PDLIM2 protein in a sample of the subject.

In certain embodiments, the sample include cells of the subject. In certain embodiments, the cells of the subject are tumor cells of the subject. In certain embodiments, the cells of the subject are non-tumor cells of the subject. In certain embodiments, cells to be used with the presently disclosed methods can be obtained by any methods known in the art, including, but not limited to, a surgical resection, as a biopsy for example but not limited to a needle biopsy, core biopsy, or aspirate, or collection from a fluid sample, such as blood, urine, cerebral spinal fluid, or cystic fluid.

Any suitable methods known in the art for measuring mRNA and protein levels can be used with the presently disclosed methods.

In certain embodiments, methods for measuring mRNA levels include, but not limited to, real-time PCR (RT-PCR), quantitative PCR, quantitative real-time polymerase chain reaction (qRT-PCR), fluorescent PCR, RT-MSP (RT methylation specific polymerase chain reaction), PicoGreen™ (Molecular Probes, Eugene, OR) detection of DNA, radioimmunoassay or direct radio-labeling of DNA, in situ hybridization visualization, fluorescent in situ hybridization (FISH), microarray In certain embodiments, methods for measuring protein levels include, but are not limited to, mass spectrometry techniques, 1-D or 2-D gel-based analysis systems, chromatography, enzyme linked immunosorbent assays (ELISAs), radioimmunoassays (RIA), enzyme immunoassays (EIA), Western Blotting, immunoprecipitation and immunohistochemistry.

5.4 Drug Screening Methods

The present disclosure provides methods for screening for candidate compounds for treating cancer. The capacity of a candidate compound to alleviate a cancer can be determined by assaying the candidate compound's ability to restore the expression of PDLIM2 in a tumor cell and/or a non-tumor cell that has suppressed expression of PDLIM2. In certain embodiments, the expression of PDLIM2 includes the level of PDLIM2 mRNA and/or the level of PDLIM2 protein.

In certain embodiments, the methods include: providing a population of cells; contacting the cells with a test compound; and measuring the expression of PDLIM2 in the cells. In certain embodiments, the methods further include selecting the test compound, if the expression of PDLIM2 is higher than a reference level. In certain embodiments, the cells comprise tumor cells, non-tumor cells, or combinations thereof.

In certain embodiments, the reference level is a predetermined level of PDLIM2 (e.g., levels of PDLIM2 mRNA and/or PDLIM2 protein). In certain embodiments, the reference level is the level of the PDLIM2 (e.g., levels of PDLIM2 mRNA and/or PDLIM2 protein) in the cells before the cells are contacted with the test compounds. In certain embodiments, the reference level is the level of the PDLIM2 in cells that are not contacted with the test compounds.

In certain embodiments, the cells are contacted with the test compounds for between about 15 minutes to about 7 days. In certain embodiments, the cells are contacted for about 2 hours and about 24 hours. In certain embodiments, the tumor cells and/or the tumor associated cells are contacted with the test compounds for about 2 hours, about 4 hours, about 8 hours, about 12 hours, about 16 hours, about 24 hours, about 36 hours, about 48 hours, about 72 hours, about 4 days, about 5 days, about 6 days, or about 7 days.

5.5 Kits

The present disclosure provides kits for treating a subject having a cancer. In certain embodiments, the kits include an effective amount of an agent for increasing the expression of PDLIM2, or a functional fragment thereof, or a composition including said agent in unit dosage form. In certain embodiments, the kits include a genetic engineering system for increasing the expression of PDLIM. Non-limiting exemplary said agents and said genetic engineering systems are disclosed in Sections 5.2.1 and 5.2.2.

In certain embodiments, the kits include a sterile container which contains the agents or the genetic engineering system; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kits include instructions for administering an agent for increasing the expression of PDLIM2, or functional fragment thereof or a composition including said agent, or a genetic engineering system for increasing the expression of PDLIM2, or a functional fragment thereof, to a subject having a cancer. The instructions can include information about the use of the agent, composition, or genetic engineering system for treating the cancer. In certain embodiments, the instructions include at least one of the following: description of the agent or the genetic engineering system; dosage schedule and administration for treating the cancer; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

The present disclosure further provides kits for diagnosing a cancer. The present disclosure further provides for determining a prognosis of a cancer. The present disclosure further provides kits for predicting a subject's responsiveness to an anti-cancer treatment. The present disclosure further provides kits for monitoring a subject's responsiveness to an anti-cancer treatment.

In certain embodiments, the kits are configured for detecting a level of a PDLIM2 biomarker, e.g., using a detector. In certain embodiments, the PDLIM2 biomarker is a PDLIM2 mRNA, a PDLIM2 protein, or a combination thereof.

Non-limiting example of detectors that can be used with the presently disclosed kits include antibodies for immunodetection of the biomarker to be identified, oligonucleotide primers suitable for polymerase chain reaction (PCR) or nucleic acid sequencing; nucleic acid probes suitable for in situ hybridization or fluorescent in situ hybridization.

In certain embodiments, the kit further includes instructions or supporting material that describe the use of the kit to diagnose a cancer and/or reference to a website or publication describing same. In certain embodiments, the kit further includes instructions or supporting material that describe the use of the kit to determine a prognosis of cancer and/or reference to a website or publication describing same. In certain embodiments, the kit further includes instructions or supporting material that describe the use of the kit to predict or monitor a subject's responsiveness to an anti-cancer treatment and/or reference to a website or publication describing same. In certain embodiments, the instructions further include selecting an effective anti-cancer treatment based on the prediction or monitoring results.

6. EXAMPLES

The presently disclosed subject matter will be better understood by reference to the following Example, which is provided as exemplary of the presently disclosed subject matter, and not by way of limitation.

Example 1: Causative Role of PDLIM2 Epigenetic Repression in Lung Cancer and Therapeutic Resistance The present example identified PDZ-LIM domain-containing protein PDLIM2, also known as SLIM or mystique (Torrado et al., *Invest. Ophthalmol. Vis. Sci.* 45, 3955-3963 (2004); Tanaka et al., *Immunity* 22, 729-736 (2005); Loughran et al., *Mol. Biol. Cell.* 16, 1811-1822 (2005)), as a bona fide tumor suppressor particularly important for lung cancer therapeutic responses. Unbiased big data indicated that PDLIM2 is epigenetically repressed in over 75% of human lung cancers, associating with poor prognosis. Global or lung epithelial-specific deletion of PDLIM2 in mice led to increased lung cancer development and chemoresistance, and remarkably, complete resistance to anti-PD-1 and epigenetic drugs. PDLIM2 re-expression reversed the malignant phenotypes of lung cancer, and epigenetic agents synergized with anti-PD-1 and particularly chemotherapeutic drugs for complete remission of almost all lung cancers in an endogenous mouse model of lung cancer. Anti-PD-1 and chemotherapeutic drugs also showed great synergy. Mechanistically, the present example discovered that chemotherapeutic and epigenetic drugs induced PD-L1 expression in lung cancer cells, and that PDLIM2 increased major histocompatibility complex I (MHC-I) expression and repressed multi-drug resistance gene (MDR1) and growth/migration/invasion-related genes through inhibiting NF-KB RelA and STAT3, two transcription factors that have been linked to lung and other cancers (Bassères et al., *Cancer Res.* 70, 3537-3546 (2010); Zhou et al., *Oncogene* 34, 3804-3814 (2015); Xiao et al., *Am. J. Cancer Res.* 1, 192-221 (2011); Yu et al., *Nat. Rev. Cancer* 9, 798-809 (2009)). These findings provided mechanistic insights into the intrinsic and acquired resistance of lung cancer to anti-PD-1/PD-L1, chemotherapy and epigenetic therapy, and also a strong rationale for the selection of different combination therapies to treat the deadliest cancer.

Methods

Animals

PDLIM2$^{flx/flx}$ mice were generated at the UC Davis Mouse Biology Program and possess loxP sites flanking exon 3 of the pdlim2 gene and express a truncated PDLIM2 with 62 amino acids instead of 349 amino acids after Cre recombination. PDLIM2-null mice, RelA$^{flx/flx}$ mice, SP-C-rtTA$^{tg/-}$/(tetO)7CMV-Cre$^{tg/tg}$ mice, STAT3$^{flx/flx}$ mice and Lox-Stop-Lox (LSL) K-Ras$^{G12D}$ mice have been described before (Steinbrecher et al., *J. Immunol.* 180, 2588-2599 (2008); Li et al., *Oncoimmunology* 7, e1435250 (2018); Zhou et al., *Cancer Immunol. Res.* 5, 257-268 (2017); Hokuto et al., *J. Clin. Invest.* 113, 28-37 (2004); Houghton et al., *Nat. Med.* 16, 219-223 (2010); Jackson et al., *Genes Dev.* 15, 3243-3248 (2001); Tanaka et al., *Immunity* 22, 729-736 (2005); Bassères et al., *Cancer Res.* 70, 3537-3546 (2010); Zhou et al., *Oncogene* 34, 3804-3814 (2015)). Except for the PDLIM2$^{-/-}$ mice used for the spontaneous tumorigenesis were under a pure BALB/c background, all transgenic mice were backcrossed to a pure FVB/N background before being used for the experimental studies. BALB/c and C57BL/6 mice were originally from The Jackson Laboratory, and the severe combined immunodeficiency (SCID) mice were form Charles River. All animals were maintained under pathogen-free conditions.

Lung Tumor Models

Spontaneous tumor model: PDLIM2-null mice and control BABL/c mice were sacrificed at different ages for examining tumors in different organs/tissues.

Urethane model: 6-8-week-old mice under FVB/N background were intraperitoneally (i.p.) injected with urethane (1 g/kg body weight, Sigma-Aldrich, St. Louis, MO, USA) once a week for six weeks. All mice were sacrificed for lung tumor examinations seven (for no drug treatment experiments) or six (for drug treatment experiments) weeks post urethane treatment. For drug treatment experiments, the epigenetic agents 5-aza-dC (1 mg/kg body weight, Sigma-Aldrich, St. Louis, MO, USA) and MS-275 (1 mg/kg body weight, Selleckchem, Houston, TX, USA), chemotherapeutic drugs carboplatin (30 mg/kg body weight, AdipoGen, San Diego, CA, USA) and paclitaxel (15 mg/kg body weight, AdipoGen, San Diego, CA, USA), and/or PD-1 neutralizing antibody (200 μg/mouse, BioXCell, West Lebanon, NH, USA) were i.p injected as indicated in FIG. 4. Surface tumors in mouse lungs were counted by three blinded readers under a dissecting microscope, and tumor diameters were measured by microcalipers. K-Ras$^{G12D}$ model: 6-8-week-old mice under FVB/N background were intranasally administered $1\times10^7$ plaque-forming units of Cre-expressing adenovirus (adenocre; Gene Transfer Vector Core, University of Iowa, Iowa City, IA). Three months post AdenoCre treatment, all mice were sacrificed for lung tumor examinations.

MAD109 syngeneic model: 6-week-old BALB/c mice were challenged subcutaneously (s.c) in the lower back with $5\times10^5$ MAD109 cells expressing ectopic PDLIM2 or an empty vector. Tumors at the injection sites were measured every three days and surgically taken out 21 days post MAD109 cell injection. All the mice were sacrificed 26 days post MAD109 cell injection and the lungs were perfused and stained with India ink (Speedball, NC, USA) for lung metastasis examinations.

LLC syngeneic model: 6-week-old C57BL/6 mice were intravenously (i.v) injected with $5\times10^5$ LLC cells expressing ectopic PDLIM2 or an empty vector. All the mice were sacrificed 21 days post cell injection for lung metastasis examinations.

SCID mouse xenograft model: SCID mice were injected s.c with $5\times10^5$ human lung cancer cells expressing ectopic PDLIM2 or an empty vector. The recipient mice were sacrificed for tumor evaluation 14 days post injection.

Flow Cytometry (FACS) Analysis

The indicated cells were fixed with paraformaldehyde (2%) and permeabilization with saponin (0.5%). Cells were then treated with the indicated antibodies. Data were acquired using FACSCalibur (BD Biosciences, Bedford, MA, USA) and analyzed using CellQuest software (Becton Dickinson, Franklin Lakes, NJ, USA) as described previously (Li et al., Oncoimmunology 7, e1435250 (2018)).

Histology and Immunohistochemistry and Human Lung Tumor Tissue Microarray (TMA) Assays.

Mouse or tissues were excised, fixed in formalin, embedded in paraffin, and cut into 4-pm-thick sections. Sections were stained with H&E, or subjected to sequential incubations with different primary antibodies and peroxidase-conjugated goat anti-rabbit secondary antibodies. The human lung tumor tissue arrays were described previously (Sun et al., *Oncogene* 35, 2299-2310 (2016)). Antibodies used for histology and FACS assays were listed in Table 1.

TABLE 1

Antibodies Used

| Antibody | Company | Cat. No. | Dose | Usage |
|---|---|---|---|---|
| Anti-Cleaved Caspase 3 | Cell Signaling Technology, Danvers, MA, USA | 9661 | 1:200 | IHC |
| Anti-Bcl-xL | Cell Signaling Technology, Danvers, MA, USA | 2764 | 1:300 | IHC |
| Anti-PD-L1 | Cell Signaling Technology, Danvers, MA, USA | 64988 | 1:200 | IHC |
| Anti-BrdU | Sigma-Aldrich, St. Louis, MO, USA | B2531 | 1:500 | IHC |
| Anti-Cyclin D1 | Santa Cruz Biotechnology, Dallas, TX, USA | sc-450 | 1:200 | IHC |
| Anti-Ki-67 | Santa Cruz Biotechnology, Dallas, TX, USA | sc-7846 | 1:500 | IHC |
| Anti-SP-C | Santa Cruz Biotechnology, Dallas, TX, USA | sc-13979 | 1:400 | IHC |
| Anti-CCSP | Santa Cruz Biotechnology, Dallas, TX, USA | sc-9772 | 1:1000 | IHC |
| Anti-CD4 | Santa Cruz Biotechnology, Dallas, TX, USA | sc-13573 | 1:50 | IHC |
| Anti-CD8 | Thermo Fisher Scientific, Waltham, MA, USA | MA1-70041 | 1:50 | IHC |
| Anti-mouse IgG Biotinylated | Vector Laboratories, Burlingame, CA, USA | BMK-2202 | 1:200 | IHC |
| Goat anti-rat IgG Biotinylated | Vector Laboratories, Burlingame, CA, USA | BA9401 | 1:100 | IHC |
| Goat anti-rabbit IgG Biotinylated | Dako, Carpinteria, CA, USA | E0432 | 1:200 | IHC |
| Rabbit anti-goat IgG Biotinylated | Santa Cruz Biotechnology, Dallas, TX, USA | sc-2774 | 1:200 | IHC |
| Anti-PDLIM2 (mouse) | Everest Biotech, Ramona, CA, USA | EB1187 8 | 1:400 | IHC |
| Anti-PDLIM2 (human) | Sigma-Aldrich, St. Louis, MO, USA | HPA003 880 | 1:250 (IHC) & 1:1000 (WB) | IHC & WB |
| Anti-STAT3 | Cell Signaling Technology, Danvers, MA, USA | 4904 | 1:1000 | IHC & WB |
| Anti-RelA | Cell Signaling Technology, Danvers, MA, USA | 8242 | 1:500 (IHC) & 1:1000 (WB) | IHC & WB |
| Anti-c-Myc | Santa Cruz Biotechnology, Dallas, TX, USA | sc-40 | 1:1000 | WB |
| Anti-Hsp90 | Santa Cruz Biotechnology, Dallas, TX, USA | sc-13119 | 1:1000 | WB |
| Anti-LaminB | Santa Cruz Biotechnology, Dallas, TX, USA | sc-6217 | 1:1000 | WB |
| Anti-Sp1 | Santa Cruz Biotechnology, Dallas, TX, USA | sc-59 | 1:1000 | WB |

TABLE 1-continued

| Antibodies Used | | | | |
|---|---|---|---|---|
| Antibody | Company | Cat. No. | Dose | Usage |
| Goat anti-mouse IgG-HRP | Santa Cruz Biotechnology, Dallas, TX, USA | sc-2055 | 1:5000 | WB |
| Goat anti-rabbit IgG-HRP | Santa Cruz Biotechnology, Dallas, TX, USA | sc-2054 | 1:5000 | WB |
| Anti-HDAC1 | Millipore, Burlington, MA, USA | 17-10199 | 2 μg (ChIP) & 1:1000 (WB) | ChIP & WB |
| Anti-phospho HDAC1 (Ser421/Ser423) | Millipore, Burlington, MA, USA | 07-1575 | 1:100 (ChIP) & 1:1000 (WB) | ChIP & WB |
| Anti-acetyl-Histone H3 (Lys14) | Millipore, Burlington, MA, USA | 07-353 | 1:50 | ChIP |
| Normal mouse IgG | Millipore, Burlington, MA, USA | 12-371B | 2 μg | ChIP |
| Normal rabbit IgG | Millipore, Burlington, MA, USA | PP64B | 2 μg | ChIP |
| Anti-Pol II | Cell Signaling Technology, Danvers, MA, USA | 2629 | 1:50 | ChIP |
| Anti-IFNγ FITC | eBioscience, San Diego, CA, USA | 11-7311-82 | 1 μl per 106 cell | FACS |
| Anti-GranzB FITC | eBioscience, San Diego, CA, USA | 11-8898-82 | 0.25 μl per 106 cell | FACS |
| Anti-CD3 PE | eBioscience, San Diego, CA, USA | 12-0031-83 | 2.5 μl per 106 cell | FACS |
| Anti-CD4 PE-Cy7 | eBioscience, San Diego, CA, USA | 25-0042-82 | 1.25 μl per 106 cell | FACS |
| Anti-CD8a APC | eBioscience, San Diego, CA, USA | 17-0081-83 | 0.625 μl per 106 cell | FACS |
| Anti-CD11c FITC | eBioscience, San Diego, CA, USA | 11-0114-82 | 0.5 μl per 106 cell | FACS |
| Anti-C11b PE | eBioscience, San Diego, CA, USA | 12-0112-82 | 0.625 μl per 106 cell | FACS |
| Anti-PD-L1 PE-Cy7 | eBioscience, San Diego, CA, USA | 25-5982-82 | 0.625 μl per 106 cell | FACS |
| Anti-F4/80 APC | eBioscience, San Diego, CA, USA | 17-4801-82 | 2 μl per 106 cell | FACS |
| Anti-PD-1 | BioXcell, West Lebanon, NH, USA | BE0273 | 200 μg per mouse | in vivo blockade |

BrdU Labeling

Mice were i.p. injected with 100 mg/kg BrdU (Sigma-Aldrich, St. Louis, MO, USA) 2 hrs prior to sacrifice. Mouse lung tissue sections were stained with a BrdU in situ detection kit (BD Biosciences, Bedford, MA, USA). More than 3000 cells per lung were counted in randomly selected fields. BrdU labeling index was calculated as the percentage of labeled cells per total cells counted.

In Vitro Transwell Migration and Invasion Assays

Cells were plated in the upper chamber of transwell coated with Matrigel (BD Biosciences, Bedford, MA, USA) (for invasion assay) or uncoated (for migration assay), and incubated for 24 h at 37° C. in 5% $CO_2$. Non-migrated cells were scraped from the upper surface of the membrane (8 μm pore size) with a cotton swab, and migrated cells remaining on the bottom surface were stained with crystal violet.

Cell Growth Assays

Cells were seeded into 12-well plates at a density of 5,000 cells per well, in the presence or absence of the indicated treatment. Cell density was determined by replacing the medium with 2 μmol/L of calcein AM in 1× dissociation solution (Trevigen) at the indicated time points. After 1 h of incubation, diesterase activity (relative fluorescence units) was measured with a Tecan Infinite 200 Microplate Reader, using an excitation wavelength of 485 nm and emission wavelength of 520 nm.

Quantitative Polymerase Chain Reaction (qPCR) Analysis

Mouse lung tissues and BAL cells were subjected to RNA extraction, RNA reverse transcription and real-time PCR as described (Li et al., Oncoimmunology 7, e1435250 (2018); Sun et al., *Bio. Protoc.* 7, pii: e2287 (2017)). Primer pairs used for qPCR were listed in Table 2.

TABLE 2

| Primers Used | | | | | |
|---|---|---|---|---|---|
| Gene | Species | Accession number | Forward (5' to 3') | Reverse (5' to 3') | Usage |
| gapdh | human | NM_002046.3 | CCGAGCCACATCGCTCAGACAC [SEQ ID NO. 1] | GTGACCAGGCGCCCAATACGAC [SEQ ID NO. 2] | RT-PCR |
| pdlim2 | human | NM_021630.5 | GTATGGCGTTGACGGTGGATGTG [SEQ ID NO. 3] | GGAGGTCAGCGTCCTTGGCTTT [SEQ ID NO. 4] | RT-PCR |
| hdac1 | human | NM_004964.2 | ACTACGACGGGGATGTTGGA [SEQ ID NO. 5] | CAGCATTGGCTTTGTGAGGG [SEQ ID NO. 6] | RT-PCR |
| bcl-2 | human | NM_000633.2 | ATGTGTGTGGAGAGCGTCAACC [SEQ ID NO. 7] | TGAGCAGAGTCTTCAGAGACAGCC [SEQ ID NO. 8] | RT-PCR |
| mmp9 | human | NM_004994.2 | GCCTTTGGACACGCACGACG [SEQ ID NO. 9] | AGCCCACTTGGTCCACCTGGTT [SEQ ID NO. 10] | RT-PCR |
| abcb1 (mdr1) | human | NM_000927.4 | GCGAGGTCGGAATGGATCTT [SEQ ID NO. 11] | GCCAAAGTTCCCACCACCAT [SEQ ID NO. 12] | RT-PCR |
| bcl2l1 (bcl-xl) | human | NM_138578.1 | GAATGACCACCTAGAGCCTTGG [SEQ ID NO. 13] | TGTTCCCATAGAGTTCCACAAAAG [SEQ ID NO. 14] | RT-PCR |

TABLE 2-continued

| Primers Used | | | | | |
|---|---|---|---|---|---|
| Gene | Species | Accession number | Forward (5' to 3') | Reverse (5' to 3') | Usage |
| birc5 (survivin) | human | NM_001168.2 | TGACGACCCCATAGAGGAACA [SEQ ID NO. 15] | CGCACTTTCTCCGCAGTTTC [SEQ ID NO. 16] | RT-PCR |
| ccnd1 (cyclin D1) | human | NM_053056.2 | GCTGCGAAGTGGAAACCATC [SEQ ID NO. 17] | GCACTTCTGTTCCTCGCAGA [SEQ ID NO. 18] | RT-PCR |
| cd274 (pd-l1) | human | NM_014143.3 | TGGCATTTGCTGAACGCATTT [SEQ ID NO. 19] | AGTGCAGCCAGGTCTAATTGT [SEQ ID NO. 20] | RT-PCR |
| cdh2 (n-cadherin) | human | NM_001792.3 | GGCTTCTGGTGAAATCGCAT [SEQ ID NO. 21] | GCAGGCTCACTGCTCTCATA [SEQ ID NO. 22] | RT-PCR |
| β-actin | mouse | NM_007393.3 | ACCCGCGAGCACAGCTTCTTTG [SEQ ID NO. 23] | CTTTGCACATGCCGGAGCCGTTG [SEQ ID NO. 24] | RT-PCR |
| gapdh | mouse | NM_008084.2 | AGTGCCAGCCTCGTCCCGTA [SEQ ID NO. 25] | CAGGCGCCCAATACGGCCAA [SEQ ID NO. 26] | RT-PCR |
| pdlim2 | mouse | NM_145978.2 | GAGAACATGCTACACGCGGA [SEQ ID NO. 27] | GGAGCCCTGGAATCTGGTTG [SEQ ID NO. 28] | RT-PCR |
| h2-k1 | mouse | NM_001001892.2 | AGGCTGGTGAAGCAGAGAGA [SEQ ID NO. 29] | ATGTCAGCAGGGTAGAAGCC [SEQ ID NO. 30] | RT-PCR |
| twist2 | mouse | NM_007855.2 | CTACCAGGTTCTCCAGAGCG [SEQ ID NO. 31] | TTGTCCAGGTGCCGAAAGTC [SEQ ID NO. 32] | RT-PCR |
| sftpc (sp-c) | mouse | NM_011359.2 | AAAGAGGTCCTGATGGAGAGTCCAC [SEQ ID NO. 33] | GCTCCTGGGACCTGCCGAGTA [SEQ ID NO. 34] | RT-PCR |
| bcl2l1 (bcl-xl) | mouse | NM_009743.4 | AGATTCAGCACGAGCAGTCA [SEQ ID NO. 35] | GGGCTCAACCAGTCCATTGT [SEQ ID NO. 36] | RT-PCR |
| ccnd1 (cyclin D1) | mouse | NM_007631.2 | CAAAATGCCAGAGGCGGATG [SEQ ID NO. 37] | CATGGAGGGTGGGTTGGAAA [SEQ ID NO. 38] | RT-PCR |
| cd274 (pd-l1) | mouse | NM_021893.3 | CCTGCTGTCACTTGCTACGG [SEQ ID NO. 39] | CACTAACGCAAGCAGGTCCA [SEQ ID NO. 40] | RT-PCR |
| cdh2 (n-cadherin) | mouse | NM_007664.4 | CCTTGCTTCAGGCGTCTGTG [SEQ ID NO. 41] | CTTGAAATCTGCTGGCTCGC [SEQ ID NO. 42] | RT-PCR |
| hdac1 | human | NM_004964.2 | CTGTGAGGAAGAGTTCGCCGA TGCTGAAGAGGAGGGAGAG [SEQ ID NO. 43] | CTCTCCCTCCTCTTCAGCATCG GCG AACTCTTCCTCACAG [SEQ ID NO. 44] | SS421/423AA mutation |
| hdac1 | human | NM_004964.2 | TGCTGCTCAACTATGGTCTCTA TTCAAGAGATAGAGACCATAG TTGAG CAGCTTTTTTC [SEQ ID NO. 45] | TCGAGAAAAAAGCTGCTCAA CTATGGTCTCTATCTCTTGAAT AGAGACCATAGTTGAGCAGCA [SEQ ID NO. 46] | Cloning for shRNA |
| hdac1 | human | NM_004964.2 | GGgcggccgcAAGATGGCGCAG ACGCAGG [SEQ ID NO. 47] | AGggatccTCAGGCCAACTTGA CCTCCTC [SEQ ID NO. 48] | Cloning for expression |
| pdlim2 | human | Gene ID: 64236 | GAAGTGAAACCGGGCTGAGG [SEQ ID NO. 49] | GCCAAAGGGAGAAGGAGAGG [SEQ ID NO. 50] | ChIP PCR |
| pdlim2 | human | Gene ID: 64236 | AGAGGAGTTTATATATATTTAGG [SEQ ID NO. 51] | TACCTAACAACCCTCTCTCC [SEQ ID NO. 52] | Bisulfite PCR |

Bisulfite Genomic DNA Sequencing

Genomic DNA from 5-aza-dC-treated or DMSO mock-treated cells were isolated using the PureLink Genomic DNA Purification Kit (Invitrogen, Carlsbad, CA, USA). Genomic DNA aliquots were then treated with sodium bisulfite using the EZ DNA Methylation-Gold Kit (Zymo Research, Irvine, CA, USA), followed by PCR to amplify the pdlim2 promoter using Hot-Start Taq enzyme (Qiagen, Hilden, Germany). Primers used for the PCR were:

```
primer forward
                                      [Seq ID No. 53]
5'-AGAGGAGTTTATATATATTTAGG
and

primer reverse
                                      [Seq ID No. 54]
5'-TACCTAACAACCCTCTCTCC.
```

The PCR products were used for DNA sequencing to determine the methylation status of the CpG dinucleotides within the pdlim2 promoter.

ChIP Assays

ChIP assays were performed essentially as described (Qing et al., Proc. Natl. Acad. Sci. USA 104, 5324-5329 (2007)). Primers for ChIP, qPCR and bisulfite genomic DNA amplification and sequencing are listed in Table 1.

Statistical Analysis

Data were reported as mean±standard deviation (SD). Student's t test (two tailed) and one way ANOVA/Tukey's or two way ANOVA/Sidak's test were used to assess significance of differences between two groups and multiple comparisons, respectively. Gehan-Breslow-Wilcoxon test and log-rank test were used to compare overall patient survival between high and low PDLIM2 expression groups. Multivariate survival analysis was also performed using Cox's proportional hazards model to statistically consider and adjust the potential effect of other clinical factors, such as age and tumor stage. The p values <0.05 and 0.01 were considered statistically significant and highly statistically significant, respectively.

Results and Discussion

In line with its role in promoting ubiquitination and proteasomal degradation of nuclear RelA and STAT3, PDLIM2 has been suggested to function as a tumor suppressor in cell line studies (Tanaka et al., *Nat. Immunol.* 8, 584-591 (2007); Tanaka et al., *Sci. Signal.* 4, ra85 (2011); Qu et al., *Cell Biosci.* 2, 23 (2012); Qu et al., *J. Biol. Chem.* 285, 11786-11792 (2010); Qu et al., *Cancer Res.* 70, 1766-1772 (2010); Sun et al., *J. Biol. Chem.* 290, 7362-7368 (2015); Yan et al., *Blood* 113, 4370-4380 (2009)). However, the pathophysiological significance of these findings and in particular the role of PDLIM2 in lung cancer has not been suitably documented. Of note, PDLIM2 is expressed highest in normal lungs (Torrado et al., *Invest. Ophthalmol. Vis. Sci.* 45, 3955-3963 (2004); Tanaka et al., *Immunity* 22, 729-736 (2005); Loughran et al., *Mol. Biol. Cell.* 16, 1811-1822 (2005)). Furthermore, whether PDLIM2 is involved in therapeutic resistance has not been suitably documented in any cancer type.

To this end, PDLIM2 expression in lung cancer was examined using The Cancer Genome Atlas (TCGA), Gene Expression Omnibus (GEO), European Genome-phenome Archive (EGA) and EMBL-EBI Expression Atlas databases.

Such public data indicated that PDLIM2 was repressed in human lung cancers and cancer cell lines, and that PDLIM2 repression associated with cancer progression and poor patient survival (FIG. 1A and FIG. 5; Tables 3 & 4). These findings were further validated by the presently disclosed lung cancer and cell line studies (FIGS. 1B-1E; Tables 5 & 6). Besides lung cancer, PDLIM2 was repressed in other cancers (FIG. 6). PDLIM2 repression is thus clinically and pathogenically relevant to human cancers, particularly lung cancer.

TABLE 3

PDLIM2 expression levels in subjects of TCGA-LUNG cohort

| TCGA-LUNG Cohort Characteristics | Expression level of PDLIM2: Low (n = 900) | High (n = 119) | Total (n = 1019) | p-value by $x^2$ test |
|---|---|---|---|---|
| Sex | | | | 0.0002 |
| Male | 558 | 53 | 611 | |
| Female | 341 | 66 | 407 | |
| N/A | 1 | 0 | 1 | |
| Age (mean = 66.28 yrs) | | | | 0.8107 |
| <mean | 410 | 52 | 462 | |
| >mean | 466 | 62 | 528 | |
| N/A | 24 | 5 | 29 | |
| Smoke | | | | 0.0144[a] |
| Non-smoker | 76 | 18 | 94 | |
| Reformed smoker (>15 yrs) | 192 | 26 | 218 | |
| Reformed smoker (≤15 yrs) | 375 | 44 | 419 | |
| Current smoker | 227 | 25 | 252 | |
| N/A | 30 | 6 | 36 | |
| T-stage | | | | 0.0002[b] |
| T1 | 234 | 50 | 284 | |
| T2 | 521 | 50 | 571 | |
| T3 | 103 | 15 | 118 | |
| T4 | 39 | 3 | 42 | |
| N/A | 3 | 1 | 4 | |
| N-stage | | | | 0.037[c] |
| N0 | 567 | 85 | 652 | |
| N1 | 204 | 23 | 227 | |
| N2 | 107 | 7 | 114 | |
| N3 | 7 | 0 | 7 | |
| N/A | 15 | 4 | 19 | |
| Clinical stage | | | | 0.0239[d] |
| I | 452 | 73 | 525 | |
| II | 256 | 30 | 286 | |
| III | 161 | 12 | 173 | |
| IV | 29 | 4 | 33 | |
| N/A | 2 | 0 | 2 | |
| Recurrence | | | | 0.9221 |
| Yes | 263 | 37 | 300 | |
| No | 501 | 69 | 570 | |
| N/A | 136 | 13 | 149 | |
| Metastasis[e] | | | | 0.0304 |
| Yes | 371 | 38 | 409 | |
| No | 345 | 57 | 402 | |
| N/A | 184 | 24 | 208 | |

[a]Non-smoker vs Reformed smoker (>15 yrs, ≤15 yrs) and Current smoker

[b]T1 vs T2, T3, and T4

[c]N0 vs N1, N2, and N3

[d]I vs II, III, and IV

[e]Metastasis was determined by M stage, N stage, and new tumor event with Distant metastasis.

TABLE 4

| Smoke characteristic of subjects of TCGA-LUNG cohort | | | | |
|---|---|---|---|---|
| | TCGA-LUNG Cohort | | | |
| Characteristics | Male (n = 611) | Female (n = 407) | Total (n = 1018) | p-value by $\chi^2$ test |
| Smoke | | | | <0.0001 |
| Non-smoker | 31 | 63 | 94 | |
| Reformed smoker (>15 yrs) | 140 | 78 | 218 | |
| Reformed smoker (≤15 yrs) | 243 | 176 | 419 | |
| Current smoker | 173 | 79 | 252 | |
| N/A | 24 | 11 | 35 | |

TABLE 5

| PDLIM2 expression levels in tissue microarray | | | | |
|---|---|---|---|---|
| | Expression level of PDLIM2 | | | |
| TMA Characteristics | Low (n = 51) | High (n = 18) | Total (n = 69) | p-value by $\chi^2$ test |
| Race | | | | 0.2860 |
| White | 44 | 17 | 61 | |
| Black | 3 | 0 | 3 | |
| N/A | 4 | 1 | 5 | |
| Sex | | | | 0.6859 |
| Female | 25 | 10 | 35 | |
| Male | 25 | 8 | 33 | |
| N/A | 1 | 0 | 1 | |
| Pleural | | | | 0.0889 |
| Yes | 26 | 5 | 31 | |
| No | 25 | 13 | 38 | |
| Inflammation | | | | 0.0422[a] |
| Mild | 41 | 18 | 59 | |
| Moderate | 7 | 0 | 7 | |
| Severe | 3 | 0 | 3 | |
| T-stage | | | | 0.0199[b] |
| T1 | 15 | 11 | 26 | |
| T2 | 28 | 7 | 35 | |
| T3 | 1 | 0 | 1 | |
| T4 | 6 | 0 | 6 | |
| N/A | 1 | 0 | 1 | |
| N-stage | | | | 0.1579[c] |
| N0 | 30 | 14 | 44 | |
| N1 | 9 | 2 | 11 | |
| N2 | 8 | 1 | 9 | |
| NX | 3 | 1 | 4 | |
| N/A | 1 | 0 | 1 | |
| Clinical stage | | | | 0.0485[d] |
| 1/1a/1b | | 26 | 14 | 40 |
| 2 | 7 | 2 | 9 | |
| 3a/3b | 14 | 1 | 15 | |
| N/A | 4 | 1 | 5 | |
| Recurrence | | | | 0.1071 |
| Yes | 25 | 5 | 30 | |
| No | 23 | 12 | 35 | |
| N/A | 3 | 1 | 4 | |
| Metastasis | | | | 0.0361 |
| Yes | 31 | 6 | 37 | |
| No | 17 | 11 | 28 | |
| N/A | 3 | 1 | 4 | |

[a]Mild vs Moderate plus Severe
[b]T1 vs T2, T3 plus T4
[c]N0 vs N1 plus N2
[d]1/1a/1b vs 2 plus 3a/3b

TABLE 6

| Clinicopathological characteristics in tissue microarray | |
|---|---|
| Characteristics | Patient (n = 69) |
| Race | |
| White | 61 |
| Black | 3 |
| N/A | 5 |
| Sex | |
| Female | 35 |
| Male | 33 |
| N/A | 1 |
| Smoke | |
| Smoker | 17 |
| Former | 42 |
| Never | 10 |
| Mutation | |
| WT | 19 |
| EGFR | 18 |
| KRAS | 32 |
| Angiogenesis | |
| Yes | 42 |
| No | 26 |
| N/A | 1 |
| Pleural | |
| Yes | 31 |
| No | 38 |
| Inflammation | |
| Mild | 59 |
| Moderate | 7 |
| Severe | 3 |
| T-stage | |
| T1 | 26 |
| T2 | 35 |
| T3 | 1 |
| T4 | 6 |
| N/A | 1 |
| N-stage | |
| N0 | 44 |
| N1 | 11 |
| N2 | 9 |
| NX | 4 |
| N/A | 1 |
| Clinical stage | |
| 1/1a/1b | 40 |
| 2 | 9 |
| 3a/3b | 15 |
| N/A | 5 |
| Recurrence | |
| Yes | 30 |
| No | 35 |
| N/A | 4 |
| Metastasis | |
| Yes | 37 |
| No | 28 |
| N/A | 4 |

TCGA data also indicated that the pdlim2 promoter was hypermethylated, and that all three functional DNA methyltransferases (DNMTs) were increased in human lung cancers, associating with pdlim2 promoter methylation positively and PDLIM2 expression negatively (FIG. 1F and FIGS. 7A-7E). Interestingly, tobacco smoking, a predominant risk factor that accounts for over 80% of lung cancer cases (American Cancer Society. Tobacco use. American Cancer Society (Ed.), Cancer facts & figures American Cancer Society, Atlanta, GA. 44-47 (2018)), was associated positively with DNMT expression and pdlim2 promoter methylation but negatively with PDLIM2 expression in human lung cancers (FIGS. 7F & 7G). Importantly, treatment with the DNMT inhibitor 5-aza-dC led to promoter hypomethylation and re-expression of PDLIM2 in human lung cancer cells (FIG. 1G and FIGS. 7H & 7I). In line with their synergistic role with DNMTs in suppressing tumor suppressor gene expression (Rountree et al., *Oncogene* 20, 3156-3165 (2001)), histone deacetylases (HDACs), particularly HDAC1 and HDAC2, were significantly increased in human lung cancers and inversely associated with PDLIM2 expression (FIGS. 8A & 8B). Accordingly, more HDAC1 and in particular its phosphorylation form, but decreased histone H3K14 acetylation and RNA polymerase II (Pol II), were found at the pdlim2 promoter in human lung cancer cells (FIG. 1I1). HDAC1 knockdown increased H3K14 acetylation at the pdlim2 promoter and PDLIM2 transcription in human lung cancer cells (FIG. 1I and FIG. 8C). Over-expression of HDAC1, but not its phosphorylation deficient mutant, further suppressed PDLIM2 expression (FIG. 1J). Treatment using HDAC inhibitors MS275 and TSA induced PDLIM2 re-expression in human lung cancer cell lines or epithelial cell lines in vitro transformed by K-Ras$^{Q61H}$ mutant (FIG. 1K and FIGS. 8D-8F). PDLIM2 was also repressed in murine lung cancers and could be restored by 5-aza-dC and MS275 both in vitro and in vivo (FIG. 1*l* and FIG. 9). Thus, PDLIM2 repression in lung cancer is mediated by its promoter hypermethylation by DMNTs and de-acetylation by HDACs.

Notably, PDLIM2-null mice started to develop spontaneous tumors at 7 months of age (FIG. 2A). By 18 months of age, over 90% of PDLIM2$^{-/-}$ mice, compared to less than 10% of wild-type (WT) mice, developed tumors. Of note, 50% of them were lung tumors (FIGS. 10A & 10B). PDLIM2$^{-/-}$ mice were also more sensitive to K-Ras$^{G12D}$-induced lung tumorigenesis (FIG. 2B).

To validate these findings, PDLIM2$^{flox/flox}$/Tet(on)/SP-C-Cre (ΔSPC) mice were created, in which PDLIM2 can be selectively deleted from SP-C$^+$ alveolar type II epithelial cells and bronchioalveolar stem cells, the cells-of-origin of lung cancer (Xu et al., *Proc. Natl. Acad. Sci. USA* 109, 4910-4915 (2012)), after doxycycline administration (FIG. 10C). In comparison to WT mice, ΔSPC mice developed significantly more and larger lung tumors in response to the carcinogen urethane (FIG. 2C and FIGS. 10D-10F).

By contrast, PDLIM2 reconstitution crippled the growth, migration and invasion ability in vitro and suppressed the tumor formation and metastasis in vivo of human and mouse lung cancer cell lines (FIGS. 2D & 2E and FIGS. 11A-11E). Remarkably, and somewhat unexpectedly, 5-aza-dC and MS275 completely lost the ability to treat lung cancer in ΔSPC mice (FIG. 2F). Similarly, shRNA blockade of PDLIM2 re-expression protected human lung cancer cells from 5-aza-dC and MS275 in vitro (FIG. 11F). Altogether, these data demonstrated that PDLIM2 functions as a bona fide lung tumor suppressor, and that PDLIM2 restoration is essential for the anti-lung cancer activity of 5-aza-dC and MS275.

Interestingly, PDLIM2 expression inversely associated with the carboplatin sensitivity of lung cancer cells, and ectopic expression of PDLIM2 remarkably increased the sensitivity (FIGS. 2G & 2H and FIG. 12A). PDLIM2 expression also overcame the acquired resistance to paclitaxel, another chemotherapeutic drug that is often combinedly used with carboplatin for the first-line treatment of lung and many other cancers (FIGS. 12B-12F). Consistent with these in vitro studies, lung tumors in ΔSPC mice were more resistant to carboplatin-paclitaxel combination treatment compared to those in WT mice (FIG. 2I). Notably, lung tumors in ΔSPC mice were completely resistant to anti-PD-1 treatment (FIG. 2J). It should be pointed out that the basal numbers of tumor-infiltrated lymphocytes (TILs) as well as those induced by chemo or anti-PD-1 treatment were comparable in ΔSPC and WT mice (FIGS. 2K & 2L and FIG. 13). However, either basal or treatment-induced apoptosis of lung cancer cells in ΔSPC mice was lower (FIGS. 2M & 2N). These data suggest that PDLIM2 repression renders lung cancer cells resist to chemotherapeutic drugs and cytotoxic T cells (CTLs).

In this regard, PDLIM2 expression in human lung cancers positively associated with T-cell activation and MHC-I expression (FIG. 3A and FIG. 14). PDLIM2 deletion decreased while its expression increased MHC-I in lung cancer cells in mouse models (FIG. 3B). In contrast, PDLIM2 deletion increased and its expression decreased expression of growth genes, including Bcl-xL and Cyclin D1 in lung cancer cells (FIGS. 3C & 3D and FIG. 15). Consistently, PDLIM2 deletion diminished T-cell activation, decreased apoptosis and increased proliferation of lung cancer cells, whereas PDLIM2 re-expression showed opposite effects (FIGS. 16A-16D). These findings suggested that PDLIM2 repression contributes to lung cancer immune evasion via repressing MHC-I expression to evade CTLs on one hand, and inducing growth genes to resist CTL cytotoxicity on the other hand. PDLIM2 repression also induced migration/invasion genes to promote lung cancer progression (FIGS. 17A-17C).

Survival gene induction by PDLIM2 repression also protects lung cancer cells from chemotherapeutic drugs. Additional mechanism underlying lung cancer chemoresistance involves paclitaxel induction of MDR1 and drug efflux, which was blocked by PDLIM2 re-expression (FIGS. 3E & 3F).

It was then examined whether PDLIM2 represses lung cancer via repressing RelA and/or STAT3, because PDLIM2 deletion increased while its expression decreased nuclear RelA and STAT3, a hallmark of NF-κB and STAT3 activation, in lung cancer cells (FIGS. 18A & 18B). Indeed, deletion of lung epithelial RelA or STAT3 from PDLIM2-null mice blocked the lung cancer increase (FIG. 3G). Consistently, RelA or STAT3 co-deletion or knockdown decreased growth gene expression and lung cancer cell growth (FIG. 3G and FIGS. 19A-19C). Interestingly, deletion of STAT3, but not RelA, increased MHC-I expression in lung cancer cells (FIG. 20A), indicating a specific role for STAT3. Conversely, PDLIM2 suppressed paclitaxel induction of MDR1 through RelA. Paclitaxel increased RelA activation and expression of the NF-κB inhibitor IκBα overcame the paclitaxel resistance of lung cancer cells (s). Nevertheless, these data indicated that PDLIM2 suppresses lung cancer and therapeutic resistance through repressing RelA and STAT3 to increase MHC-I expression and repress MDR1 and cancer-related genes.

In further support, epigenetic drugs, which could restore PDLIM2 expression and suppress lung cancer in WT mice but have no effect in ΔSPC mice, inhibited RelA and STAT3 activation and Bcl-xL and Cyclin D1 expression in PDLIM2 WT but not null lung tumors (FIGS. 3H & 3I). Epigenetic drugs could also induce MHC-I expression in lung cancer cells (FIG. 3J).

Based on these findings, it was hypothesized that through restoring PDLIM2 expression to repress RelA and STAT3 activation, epigenetic drugs render lung cancer vulnerable to chemotherapeutic drugs and anti-PD-1 (FIG. 4A). It was also hypothesized that PD-1 blockade overcomes the acquired immunoresistance induced by chemo and epigenetic therapy, because it was found that chemotherapeutic or epigenetic drugs induced PD-L1 in lung tumor cells and macrophages, independently of PDLIM2 (FIGS. 4A-4F and FIGS. 21A-21C & 22A-22D). Epigenetic agents indeed sensitized lung cancer cells to chemotherapeutic drugs in vitro (FIGS. 4G & 4H). More importantly, their combination led to complete remission of almost all lung cancers in mouse model (FIG. 4I). Epigenetic drugs and anti-PD-1 as well as anti-PD-1 and chemotherapeutic drugs also showed great synergies (FIGS. 4J & 4K).

Overall, the presently disclosed data demonstrated PDLIM2 epigenetic repression and RelA/STAT3 regulation of MHC-1, MDR1 and cancer-related genes as a previously unknown mechanism underlying lung cancer and resistance to PD-1 blockade and chemo-therapy. The presently disclosed data also identified PDLIM2 restoration as a critical mechanism of epigenetic therapy, and PD-L1 induction as a new mechanism of acquired immunoresistance induced by chemo and epigenetic drugs. These data thus not only help understand lung cancer and therapeutic resistance, but also provide a firm basis to use combination therapies of anti-PD, chemotherapeutic and/or epigenetic drugs for lung cancer.

Example 2: PDLIM2 and Tumor

The present example describes the role of PDLIM2 as potential biomarker for cancer therapy and in particular for immunotherapy resistance. PDLIM2 expression was repressed in various human cancers. PDZ-LIM domain containing protein 2 (PDLIM2, also known as Mystique, or Slim) was recently identified as a tumor suppressor whose expression is repressed in various cancer cell lines, including cell lines of colon cancer, adult T cell leukemia, primary effusion lymphoma (Yan et al., Blood. 2009; 113(18):4370-4380; Yan et al., Neoplasia. 2009; 11(10):1036-1041; Qu et al., Cancer Res. 2010; 70(5):1766-1772; Qu et al., J Biol Chem. 2010; 285(16):11786-11792). PDLIM2 expression was also significantly repressed in many lung cancer cell lines (FIG. 23A). A significant decrease in PDLIM2 expression (<40% of the level in matched normal controls) was also found in 28 out of 36 (based on the RNA level) and 51 out of 69 (based on the protein level) of lung cancer samples directly isolated from patients (FIGS. 23B & 23C). In addition, the presently disclosed analysis of The Cancer Genome Atlas (TCGA) database revealed that in comparison to control normal tissues, PDLIM2 was significantly decreased in various cancers including Bladder Urothelial Carcinoma (BLCA), Cervical squamous cell carcinoma and endocervical adenocarcinoma (CESC), Cholangiocarcinoma (CHOL), Colon adenocarcinoma (COAD), Head and Neck squamous cell carcinoma (HNSC), Kidney Chromophobe (KICH), Kidney renal papillary cell carcinoma (KIRP), Liver hepatocellular carcinoma (LIHC), Lung adenocarcinoma (LUAD), Lung squamous cell carcinoma (LUSC), Prostate adenocarcinoma (PRAD), Rectum adenocarcinoma (READ), Stomach adenocarcinoma (STAD), Uterine Corpus Endometrial Carcinoma (UCEC) (FIG. 23D).

PDLIM2 repression in tumors was associated with poor patient survival. Not only PDLIM2 expression is repressed in various cancers including lung cancer, the presently disclosed tissue array analysis revealed that low PDLIM2 protein expression in lung tumors is associated with poor overall survival of lung cancer patients (FIG. 24A). Through an online analysis tool (http://kmplot.com/analysis/index.php?p=service&cancer=lung), it was also found that low PDLIM2 RNA expression was associated with poor patient survival, including overall survival (FIG. 24B), progression-free survival (FIG. 24C), and post-progression survival (FIG. 24D).

PDLIM2 loss led to spontaneous cancer development and promotes cancer development and progression induced by chemical carcinogen or oncogenic mutation. In line with the in vitro cancer cell line studies suggesting a tumor suppressor role of PDLIM2 (Yan et al., Blood. 2009; 113(18):4370-4380; Yan et al., Neoplasia. 2009; 11(10):1036-1041; Qu et al., Cancer Res. 2010; 70(5):1766-1772; Qu et al., J Biol Chem. 2010; 285(16):11786-11792; Fu et al., Onocogene. 2010; 29(49):6499-6507; Sun et al., J Biol Chem. 2015; 290(12):7362-7368), PDLIM2$^{-/-}$ (KO) mice started to develop spontaneous tumors at 7 months of age (FIG. 25A). By 18 months of age, over 90% of PDLIM2$^{-/-}$ mice, compared to less than 10% of PDLIM2$^{+/+}$ (WT) mice, developed tumors. Remarkably, 50% of the tumors were lung carcinomas (FIG. 25B). These data are highly consistent with the fact that PDLIM2 is ubiquitously expressed, with the highest level in normal lungs (Torrado et al., *Invest. Ophthalmol. Vis. Sci.* 45, 3955-3963 (2004); Tanaka et al., *Immunity* 22, 729-736 (2005); Loughran et al., *Mol. Biol. Cell.* 16, 1811-1822 (2005)). Moreover, PDLIM2$^{-/-}$ mice were more sensitive to lung tumorigenesis induced by oncogenic K-Ras (FIG. 25C) or the chemical carcinogen urethane (FIG. 25D).

PDLIM2 reconstitution blocked cancer cell growth and metastasis. PDLIM2 reconstitution in various types of cancer cells, such as breast cancer cells, colorectal cancer cells, HTLV-I transformed lymphoma cells, and KSHV associated cancer cells, can block cancer cell growth in vitro and in vivo. PDLIM2 reconstitution unexpectedly blocked not only primary tumor growth at the original inoculation sites, but also tumor cell metastasis to lung in syngeneic mouse model of lung cancer (FIG. 26A-26B). It indicates that restoration of PDLIM2 expression is an effective approach to treat cancer and cancer metastasis.

Figure 27F:
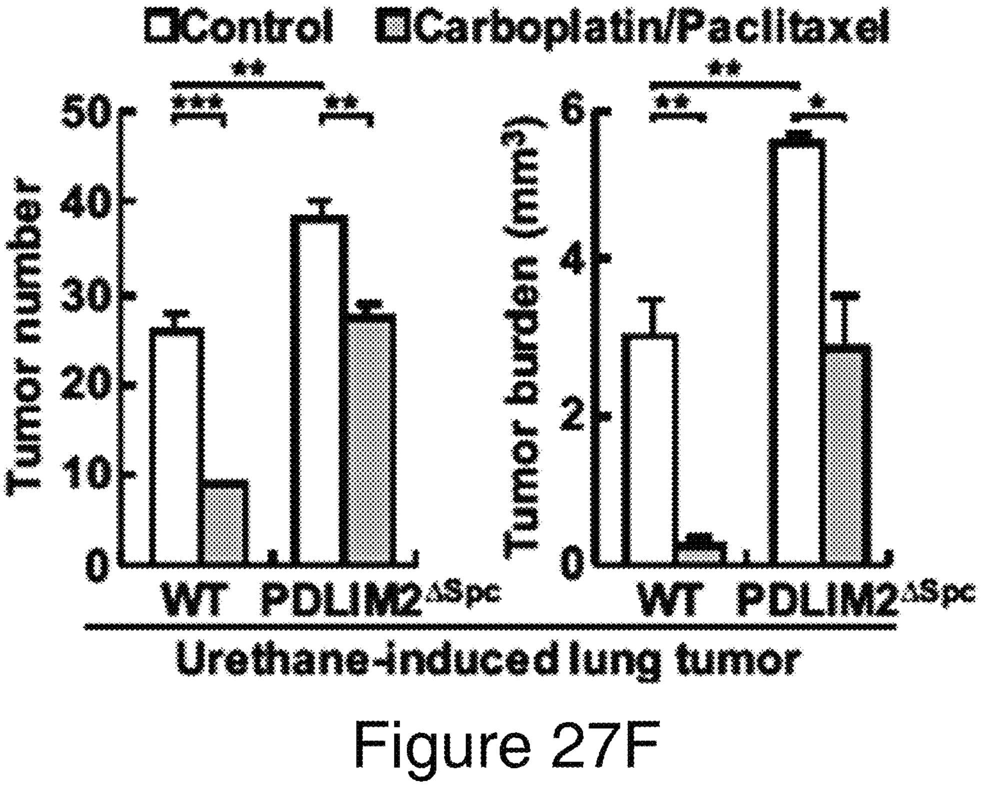

PDLIM2 repression was associated with cancer chemotherapy resistance and PDLIM2 reconstitution sensitizes cancer cells to chemotherapy reagents treatment. Chemotherapy is the mainstay of cancer treatment. However, intrinsic or acquired chemotherapy resistance often limits its effectiveness. Interestingly, it was found that PDLIM2 repression was linked to chemotherapy resistance. PDLIM2 expression level in lung cancer cells was inversely associated with the sensitivity of these cells to the drug carboplatin commonly used in cancer chemotherapy (FIG. 27A). In addition, in cancer cells with low expression, ectopic PDLIM2 expression sensitized these cells to carboplatin treatment (FIG. 27B). In FIGS. 27D and 27E, The cells underwent 4 consecutive 9-day cycles of paclitaxel treatment. In each 9-day cycle, the cells were treated with paclitaxel for the initial 2 days, then the drug was withdrawn from culture and the cells were left untreated for the rest 7 days. Although PDLIM2 expression level in lung cancer cells was not found to be associated with the sensitivity of these cells to paclitaxel, another commonly used cancer chemotherapy drug, ectopic PDLIM2 expression can block acquired resistance of lung cancer cells to paclitaxel (FIGS. 27C-27E). Moreover, lung tumors with PDLIM2 deleted were more resistant to carboplatin and paclitaxel treatment in mouse model of lung cancer induced by chemical carcinogen urethane (FIG. 27F). These results suggested that PDLIM2 expression can be used as a predictive biomarker for chemotherapy resistance and that PDLIM2 expression restoration combined with chemotherapy can be an effective approach in cancer treatment.

PDLIM2 repression was associated with cancer immunotherapy resistance. Overall, clinical benefit of cancer immunotherapy is still very limited, particularly for solid tumors. One cause can be the cancer immunosurveillance evasion through decreased antigen presentation in tumor cells. The presently disclosed analysis of the TCGA data revealed positive associations of PDLIM2 expression with antigen presenting genes, including HLA-A, HLA-B, and HLA-C in lung cancer and various other cancers (FIG. 28A). The presently disclosed animal studies also indicated decreased antigen presenting gene H2-K1 expression in PDLIM2 deficient lung tumors (FIG. 28B). On the other hand, PDLIM2 reconstitution in lung tumor cells led to increased H2-K1 expression (FIG. 28C). In addition, lung tumors with PDLIM2 deleted were resistant to PD-1 blockade immunotherapy, and PD-1 blockade immunotherapy combined with carboplatin/paclitaxel chemotherapy in the presently disclosed mouse model of lung cancer induced by chemical carcinogen urethane (FIG. 28D). These results indicated that PDLIM2 expression can also be used as a predictive biomarker for immunotherapy resistance, and that PDLIM2 expression restoration can be combined with immune- and/or chemo-therapy to increase treatment efficiency.

Example 3: ROS-Induced Inactivation of PDLIM2

The present example illustrates the effects of reactive oxygen species in the inactivation of PDLIM2 and the potential role of anti-oxidant agents for restoring the physiological expression levels and activity of PDLIM2. Here, the present example reports that alveolar macrophages (AMs) constitutively express the immune inhibitory molecule PD-L1 (programmed death-1 (PD-1) ligand 1) to increase their phagocytosis and repress cytotoxic T lymphocytes (CTLs) via cis- and trans-interacting with the co-stimulatory molecule CD80 (B7-1) and the immune checkpoint PD-1 (CD279), respectively. Genetic evidence showed that PDLIM2 increases CD80 expression and AM phagocytosis during lung tumorigenesis. Further, the pulmonary recruitment of monocytes and subsequent differentiation into interstitial macrophages (IMs) and AMs as well as AM protumorigenic activation was restricted via repression of STAT3 but not RelA, thereby relieving CTL suppression and preventing lung cancer. PDLIM2 was decreased in lung macrophages by oxidative stress-activated transcription repressor BTB and CNC homology 1 (BACH1) and that PDLIM2 repression is associated with poor survival of lung cancer patients. These findings provide mechanistic insights into how the lung maintains immune and tissue homeostasis for its physiological function and how this unique immunosuppressive environment is hijacked for the pathogenesis of lung tumor and other lung diseases associated with oxidative stress. These findings also reveal the role of PD-L1 and CD80 in innate immunity.

Methods

Animals and Lung Carcinogenesis

The animal experiments were performed in accordance with the US National Institutes of Health (NIH) Guidelines on the Use of Laboratory Animals. All animals were maintained under pathogen-free conditions. PDLIM2flx/flx mice, STAT3flx/flx mice, RelAflx/flx mice and Lysozyme M-Cre mice have been described before (Sun et al., Nat Commun 2019; 10:5324; Zhou et al., Oncogene 2015; 34:3804-3814; Zhou et al., Cancer Immunol Res 2017; 5:257-268; Li et al., Oncoimmunology 2018; 7:e1435250). Luciferase-expressing mice, PD-1 deficient mice and CD80/CD86 deficient mice were purchased from The Jackson Laboratory. Except for the PD-1 deficient mice and CD80/CD86 deficient mice, which are under C56BL/6 background, all other mice were backcrossed to FVB/N mice (The Jackson Laboratory) for more than ten generations, and then used to generate the experimental mice. For lung carcinogenesis, mice were intraperitoneally (i.p.) injected with urethane (1 mg/g body weight, Sigma-Aldrich, St. Louis, MO, USA) once a week for six consecutive weeks (8-10). Mice were sacrificed for lung inflammation and tumor examinations at one week or six weeks post urethane treatment, except for those also treated with PD-L1 antibodies or their control antibodies, which were sacrificed at three weeks post urethane treatment. Surface tumors in mouse lungs were counted by three blinded readers under a dissecting microscope, and tumor diameters were measured by microcalipers. For PD-L1 antibody treatment, mice were i.p. injected with PD-L1 or control antibodies (7 μg/g body weight, BioXCell, West Lebanon, NH, USA) two times per week for six consecutive weeks starting at the first day of urethane injection. For the treatment of N-Acetyl-L-cysteine (NAC), mice were administered with NAC (5 mg/ml in drinking water, Sigma-Aldrich, St. Louis, MO, USA. Water was changed daily and mice drink ad libitum) starting at the first day of urethane treatment until their euthanasia at one week post last urethane treatment.

Bronchioalveolar Lavage (BAL)

Upon sacrifice, mice lungs were lavaged with phosphate buffered saline. The recovered BAL fluids (BALF) were centrifuged. Pelleted cells from BALF were used for by immunofluorescent (IF), immunohistochemistry (IHC), flow cytometry (FACS), and/or quantitative polymerase chain reaction (qPCR) analysis.

IF Analysis, Histology, IHC and Human Lung Tumor Tissue Array Assays

Cells were fixed, permeabilized, and subsequently incubated with the indicated primary antibodies, followed by FITC- or TRITC-conjugated secondary antibodies. Cells were also counterstained with DAPI for nuclear staining. Stained proteins and their subcellular localizations were detected using a fluorescence microscope.

Lung tissues were excised, fixed in formalin, embedded in paraffin, and cut into 4-μm-thick sections. Sections were stained with H&E or subjected to sequential incubations with the indicated primary antibodies, biotinylated secondary antibodies and streptavidin-HRP. The human lung tumor tissue microarrays (TMAs) were described previously (Sun et al., Nat Commun 2019; 10:5324; Zhou et al., Cancer Immunol Res 2017; 5:257-268; Li et al., Oncoimmunology 2018; 7:e1435250). In the TMA stained with PDLIM2 antibody, myeloid cells with obvious PDLIM2 staining were scored as 1 or above. Scores were averaged for each sample and used for the cutoff of high (≥1) and low (<1) PDLIM2 expression.

In Vivo BrdU Labeling, qPCR Analysis and FACS Analysis

Mice were i.p. injected with 50 mg/kg BrdU (Sigma-Aldrich, St. Louis, MO, USA) 24 h prior to sacrifice. Mouse lung tissue sections were stained with anti-BrdU (Sigma-Aldrich, St. Louis, MO, USA). BrdU labeling index was calculated as the percentage of labeled cells per total cells counted (more than 500 cells in each counted tumor-containing area).

The indicated tissues or cells were subjected to RNA extraction, RNA reverse transcription and real-time PCR using trizol, reverse transcriptase, and Power SYBR Green PCR Master Mix (Thermo Fisher Scientific, Waltham, MA USA).

The cells were incubated with the antibodies against cell surface antigens after blocking with αCD16/CD32. The cells were then fixed with paraformaldehyde (2%), permeabilized with saponin (0.5%), and incubated with antibodies against intracellular antigens if needed. For IFNγ staining, cells were treated with phorbol 12-myristate 13-acetate (PMA, 50 ng/ml), ionomycin (1 μM), brefeldin A (BFA, 3 μg/ml) and monensin (2 μM) for 4 h before they were stained for FACS analysis. Data were acquired and analyzed by Accuri C6 or BD LSRFortessa I (BD Biosciences, Bedford, MA, USA) or analyzed using the FlowJo software.

Peritoneal Cell Preparation, In Vitro AM Like Cell Differentiation of Bone Marrow-Derived Monocytes (BMDMs) and, In Vivo Pulmonary Recruitment and AM Differentiation of BMDMs During Tumorigenesis Ice-cold phosphate-buffered saline (PBS) was injected into mouse peritoneal cavity and then recovered from peritoneal cavity after peritoneum was gently and completely massaged. Peritoneal cells obtained were then used for FACS analysis.

For BMDM preparation, bone marrow cells were flushed from femurs of mice and cultured for 8 days with 10 ng/mL macrophage colony-stimulating factor (M-CSF). Non-attached cells were washed away and adherent cells were IM-like and AM-like cells.

WT mice treated with urethane (1 mg/g body weight, Sigma-Aldrich, St. Louis, MO, USA, i.p. injection 2 times per week for 3 consecutive weeks) were intravenously (i.v.) injected with carboxy-fluorescein succinimidyl ester (CFSE)-labeled BMDMs ($6\times10^6$ cells/mouse) isolated by monocyte isolation kit (Miltenyi Biotec, San Diego, CA, USA) from in vitro differentiated bone marrow cells [cultured with M-CSF (20 ng/ml) for 5 days in ultra-low attachment plate (Corning Inc. Corning, NY, USA)] of the indicated mice treated with urethane, or bone marrow cells from the indicated luciferase-expressing mice ($10^7$ cells/mouse). Mice were sacrificed 5 days (BMDMs) or 10 days (bone marrow) post cell injection and the lung tissues were then subjected to FACS to detect $CFSE^+$ $CD11b^+$ cells or luciferase-expressing AMs and IMs.

In Vitro CTL Suppression by AMs and BMDM-Derived AM-Like Cells and Ex Vivo Phagocytosis Assays Splenic $CD3^+$ T cells from WT mice were co-cultured with AMs from WT mice or macrophages in vitro differentiated from the indicated BMDMs (1:0.05 ratio) in the presence or absence of PD-L1 antibody (20 μg/ml) or PD-1 antibody (20 μg/ml) or control IgG in CD3 and CD28 antibody coated plates for 3 days, followed by FACS analysis to detect granzyme $B^+$ and $IFN\gamma^+$ $CD8^+$ T cells.

Macrophages harvested from fresh mouse lung tissues were seeded in ultra-low attachment plate (Corning Inc. Corning, NY, USA) for 20 min with or without indicated antibody, then directly added Latex Beads-Rabbit IgG-FITC Complex (Cayman Chemical, Ann Arbor, MI, USA. 1:100) and cultured for 2 hours. The phagocytic ability of macrophages was determined by FACS.

Chromatin Immunoprecipitation (ChIP) Assays and Subcellular Fractionation and Immunoblotting (IB) Assays Cells were collected after formaldehyde treatment. The chromatin DNA was extracted, broken into fragments of 300-1000 bp in length by sonication, and immunoprecipitated with antibodies to the target. IgG was used in immunoprecipitation as a control for nonspecific signal. DNA in the immunoprecipitation product was amplified by PCR.

Whole-cell extracts were prepared by lysing cells in RIPA buffer. Nuclear extracts were prepared by lysing pellets in insoluble nuclear buffer (20 mM Tris, pH 8.0, 150 mM NaCl, 1% [wt/vol] SDS, 1% [vol/vol] NP-40, and 10 mM iodoacetamide) after the cytoplasm was extracted with the hypotonic buffer (20 mM HEPES, pH 8.0, 10 mM KCl, 1 mM MgCl2, 0.1% [vol/vol] Triton X-100, and 20% [vol/vol] glycerol). The purity of the nuclear fractions was confirmed by checking Hsp90 (cytoplasm) or lamin B/C (nuclear fraction). All the lysis buffers were supplemented with 1 mM PMSF and a protease inhibitor cocktail (Roche Molecular Biochemicals). The cell extracts were used for D3 assays. Briefly, the cell extracts were separated on polyacrylamide gels followed by electrotransfer onto nitrocellulose membranes. After blocking nonspecific protein binding with 5% dry milk, the membranes were sequentially incubated with appropriate primary and horseradish peroxidase-conjugated secondary antibodies, with extensive wash with PBST after each of the incubation steps. Specific immune complexes were detected by enhanced chemiluminescence as specified by the manufacturer (Western Lightning ECL Pro; Amersham).

Statistical Analysis

Measurements were taken from distinct samples. Student's t test (two tailed) and one way ANOVA/Tukey's or two way ANOVA/Sidak's test were used to assess significance of differences between two groups and multiple comparisons, respectively. Gehan-Breslow-Wilcoxon test was used to compare overall patient survival between high and low myeloid PDLIM2 expression groups. Multivariate survival analysis was also performed using Cox's proportional hazards model to statistically consider and adjust the potential effect of other clinical factors, such as age and tumor stage. Pearson's correlation test was used to assess associations in expression between different genes. All bars in figures represent means±standard error of the mean (SEM). The P values are indicated as $*P<0.05$, $**P<0.01$, ns, not statistically significant, except for those shown in figures. The P values $<0.05$ and 0.01 are considered statistically significant and highly statistically significant, respectively.

Results and Discussion

The lung is constantly exposed to airborne substances, the majority of which are harmless while some are pathogenic. Thus, it is critical for AMs, the first sentinels and the most abundant immune cells in the lung, to maintain immune tolerance to innocuous inhaled substances and also to ensure the rapid initiation but timely termination of the immune response to invading pathogens, preventing any unnecessary inflammation and potential injury within this essential organ. To define the mechanism underlying this pathophysiologically important function of AMs, the expression levels of the immune inhibitory molecules PD-L1 and PD-L2 (B7-DC, CD273) on the surface of AMs were examined. Both PD-L1 and PD-L2, in particular PD-L1, play important roles in immune tolerance and immune response termination by physically interacting with their receptor PD-1 on immune effector cells and activated CTLs in particular (Keir et al., Annu Rev Immunol 2008; 26:677-704). PD-L1 expression was quantified on lung monocyte/macrophage populations as well as on non-lung control populations. PD-L1 was detected on all AMs, but not other cells (FIG.

29A), suggesting the high AM specificity of PD-L1 expression. Neither AMs nor IMs expressed detectable PD-L2 on the surface (FIG. 37B). The AM specificity for PD-L1 expression was validated in mice under different strains (FIG. E2C in the online supplement). In line with the ability of PD-L1 in trans-interacting with PD-1 on CTLs for suppression, AMs strongly repressed CTL activity when they were co-cultured with activated CTLs (FIG. 29B). Thus, PD-L1 expression renders AMs capable of repressing CTLs.

It has been reported that PD-L1 on tumor cells can bind to PD-1 on tumor-associated macrophages (TAMs) to block TAM phagocytosis (Gordon et al., Nature 2017; 545:495-499). Thus, it was examined whether normal AMs also expressed PD-1. Of note, TAMs in lung tumors are derived largely from AMs (Sun et al., J Immunother Cancer 2020; 8). As shown in FIG. 29C, most AMs, but only a minority of IMs, expressed PD-1 on the surface. PD-1 expression on AMs also inhibits phagocytosis, because genetic deletion of PD-1 from AMs dramatically enhanced their phagocytic ability (FIG. 29D). However, AMs are the primary phagocytes in the lung. Thus, the phagocytic activities of AMs and IMs were compared in the same system, particularly given that unlike AMs, IMs do not express PD-L1 and only express minimal PD-1. AMs displayed much higher phagocytic activity compared to IMs (FIG. 29E). Therefore, the role of cell-intrinsic PD-L1 in AM phagocytosis was examined. Remarkably, genetic deletion of PD-L1 significantly decreased AM phagocytosis (FIG. 29F). These data suggested that PD-L1 promotes AM phagocytosis and dominates the negative effect of PD-1, thereby rendering AMs superior phagocytic ability. These data also implied that other receptor(s) on AMs compete with PD-1 for PD-L1 engagement to enhance AM phagocytosis.

CD80 is the only known PD-L1 receptor/ligand other than PD-1, and binds to PD-L1 only in cis on the same cell surface (Butte et al., Immunity 2007; 27:111-122; Chaudhri et al., Cancer Immunol Res 2018; 6:921-929). It should be pointed out that all AMs express PD-L1 on the surface. To examine whether cis-CD80/PD-L1 ligation increases AM phagocytosis, CD80 expression on AMs were first examined. CD86 (B7-2) was also included in the assays. Both CD80 and CD86 were found on AMs, although at relatively low levels (FIGS. 29G and 37D). Importantly, CD80-blocking antibody decreased AM phagocytosis, while CD86-blocking antibody had no significant effect (FIG. 29H). Consistently, AMs expressing high levels of CD80 showed a significantly higher phagocytic ability compared to those with low CD80 expression (FIG. 29I). Genetic deletion of CD80 and CD86 decreased the phagocytic ability of AMs (FIG. 29J). These data suggested that cis-CD80/PD-L1 interaction contributes to the high phagocytic ability of AMs. AM-intrinsic PDLIM2 is indispensable for AM phagocytosis as well as for restricting the pro-tumorigenic activation and CTL suppression activity of AMs in lung tumorigenesis The next step was to determine the significance of PDLIM2 in AMs, given its tumor suppressor role in lung cancer and its high expression in AMs (Sun et al., Nat Commun 2019; 10:5324). PDLIM2flx/flx/lysozyme M-Cre mice (PDLIM2mKO) in which PDLIM2 is selectively deleted from myeloid cells (FIG. 38A) were generated. Like PDLIM2−/− mice, under pathogen-free conditions PDLIM2mKO mice were healthy and showed no apparent abnormalities in the development of myeloid cells, including AMs, IMs, lung monocytes and neutrophils (FIG. 38B). PDLIM2−/− AMs exhibited similar expression of PD-L1, CD80 and PD-1 as wild type (WT) AMs (FIG. 38C). Consistently, PDLIM2−/− AMs had a phagocytic ability similar to WT AMs (FIG. 38D).

Next, it was examined whether PDLIM2 is involved in AM regulation during lung pathogenesis. Urethane-treated mice, a faithful model of lung cancer relevant to humans, and in particular adenocarcinoma, was used. Interestingly, PDLIM2 plays a major role in AM phagocytosis in lung tumorigenesis, as evidenced by the dramatically lower phagocytic ability of AMs in urethane-treated PDLIM2mKO mice in comparison to those in WT mice under the same treatment (FIG. 30A). The lower phagocytosis was associated with lower expression of CD80 on the AMs of urethane-treated PDLIM2mKO mice (FIG. 30B). The expression levels of PD-L1 and PD-1 on those AMs were comparable. Thus, cell-intrinsic PDLIM2 is required for CD80 expression and AM phagocytosis during lung tumorigenesis, although it is dispensable for the development and functions of AMs under pathogen-free conditions. PDLIM2 also controls AM pro-tumorigenic polarization/activation during lung tumorigenesis. In comparison to those AMs in WT mice treated with urethane, AMs in urethane-treated PDLIM2mKO mice expressed significantly more arginase, vascular endothelial growth factor (VEGF) and mannose receptor (MR, CD206), hallmarks of macrophage pro-tumorigenic polarization (FIGS. 30C and 30D). In contrast, PDLIM2mKO mice had significantly lower activation of pulmonary CD8+ T cells compared to WT mice, as evidenced by decreased expression of interferon-γ (IFNγ), granzyme B and CD44 in those CTLs (FIGS. 30E and 30F). The total numbers of lung CD4+ and CD8+ T cells as well as CD4+ T-cell activation and Treg cell differentiation were comparable in those mice (FIG. 39). These data suggested that during lung tumorigenesis cell-intrinsic PDLIM2 restricts lung macrophages and AMs in particular from repressing lung CD8+ CTLs in a manner independent of CD4+ T cells.

Further, the present example determined whether myeloid cell-intrinsic PDLIM2 promoted the activity of pulmonary CD8+ CTLs during lung tumorigenesis. The total number of lung macrophages in the PDLIM2mKO mice was much greater compared to the WT mice with the same urethane treatment (FIG. 31A). Interestingly, the ratio of AMs in total lung macrophages was increased whereas IMs'ratio was decreased in PDLIM2mKO mice (FIG. 31B). Lung monocytes showed a decreased pattern similar to IMs in PDLIM2mKO mice (FIG. 31C). These data indicated that PDLIM2 limits the expansion of AMs, which constitutively express PD-L1, thereby releasing the brake on lung CD8+ CTLs and that PDLIM2 exerts this effect through constraining monocytes differentiation into IMs and finally AMs. To test this hypothesis, bone marrow cells of WT and PDLIM2mKO mice were used for the in vitro macrophage differentiation assay of BMDMs. Both WT and PDLIM2−/− BMDMs could differentiate into IM-like and AM-like cells as evidenced by the expressions of PD-L1, CD11b, CD11c and F4/80 (FIGS. 31D and 40A-40D). Importantly, PDLIM2−/− BMDMs differentiated into significantly more AM-like cells associating with fewer IM-like cells. Moreover, PDLIM2−/− BMDMs migrated, at a significantly higher rate, into the lung during lung tumorigenesis. Significantly more CF SE-labeled cells were detected in the lung of urethane-treated mice i.v. injected with the same numbers of CFSE-labeled WT or PDLIM2−/− BMDMs (FIG. 31E). To further validate those studies, luciferase-expressing PDLIM2−/− or WT bone marrow cells were i.v. injected into urethane-treated WT mice. Luciferase-expressing AMs and IMs were detected in all the mice (FIGS. 31F and 31G). However, mice injected with PDLIM2−/−cells had significantly more luciferase-expressing AMs and IMs. These data together implied that during lung tumorigenesis BMDMs are recruited from the circulation into the lung to sequentially differentiate into IMs and AMs, and that PDLIM2 serves as an intrinsic checkpoint refraining this potentially pathogenic process.

The present example also validated the role of PD-L1 inherently expressed on AMs in lung tumorigenesis. Urethane treatment induced lung cancers in both WT and PDLIM2mKO mice (FIG. 32A). However, PDLIM2mKO mice developed significantly more lung tumors with larger tumor burden compared to WT mice. The lung tumors in PDLIM2mKO mice had much higher angiogenesis and proliferation but decreased apoptosis (FIG. 32B). These data demonstrated that PDLIM2 prevents myeloid cells and AMs from promoting lung cancer. Although PDLIM2 is dispensable for PD-L1 expression on AMs under either physiological or lung cancer pathogenic conditions, PDLIM2mKO mice have significantly more AMs during lung tumorigenesis. The present example examined whether PD-L1 blockade blocked the increased lung cancer development in the urethane-treated PDLIM2mKO mice. PD-L1 blockade before lung tumors developed indeed reversed the decreased lung CTL activation, the increased CTL apoptosis and the elevated lung tumorigenesis in PDLIM2mKO mice (FIGS. 32C-32E). In agreement with the fact that activated but not naïve CD8+ T cells express PD-1, PD-L1/PD-1 blockade prevented the apoptosis of activated pulmonary CD8+ T cells, but had no effect on the basal apoptosis of un-activated pulmonary CD8+ T cells in the mice. Altogether, these data suggested that PDLIM2 restrains AM differentiation and expansion, lowering the potential PD-L1/PD-1 interaction between AMs and CTLs and thereby releasing the brake on CTL antitumor activity.

The present example investigated the mechanism underlying the tumor-suppressive role of myeloid-intrinsic PDLIM2 in lung cancer by deleting STAT3 or RelA from myeloid cells in PDLIM2mKO mice. STAT3 co-deletion completely blocked the increased lung tumorigenesis in PDLIM2mKO mice by urethane, but RelA deletion had no significant effect (FIG. 33A), indicating that myeloid PDLIM2 suppresses lung cancer through targeting STAT3 but independent of RelA. In line with this, much higher STAT3 activation but comparable RelA activation was detected in AMs from PDLIM2mKO mice compared to WT mice (FIGS. 33B and 41). This is contrast to the tumor suppression by cancer cell-intrinsic PDLIM2, which depends on both STAT3 and RelA (Sun et al., Nat Commun 2019; 10:5324). STAT3 co-deletion in myeloid cells reversed all those changes by PDLIM2 deletion during lung tumorigenesis: elevated pulmonary recruitment of BMDMs, expanded AM differentiation from IMs and BMDMs, heightened AM pro-tumorigenic activation, decreased lung CTL activation, increased tumor angiogenesis and tumor cell proliferation, and reduced tumor cell apoptosis (FIGS. 33C-33J and 42). To define the mechanism by which PDLIM2/STAT3 signaling controls the pulmonary recruitment of BMDMs, the prerequisite for AM expansion and lung cancer promotion, the expression levels of CCR2 (CD192) in the BMDMs of WT, PDLIM2mKO, and PDLIM2/STAT3mKO mice treated with urethane were examined. CCR2 is a key determinant of monocytes trafficking, through binding its ligand monocyte chemoattractant protein-1 (MCP-1/CCL2) (Rose et al., Microcirculation 2003; 10:273-288). Indeed, CCR2 expression in BMDMs was significantly increased by PDLIM2 deletion, and the increase was blocked by STAT3 co-deletion (FIG. 33K). Of note, CCL2 expression was increased in the lung during lung tumorigenesis, but to a similar level in the PDLIM2mKO and WT mice (FIG. 33L). These data suggested that PDLIM2 restricts the lung recruitment of monocytes through preventing STAT3 from inducing CCR2 on monocytes, thereby limiting AM differentiation and expansion for lung tumor promotion.

Further, the present example investigated the pathogenic and clinical relevance of PDLIM2 in lung cancer and therefore the expression of PDLIM2 was analyzed in BAL cells from urethane-treated mice. PDLIM2 expression in BAL cells was significantly decreased one-week post urethane treatment, and the suppression persisted thereafter (FIG. 34A). This was confirmed by IF staining of BAL cells and IHC staining of lung tissues (FIGS. 34B and 34C). Thus, the expression of PDLIM2 is repressed in AMs in the mouse model of lung cancer. Next, the mouse studies were validated using human clinical samples of lung cancer patients. PDLIM2 was repressed in TAMs/AMs (FIG. 34D). Of note, the low PDLIM2 expression correlated with poor survival of lung cancer patients (FIG. 34E). PDLIM2 repression in AMs is thus both clinically and pathogenically relevant to lung cancer. To define the mechanism by which PDLIM2 is repressed in AMs for lung tumor promotion, the pdlim2 promoter was analyzed and a putative BACH1-binding site was identified (FIG. 35A). BACH1 is a transcription repressor of genes involved in the oxidative stress response (Zhou et al., Clin Rev Allergy Immunol 2016; 50:345-356). Of note, oxidative stress is a causative driver of lung diseases and lung cancer in particular (Lawless et al., J Cell Mol Med 2009; 13:2800-2821). ChIP assays detected BACH1 at the BACH1-binding site in $H_2O_2$-treated but not untreated macrophages, which was inversely associated with RNA polymerase II (Pol II) at the pdlim2 promoter (FIG. 35B). Consistently, H2O2 induced BACH1 nuclear translocation and PDLIM2 expression decrease in macrophages (FIGS. 35C and 35D), as did ectopic BACH1 expression (FIG. 35E). In contrast, the reactive oxygen species (ROS) inhibitor NAC could block the PDLIM2 suppression in macrophages induced by lung tumor cell co-culture (FIG. 35F). Consistent with the in vitro data, BACH1 was mainly in the nucleus of AMs in mice with lung cancer but in the cytoplasm in untreated mice (FIG. 35G). BACH1 nuclear translocation and PDLIM2 repression in AMs in urethane-treated mice could efficiently be blocked by NAC (FIGS. 35H-J). These data indicated that PDLIM2 repression in AMs in lung tumorigenesis is mediated by oxidative stress, which induces BACH1 to enter the nucleus to bind to the pdlim2 promoter and repress PDLIM2 transcription.

In the present example, it is shown that alveolar macrophages (AMs), but not interstitial macrophages (IMs), peritoneal macrophages (PMs), splenic macrophages (SMs) and monocytes, inherently express PD-L1 on the surface and thereby are bestowed simultaneously with high phagocytic and CTL-suppressive activities to exert those pathophysiologically important roles. PD-L1 increases AM phagocytosis through interacting with CD80 in cis while terminating CTL activation via binding to PD-1 on activated CTLs. Many AMs also express PD-1 on the surface to refine/restrict AM phagocytosis by outcompeting with CD80 for PD-L1 engagement. Until now, studies on PD-L1, CD80, PD-1 and other immune co-stimulatory or -inhibitory molecules have been focusing mainly on their roles in adaptive immunity and CTL regulation in particular (Chen, Nat Rev Immunol 2004:4:336-347; Schildberg et al., Immunity 2016; 44:955-972). Mutual competition between CD80 and PD-1 to engage with PD-L1 for T-cell regulation has been described recently (Sugiura et al., Science 2019; 364:558-566; Zhao et al., Immunity 2019; 51:1059-1073). Cis-interaction between CD80 and PD-L1 on antigen-presenting cells (APCs) blocks the trans-interaction of PD-L1 with PD-1 and also CD80 with the immune checkpoint CD152/cytotoxic T-Lymphocyte associated protein 4 (CTLA4) on CTLs for optimal T-cell response. Thus, the competition between CD80 and PD-1 for PD-L1 binding is a common mechanism controlling innate and adaptive immune responses. Of note, although constitutive PD-L1 expression is specific for AMs, this important immune regulatory molecule is induced in many other macrophage types and other immune cells under pathogenic conditions, such as in tumorigenesis. It should also be pointed out, however, that while PD-1 or CD80 has the same effect on both innate and adaptive immunity (PD-1 suppresses and CD80 increases), the overall functions of PD-L1 in innate and adaptive immunity are complex but generally opposite (increasing innate immunity by binding to CD80 in cis but repressing adaptive immunity by binding to PD-1 in trans, although it can also be required for the optimal T-cell activation by cis-binding to CD80 on APCs and suppression of TAM/macrophage phagocytosis by trans-binding to PD-1 on TAMs). In line with this, PD-1-blocking antibody showed a better efficacy than PD-L1 antibody in animal model of lung cancer (FIG. 43). Logically, blocking PD-1/PD-L2 engagement can also contribute to the therapeutic efficacy of PD-1 antibody. Also, the present disclosure identifies the tumor suppressor PDLIM2 as an intrinsic checkpoint of AMs and monocytes for lung cancer suppression. Similar to its repression or loss in lung precancerous and cancer cells, PDLIM2 down-regulation in myeloid cells and in particular AMs is also an important mechanism promoting lung cancer. Although dispensable for PD-L1 or PD-1 expression on AMs, PDLIM2 down-regulation decreases CD80 and AM phagocytosis while increasing STAT3 activation and promoting AM pro-tumorigenic polarization as well as BMDM pulmonary recruitment and differentiation into AMs to repress CTLs, thereby suppressing both innate and adaptive immunity against lung tumorigenesis. PDLIM2 expression in AMs and monocytes is down-regulated by ROS-activated BACH1. Given high ROS production in tumor cells (Storz and Liou, Free Radic Res 2010; 44:479-496), this mechanism can also contribute to PDLIM2 repression in tumor cells. On the other hand, ROS released by tumor cells can contribute to PDLIM2 downregulation in tumor-associated cells, such as TAMs.

In summary, the presented data provide mechanistic insights into lung physiology, lung cancer and PD-L1/PD-1-targeted immunotherapies. Unlike their precursors and counterparts in other tissues, AMs have both superior phagocytic activity and inherent CTL-suppressive capability by constitutively expressing PD-L1 on the surface to respectively cis- and trans-interacting with CD80 on the same cells and PD-1 on CTLs, thereby assuring optimal protective immunity and tolerance within the lung. The data presented herein also identify PDLIM2 down-regulation in AMs and monocytes by ROS-activated BACH1 to restrict CD80 expression and increase STAT3 activation as a previously unknown mechanism driving these immune cells to promote lung cancer. These pieces of knowledge are applicable to other inflammation-associated diseases because a causal link between oxidative stress and inflammation has been well established in many diseases other than lung cancer and lung diseases. In addition, although PD-L1 is not expressed on macrophages and other phagocytic cells located at many tissues and organs other than the lung, its up-regulation on these cells is common in response to pathophysiological stimuli.

Example 4: Nanoparticle-Delivered PDLIM2 Dramatically Improves the Efficacy of Chemotherapy and Immune Checkpoint Inhibitors in Lung Cancer The present example examined whether and how PDLIM2 can be targeted to treat lung cancer in a faithful mouse model of human lung cancer. In particular, it was tested whether systemic administration of PDLIM2 expression plasmids encapsulated by nanoparticles synergizes with anti-PD-1 and chemotherapeutic drugs. It was also examined whether PDLIM2 repression in human lung cancer involves genetic deletion and its relationship with epigenetic silencing. These studies indicate that besides epigenetic repression, PDLIM2 also undergoes loss of heterozygosity (LOH) in about 58% of human lung cancers, and that PDLIM2 heterozygous deletion (PDLIM2$^{+/-}$) mice develop spontaneous lung and other tumors. Notably, systemic administration of nanoparticle-encapsulated PDLIM2 plasmids reverses the phenotypes by PDLIM2 repression, and induces complete remission of all lung cancers in most mice without further increasing toxicity when combined with anti-PD-1 and chemotherapeutic drugs. These findings provide a firm basis to combine ICIs and chemotherapeutic drugs with PDLIM2-targeted therapy for the treatment of lung and other cancers.

Methods

Animals and Lung Carcinogenesis

PDLIM2flx/flx/SP-C-rtTAtg/−/(tetO)7CMV-Cretg/tg (ΔSPC) mice under a pure FVB/N background and PDLIM2−/− mice under a pure BABL/C background have been described before (Sun et al., Nat. Commun. 2019. 10, 5324). For lung carcinogenesis, six to eight week old ΔSPC and wild type FVB/N mice were intraperitoneally (i.p.) injected with urethane (1 mg/g body weight, Sigma-Aldrich, St. Louis, MO, USA) once a week for six consecutive weeks, followed by different treatment as shown in FIGS. 45A and 49A. Mice were sacrificed for lung inflammation and tumor examinations at six weeks post urethane treatment. Surface tumors in mouse lungs were counted blinded under a dissecting microscope, and tumor diameters were measured by microcalipers.

Preparation of PDLIM2-Expression Plasmid or Empty Plasmid Nanoparticles

The in vivo-jetPEI (Polyplus Transfection, New York, NY, USA) and plasmid DNA complexes at a nitrogen-to-phosphate ratio of 8 (N/P8) were prepared according to the manufacturer's instructions. Briefly, 25 μg of pCMV-myc-PDLIM2 or empty plasmids in 100 μl of a 5% glucose solution were mixed with the in vivo-jetPEI reagent (4 μl) diluted into 100 μl of a 5% glucose solution. After 15 minutes of incubation at room temperature, the mixed solution (200 μl/mouse) was injected i.v. via the tail vein.

IF Analysis, Histology and IHC Analysis

Cells were fixed, permeabilized, and subsequently incubated with the indicated primary antibodies, followed by FITC- or TRITC-conjugated secondary antibodies. Cells were also counterstained with DAPI for nuclear staining. Stained proteins and their subcellular localizations were detected using a fluorescence microscope.

Lung tissues were excised, fixed in formalin, embedded in paraffin, and cut into 4-μm-thick sections. Sections were stained with H&E, or subjected to sequential incubations with the indicated primary antibodies, biotinylated secondary antibodies and streptavidin-HRP.

In Vivo BrdU Labeling and Flow Cytometry (FACS) Analysis

Mice were i.p. injected with 50 mg/kg BrdU (Sigma-Aldrich, St. Louis, MO, USA) 24 h prior to sacrifice. Mouse lung tissue sections were stained with anti-BrdU (Sigma-Aldrich, St. Louis, MO, USA). BrdU labeling index was calculated as the percentage of labeled cells per total cells counted (more than 500 cells in each counted tumor-containing area).

The cells were incubated with the antibodies against cell surface antigens after blocking with αCD16/CD32. The cells were then fixed with paraformaldehyde (2%), permeabilized with saponin (0.5%), and incubated with antibodies against intracellular antigens if needed. For IFNγ staining, cells were treated with phorbol 12-myristate 13-acetate (PMA, 50 ng/ml), ionomycin (1 μM), brefeldin A (BFA, 3 μg/ml) and monensin (2 μM) for 4 h before they were stained for FACS analysis. Data were acquired and analyzed by Accuri C6 or BD LSRFortessa I (BD Biosciences, Bedford, MA, USA) or analyzed using the FlowJo software.

qPCR Analysis

The indicated tissues or cells were subjected to DNA or RNA extraction, RNA reverse transcription and real-time PCR using trizol, reverse transcriptase, and Power SYBR Green PCR Master Mix (Thermo Fisher Scientific, Waltham, MA USA) according to the product manufacture's protocol.

Microsatellite and Gene-Specific PCR-Based LOH Analysis of PDLIM2

Genomic DNAs were isolated from human lung tumors and their matched normal tissues using the PureLink Genomic DNA Purification Kit (Invitrogen, Carlsbad, CA, USA), and subjected to semi-quantitative PCR using the primers specific for the microsatellite markers D8S1786 and D8S1752 that straddle the pdlim2 genetic locus or the pdlim2 genetic locus itself.

Bisulfite Genomic DNA Sequencing

Genomic DNA aliquots from the indicated cells were treated with sodium bisulfite using the EZ DNA Methylation-Gold Kit (Zymo Research, Irvine, CA, USA), followed by PCR to amplify the pdlim2 promoter using Hot-Start Taq enzyme (Qiagen, Hilden, Germany). The PCR products were used for DNA sequencing to determine the methylation status of the CpG dinucleotides within the pdlim2 promoter.

Statistical Analysis

Measurements were taken from distinct samples. Student's t test (two tailed) and one way ANOVA/Tukey's or two way ANOVA/Sidak's test were used to assess significance of differences between two groups and multiple comparisons, respectively. Pearson's correlation test was used to assess association between PDLIM2 expression with its promoter methylation or genetic deletion and the overlap between PDLIM2 promoter methylation and genetic deletion. All bars in figures represent means±standard error of the mean (SEM). The p values are indicated as *p<0.05, **p<0.01, ns, not statistically significant, except for those shown in figures. The p values <0.05 and 0.01 are considered statistically significant and highly statistically significant, respectively.

Results and Discussion

Previously using 40% of the expression level in matched normal lung tissues as the cut-off, it was found that PDLIM2 is repressed in over 75% of human lung cancers (Sun et al., Nat. Commun. 2019. 10, 5324). If using 50% as the cut-off, it was found that PDLIM2 was repressed in about 93% of human lung cancers (FIG. 44A). Using 125% of the methylation level of the pdlim2 promoter in normal lung tissues as the cut-off to analyze The Cancer Genome Atlas (TCGA) database, over 70% of human lung cancers with decreased PDLIM2 expression were found to have hypermethylation of the pdlim2 promoter (FIG. 44B), further validating previous finding of epigenetic silencing as the main mechanism underlying PDLIM2 repression (Sun et al., Nat. Commun. 2019. 10, 5324). In line with PDLIM2's location on chromosome 8p21.3, a frequent LOH region in lung and other tumors, analysis of TCGA database revealed that the expression of PDLIM2 was positively associated with its gene copy numbers, and that about 58% of human lung cancers with decreased PDLIM2 expression had genetic deletion of the pdlim2 gene if the gene copy number of 1.5 was used as the cut-off for the gene deletion (FIG. 44C). Further analysis indicated that about 44% of human lung cancers with decreased PDLIM2 expression simultaneously harbored the promoter hypermethylation and LOH of PDLIM2, and about 26% and 14% of them only having the promoter hypermethylation or LOH of PDLIM2, respectively (FIG. 44D). Around 16% of lung cancers possessed no epigenetic or genetic alterations of PDLIM2. These findings were confirmed by microsatellite and gene-specific PCR-based LOH analysis of human primary lung cancer tissues and cell lines (FIGS. 44E and 44F). These data suggested that PDLIM2 repression in lung cancer involves both epigenetic silencing and genetic deletion.

The present example determined the significance of PDLIM2 LOH in lung tumors by examining whether PDLIM2 heterozygous deletion leads to decreased PDLIM2 expression and spontaneous lung tumors in mice. Unlike its absolute absence in PDLIM2 homozygous deletion (PDLIM2−/−) mice, PDLIM2 was detected in the lung of PDLIM2+/− mice, but at a much lower level compared to wild type (WT) mice (FIGS. 45A and 45B).

Importantly, PDLIM2+/− mice developed spontaneous tumors, though at a delayed onset compared to PDLIM2−/− mice (FIG. 45C). Of note, similar to those in PDLIM2−/− mice (Sun et al., Nat. Commun. 2019. 10, 5324), over 50% of tumors developed in PDLIM2+/− mice were lung adenocarcinomas (ACs), the most common type that accounts for about 40% of all lung cancers (FIGS. 45D-45E). These data were also highly consistent with the fact that PDLIM2 is ubiquitously expressed under physiological conditions, with the highest level in the lung and lung epithelial cells in particular (Sun et al., Nat. Commun. 2019. 10, 5324; Torrado et al., Invest. Ophthalmol. 2004. Vis. Sci. 45, 3955-3963; Tanaka et al., Immunity. 2005. 22, 729-736; Loughran et al., Mol. Biol. Cell. 2005 16, 1811-1822). Thus, PDLIM2 is a haploinsufficient tumor suppressor that is particularly important for lung tumor suppression.

Although reversal of PDLIM2 epigenetic repression by epigenetic drugs to restore PDLIM2 expression in cancer cells can be used to treat lung cancers, this approach cannot be applied to lung cancers involving PDLIM2 LOH, which accounts for about 58% of all lung cancer cases. To overcome this limitation and expand PDLIM2-targeted therapy to all lung cancers with PDLIM2 repression regardless of the involved mechanisms, the therapeutic efficacy of systemic administration of PDLIM2-expression plasmids encapsulated by the clinically feasible polyethylenimine (PEI)-based nanoparticles was tested. To this end, mouse lung cancers induced by urethane, a faithful model of human lung cancer and AC in particular was used (Sun et al., Nat. Commun. 2019. 10, 5324; Sun et al., J. Immunother. 2020. Cancer 8; Zhou et al., Oncogene. 2015. 34, 3804-3814; Qu et al., Cancer Res. 2015. 75, 3209-3215). Urethane is a chemical carcinogen present in fermented food, alcoholic beverage and also cigarette smoke, the predominant risk factor accounting for about 90% of human lung cancers. Like its human counterpart, the murine lung cancer by urethane also shares PDLIM2 repression, in addition to their similarities in histology, genetics, molecular biology and immunology (FIGS. 45B and 47A for PDLIM2 repression). WT mice with lung tumors induced by urethane were intravenously (i.v.) injected with nanoparticle-encapsulated PDLIM2 plasmids or empty plasmids. Six weeks post the initial treatment of nanotherapy, mice were sacrificed and lung tissues were collected (FIG. 46A). Compared to the plasmid mock-treated group (Vec), PDLIM2-treated mice had a significantly reduced tumor burden in their lungs, although tumor numbers were not decreased significantly in those mice (FIG. 46B). Thus, systemic administration of PDLIM2 plasmid nanoparticles alone shrinks but does not ablate individual lung nodules in this model of refractory lung cancer.

In line with tumor shrinkage, PDLIM2 plasmid administration decreased nuclear RelA and STAT3, a hallmark of NF-KB and STAT3 activation, thereby resulting in reduction in the expression of the cell survival gene Bcl-xL and the cell proliferation gene Cyclin D1 and subsequently increase in apoptosis and decrease in proliferation of lung cancer cells (FIGS. 46C-46E). These data indicated that intravenous injection of nanoparticle-encapsulated PDLIM2 plasmids show efficacy in suppressing oncogenic RelA and STAT3 activation and in treating lung cancer. To characterize the potential new lung cancer therapy, the expression levels of PDLIM2 in lung tumors and several organs and tissues, including the liver, kidney and spleen were analyzed. Consistent with the treatment efficacy, a high level of PDLIM2 was detected in the lung tumors from mice treated with the PDLIM2 plasmid nanoparticles, whereas no obvious PDLIM2 was found in the lung tumors from mice treated with the control plasmid nanoparticles (FIG. 47A). It should be pointed out that the tumor delivery efficiency of PDLIM2-expression or control plasmid nanoparticles was similarly high (FIG. 47B). However, either PDLIM2-expression or control plasmids were hardly detected in other organs/tissues of the same mice, such as the liver, kidney and spleen. Consistently, the protein levels of PDLIM2 in these tissues were comparable (FIG. 47C), suggesting that PDLIM2 proteins detected are endogenous instead of being expressed ectopically by nanoparticle-delivered PDLIM2 plasmids. In further support of the lung tumor-specific delivery, the i.v. injection of either PDLIM2-expression or control plasmid nanoparticles showed no obvious toxicity to animals, as evidenced by no significant changes in the animal body weight or histology of all organs/tissues examined, including the spleen, kidney and liver (FIGS. 47D-47E). Mouse appearance and behaviors, such as eating, drinking, defecating, urinating, sniffing, grooming and digging, were indiscriminate, too (data not shown). Taken together, these data suggested the therapeutic efficacy and low toxicity of PDLIM2-based nanotherapy in the mouse model of lung cancer.

Given the role of PDLIM2 in inhibiting the expression of cell survival and proliferation genes in tumor cells and the role of cell survival and proliferation genes in cancer cell resistance to chemotherapy, it was tested whether PDLIM2 nanotherapy increases the therapeutic efficacy of chemotherapy in the mouse model of lung cancer. Treatment with carboplatin and paclitaxel, two chemotherapeutic drugs that are often used together as the first-line treatment for lung and many other cancers, led to significant decrease in tumor number and tumor burden (FIG. 48A). Importantly, combination with PDLIM2 plasmid nanoparticles further significantly decreased both tumor number and tumor burden, suggesting a promising synergy between PDLIM2 nanotherapy and chemotherapy in lung cancer treatment. Consistently, significantly higher tumor cell apoptosis was detected in mice treated with the combination therapy, in comparison to those with the single treatment of nanotherapy or chemotherapy (FIG. 48B). Another important mechanism contributing to the synergy between these two therapies involves PDLIM2 nanotherapy blockade of the acquired chemoresistance of lung cancer cells. Chemotherapy induced strong RelA activation/nuclear expression and MDR1 expression (FIGS. 48C-48D). PDLIM2 nanotherapy not only repressed the constitutive activation of RelA in cancer cells but also prevented the strong induction of RelA activation and MDR1 expression by the chemotherapy. Thus, PDLIM2 nanotherapy improves the therapeutic efficacy of chemotherapy through blocking both intrinsic and acquired chemoresistance of lung cancer cells.

High expression of cell survival genes also renders tumor cells resistant to the tumoricidal activity of cytotoxic T lymphocytes (CTLs), including those unleashed by ICIs. PDLIM2 nanotherapy should also synergize with immunotherapy, given its ability in suppressing the expression of cell survival genes. Furthermore, PDLIM2 nanotherapy increased the number of TILs and the expression of MHC-I, the most important and core components of immunotherapies including PD-1 immune checkpoint blockade therapy (FIGS. 49A-49B). PD-1 blocking antibody, like PDLIM2 nanotherapy, showed some efficacies in the mouse model of lung cancer, as evidenced by the significant decrease in tumor burden (FIG. 49C). Combining with PDLIM2 nanotherapy further significantly decreased tumor burden, although not tumor number. Consistently, significant increases in both CD4+ and CD8+ TILs, CD8+ CTL activation and lung tumor cell death were detected (FIGS. 49D-49F). These data together suggested a moderate synergy between PDLIM2 nanotherapy and PD-1 blockade therapy.

Like most human lung cancers, lung cancers in the animal model of the present example also decrease PD-L1 on the surface, in additional to the low expression of MHC-I and low number of TILs. However, PDLIM2 nanotherapy failed to induce PD-L1 expression, which was in contrast to chemotherapy (FIG. 50A). That could explain why the synergy between PDLIM2 nanotherapy and PD-1 blockade therapy is only moderate. Although it dramatically increases TILs as well, chemotherapy also induced the expression of PD-L1 on cancer cells, which presumably protects cancer cells from immune attack and thereby restricts further efficacy improvement of its combination with PDLIM2 nanotherapy. But this can increase the sensitivity of cancer cells to PD-1 blockade therapy. Indeed, chemotherapy and PD-1 blockade therapy showed a promising synergy, as evidenced by the further significant decrease in both tumor number and tumor burdens in comparison to the individual treatment of chemotherapy or PD-1 blockade therapy (FIGS. 50B-50C). The synergy was largely blocked when PDLIM2 was genetically deleted from lung cancer cells (ΔSPC), suggesting an important role of PDLIM2 in the combination therapy of chemotherapeutic drugs and anti-PD-1. Whereas PDLIM2 nanotherapy increases MHC-I expression on tumor cells for better recognition and killing by CD8+ CTLs, chemotherapy alone or combined with anti-PD-1 failed to do so (FIG. 50D). Anti-PD-1 and chemotherapeutic drug combinational therapy, like the combination therapies of PDLIM2 plasmid nanoparticles with anti-PD-1 or chemotherapeutic drugs, also failed to induce a complete remission of lung cancers in any mice. Given their overlap role in increasing TILs and in particular their complement roles in inducing MHC-I and PD-L1 expression on tumor cells for turning tumor hot and sensitive to PD-1 blockade, simultaneous combination of PDLIM2 nanoparticles and chemotherapeutic drugs with anti-PD-1 should show better efficacy than any therapies combining only two of them. Indeed, combination of all three showed great synergy and induced complete remission of all lung cancers in 60% of mice (FIG. 50E). The remaining tumors shrunk much more dramatically, in comparison to those treated with two combined drugs. In line with the high therapeutic efficacy, the numbers and/or activation of CD4+ and CD8+ T cells were further significantly increased in the lung (FIGS. 50F-50G). It should be pointed out that consistent with the undetectable toxicity of PDLIM2 nanotherapy, its combination did not further increase the toxicity of anti-PD-1 and chemotherapeutic drugs. There was no obvious histological difference of major organs, including the liver, lung, kidney, and spleen (FIG. 51). Moreover, no significant differences in animal body weights were observed by additional PDLIM2 nanotherapy, in comparison to the mice received the combinational treatment of anti-PD-1 and chemotherapeutic drugs in the presence or absence of empty plasmid nanoparticles (FIG. 50H). These data suggested a novel combination therapy, with very high therapeutic efficacy and no increased toxicity, for lung cancer and refractory lung cancer in particular.

Using an authentic mouse model of lung cancer, the present example shows that PDLIM2 nanotherapy has efficacy and high safety, and more importantly, induces complete remission of all lung cancers in most animals when it is combined with anti-PD-1 and chemotherapeutic drugs. Most human lung cancers and also lung cancer in the presently disclosed animal model have low numbers of TILs and decreased expression of PD-L1 and MHC-I on the cell surface, all of which are important mechanisms contributing to the resistance to PD-1 blockade therapy. Through inducing immunogenic cell death (ICD) of cancer cells, chemotherapy is able to increase TILs and also PD-L1 expression, and thereby synergize with anti-PD-1. However, chemotherapy cannot induce MHC-I expression, which limits further improvement of their synergy for complete cancer remission.

On the other hand, PDLIM2 nanotherapy induces MHC-I expression and also lymphocyte tumor infiltration but fails to up-regulate PD-L1. PDLIM2 nanotherapy improves the efficacy of PD-1 blockade therapy but cannot induce complete tumor remission either. Because of these important functions of PDLIM2 nanotherapy and in particular its complementary role in inducing MHC-I and PD-L1 expression on cancer cells with chemotherapy, however, combination of PDLIM2 nanotherapy and chemotherapy is an ideal approach to turn cold tumor hot and sensitive to PD-1 blockade, resulting in complete cancer remission. Moreover, PDLIM2 nanotherapy prevents the induction of MDR1 and the expression of tumor-related genes and in particular cell survival genes, further sensitizing tumor cells to the cytotoxicity of chemotherapeutic drugs and immune cells including those activated by chemotherapy and unleashed by PD-1 blockade.

Another important clinical characteristic of PDLIM2 nanotherapy is its tumor-specificity and high safety profile. Surprisingly, it delivers PDLIM2-expression plasmids to tumor tissues in a specific manner much beyond expectation and shows undetectable toxicity in the animal model. Its combination does not further increase the toxicity of anti-PD-1 and chemotherapeutic drugs. This is sharp contrast to the FDA-approved epigenetic drugs, which can restore PDLIM2 expression in cancer cells with PDLIM2 epigenetic repression (Sun et al., Nat. Commun. 2019. 10, 5324; Qu et al., J. Biol. Chem. 2010. 285, 11786-11792; Qu et al., Cancer Res. 2010. 70, 1766-1772; Sun et al., J. Biol. Chem. 2015. 290, 7362-7368; Yan et al., Neoplasia. 2009. 11, 1036-1041; Vanoirbeek et al., Oncogene. 2014. 33, 1904-1911). Epigenetic drug treatment lead to dramatic body weight loss of animals, especially during the first cycles of the treatment (FIG. 52). This is much worse when epigenetic drugs are combined with chemotherapy.

Both epigenetic therapies and PDLIM2 nanotherapy show significant efficiency in reducing number of tumor cells and tumor burden (FIG. 53). However, the use of epigenetic therapy is limited to lung cancers having epigenetic repression only. About 58% of lung cancers harboring PDLIM2 LOH are not suitable for epigenetic therapies, although most of them are also with epigenetic alterations of the pdlim2 gene. It is noteworthy that the therapeutic efficiency of epigenetic therapy depends on PDLIM2 expression (Sun et al., Nat. Commun. 2019. 10, 5324), and that PDLIM2 heterozygous loss causes spontaneous lung and other cancers. Therefore, PDLIM2 nanotherapy, alone or in combination with chemotherapy and/or immunotherapy, can be administered to a larger population of cancer patients as compared to the epigenetic drugs.

In summary, the present example identifies genetic deletions as the main mechanism for PDLIM2 repression in human lung cancers, and PDLIM2 as a haploinsufficient tumor suppressor particularly important for suppressing lung cancer and therapy resistance. More importantly, these data establish a novel combination treatment of PDLIM2 nanotherapy and PD-1 blockade therapy and chemotherapy that induces complete remission of all lung cancers in most animals and is also with high safety profile. These results are applicable to other cancers linked to PDLIM2 repression.

Although the presently disclosed subject matter and its advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, and composition of matter, and methods described in the specification. As one of ordinary skill in the art will readily appreciate from the disclosure of the presently disclosed subject matter, processes, machines, manufacture, compositions of matter, or methods, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, or methods.

Various patents, patent applications, publications, product descriptions, protocols, and sequence accession numbers are cited throughout this application, the disclosure of which are incorporated herein by reference in their entireties for all purposes.

What is claimed is:

1. A method for treating a subject having a cancer, comprising administering to the subject an agent for increasing the expression of PDZ-LIM domain containing protein 2 (PDLIM2), or a functional fragment thereof, and a second anti-cancer treatment selected from the group consisting of a chemotherapy, a radiotherapy, a targeted drug therapy, an immunotherapy, and a combination thereof, in the subject; wherein the agent is an epigenetic modulating agent selected from the group consisting of DNA methyltransferase inhibitor, histone deacetylase inhibitor, and combination thereof.

2. The method of claim 1, wherein the DNA methyltransferase inhibitor is selected from the group consisting of 5-azadeoxycitidine, 5-aza-cytidine, SGI-110, procainamide, epigallocathechin 3-gallate, RG108, hydralazine, and a combination thereof.

3. The method of claim 1, wherein the histone deacetylase inhibitor is selected from the group consisting of a HDAC1 inhibitor, a HDAC2 inhibitor, a HDAC3 inhibitor, a pan-HDAC inhibitor, and a combination thereof.

4. The method of claim 1, wherein the histone deacetylase inhibitor is selected from the group consisting of entinostat, trichostatin A, vorinostat, panobinostat, romidepsin, belinostat, and a combination thereof.

5. The method of claim 1, wherein the chemotherapy comprises a chemotherapeutic agent selected from the group consisting of cisplatin, carboplatin, docetaxel, gemcitabine, paclitaxel, paclitaxel, vinorelbine, pemetrexed, and a combination thereof.

6. The method of claim 1, wherein the immunotherapy comprises an immune checkpoint inhibitor selected from the group consisting of an anti-PD1 antibody, an anti-PD-L1 antibody, an anti-CTLA-4 antibody, and a combination thereof.

7. The method of claim 1, wherein the cancer is selected from bladder urothelial carcinoma and endocervical carcinoma, cervical squamous cell adenocarcinoma, cholangiocarcinoma, colon adenocarcinoma, head and neck squamous cell carcinoma, kidney chromophobe, kidney renal papillary cell carcinoma, liver hepatocellular carcinoma, lung adenocarcinoma, lung squamous cell carcinoma, prostate adenocarcinoma, rectum adenocarcinoma, stomach adenocarcinoma, and uterine corpus endometrial carcinoma.

8. The method of claim 1, comprising:

a) determining the level of a PDLIM2 biomarker in a sample from the subject;
b) comparing the level of the PDLIM2 biomarker to a reference level; and
c) identifying the subject as not responsive to the second anti-cancer treatment if the PDLIM2 biomarker is lower than the reference level; and
d) treating the subject with the agent for increasing the expression of PDLIM2, or a functional fragment thereof, if the subject is predicted to not be responsive to the anti-cancer treatment.

9. The method of claim 8, wherein the anti-cancer treatment increasing the expression of PDLIM2 or a functional fragment thereof, comprises:

a. a DNA methyltransferase inhibitor selected from 5-azadeoxycitidine, 5-aza-cytidine, SGI-110, procainamide, epigallocathechin 3-gallate, RG108, hydralazine, and combinations thereof;
b. a histone deacetylase inhibitor is selected from HDAC1 inhibitors, HDAC2 inhibitors, HDAC3 inhibitors, pan-HDAC inhibitors, and combinations thereof; and/or
c. a histone deacetylase inhibitor is selected from entinostat, trichostatin A, vorinostat, panobinostat, romidepsin, belinostat, and combinations thereof.

10. The method of claim 8, wherein the chemotherapy comprises a chemotherapeutic agent selected from the group consisting of cisplatin, carboplatin, docetaxel, gemcitabine, paclitaxel, paclitaxel, vinorelbine, pemetrexed, and combinations thereof.

11. The method of claim 8, wherein the immunotherapy comprises an immune checkpoint inhibitor selected from the group consisting of an anti-PD1 antibody, an anti-PD-L1 antibody, an anti-CTLA-4 antibody, and a combination thereof.

12. The method of claim 8, wherein the cancer is selected from bladder urothelial carcinoma, cervical squamous cell carcinoma and endocervical adenocarcinoma, cholangiocarcinoma, colon adenocarcinoma, head and neck squamous cell carcinoma, kidney chromophobe, kidney renal papillary cell carcinoma, liver hepatocellular carcinoma, lung adenocarcinoma, lung squamous cell carcinoma, prostate adenocarcinoma, rectum adenocarcinoma, stomach adenocarcinoma, and uterine corpus endometrial carcinoma.

* * * * *